(12) United States Patent
Beard et al.

(10) Patent No.: US 8,524,917 B2
(45) Date of Patent: *Sep. 3, 2013

(54) 6-SUBSTITUTED INDOLE-3-CARBOXYLIC ACID AMIDE COMPOUNDS HAVING SPHINGOSINE-1-PHOSPHATE (S1P) RECEPTOR ANTAGONIST BIOLOGICAL ACTIVITY

(75) Inventors: Richard L. Beard, Newport Beach, CA (US); Haiqing Yuan, Irvine, CA (US); John E. Donello, Dana Point, CA (US); Xiaoxia Liu, Lake Forest, CA (US); Tien Duong, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 675 days.

This patent is subject to a terminal disclaimer.

(21) Appl. No.: 12/013,239

(22) Filed: Jan. 11, 2008

(65) Prior Publication Data

US 2008/0171772 A1   Jul. 17, 2008

Related U.S. Application Data

(60) Provisional application No. 60/884,470, filed on Jan. 11, 2007.

(51) Int. Cl.
- A61K 31/444   (2006.01)
- A61K 31/4439  (2006.01)
- A61K 31/404   (2006.01)
- C07D 209/42   (2006.01)
- C07D 401/14   (2006.01)
- C07D 401/12   (2006.01)
- C07D 401/06   (2006.01)

(52) U.S. Cl.
USPC ........ 548/492; 546/256; 546/278.1; 548/466; 514/333; 514/339; 514/414; 514/419

(58) Field of Classification Search
USPC ...................................................... 548/492
See application file for complete search history.

(56) References Cited

U.S. PATENT DOCUMENTS

| | | | |
|---|---|---|---|
| 4,619,941 A * | 10/1986 | Wright et al. | 514/397 |
| 4,952,683 A | 8/1990 | Tschannen et al. | |
| 5,026,722 A * | 6/1991 | Oxford et al. | 514/397 |
| 5,102,901 A | 4/1992 | vanWijngaarden et al. | |
| 5,110,987 A | 5/1992 | Liotta et al. | |
| 5,294,722 A | 3/1994 | Kim | |
| 5,403,851 A | 4/1995 | D'Orlando et al. | |
| 5,580,878 A | 12/1996 | D'Orlando et al. | |
| 5,994,378 A | 11/1999 | Matsuo et al. | |
| 6,235,912 B1 | 5/2001 | Takesako et al. | |
| 6,239,297 B1 | 5/2001 | Takesako et al. | |
| 6,342,516 B1 * | 1/2002 | Umeda et al. | 514/397 |
| 6,951,848 B2 * | 10/2005 | Harriman et al. | 514/183 |
| 7,737,173 B2 * | 6/2010 | Beard et al. | 514/419 |
| 2003/0125371 A1 | 7/2003 | Elokdah et al. | |
| 2007/0191313 A1 | 8/2007 | Liu et al. | |
| 2007/0232682 A1 | 10/2007 | Beard et al. | |

FOREIGN PATENT DOCUMENTS

| | | |
|---|---|---|
| DE | 197 53 522 A1 | 6/1999 |
| FR | 2 121 394 | 8/1972 |
| WO | WO 99/33800 | 7/1999 |
| WO | WO 00/42045 | 7/2000 |
| WO | WO-00/42045 A2 * | 7/2000 |
| WO | WO 01/98301 A | 12/2001 |
| WO | WO03-062252 | 7/2003 |
| WO | WO 03/070691 A | 8/2003 |
| WO | WO2004-096752 | 7/2004 |
| WO | WO2004-071442 | 8/2004 |
| WO | WO2004-103306 | 12/2004 |
| WO | WO 2007/095561 | 8/2007 |
| WO | WO 2007/095561 A | 8/2007 |
| WO | WO 2008/016883 | 2/2008 |
| WO | WO 2008/089015 | 7/2008 |
| WO | WO 2008/141013 | 11/2008 |

OTHER PUBLICATIONS

Heckel et al., Chemical Abstract 131:31874, 1999.*
Daryl R. Sauer et al.: "Microwave-Assisted Synthesis Utilizing-Supported Reagents: a Rapid and Efficient Acylation Procedure" Organic Letters, vol. 5, No. 24, 2003, pp. 4721-4724.
Di Santo R. et. al.: "N-(1-Naphthylmethyl)-n-(1-alky1-4-aryl-Inpyrrol-3-Ylmethyl)Methylam inres Related to Naftifine. Synthesis and Antifungal Activity" Medicinal Chemistry Research, Birkhaeuser, Boston, US, vol. 7, No. 2, 1997, pp. 98-108.
Domschke G. et. al.: "N-Substituierte 1-Benzyl-2-Methyl-3-Aminomethyl-5-Methoxy-Indole Und Verwandte Verbindungen" Chemische Berichte, Verlag Chemie GMBH. Weinheim, DE, vol. 93, 1960, pp. 2097-2106.
Joginder S. Bajwa: "Chemoselective Deprotection of Benzyl Esters in the Presence of Benzyl Ethers, Benzyloxymethyl Ether and N-Benzyl Groups by Catalytic Transfer Hydrogenation" Tetrahedron Letters, vol. 33, No. 17, 1992, pp. 2299-2302.
John T. Carlock et al.: "3-diazo-4-oxo-3, 4-Dihydroquinoline. A Novel Synthon for Indole-3-Carboxamides" Journal of Organic Chemistry, vol. 42, No. 11, 1977, pp. 1883-1885.

(Continued)

Primary Examiner — Laura L. Stockton
(74) Attorney, Agent, or Firm — Doina G. Ene

(57) ABSTRACT

The invention provides compounds represented by the formula I, each of which compounds may have sphingosine-1-phosphate receptor agonist and or antagonist biological activity:

Formula I

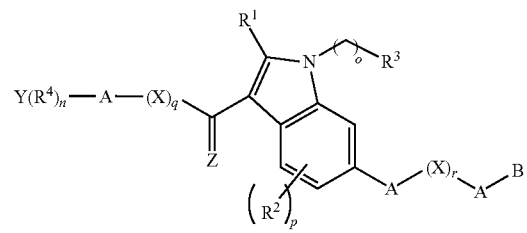

and wherein the variables Y, $R^4$, n, o, A, $A^1$, $A^2$, X, Z, $R^1$, $R^3$, $R^2$, p, q and r are as defined in the specification. These compounds are useful for treating a disease or condition selected from the group consisting of glaucoma, dry eye, angiogenesis, cardiovascular conditions and diseases, and wound healing.

14 Claims, No Drawings

(56) References Cited

OTHER PUBLICATIONS

Jonathan Clayden et al.: "Nucleophilic Addition to Election-rich Heteroaromatics: Dearomatizing Anionic Cyclizations of Pyrrolecarboxamides" Organic Letters, vol. 6, No. 4, 2004, pp. 609-611.
Kutschy P. et. al.: "Synthesis of Some Analogs of Indole Phytoalexins Brassinin and Methoxybras Sinin B and Their Postional Isomers" Collection of Czechoslovak Chemical Communications, Institute or Organic Chemistry & Biochemistry, Prague, CZ, vol. 64, No. 2, Feb. 1999, pp. 348-362.
Nagashima et. al.: "Fluorous 2-Chloropyridinium Salt (Mukaiyama Condensation Reagent) for Amide Formation Reactions" Tetrahedron Letters, Elsevier, Amsterdam, NL, vol. 46, No. 38, Sep. 19, 2005, pp. 6585-6588.
STN Database Accession No. 2003:678775, RN 591218-03-0, XP002444827, 2003.
STN Database Accession No. 2023870141, RN 866145-24-6, XP002444828, 2005.
STN Database Accession No. 131:31874, RN 226901-36-6, XP002481307, 1999.
Clemens et al, Bioorg. Med. Chem. Lett. 13, 3401-3404, 2003.
Hale et al, Bioorg. Med. Chem. Lett. 14, 3351-3355, 2004.
Hale et al, Bioorg. Med. Chem. Lett. 14, 3495-3499, 2004.
Yan et al, Bioorg. Med. Chem. Lett. 14, 4861-4866, 2004.
Clemens et al, Bioorg. Med. Chem. Lett. 14, 4903-4906, 2004.
Hale et al, Bioorg. Med. Chem. Lett. 14, 3501-3505, 2004.
Hale et al, J.. Med. Chem., 47, 6662-6665, 2004.
Matter, H.; et al.: Design and Quantitative Structure-Activity Relationship of 3-Amidinobenzyl-1H-indole-2-carboxamides . . . J. Med. Chem. vol. 45; Jan. 1, 2002. p. 2749-2769.
Olgen; et al.: Synthesis and Evaluation of N-substituted Indole-3-Carboxamide Derivatives as Inhib . . . J. Enzyme Inhibition and Med. Chem. vol. 23, No. 3, Jun. 2008, p. 334-340.
Sureyya, Olegen; et al.: New Potent Indole Derivatives as Hyaluronidase Inhibitors. Chem. Biol. Drug Des, vol. 70, 2007, pp. 547-551.

* cited by examiner

6-SUBSTITUTED INDOLE-3-CARBOXYLIC ACID AMIDE COMPOUNDS HAVING SPHINGOSINE-1-PHOSPHATE (S1P) RECEPTOR ANTAGONIST BIOLOGICAL ACTIVITY

CROSS-REFERENCE TO RELATED APPLICATION

This application is based on, and claims priority under 35 U.S.C. §120 to U.S. Provisional Application No. 60/884,470, filed on Jan. 11, 2007, and which is incorporated herein by reference.

BACKGROUND OF THE INVENTION

1. Field of the Invention

The present invention relates to derivatives and/or analogues of sphingosine and pharmaceutical compositions, including such derivatives and/or analogues, which are useful as drugs for the treatment of fungal infections, allergic diseases, immune disorders, etc.

2. Summary of the Art

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

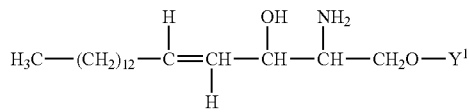

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by spingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 μM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or spingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

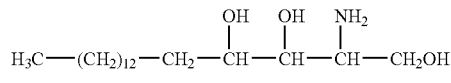

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683; 5,110, 987; 6,235,912 B1 and 6,239,297 B1.

Also, compounds which are similar to certain spingosine derivatives, but which are not reported as being ligands for the spingosine receptors are reported in various patents and published patent applications. See for example, U.S. Pat. Nos. 5,294,722; 5,102,901; 5,403,851 and 5,580,878. U.S. Patent Application Publication No. U.S. 2003/0125371 A2. While certain of the compounds reported in the above patents are indoles, it does not appear that indole compounds have been reported as being ligands for sphingosine receptor or having activity as sphingosine agonists or antagonists.

SUMMARY OF THE INVENTION

The present invention provides a derivative or analogue of sphingosine that is able to regulate the functions of sphingolipid, and pharmaceutical compositions comprising said derivative or analogue.

Compounds represented by the formula I having sphingosine-1-phosphate receptor agonist and or antagonist biological activity:

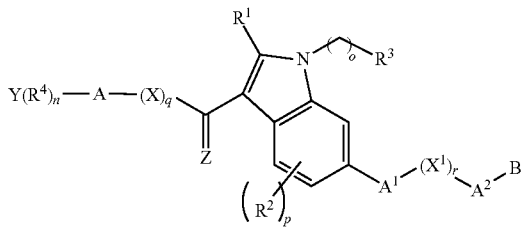

Formula I wherein:
$R^1$ $R^2$, $R^3$ and $R^4$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, carbocyclic hydrocarbon groups having from 3 to 20 carbon atoms, heterocyclic groups having up to 20 carbon atoms and at least one of oxygen, nitrogen and/or sulfur in the ring, halo, $C_1$ to $C_{12}$ haloalkyl, hydroxyl, $C_1$ to $C_{12}$ alkoxy, $C_3$ to $C_{20}$ arylalkyloxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, and sulfonyl groups;
X and $X^1$ are independently selected from the group consisting of $NR^5$, O and S; $R^5$ is hydrogen, an alkyl group of 1 to 10 carbons, a cycloalkyl group of 5 to 10 carbons, phenyl or lower alkylphenyl; Y is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;
Z is O or S;
n is 0 or an integer of from 1 to 5;
o is 0 or an integer of from 1 to 3;
p is 0 or an integer of from 1 to 3;
q is 0 or 1;
r is 0 or 1;
A, $A^1$ and $A^2$ are independently selected from the group consisting of $(CH_2)_v$ wherein v is 0 or an integer of from 1 to 12, branched chain alkyl having 3 to 12 carbons, cycloalkyl having 3 to 12 carbons, alkenyl having 2 to 10 carbons and 1-3 double bonds and alkynyl having 2 to 10 carbons and 1 to 3 triple bonds;
B is selected from the group consisting of hydrogen, $OR^6$, $COOR^7$, $NR^8R^9$, $CONR^8R^9$, $COR^{10}$, $CH=NOR^{11}$, $CH=NNR^{12}R^{13}$ wherein $R^6$, $R^7$, $R^{10}$ and $R^{11}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, $R^8$, $R^9$, $R^{12}$ and $R^{13}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, or $R^8$ and $R^9$ and/or $R^{12}$ and $R^{13}$, together, can form a divalent carbon radical of 2 to 5 carbons to form a heterocyclic ring with nitrogen, wherein any of $R^6$, $R^7$, $R^8$, $R^9$, $R^{10}$, $R^{11}$, $R^{12}$ or $R^{13}$ may be substituted with one or more halogen, hydroxy, alkyloxy, cyano, nitro, mercapto or thiol radical; provided however, when v is 0, and r is 0, B is not hydrogen; or B is a carbocyclic hydrocarbon group having from 3 to 20 carbon atoms, or a heterocyclic group having up to 20 carbon atoms and at least one of oxygen, nitrogen and/or sulfur in the ring, and wherein when said B is a carbocyclic or heterocyclic group B may be bonded to $A^2$ at any position, or a pharmaceutically acceptable salt of said compound.

The aryl group is a carbocyclic aryl or heterocyclic aryl group wherein said carbocylic aryl comprises from 6 to 20 atoms and said heterocyclic aryl comprise from 2 to 20 carbon atoms and from 1 to 5 heteroatoms selected from the group consisting of nitrogen, oxygen and sulfur, and preferably said aryl group is selected from the group consisting of benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone. Said aryl groups can be bonded to the above moiety at any position. Said aryl group may itself be substituted with any common organic functional group including but not limited to $C_1$ to $C_{12}$ alkyl, $C_2$ to $C_6$ alkenyl, $C_2$ to $C_6$ alkynyl, halo, $C_1$ to $C_{12}$ haloalkyl, hydroxyl, $C_1$ to $C_{12}$ alkoxyl, $C_1$ to $C_{12}$ alkylcarbonyl, formyl, oxycarbonyl, carboxyl, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups.

Preferably Z is O.
Preferably, the carbocyclic aryl group will comprise from 6 to 14 carbon atoms, e.g. from 6 to 10 carbon atoms. Preferably the heterocyclic aryl group will comprise from 2 to 14 carbon atoms and one or more, e.g. from 1 to 3 heteroatoms selected from the group consisting of nitrogen, oxygen and sulfur.
Preferably, A is $CH_2$.
Preferably, X is NH.
Preferably, n is 0 or an integer of 1 or 2 and $R^4$ is fluoro.
Preferably, $R^1$ is i-propyl.
Preferably, $R^3$ is selected from the group consisting of phenyl, which may be substituted with one or two flouro groups, and pyridyl.
Preferably, p is 0.
Preferably, $A^1$ and $A^2$ are absent.
Preferably, B is $OR^6$ or $COOR^7$.

Preferably, X is O, r is 1, $A^1$ is absent, $A^2$ is $(CH_2)_v$, wherein v is 1 or 2, and B is $OR^6$ or $NR^8R^9$ and $R^6$, $R^8$ and $R^9$ are methyl.

Preferably, B is $CR^{10}=NOR^{11}R^{10}$ wherein $R^{10}$ is H and $R^{11}$ is methyl or i-butyl or B is $CONR^8R^9$ wherein $R^8$ and $R^9$ are selected from the group consisting of H, methyl, ethyl and propyl, or $R^8$ and $R^9$, together with N, form a 5-member ring.

Preferably, $A^1$ is absent, r is 0, $A^2$ is $CH_2$ and B is $OR^6$, wherein $R^6$ is H, or X is O, r is 1 and B is $COR^{10}$, wherein $R^{10}$ is methyl.

Specific Examples of the compounds of formula I include

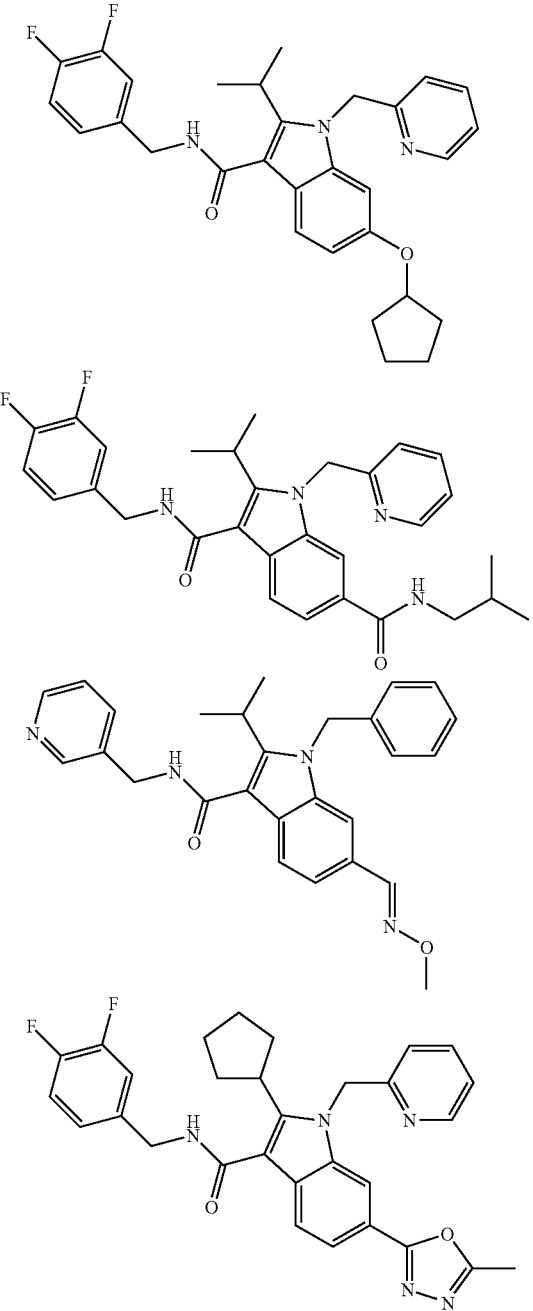

pound (e.g. benzyl bromide) in the presence of an weak base (e.g. potassium carbonate) to produce an N-alkylated indole (e.g. methyl 1-benzyl-6-methoxyindole-2-carboxylate). The 2-carboxylate group is converted to an alkyl group by a three-step process: Grignard reaction, elimination, and hydrogenation. The resulting 2-alkyl indole is carboxylated in the 3-position by treatment with dimethylformamide and phosphorus oxychloride followed by sodium hypochlorite oxidation of the resulting aldehyde. The carboxylic acid may be further functionalized by treatment with an amine in the presence of N-(3-dimethylaminopropyl)-N'-ethylcarbodimide (EDC) to produce a 6-methoxyindole-3-carboxamide derivative (e.g. 3,4-difluorophenylmethyl6-methoxy-2-isopropyl-1-benzylindole-3-carboxamide). The carboxylic acid may also be treated with an alcohol or thiol in the presence of EDC to produce an ester and thiol ester derivatives, respectively. The 6-methoxy group may then be deprotected using boron tribromide and the resulting hydroxide subjected to alkylating (e.g. cyclopentyl iodide/potassium carbonate) or acylating (e.g. pivaloyl chloride/pyridine) reagents to produce a large variety of 6-substituted indole homologs and derivatives within the scope of the invention.

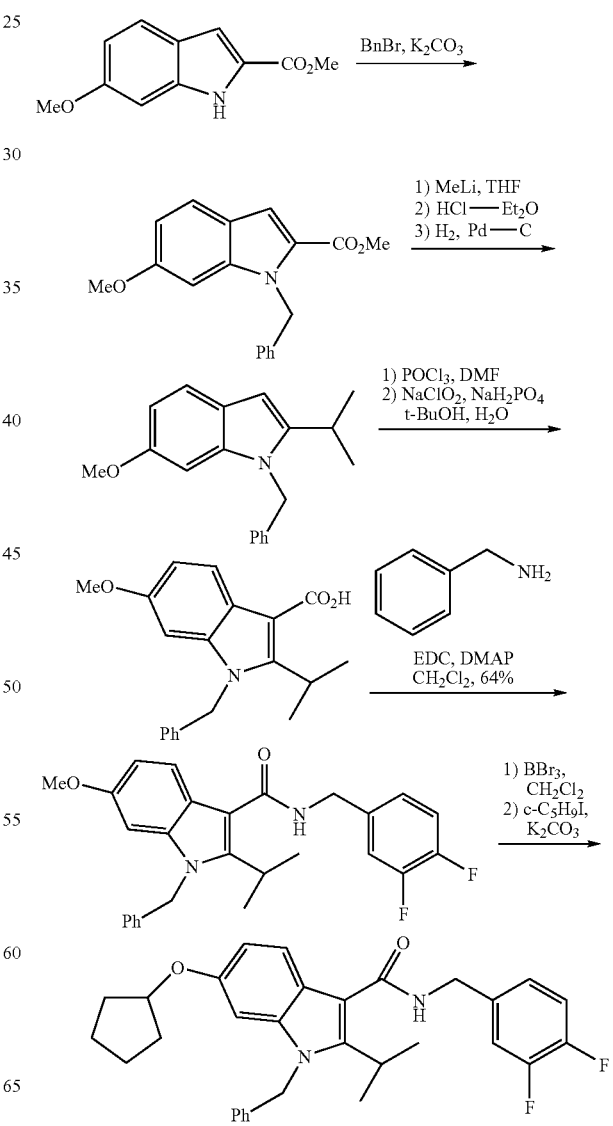

Some compounds within the scope of the invention may be prepared as depicted in Scheme 1. Thus, methyl 6-methoxyindole-2-carboxylate is treated with an electrophilic com- Many other compounds within the scope of the invention may be prepared as depicted in Scheme 2. Thus, ethyl 4-iodobenzoate may be nitrated in the 3-position with fuming nitric acid and the resulting nitro compound reduced under mild conditions (e.g. $SnCl_2$—$H_2O$) to produce ethyl 3-amino-4-iodobenzoate. This compound may be converted to the indole by treatment with a terminal alkyne (e.g. 3-methylbutyne) in the presence of a palladium catalyst and copper iodide followed by heating the aryl alkyne in the presence of copper iodide. The resulting 2-alkyl indole may then be carbonylated in the 3-position by treatment with dimethylformamide and phosphorus oxychloride and N-alkylated as described above (benzyl bromide, potassium carbonate), followed by sodium hypochlorite oxidation to produce an N-alkylindole-3-carboxylic acid. The carboxylic acid may be further functionalized by treatment with an amine in the presence of EDC to

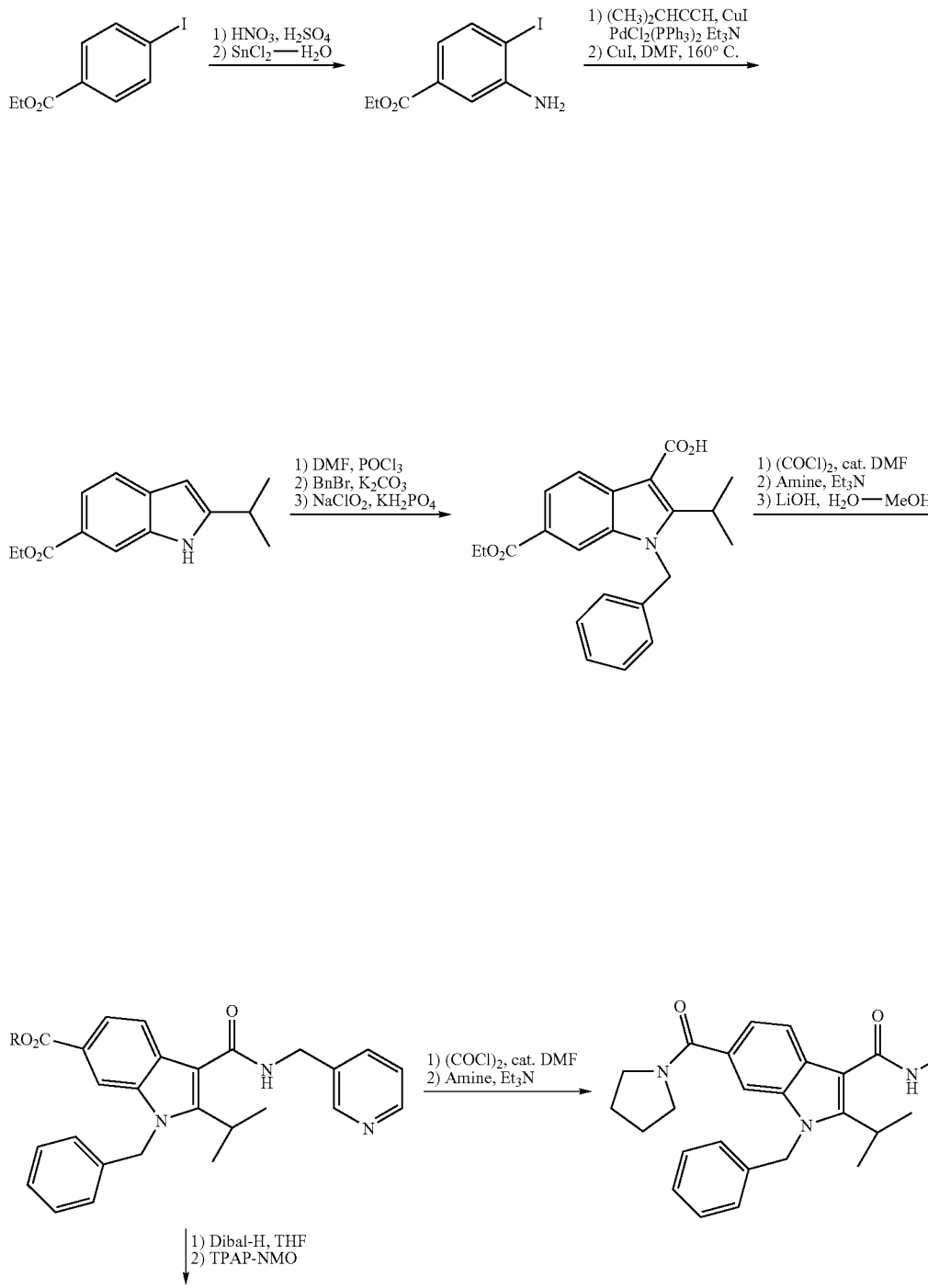

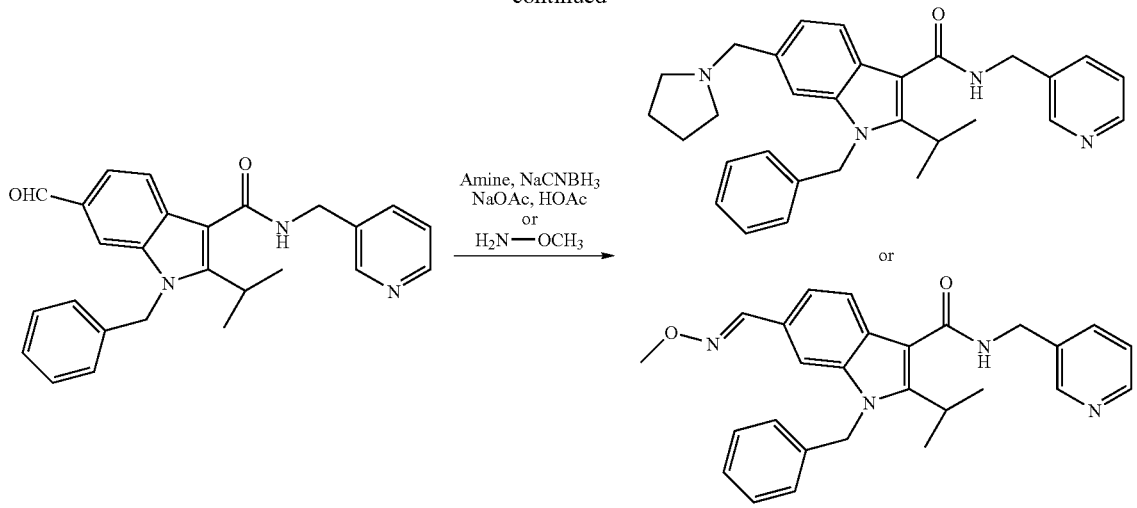

produce a 6-methoxyindole-3-carboxamide derivative (e.g. 3-pyridylmethyl 1-benzyl-6-carboethoxy-2-isopropylindole-3-carboxamide). The carboxylic acid may also be treated with an alcohol or thiol in the presence of EDC to produce an ester and thiol ester derivatives, respectively. The 6-carboethoxy group may be further functionalized to produce a large variety of 6-substituted indole homologs and derivatives within the scope of the invention. For example, the 6-carboethoxy group be hydrolyzed with strong base and the resulting carboxylic acid converted to the carboxylic acid chloride, which could be reacted with various alcohols or amines in the presence of base to produce ester or amide derivatives, respectively, such as 3-pyridylmethyl1-benzyl-2-isopropyl-6-(1-pyrrolidinylcarbamoyl)indole-3-carboxamide. Alternatively, the 6-carboethoxy group could be reduced to an alcohol and re-oxidized to an aldehyde intermediate, which may then be treated with an amine under reducing conditions to give amine derivatives such as 3-pyridylmethyl1-benzyl-2-isopropyl-6-(1-pyrrolidinylmethyl)-indole-3-carboxamide. The aldehyde may also be treated with oxime or hydrazine compounds to produce oxime and hydrazone derivatives, respectively. Thus, many compounds within the scope of the invention may be produced by the general route depicted in Scheme 2. Additional compounds within the scope of the invention are exemplified in Tables 1 and 1A.

DETAILED DESCRIPTION OF THE INVENTION

Unless otherwise indicated, the following terms as used throughout this specification have the following meanings:

"Me" refers to methyl.
"Et" refers to ethyl.
"tBu" refers to t-butyl.
"iPr" refers to i-propyl.
"Ph" refers to phenyl.
"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino and SH.

"Alkynyl" refers to a straight-chain, branched or cyclic unsaturated hydrocarbon containing at least one carbon-carbon triple bond. Preferably, the alkynyl group has 2 to 12 carbons. More preferably it is a lower alkynyl of from 2 to 7 carbons, most preferably 2 to 4 carbons. The alkynyl group may be optionally substituted with one or more substituents selected from the group consisting of hydroxyl, cyano, alkoxy, O, S, $NO_2$, halogen, dimethyl amino and SH.

"Alkoxy" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Aryloxy" refers to an "O-aryl" group.

"Arylalkyloxy" refers to an "O-alkaryl" group.

"Carbocyclic" refers to cyclic saturated or unsaturated aliphatic hydrocarbon and aryl hydrocarbon groups wherein the ring atoms are exclusively carbons, and comprises from 6 to 20 carbon atoms, including said ring atoms.

"Carbocyclic aryl" refers to an aryl group wherein the ring atoms are carbon.

"Heterocyclic" refers to cyclic groups wherein the ring atoms comprise carbon atoms and at least one oxygen, nitrogen, and/or sulfur atom and may be saturated, unsaturated, i.e.

have one or more double bonds, or aryl, and comprises up to 20 carbon atoms and from 1 to 5 of the above heteroatoms.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Ester" refers to —C(O)—O—R', wherein R' is alkyl, aryl or alkylaryl.

"Thioamide" refers to —C(S)—NH—R', wherein R' is alkyl, aryl, alkylaryl or hydrogen.

"Thiol ester" refers to —C(O)—S—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$ CN, alkyaryl, sulfonamide, NH-alkyl, NH-alkylaryl, or NH-aryl.

Also, alternatively the substituent on the phenyl moiety, as shown below, is referred to as an o, m or p substituent or a 2, 3 or 4 substituent, respectively. (Obviously, the 5 substituent is also a m substituent and the 6 substituent is an o substituent.)

Specific compounds of the invention, that are prepared according to Example 2 through 199 and/or Schemes 1 through 16, are able to inhibit the activity of sphingosine-1-phosphate receptors reported in Table I, below. Compounds were assessed for their ability to activate or block activation of the human S1P3 receptor in T24 cells stably expressing the human S1P3 receptor. Ten thousand cells/well were plated into 384-well poly-D-lysine coated plates one day prior to use. The growth media for the S1P3 receptor expressing cell line was McCoy's 5A medium supplemented with 10% charcoal-treated fetal bovine serum (FBS), 1% antibiotic-antimycotic and 400 µg/ml geneticin. On the day of the experiment, the cells were washed twice with Hank's Balanced Salt Solution supplemented with 20 mM HEPES (HBSS/Hepes buffer). The cells were then dye loaded with 2 uM Fluo-4 diluted in the HBSS/Hepes buffer with 1.25 mM Probenecid and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. The positive control, Sphingosine-1-Phosphate (S1P), was diluted in HBSS/Hepes buffer with 4 mg/ml fatty acid free bovine serum albumin. The FLIPR transferred 12.5 µl from the ligand microplate to the cell plate and took fluorescent measurements for 75 seconds, taking readings every second, and then for 2.5 minutes, taking readings every 10 seconds. Drugs were tested over the concentration range of 0.61 nM to 10,000 nM. Data for Ca$^{+2}$ responses were obtained in arbitrary fluorescence units and not translated into Ca$^{+2}$ concentrations. IC$_{50}$ values were determined through a linear regression analysis using the Levenburg Marquardt algorithm.

TABLE 1

| Compound Number | Structure | S1P3 IC$_{50}$ (% inh) Kb |
|---|---|---|
| 7 | 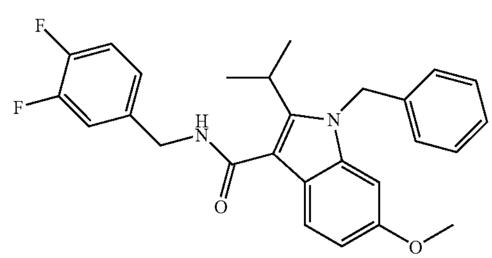 [SMILES: COc1ccc2c(C(=O)NCc3ccc(F)c(F)c3)c(C(C)C)n(Cc3ccccc3)c2c1] | 560 nM (98) |
| 8 | 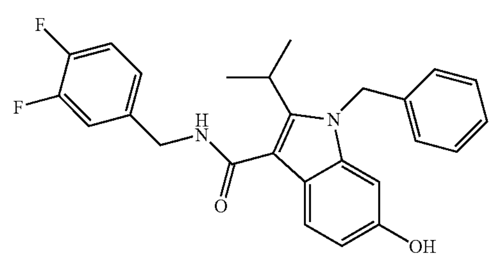 [SMILES: CC(C)c1c(C(=O)NCc2ccc(F)c(F)c2)c2ccc(O)cc2n1Cc1ccccc1] | 3.1 µM (71) |

TABLE 1-continued

| Compound Number | Structure | S1P3 IC$_{50}$ (% inh) Kb |
|---|---|---|
| 9 | 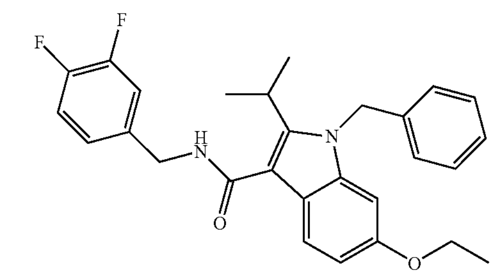 | 19 nM (100) |
| 10 | 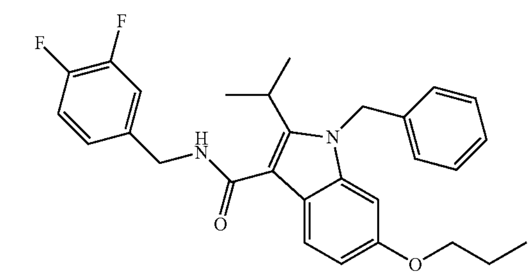 | 5 nM (100) 2 nM |
| 11 | 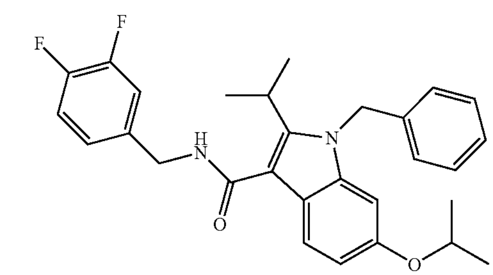 | 6 nM (100) 2 nM |
| 12 | 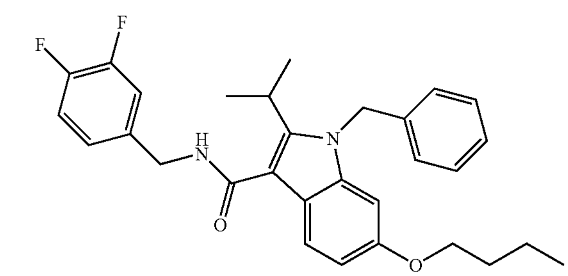 | 3 nM (100) |
| 13 | 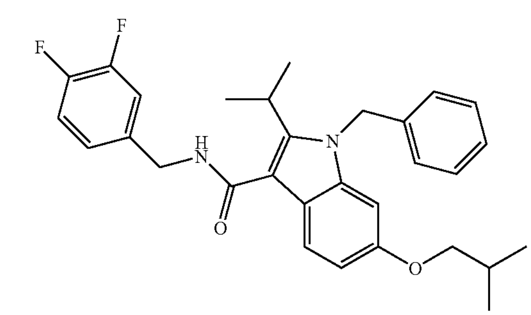 [SMILES: CC(C)COc1ccc2c(C(=O)NCc3ccc(F)c(F)c3)c(C(C)C)n(Cc3ccccc3)c2c1] | 1.2 nM (100) 1.6 nM |

TABLE 1-continued

| Compound Number | Structure | S1P3 IC$_{50}$ (% inh) Kb |
|---|---|---|
| 14 | 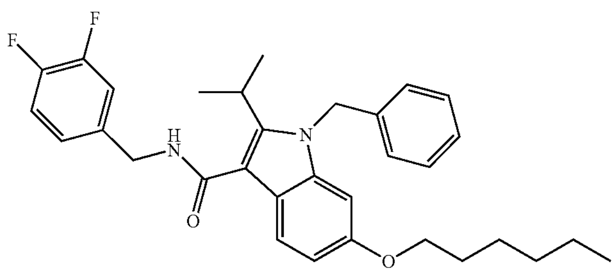 [SMILES: CCCCCCOc1ccc2c(C(=O)NCc3ccc(F)c(F)c3)c(C(C)C)n(Cc3ccccc3)c2c1] | 3.1 μM (96) |
| 15 | 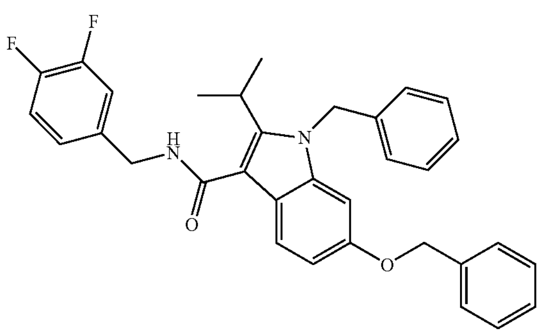 [SMILES: CC(C)c1c(C(=O)NCc2ccc(F)c(F)c2)c2ccc(OCc3ccccc3)cc2n1Cc1ccccc1] | 260 nM (100) |
| 16 | 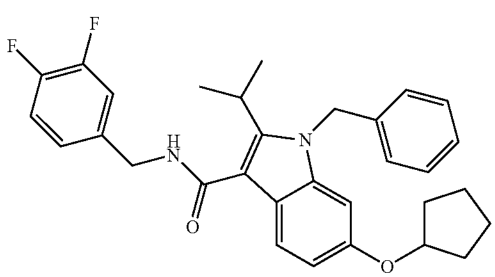 [SMILES: CC(C)c1c(C(=O)NCc2ccc(F)c(F)c2)c2ccc(OC3CCCC3)cc2n1Cc1ccccc1] | 3 nM (100) 1.2 nM |
| 17 | 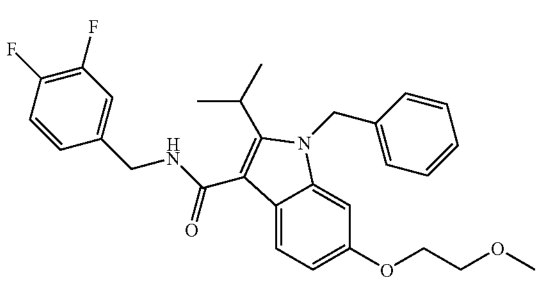 | 6.5 nM (99) |
| 18 | 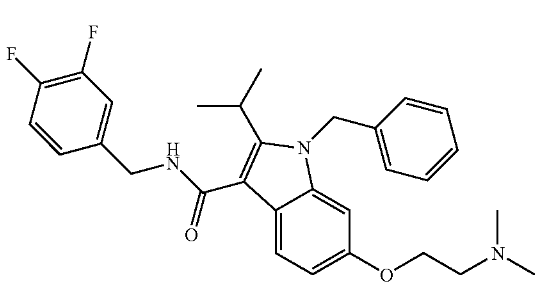 [SMILES: CC(C)c1c(C(=O)NCc2ccc(F)c(F)c2)c2ccc(OCCN(C)C)cc2n1Cc1ccccc1] | 242 nM (94) |

TABLE 1-continued

| Compound Number | Structure | S1P3 IC$_{50}$ (% inh) Kb |
|---|---|---|
| 19 | 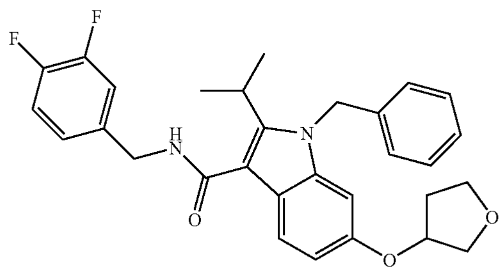 | 6 nM (100) |
| 20 | 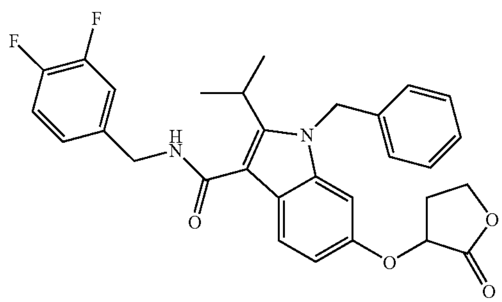 [SMILES: CC(C)c1c(C(=O)NCc2ccc(F)c(F)c2)c2ccc(OC3CCOC3=O)cc2n1Cc1ccccc1] | 81 nM (100) |
| 21 | 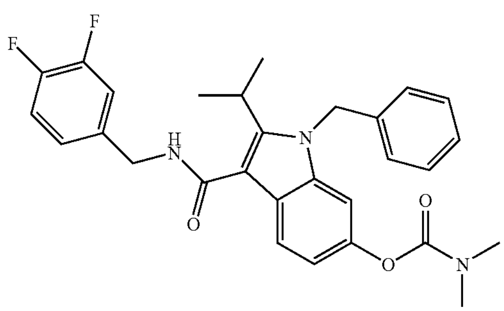 | 24 nM (99) |
| 22 | 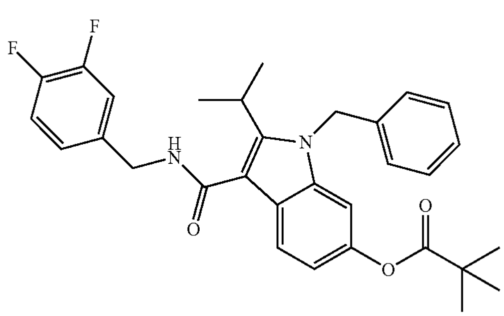 [SMILES: CC(C)c1c(C(=O)NCc2ccc(F)c(F)c2)c2ccc(OC(=O)C(C)(C)C)cc2n1Cc1ccccc1] | 4 nM (99) |
| 23 | 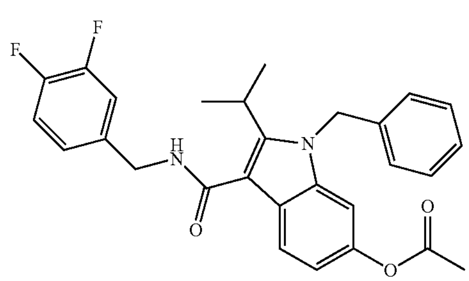 [SMILES: CC(=O)Oc1ccc2c(C(=O)NCc3ccc(F)c(F)c3)c(C(C)C)n(Cc3ccccc3)c2c1] | 14 nM (100) |

TABLE 1-continued

| Compound Number | Structure | S1P3 IC$_{50}$ (% inh) Kb |
|---|---|---|
| 24 | 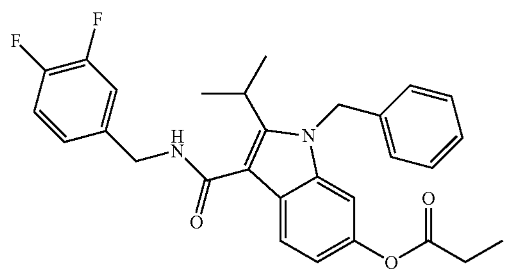 [SMILES: CCC(=O)Oc1ccc2c(C(=O)NCc3ccc(F)c(F)c3)c(C(C)C)n(Cc3ccccc3)c2c1] | 20 nM (100) |
| 25 | 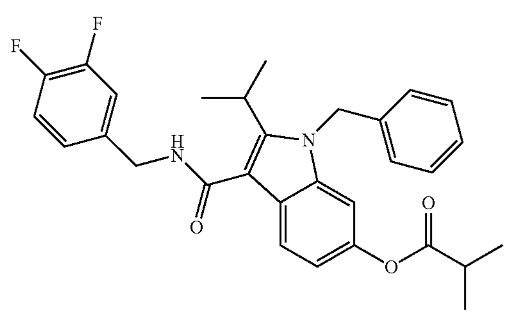 [SMILES: CC(C)C(=O)Oc1ccc2c(C(=O)NCc3ccc(F)c(F)c3)c(C(C)C)n(Cc3ccccc3)c2c1] | 14 nM (100) |
| 26 | 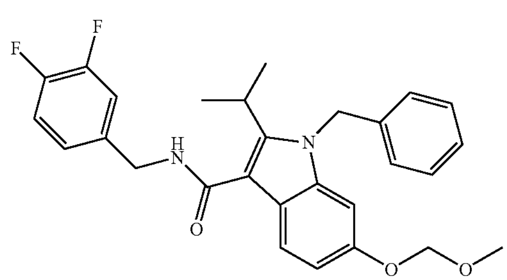 | 39 nM (100) 13 nM |
| 27 | 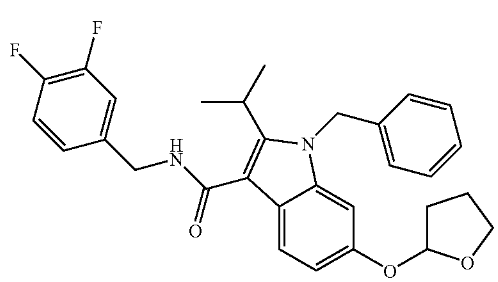 [SMILES: CC(C)c1c(C(=O)NCc2ccc(F)c(F)c2)c2ccc(OC3CCCO3)cc2n1Cc1ccccc1] | 6 nM (100) 11 nM |
| 43 | 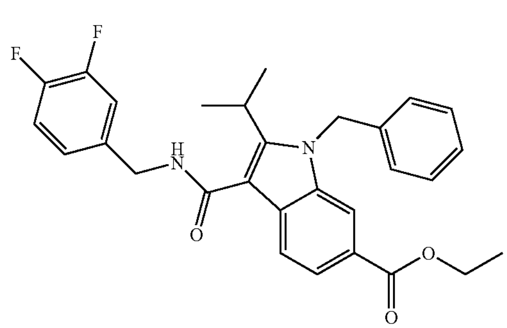 [SMILES: CCOC(=O)c1ccc2c(C(=O)NCc3ccc(F)c(F)c3)c(C(C)C)n(Cc3ccccc3)c2c1] | 7 nM (100) 8 nM |

TABLE 1-continued

| Compound Number | Structure | S1P3 IC$_{50}$ (% inh) Kb |
|---|---|---|
| 44 | 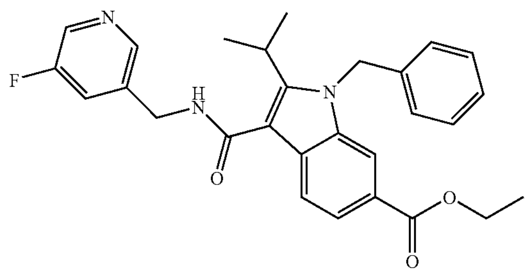 [SMILES: CCOC(=O)c1ccc2c(C(=O)NCc3cncc(F)c3)c(C(C)C)n(Cc3ccccc3)c2c1] | 24 nM (100) |
| 45 | 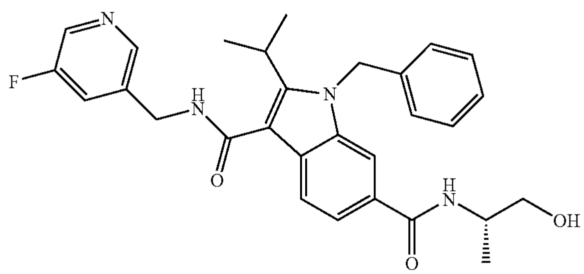 [SMILES: CC(C)c1c(C(=O)NCc2cncc(F)c2)c2ccc(C(=O)N[C@@H](C)CO)cc2n1Cc1ccccc1] | NA |
| 46 | 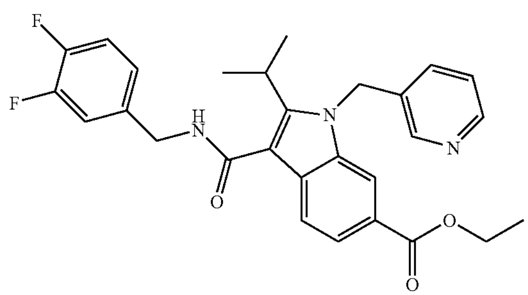 [SMILES: CCOC(=O)c1ccc2c(C(=O)NCc3ccc(F)c(F)c3)c(C(C)C)n(Cc3cccnc3)c2c1] | 241 nM (100) |
| 47 | 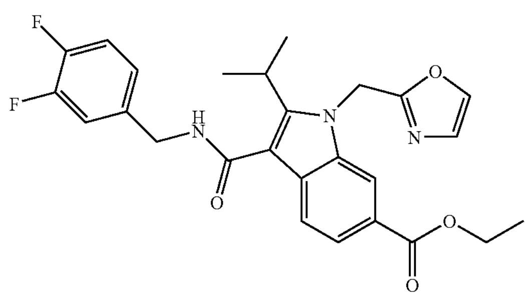 [SMILES: CCOC(=O)c1ccc2c(C(=O)NCc3ccc(F)c(F)c3)c(C(C)C)n(Cc3ncco3)c2c1] | 350 nM (100) |
| 48 | 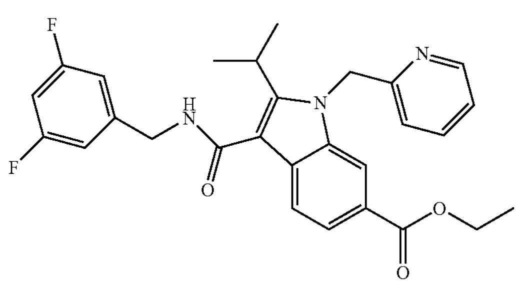 [SMILES: CCOC(=O)c1ccc2c(C(=O)NCc3cc(F)cc(F)c3)c(C(C)C)n(Cc3ccccn3)c2c1] | 24 nM (100) |

TABLE 1-continued

| Compound Number | Structure | S1P3 IC$_{50}$ (% inh) Kb |
|---|---|---|
| 49 | 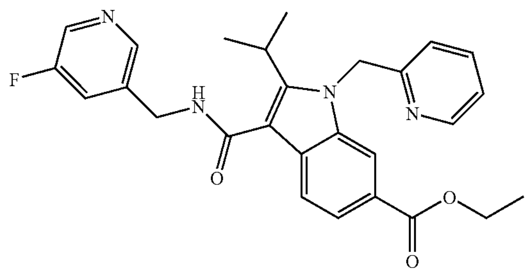 [SMILES: CCOC(=O)c1ccc2c(C(=O)NCc3cncc(F)c3)c(C(C)C)n(Cc3ccccn3)c2c1] | 870 nM (100) |
| 50 | 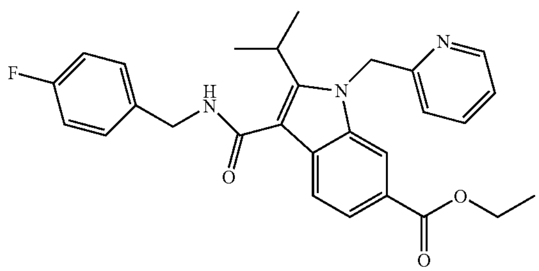 [SMILES: CCOC(=O)c1ccc2c(C(=O)NCc3ccc(F)cc3)c(C(C)C)n(Cc3ccccn3)c2c1] | 69 nM (100) |
| 51 | 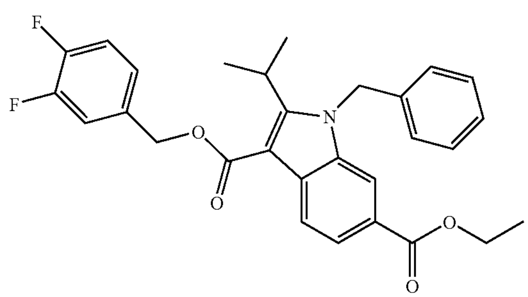 [SMILES: CCOC(=O)c1ccc2c(C(=O)OCc3ccc(F)c(F)c3)c(C(C)C)n(Cc3ccccc3)c2c1] | NA |
| 52 | 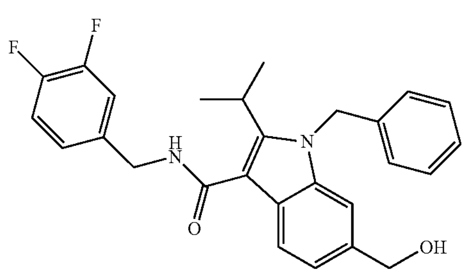 [SMILES: CC(C)c1c(C(=O)NCc2ccc(F)c(F)c2)c2ccc(CO)cc2n1Cc1ccccc1] | 2.0 μM (85) |
| 54 | 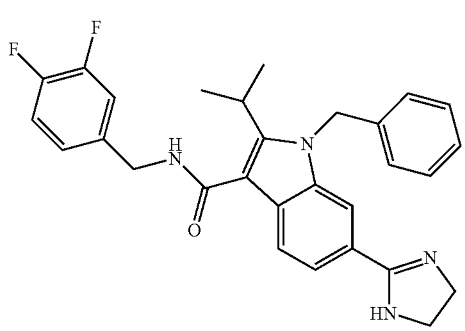 [SMILES: CC(C)c1c(C(=O)NCc2ccc(F)c(F)c2)c2ccc(C3=NCCN3)cc2n1Cc1ccccc1] | NA |

TABLE 1-continued

| Compound Number | Structure | S1P3 IC$_{50}$ (% inh) Kb |
|---|---|---|
| 55 | 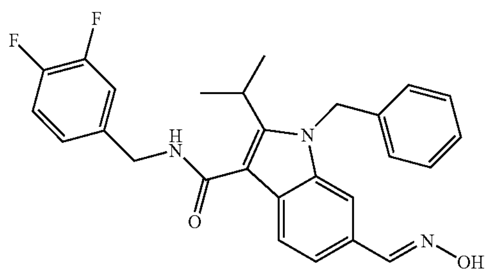 [SMILES: CC(C)c1c(C(=O)NCc2ccc(F)c(F)c2)c2ccc(/C=N/O)cc2n1Cc1ccccc1] | 234 nM (100) |
| 69 | 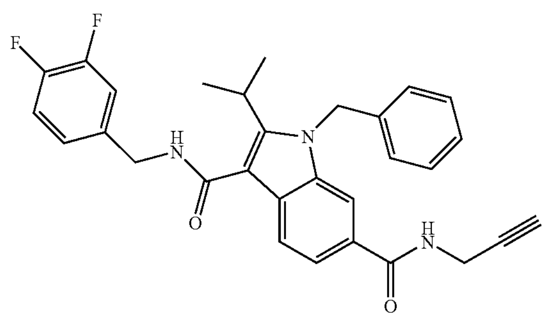 [SMILES: C#CCNC(=O)c1ccc2c(C(=O)NCc3ccc(F)c(F)c3)c(C(C)C)n(Cc3ccccc3)c2c1] | 5.0 µM (98) |
| 70 | 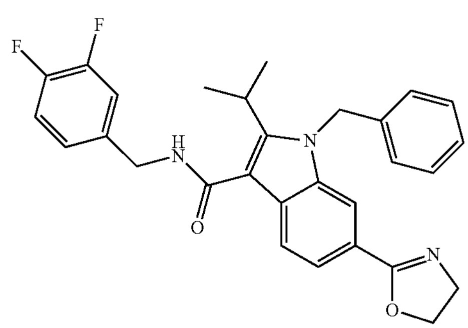 [SMILES: CC(C)c1c(C(=O)NCc2ccc(F)c(F)c2)c2ccc(C3=NCCO3)cc2n1Cc1ccccc1] | 36 nM (100) |
| 71 | 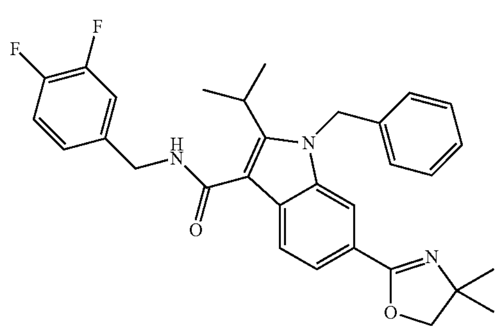 [SMILES: CC(C)c1c(C(=O)NCc2ccc(F)c(F)c2)c2ccc(C3=NC(C)(C)CO3)cc2n1Cc1ccccc1] | 47 nM (97) |
| 72 | 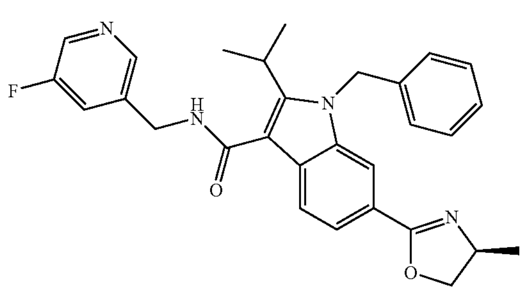 [SMILES: CC(C)c1c(C(=O)NCc2cncc(F)c2)c2ccc(C3=N[C@@H](C)CO3)cc2n1Cc1ccccc1] | 43 nM (99) |

TABLE 1-continued

| Compound Number | Structure | S1P3 IC$_{50}$ (% inh) Kb |
|---|---|---|
| 73 | 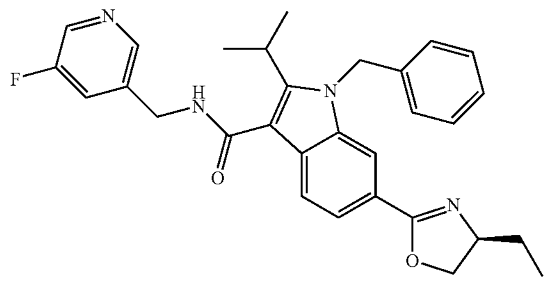 [SMILES: CC[C@H]1COC(c2ccc3c(C(=O)NCc4cncc(F)c4)c(C(C)C)n(Cc4ccccc4)c3c2)=N1] | 35 nM (100) |
| 74 | 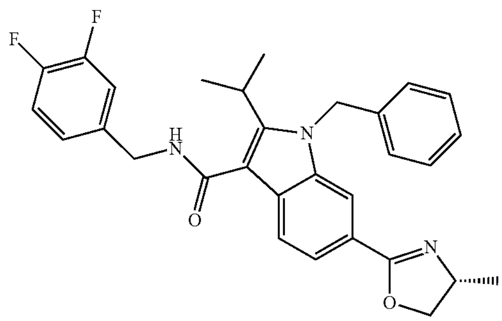 [SMILES: CC(C)c1c(C(=O)NCc2ccc(F)c(F)c2)c2ccc(C3=N[C@H](C)CO3)cc2n1Cc1ccccc1] | 49 nM (99) |
| 75 | 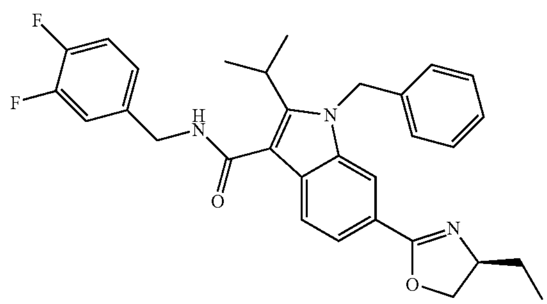 | 17 nM (97) |
| 76 | 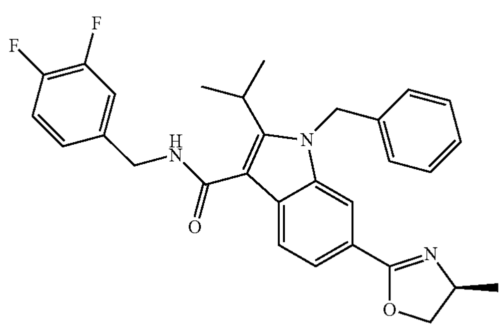 [SMILES: CC(C)c1c(C(=O)NCc2ccc(F)c(F)c2)c2ccc(C3=N[C@@H](C)CO3)cc2n1Cc1ccccc1] | 33 nM (99) |
| 77 | 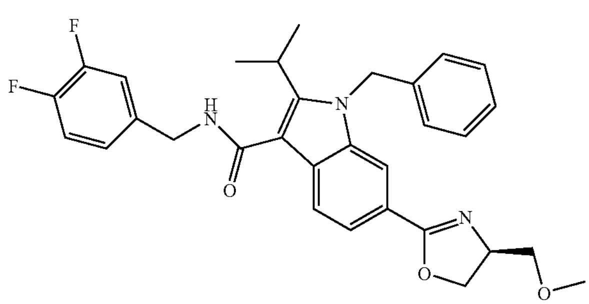 [SMILES: COC[C@H]1COC(c2ccc3c(C(=O)NCc4ccc(F)c(F)c4)c(C(C)C)n(Cc4ccccc4)c3c2)=N1] | 46 nM (96) |

TABLE 1-continued

| Compound Number | Structure | S1P3 IC$_{50}$ (% inh) Kb |
|---|---|---|
| 78 | 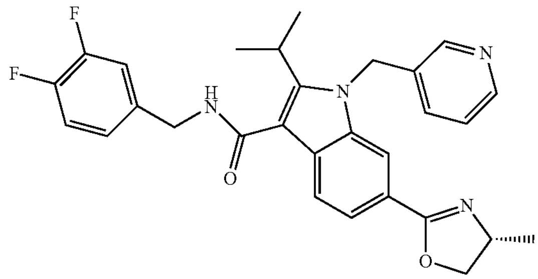 [SMILES: CC(C)c1c(C(=O)NCc2ccc(F)c(F)c2)c2ccc(C3=N[C@H](C)CO3)cc2n1Cc1cccnc1] | 78 nM (100) |
| 79 | 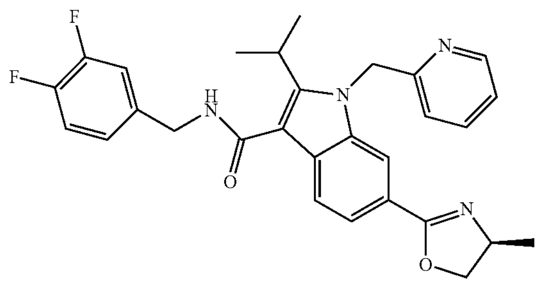 [SMILES: CC(C)c1c(C(=O)NCc2ccc(F)c(F)c2)c2ccc(C3=N[C@@H](C)CO3)cc2n1Cc1ccccn1] | 25 nM (96) |
| 80 | 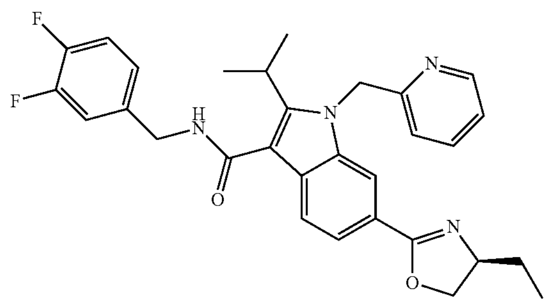 [SMILES: CC[C@H]1COC(c2ccc3c(C(=O)NCc4ccc(F)c(F)c4)c(C(C)C)n(Cc4ccccn4)c3c2)=N1] | 7 nM (99) |
| 81 | 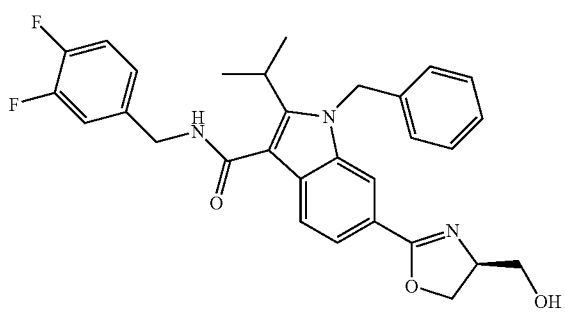 [SMILES: CC(C)c1c(C(=O)NCc2ccc(F)c(F)c2)c2ccc(C3=N[C@@H](CO)CO3)cc2n1Cc1ccccc1] | 1.6 μM (81) |
| 82 | 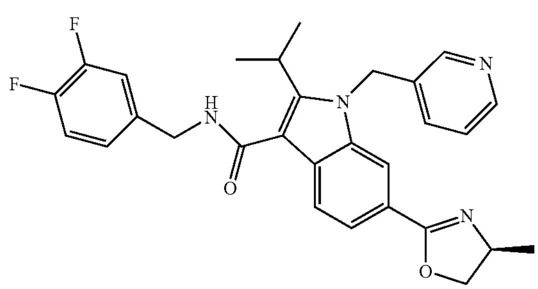 [SMILES: CC(C)c1c(C(=O)NCc2ccc(F)c(F)c2)c2ccc(C3=N[C@@H](C)CO3)cc2n1Cc1cccnc1] | 44 nM (100) |

TABLE 1-continued

| Compound Number | Structure | S1P3 IC$_{50}$ (% inh) Kb |
|---|---|---|
| 83 | 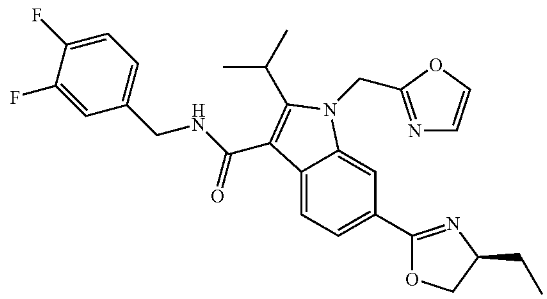 [SMILES: CC[C@H]1COC(c2ccc3c(C(=O)NCc4ccc(F)c(F)c4)c(C(C)C)n(Cc4ncco4)c3c2)=N1] | 280 nM (99) |
| 84 | 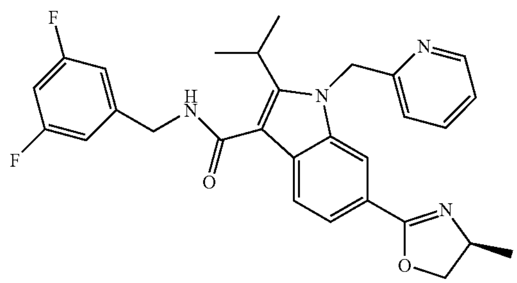 [SMILES: CC(C)c1c(C(=O)NCc2cc(F)cc(F)c2)c2ccc(C3=N[C@@H](C)CO3)cc2n1Cc1ccccn1] | 40 nM (89) |
| 85 | 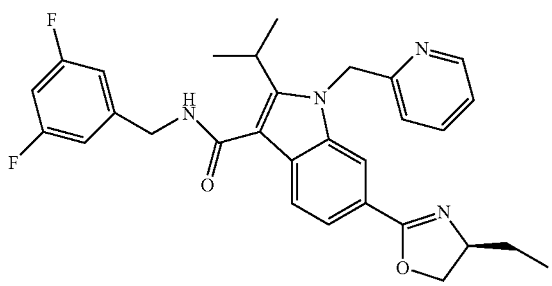 [SMILES: CC[C@H]1COC(c2ccc3c(C(=O)NCc4cc(F)cc(F)c4)c(C(C)C)n(Cc4ccccn4)c3c2)=N1] | 18 nM (100) |
| 86 | 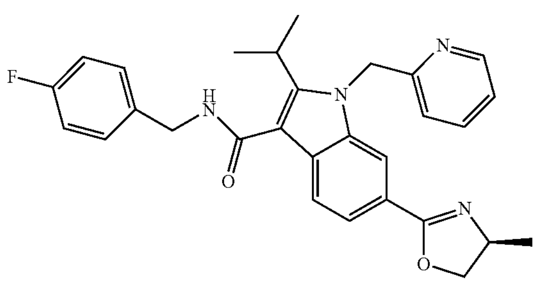 [SMILES: CC(C)c1c(C(=O)NCc2ccc(F)cc2)c2ccc(C3=N[C@@H](C)CO3)cc2n1Cc1ccccn1] | 48 nM (100) |
| 87 | 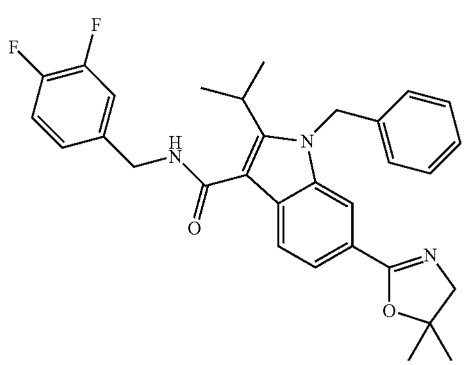 [SMILES: CC(C)c1c(C(=O)NCc2ccc(F)c(F)c2)c2ccc(C3=NCC(C)(C)O3)cc2n1Cc1ccccc1] | 115 nM (100) |

TABLE 1-continued
| Compound Number | Structure | S1P3 IC$_{50}$ (% inh) Kb |
|---|---|---|
| 89 | 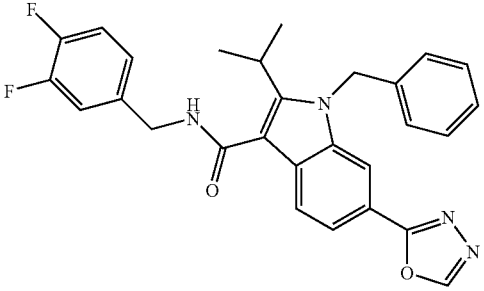 [SMILES: CC(C)c1c(C(=O)NCc2ccc(F)c(F)c2)c2ccc(-c3nnco3)cc2n1Cc1ccccc1] | 59 nM (98) |
| 93 | 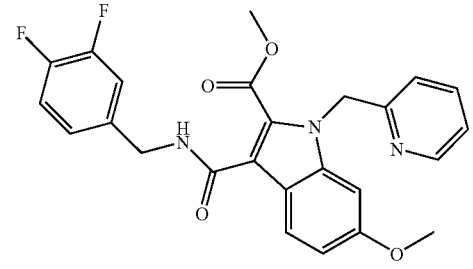 [SMILES: COC(=O)c1c(C(=O)NCc2ccc(F)c(F)c2)c2ccc(OC)cc2n1Cc1ccccn1] | NA |
| 98 | 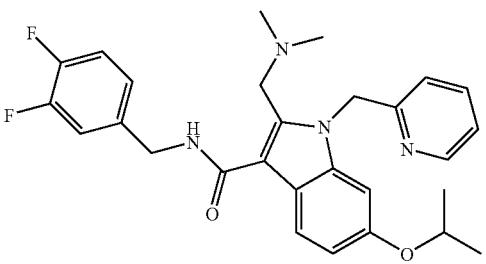 [SMILES: CC(C)Oc1ccc2c(C(=O)NCc3ccc(F)c(F)c3)c(CN(C)C)n(Cc3ccccn3)c2c1] | 632 nM (100) |
| 100 | 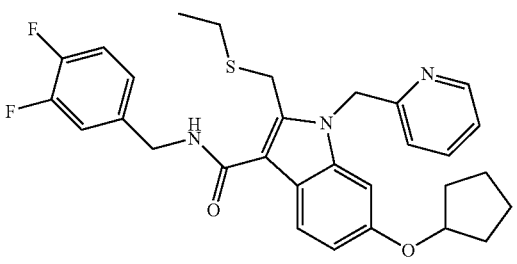 [SMILES: CCSCc1c(C(=O)NCc2ccc(F)c(F)c2)c2ccc(OC3CCCC3)cc2n1Cc1ccccn1] | NA |
| 103 | 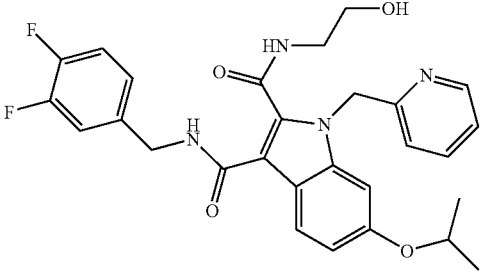 [SMILES: CC(C)Oc1ccc2c(C(=O)NCc3ccc(F)c(F)c3)c(C(=O)NCCO)n(Cc3ccccn3)c2c1] | NA |

TABLE 1-continued

| Compound Number | Structure | S1P3 IC$_{50}$ (% inh) Kb |
|---|---|---|
| 104 | 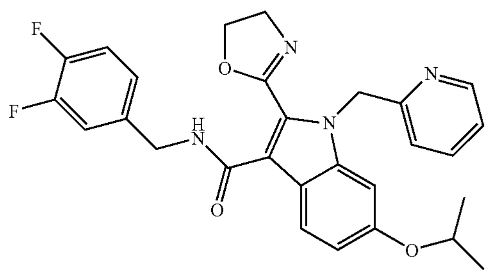 [SMILES: CC(C)Oc1ccc2c(C(=O)NCc3ccc(F)c(F)c3)c(C3=NCCO3)n(Cc3ccccn3)c2c1] | 3.9 μM (50) |
| 105 | 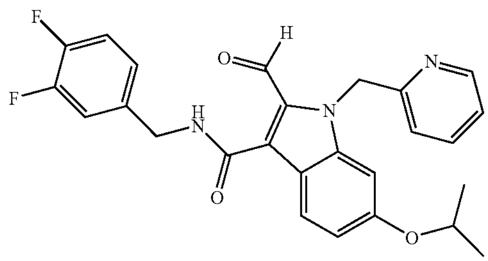 [SMILES: CC(C)Oc1ccc2c(C(=O)NCc3ccc(F)c(F)c3)c(C=O)n(Cc3ccccn3)c2c1] | 485 nM (98) |
| 106 | 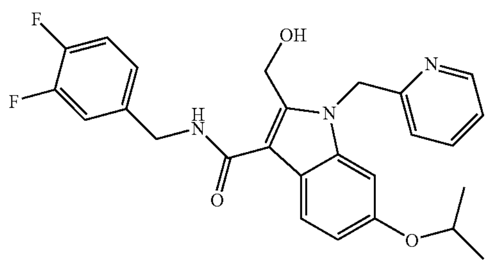 [SMILES: CC(C)Oc1ccc2c(C(=O)NCc3ccc(F)c(F)c3)c(CO)n(Cc3ccccn3)c2c1] | 689 nM (96) |
| 107 | 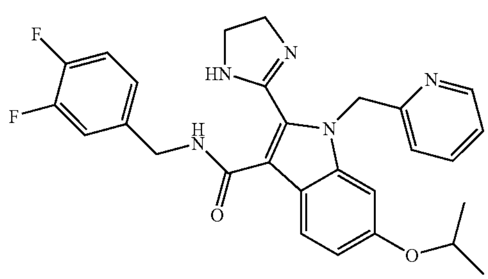 [SMILES: CC(C)Oc1ccc2c(C(=O)NCc3ccc(F)c(F)c3)c(C3=NCCN3)n(Cc3ccccn3)c2c1] | NA |
| 108 | 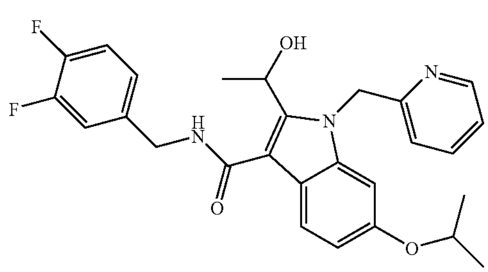 [SMILES: CC(C)Oc1ccc2c(C(=O)NCc3ccc(F)c(F)c3)c(C(C)O)n(Cc3ccccn3)c2c1] | 15 nM (98) |

TABLE 1-continued

| Compound Number | Structure | S1P3 IC$_{50}$ (% inh) Kb |
|---|---|---|
| 109 | 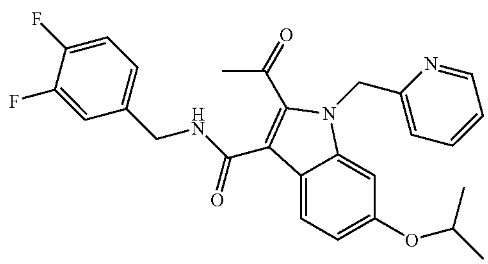 [SMILES: CC(=O)c1c(C(=O)NCc2ccc(F)c(F)c2)c2ccc(OC(C)C)cc2n1Cc1ccccn1] | 21 nM (99) |
| 110 | 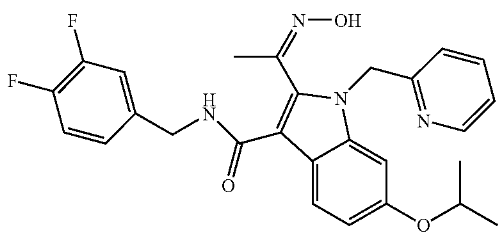 [SMILES: C/C(=N/O)c1c(C(=O)NCc2ccc(F)c(F)c2)c2ccc(OC(C)C)cc2n1Cc1ccccn1] | 384 nM (100) |
| 111 | 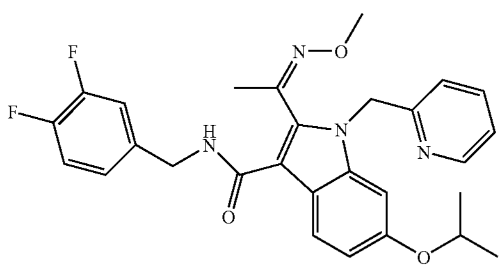 [SMILES: CO/N=C(/C)c1c(C(=O)NCc2ccc(F)c(F)c2)c2ccc(OC(C)C)cc2n1Cc1ccccn1] | 263 nM (100) |
| 116 | 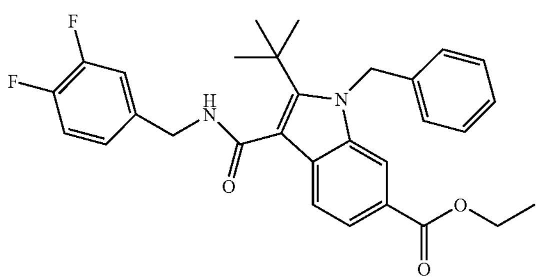 [SMILES: CCOC(=O)c1ccc2c(C(=O)NCc3ccc(F)c(F)c3)c(C(C)(C)C)n(Cc3ccccc3)c2c1] | |
| 124 | 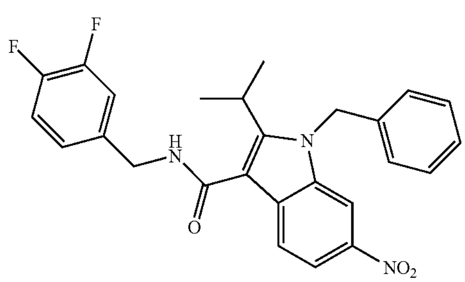 [SMILES: CC(C)c1c(C(=O)NCc2ccc(F)c(F)c2)c2ccc([N+](=O)[O-])cc2n1Cc1ccccc1] | 242 nM (90) |

TABLE 1-continued

| Compound Number | Structure | S1P3 IC$_{50}$ (% inh) Kb |
|---|---|---|
| 125 | 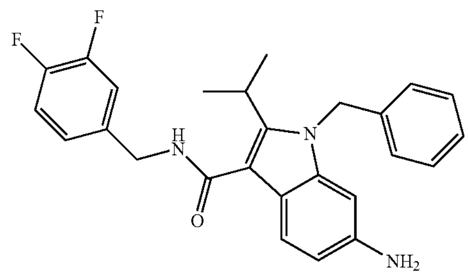 | 1.7 μM (90) |
| 126 | 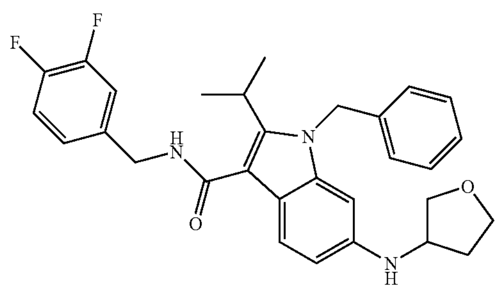 | 177 nM (100) |
| 127 | 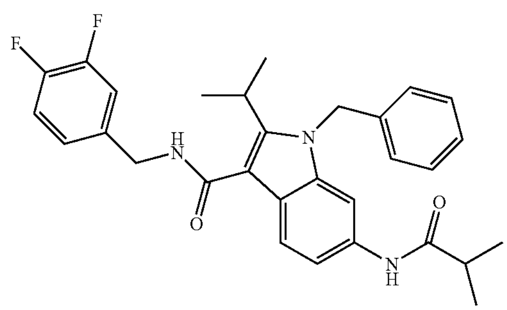 [SMILES: CC(C)C(=O)Nc1ccc2c(C(=O)NCc3ccc(F)c(F)c3)c(C(C)C)n(Cc3ccccc3)c2c1] | 890 nM (97) |
| 128 | 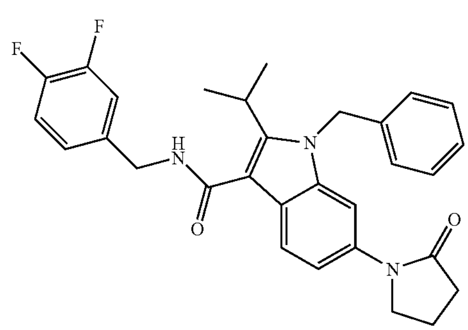 [SMILES: CC(C)c1c(C(=O)NCc2ccc(F)c(F)c2)c2ccc(N3CCCC3=O)cc2n1Cc1ccccc1] | 502 nM (99) |
| 130 | 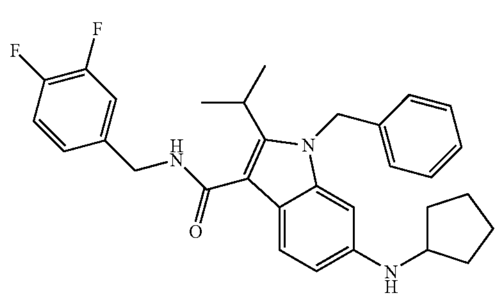 [SMILES: CC(C)c1c(C(=O)NCc2ccc(F)c(F)c2)c2ccc(NC3CCCC3)cc2n1Cc1ccccc1] | 44 nM (99) |

TABLE 1-continued

| Compound Number | Structure | S1P3 IC$_{50}$ (% inh) Kb |
|---|---|---|
| 131 | 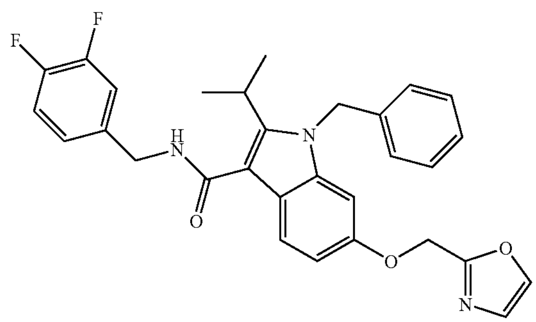 [SMILES: CC(C)c1c(C(=O)NCc2ccc(F)c(F)c2)c2ccc(OCc3ncco3)cc2n1Cc1ccccc1] | 890 nM (96) |
| 132 | 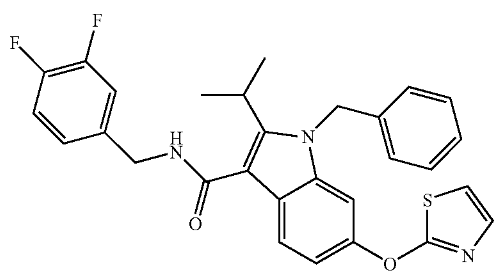 [SMILES: CC(C)c1c(C(=O)NCc2ccc(F)c(F)c2)c2ccc(Oc3nccs3)cc2n1Cc1ccccc1] | 16 nM (99) |
| 133 | 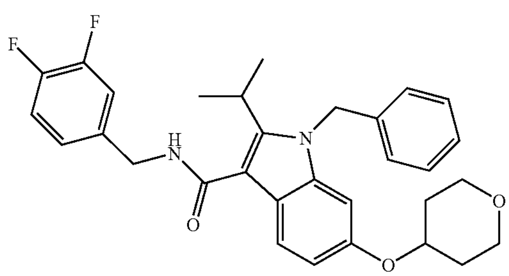 [SMILES: CC(C)c1c(C(=O)NCc2ccc(F)c(F)c2)c2ccc(OC3CCOCC3)cc2n1Cc1ccccc1] | 36 nM (99) |
| 140 | 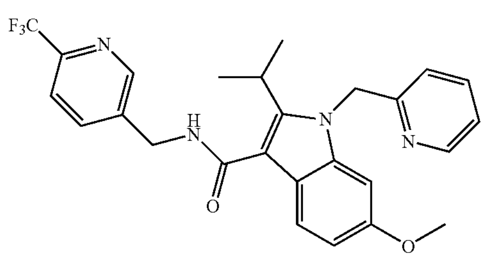 [SMILES: COc1ccc2c(C(=O)NCc3ccc(C(F)(F)F)nc3)c(C(C)C)n(Cc3ccccn3)c2c1] | NA |
| 141 | 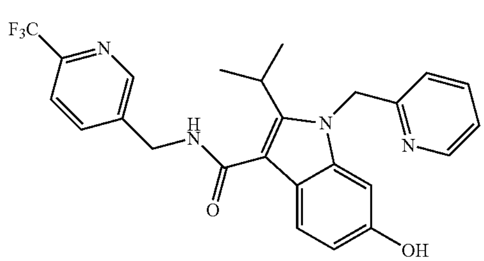 [SMILES: CC(C)c1c(C(=O)NCc2ccc(C(F)(F)F)nc2)c2ccc(O)cc2n1Cc1ccccn1] | NA |

TABLE 1-continued

| Compound Number | Structure | S1P3 IC$_{50}$ (% inh) Kb |
|---|---|---|
| 142 | 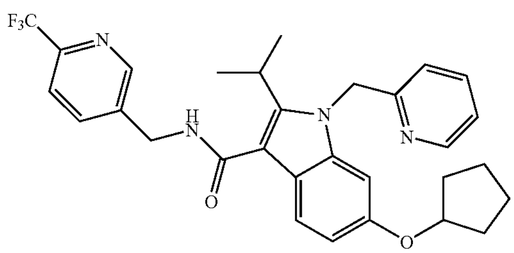 [SMILES: CC(C)c1c(C(=O)NCc2ccc(C(F)(F)F)nc2)c2ccc(OC3CCCC3)cc2n1Cc1ccccn1] | 48 nM (99) |
| 143 | 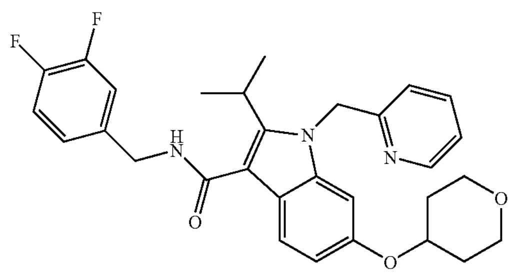 [SMILES: CC(C)c1c(C(=O)NCc2ccc(F)c(F)c2)c2ccc(OC3CCOCC3)cc2n1Cc1ccccn1] | 36 nM (99) |
| 146 | 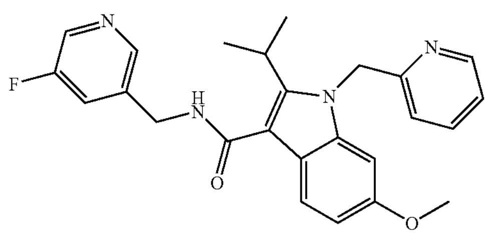 [SMILES: COc1ccc2c(C(=O)NCc3cncc(F)c3)c(C(C)C)n(Cc3ccccn3)c2c1] | NA |
| 147 | 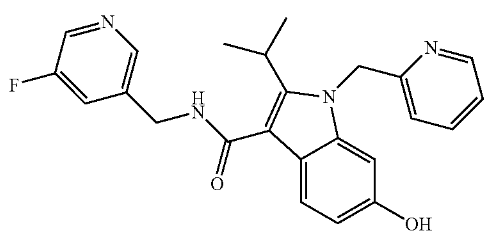 [SMILES: CC(C)c1c(C(=O)NCc2cncc(F)c2)c2ccc(O)cc2n1Cc1ccccn1] | NA |
| 148 | 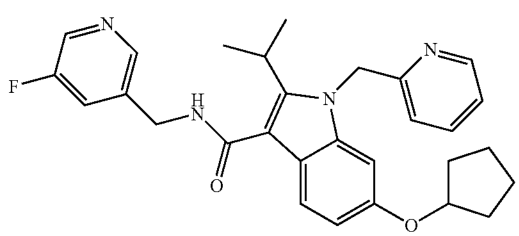 [SMILES: CC(C)c1c(C(=O)NCc2cncc(F)c2)c2ccc(OC3CCCC3)cc2n1Cc1ccccn1] | 13 nM (100) |
| 149 | 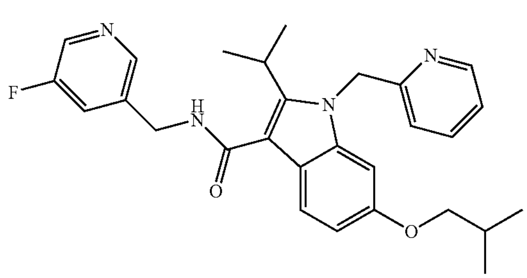 [SMILES: CC(C)COc1ccc2c(C(=O)NCc3cncc(F)c3)c(C(C)C)n(Cc3ccccn3)c2c1] | 29 nM (100) |

TABLE 1-continued
| Compound Number | Structure | S1P3 IC$_{50}$ (% inh) Kb |
|---|---|---|
| 150 | 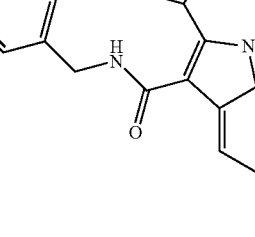 | 5 nM (100) |
| 151 | 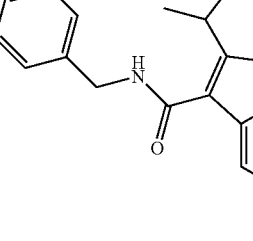 | 65 nM (98) |
| 152 | 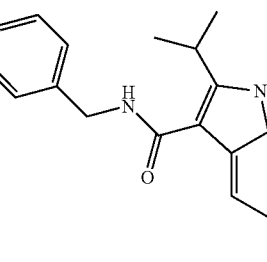 | 17 nM (97) |
| 153 | 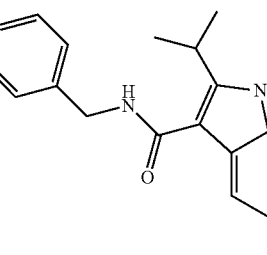 | 5 nM (99) |
| 154 | 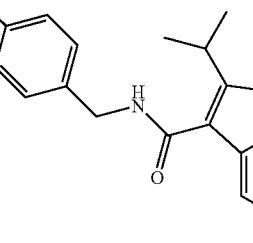 | 15 nM (100) |
| 156 | 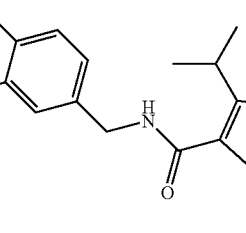 | NA |

TABLE 1-continued

| Compound Number | Structure | S1P3 IC$_{50}$ (% inh) Kb |
|---|---|---|
| 157 | 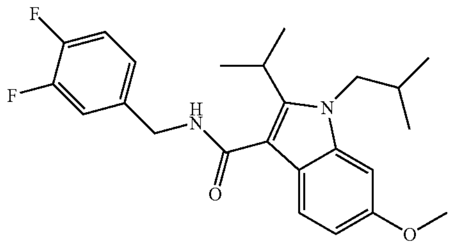 [SMILES: COc1ccc2c(C(=O)NCc3ccc(F)c(F)c3)c(C(C)C)n(CC(C)C)c2c1] | NA |
| 158 | 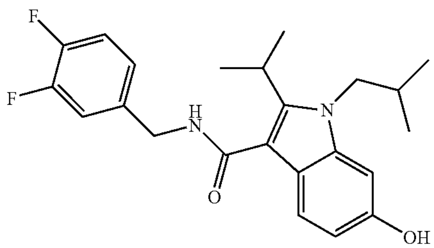 [SMILES: CC(C)Cn1c(C(C)C)c(C(=O)NCc2ccc(F)c(F)c2)c2ccc(O)cc21] | NA |
| 159 | 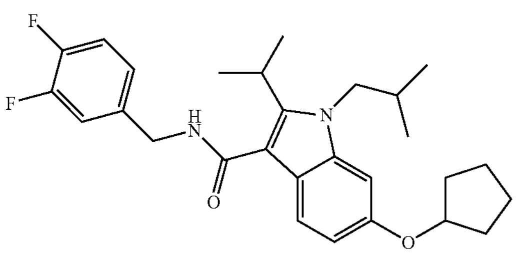 [SMILES: CC(C)Cn1c(C(C)C)c(C(=O)NCc2ccc(F)c(F)c2)c2ccc(OC3CCCC3)cc21] | 41 nM (96) |
| 161 | 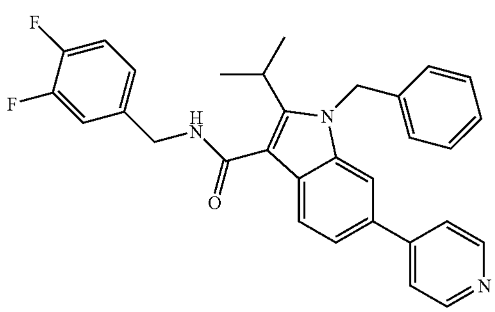 [SMILES: CC(C)c1c(C(=O)NCc2ccc(F)c(F)c2)c2ccc(-c3ccncc3)cc2n1Cc1ccccc1] | 22 nM (100) |
| 162 | 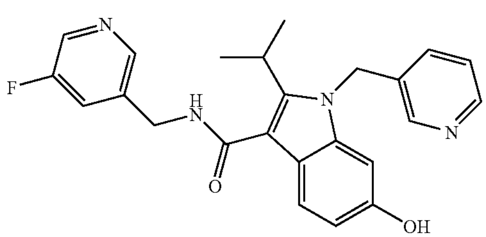 [SMILES: CC(C)c1c(C(=O)NCc2cncc(F)c2)c2ccc(O)cc2n1Cc1cccnc1] | NA |
| 163 | 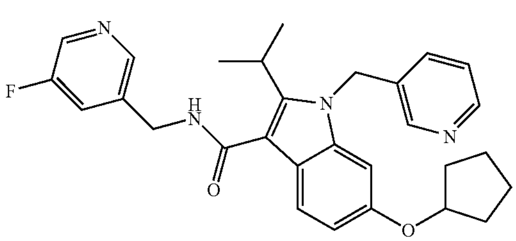 [SMILES: CC(C)c1c(C(=O)NCc2cncc(F)c2)c2ccc(OC3CCCC3)cc2n1Cc1cccnc1] | 55 nM (100) |

TABLE 1-continued

| Compound Number | Structure | S1P3 IC$_{50}$ (% inh) Kb |
|---|---|---|
| 164 | 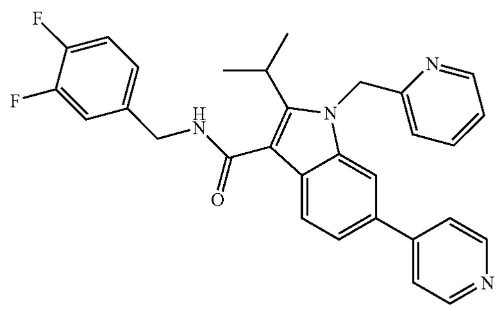 [SMILES: CC(C)c1c(C(=O)NCc2ccc(F)c(F)c2)c2ccc(-c3ccncc3)cc2n1Cc1ccccn1] | 42 nM (100) |
| 165 | 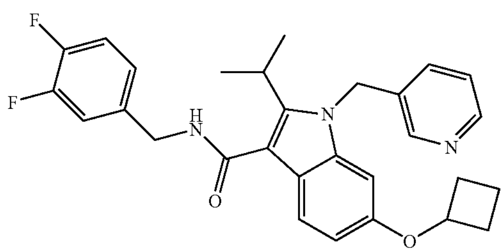 [SMILES: CC(C)c1c(C(=O)NCc2ccc(F)c(F)c2)c2ccc(OC3CCC3)cc2n1Cc1cccnc1] | 7 nM (100) |
| 171 | 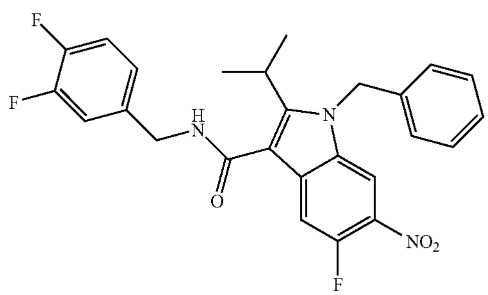 | NA |
| 172 | 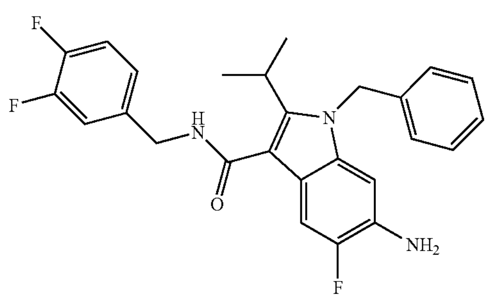 [SMILES: CC(C)c1c(C(=O)NCc2ccc(F)c(F)c2)c2cc(F)c([N+](=O)[O-])cc2n1Cc1ccccc1] | NA |
| 173 | 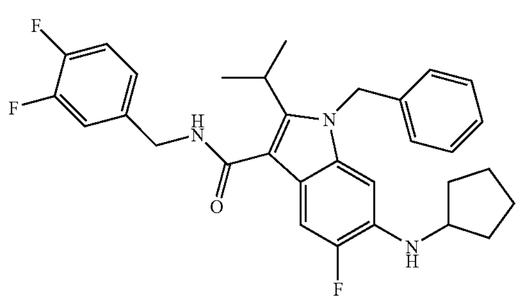 [SMILES: CC(C)c1c(C(=O)NCc2ccc(F)c(F)c2)c2cc(F)c(NC3CCCC3)cc2n1Cc1ccccc1] | NA |

TABLE 1-continued
| Compound Number | Structure | S1P3 IC$_{50}$ (% inh) Kb |
|---|---|---|
| 174 | 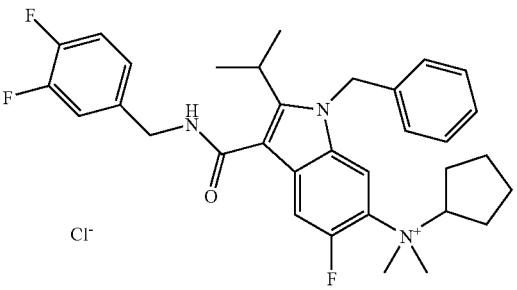 [SMILES: CC(C)c1c(C(=O)NCc2ccc(F)c(F)c2)c2cc(F)c([N+](C)(C)C3CCCC3)cc2n1Cc1ccccc1 ; [Cl-]] | NA |
| 175 | 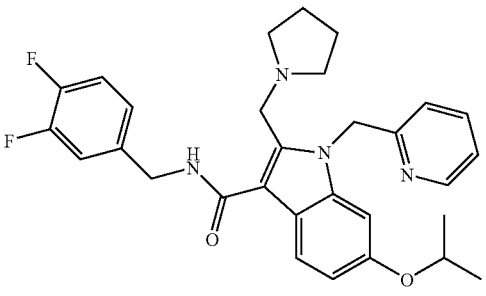 [SMILES: CC(C)Oc1ccc2c(C(=O)NCc3ccc(F)c(F)c3)c(CN3CCCC3)n(Cc3ccccn3)c2c1] | 1.1 µM (100) |
| 176 | 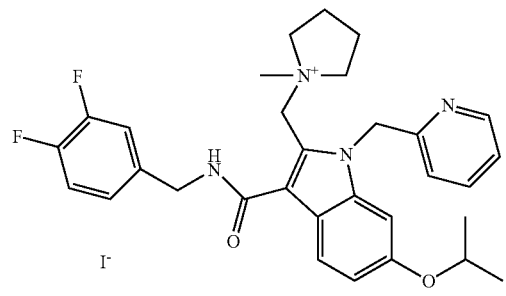 [SMILES: CC(C)Oc1ccc2c(C(=O)NCc3ccc(F)c(F)c3)c(C[N+]3(C)CCCC3)n(Cc3ccccn3)c2c1 ; [I-]] | 7.6 µM (98) |
| 177 | 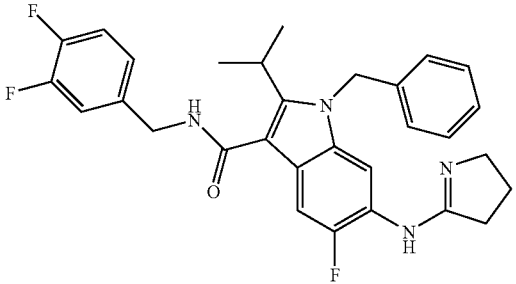 | NA |
| 178 | 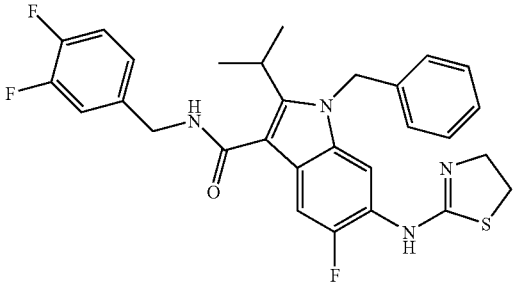 [SMILES: CC(C)c1c(C(=O)NCc2ccc(F)c(F)c2)c2cc(F)c(NC3=NCCC3)cc2n1Cc1ccccc1] | NA |

TABLE 1-continued

| Compound Number | Structure | S1P3 IC$_{50}$ (% inh) Kb |
|---|---|---|
| 180 | 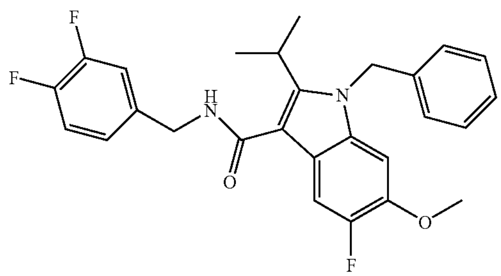 [SMILES: COc1cc2c(cc1F)c(C(=O)NCc1ccc(F)c(F)c1)c(C(C)C)n2Cc1ccccc1] | NA |
| 181 | 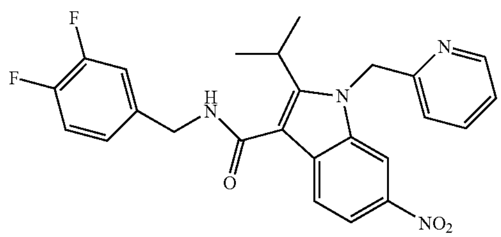 [SMILES: CC(C)c1c(C(=O)NCc2ccc(F)c(F)c2)c2ccc(N)cc2n1Cc1ccccn1] | 500 nM (100) |
| 182 | 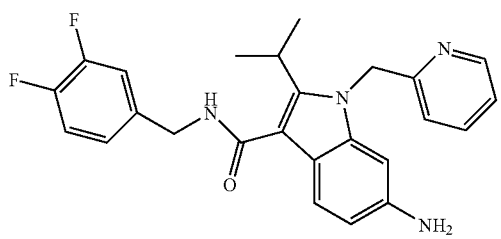 | NA |
| 183 | 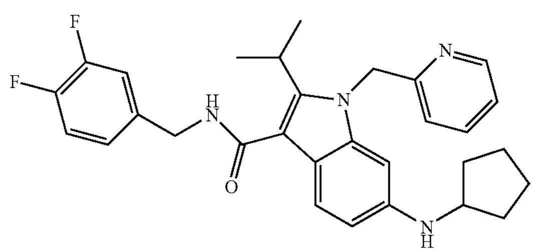 [SMILES: CC(C)c1c(C(=O)NCc2ccc(F)c(F)c2)c2ccc(NC3CCCC3)cc2n1Cc1ccccn1] | 152 nM (100) |
| 184 | 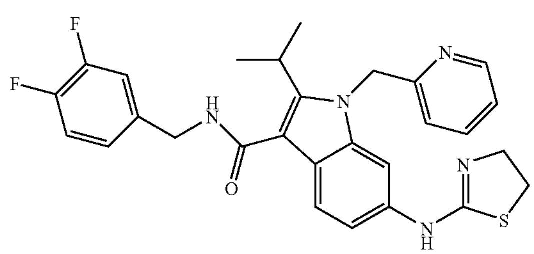 | >8.3 µM (80) |
| 186 | 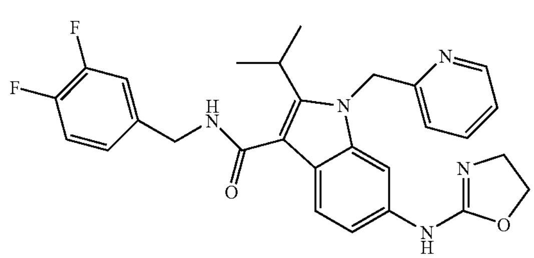 [SMILES: CC(C)c1c(C(=O)NCc2ccc(F)c(F)c2)c2ccc(NC3=NCCS3)cc2n1Cc1ccccn1] | NA |

TABLE 1-continued

| Compound Number | Structure | S1P3 IC$_{50}$ (% inh) Kb |
|---|---|---|
| 187 | 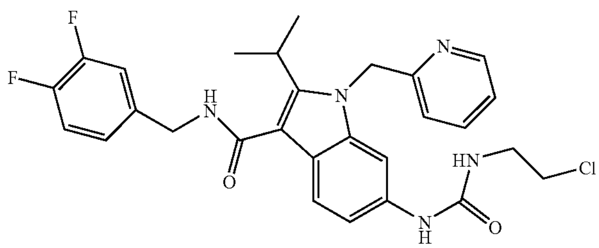 [SMILES: CC(C)c1c(C(=O)NCc2ccc(F)c(F)c2)c2ccc(NC(=O)NCCCl)cc2n1Cc1ccccn1] | NA |
| 188 | 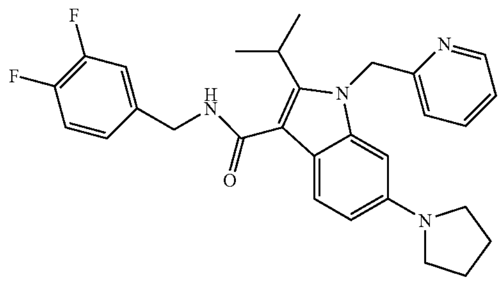 [SMILES: CC(C)c1c(C(=O)NCc2ccc(F)c(F)c2)c2ccc(N3CCCC3)cc2n1Cc1ccccn1] | 120 nM (100) |
| 189 | 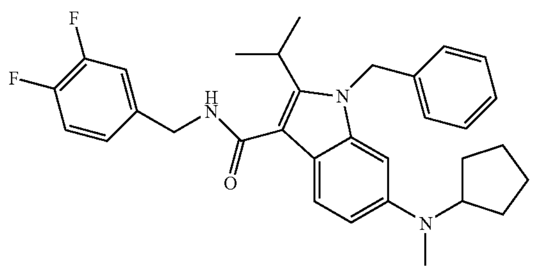 [SMILES: CC(C)c1c(C(=O)NCc2ccc(F)c(F)c2)c2ccc(N(C)C3CCCC3)cc2n1Cc1ccccc1] | 87 nM (100) |
| 190 | 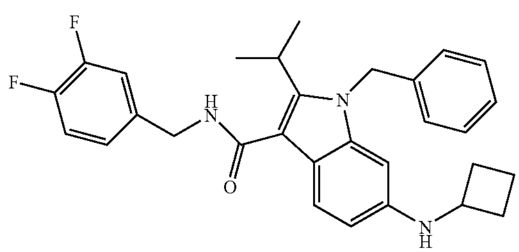 [SMILES: CC(C)c1c(C(=O)NCc2ccc(F)c(F)c2)c2ccc(NC3CCC3)cc2n1Cc1ccccc1] | 13 nM (100) |
| 191 | 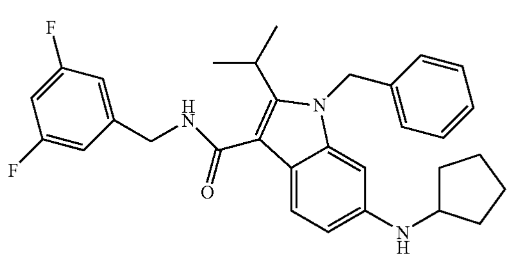 [SMILES: CC(C)c1c(C(=O)NCc2cc(F)cc(F)c2)c2ccc(NC3CCCC3)cc2n1Cc1ccccc1] | 38 nM (99) |

TABLE 1-continued

| Compound Number | Structure | S1P3 IC$_{50}$ (% inh) Kb |
|---|---|---|
| 192 | 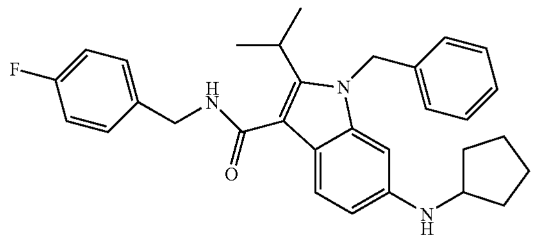 [SMILES: CC(C)c1c(C(=O)NCc2ccc(F)cc2)c2ccc(NC3CCCC3)cc2n1Cc1ccccc1] | 70 nM (100) |
| 193 | 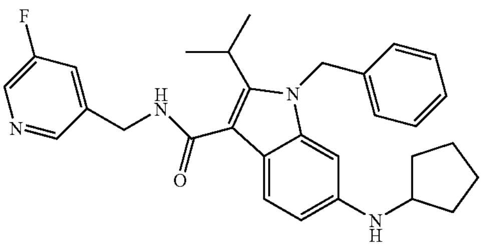 [SMILES: CC(C)c1c(C(=O)NCc2cncc(F)c2)c2ccc(NC3CCCC3)cc2n1Cc1ccccc1] | 163 nM (100) |
| 194 | 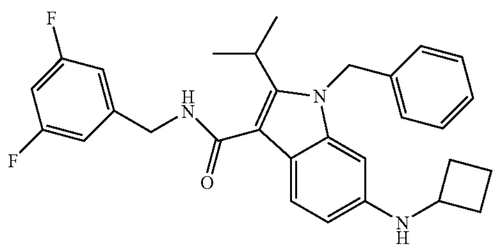 [SMILES: CC(C)c1c(C(=O)NCc2cc(F)cc(F)c2)c2ccc(NC3CCC3)cc2n1Cc1ccccc1] | 20 nM (100) |
| 195 | 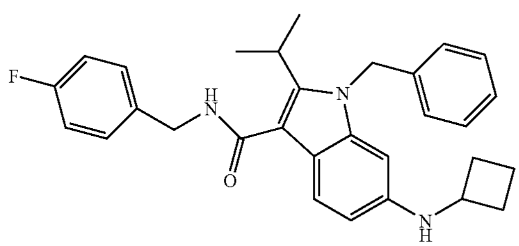 [SMILES: CC(C)c1c(C(=O)NCc2ccc(F)cc2)c2ccc(NC3CCC3)cc2n1Cc1ccccc1] | 51 nM (99) |
| 196 | 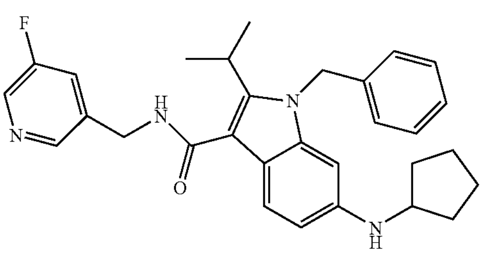 [SMILES: CC(C)c1c(C(=O)NCc2cncc(F)c2)c2ccc(NC3CCCC3)cc2n1Cc1ccccc1] | 70 nM (100) |
| 197 | 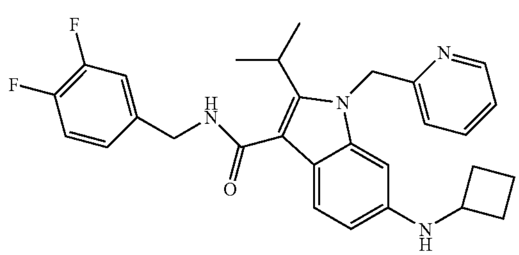 [SMILES: CC(C)c1c(C(=O)NCc2ccc(F)c(F)c2)c2ccc(NC3CCC3)cc2n1Cc1ccccn1] | 67 nM (100) |

TABLE 1-continued
| Compound Number | Structure | S1P3 IC$_{50}$ (% inh) Kb |
|---|---|---|
| 198 | 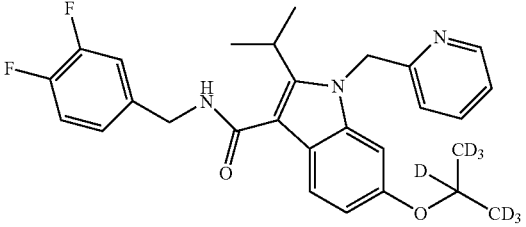 [SMILES: [2H]C([2H])([2H])C([2H])(Oc1ccc2c(C(=O)NCc3ccc(F)c(F)c3)c(C(C)C)n(Cc3ccccn3)c2c1)C([2H])([2H])[2H]] | 10 nM (100) |
| 199 | 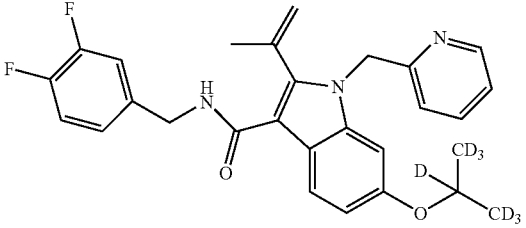 [SMILES: [2H]C([2H])([2H])C([2H])(Oc1ccc2c(C(=O)NCc3ccc(F)c(F)c3)c(C(=C)C)n(Cc3ccccn3)c2c1)C([2H])([2H])[2H]] | 51 nM (100) |
| 203 | 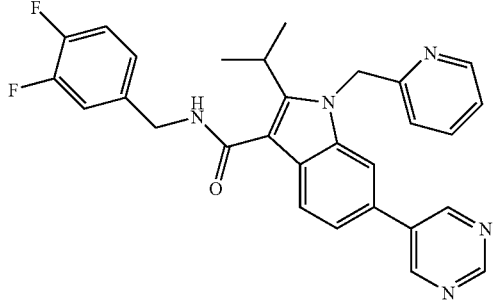 [SMILES: CC(C)c1c(C(=O)NCc2ccc(F)c(F)c2)c2ccc(-c3cncnc3)cc2n1Cc1ccccn1] | 580 nM (98) |
| 204 | 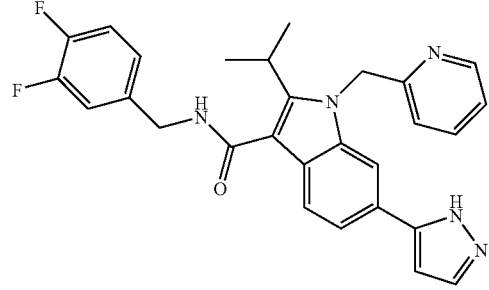 | 1.6 µM (97) |
| 205 | 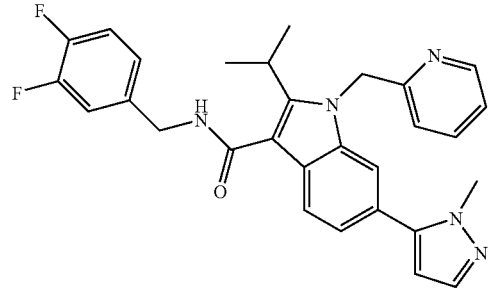 [SMILES: CC(C)c1c(C(=O)NCc2ccc(F)c(F)c2)c2ccc(-c3ccnn3C)cc2n1Cc1ccccn1] | 376 nM (97) |

TABLE 1-continued

| Compound Number | Structure | S1P3 IC$_{50}$ (% inh) Kb |
|---|---|---|
| 206 | 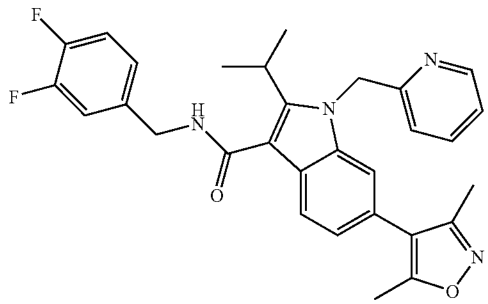 [SMILES: Cc1noc(C)c1-c1ccc2c(C(=O)NCc3ccc(F)c(F)c3)c(C(C)C)n(Cc3ccccn3)c2c1] | 390 nM (99) |
| 207 | 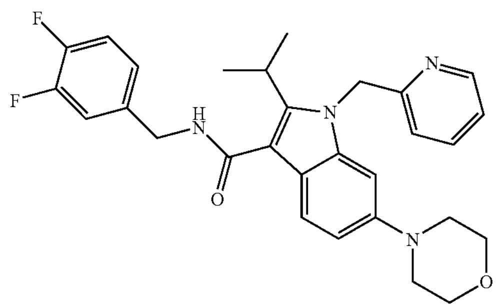 [SMILES: CC(C)c1c(C(=O)NCc2ccc(F)c(F)c2)c2ccc(N3CCOCC3)cc2n1Cc1ccccn1] | 130 nM (97) |
| 211 | 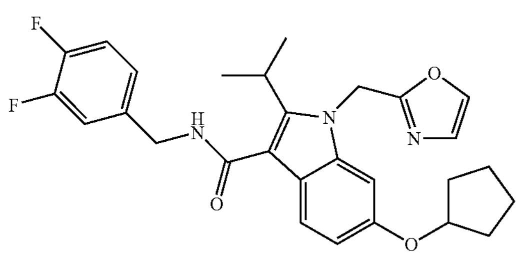 [SMILES: CC(C)c1c(C(=O)NCc2ccc(F)c(F)c2)c2ccc(OC3CCCC3)cc2n1Cc1ncco1] | 10 nM (100) |
| 212 | 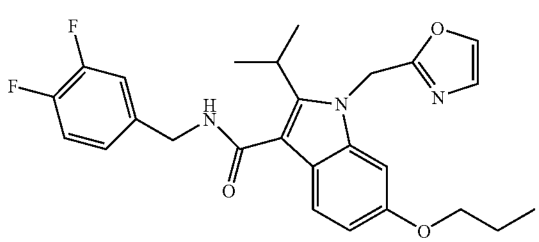 [SMILES: CCCOc1ccc2c(C(=O)NCc3ccc(F)c(F)c3)c(C(C)C)n(Cc3ncco3)c2c1] | 393 nM (100) |
| 213 | 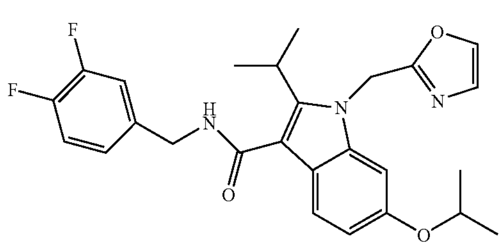 [SMILES: CC(C)Oc1ccc2c(C(=O)NCc3ccc(F)c(F)c3)c(C(C)C)n(Cc3ncco3)c2c1] | 189 nM (100) |

TABLE 1-continued

| Compound Number | Structure | S1P3 IC$_{50}$ (% inh) Kb |
|---|---|---|
| 214 | 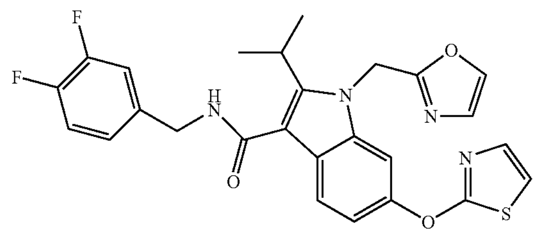 [SMILES: CC(C)c1c(C(=O)NCc2ccc(F)c(F)c2)c2ccc(Oc3nccs3)cc2n1Cc1ncco1] | 53 nM (100) |
| 215 | 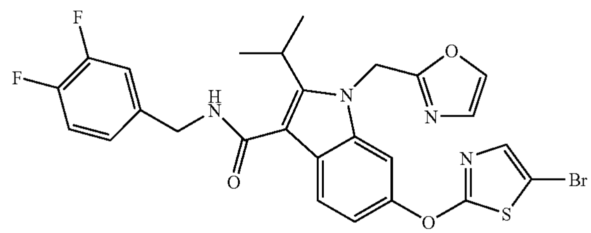 [SMILES: CC(C)c1c(C(=O)NCc2ccc(F)c(F)c2)c2ccc(Oc3ncc(Br)s3)cc2n1Cc1ncco1] | 23 nM (99) |
| 218 | 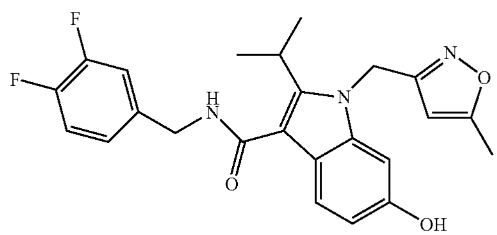 [SMILES: Cc1cc(Cn2c(C(C)C)c(C(=O)NCc3ccc(F)c(F)c3)c3ccc(O)cc32)no1] | 5.4 µM (67) |
| 219 | 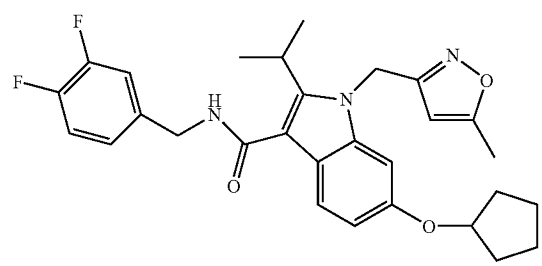 [SMILES: Cc1cc(Cn2c(C(C)C)c(C(=O)NCc3ccc(F)c(F)c3)c3ccc(OC4CCCC4)cc32)no1] | 38 nM (99) |
| 221 | 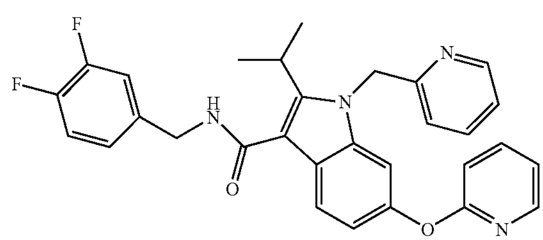 [SMILES: CC(C)c1c(C(=O)NCc2ccc(F)c(F)c2)c2ccc(Oc3ccccn3)cc2n1Cc1ccccn1] | 21 nM (100) |
| 222 | 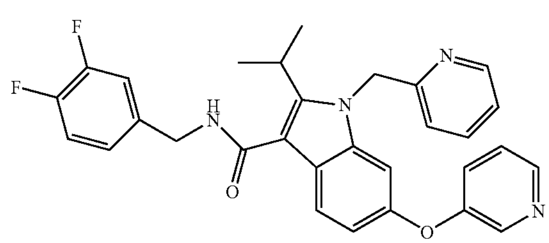 [SMILES: CC(C)c1c(C(=O)NCc2ccc(F)c(F)c2)c2ccc(Oc3cccnc3)cc2n1Cc1ccccn1] | 10 nM (100) |

TABLE 1-continued

| Compound Number | Structure | S1P3 IC$_{50}$ (% inh) Kb |
|---|---|---|
| 223 | 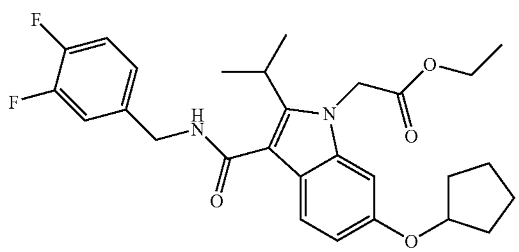 [SMILES: CCOC(=O)Cn1c(C(C)C)c(C(=O)NCc2ccc(F)c(F)c2)c2ccc(OC3CCCC3)cc21] | 24 nM (100) |
| 224 | 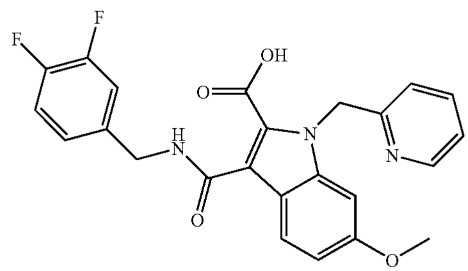 [SMILES: COc1ccc2c(C(=O)NCc3ccc(F)c(F)c3)c(C(=O)O)n(Cc3ccccn3)c2c1] | NA |
| 225 | 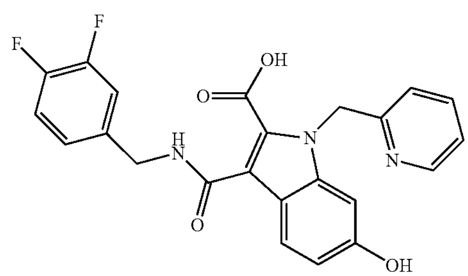 [SMILES: O=C(NCc1ccc(F)c(F)c1)c1c(C(=O)O)n(Cc2ccccn2)c2cc(O)ccc12] | NA |
| 226 | 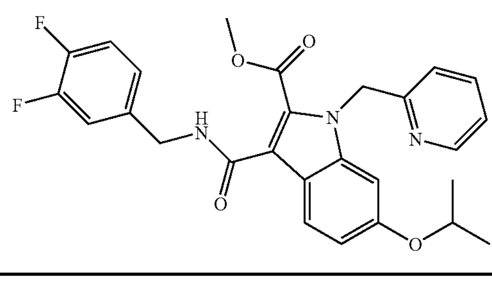 | 87 nM (100) |

The compounds of Table 1B are prepared according to procedures analogous to the procedures of Schemes 1 through 19 and/or Examples 2 through 226. These compounds are also tested for ability to inhibit the activity of the S1P3 receptor.

TABLE 1B

| Compound Number | Structure | S1P3 IC$_{50}$ (% inh) Kb |
|---|---|---|
|  |  | 12 nM (100) |
|  |  | >10 µM (40) |
|  |  | 170 nM (100) |
|  |  | 197 nM (100) |

TABLE 1B-continued

| Compound Number | Structure | S1P3 IC$_{50}$ (% inh) Kb |
|---|---|---|
| | | 634 nM (100) |
| | | 346 nM (99) |
| | | 146 nM (99) |
| | | 362 nM (93) |
| | | 990 nM (98) |

TABLE 1B-continued

| Compound Number | Structure | S1P3 IC$_{50}$ (% inh) Kb |
|---|---|---|
| | | 2.3 μM (84) |
| | | 2.5 μM (87) |
| | | 2.6 μM (77) |
| | | 12 nM (97) |
| | | 4 nM (97) |

TABLE 1B-continued
| Compound Number | Structure | S1P3 IC$_{50}$ (% inh) Kb |
|---|---|---|
| | 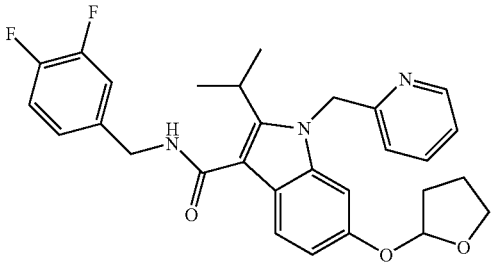 [SMILES: CC(C)c1c(C(=O)NCc2ccc(F)c(F)c2)c2ccc(OC3CCCO3)cc2n1Cc1ccccn1] | 9 nM (100) |
| | 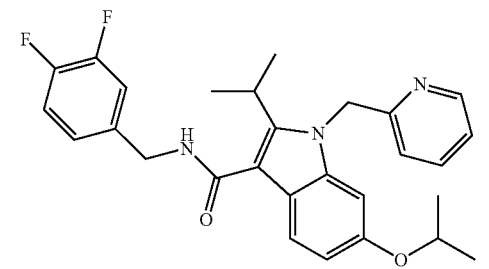 [SMILES: CC(C)Oc1ccc2c(C(=O)NCc3ccc(F)c(F)c3)c(C(C)C)n(Cc3ccccn3)c2c1] | 0.9 nM (100) |
| | 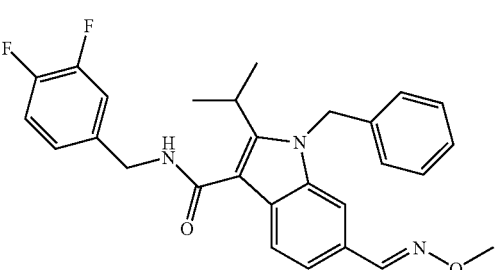 | 21 nM (99) |
| | 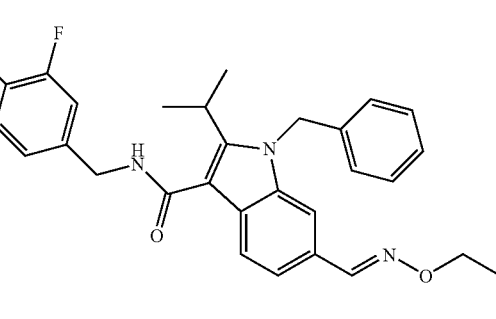 | 88 nM (100) |
| | 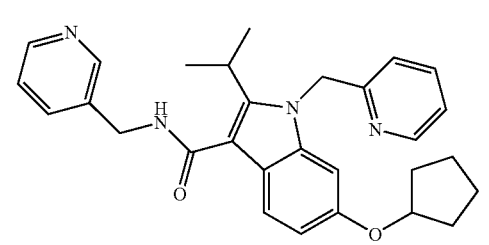 [SMILES: CC(C)c1c(C(=O)NCc2cccnc2)c2ccc(OC3CCCC3)cc2n1Cc1ccccn1] | 86 nM (95) |

TABLE 1B-continued

| Compound Number | Structure | S1P3 IC$_{50}$ (% inh) Kb |
|---|---|---|
| | | 9 nM (100) |
| | | 9 nM (96) |
| | | 187 nM (95) |
| | | 145 nM (99) |
| | | ND (98) |

TABLE 1B-continued

| Compound Number | Structure | S1P3 IC$_{50}$ (% inh) Kb |
|---|---|---|
| | | 1.2 µM (99) |
| | | 124 nM (99) |
| | | ND (54) |
| | | 42 nM (99) |
| | | 43 nM (99) |

TABLE 1B-continued

| Compound Number | Structure | S1P3 IC$_{50}$ (% inh) Kb |
|---|---|---|
| | | 45 nM (99) |
| | | 145 nM (99) |
| | | 262 nM (98) |
| | | 147 nM (100) |
| | | NA |

TABLE 1B-continued

| Compound Number | Structure | S1P3 IC$_{50}$ (% inh) Kb |
|---|---|---|
| | | 673 nM (100) |
| | | 2.4 μM (80) |
| | | 174 nM (100) |
| | | 58 nM (100) |
| | | 19 nM (100) 21 nM |

TABLE 1B-continued
| Compound Number | Structure | S1P3 IC$_{50}$ (% inh) Kb |
|---|---|---|
| | 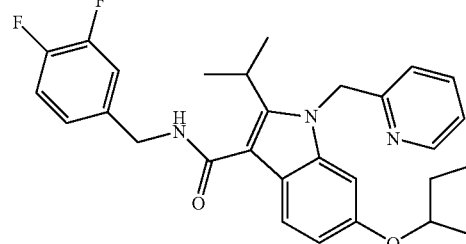 | 3 nM (100) 4 nM |
| | 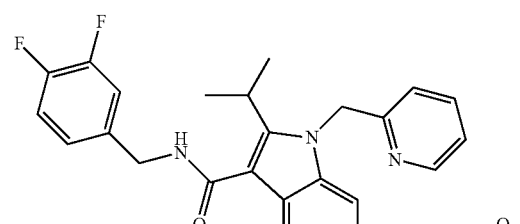 | 288 nM (100) |
| | 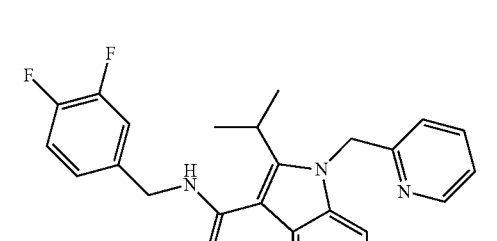 | 324 nM (99) |
| | 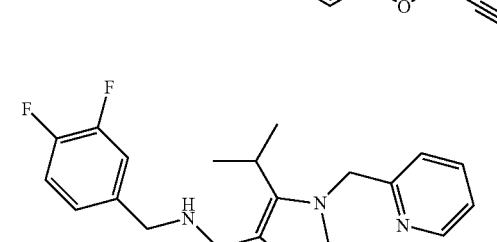 | 5 nM (100) 9 nM |
| | 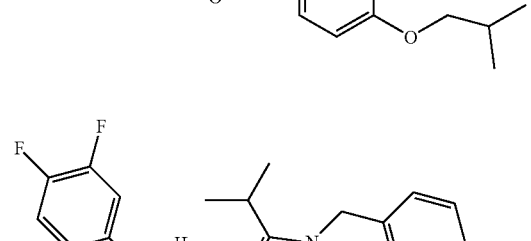 | 8 nM (100) |

TABLE 1B-continued

| Compound Number | Structure | S1P3 IC$_{50}$ (% inh) Kb |
|---|---|---|
| | (3,4-difluorobenzyl)-2-isopropyl-1-(pyridin-2-ylmethyl)-6-propoxy-1H-indole-3-carboxamide | 15 nM (100) 13 nM |
| | (3-fluorobenzyl)-6-(hydroxymethyl)-2-isopropyl-1-(pyridin-2-ylmethyl)-1H-indole-3-carboxamide | NA |
| | (3,4-difluorobenzyl)-6-formyl-2-isopropyl-1-(pyridin-2-ylmethyl)-1H-indole-3-carboxamide | ND (65) |
| | (3,4-difluorobenzyl)-6-((dimethylhydrazono)methyl)-2-isopropyl-1-(pyridin-2-ylmethyl)-1H-indole-3-carboxamide | 93 nM (100) |
| | (3,4-difluorobenzyl)-2-isopropyl-6-((methoxyimino)methyl)-1-(pyridin-2-ylmethyl)-1H-indole-3-carboxamide | 137 nM (100) |

As a result of the above activity of the compounds utilized in the method of the present invention, it is clear that such compounds may be used in treating the following diseases and conditions for the following reasons.

Glaucoma
S1P3 subtypes are expressed in primary human trabecular meshwork cells and S1P decreases outflow facility >30% in perfused porcine eyes (See IOVS 45, 2263; 2004) by altering paracellular permeability.

Dry Eye/Immunology
Induces lymphocyte sequestration without affecting T cell proliferation.

Angiogenesis Disorders
S1P3 receptor subtype is expressed in vascular endothelial cells and siRNA knockdown of S1P1 and S1P3 inhibits angiogenesis. S1P also promotes vascular endothelial cell migration and promotes barrier assembly and integrity.

Cardiovascular (S1P3)
S1P3 "knock out" mice lack S1P induced pulmonary edema.

The invention is further illustrated by the following examples which are illustrative of a specific mode of practicing the invention and are not intended as limiting the scope of the claims.

Unless otherwise indicated, the following Chemical Abbreviations are used in the examples:
AlCl$_3$; aluminum chloride
BBr$_3$: boron tribromide
BOP:benzotriazole-1-yl-oxy-tris-(dimethylamino)-phosphonium hexafluorophosphate
C$_3$D$_7$I: 2-iodopropane-d$_7$
CeCl$_3$: cerium chloride
Cs$_2$CO$_3$: cesium carbonate
CH$_2$Cl$_2$: methylene chloride
CH$_3$CN: acetonitrile
ClCH$_2$CH$_2$Cl: 1,2-dichloroethane
(COCl)$_2$: oxalyl chloride
CuI: copper(I) iodide
DIBAL: diisobutylaluminium hydride
DMAP: 4-dimethylaminopyridine
DMF: N,N-dimethylformamide
DMSO: dimethyl sulfoxide
Et$_2$O: diethyl ether
Et$_3$N: triethylamine
EtOAc: Ethyl acetate
EtOH: ethanol
EtSH: ethane thiol
H$_2$: hydrogen
H$_2$O: water
H$_2$SO$_4$: sulfuric acid
HBr: hydrogen bromide
HCl: hydrogen chloride
HOAc: acetic acid
HONH$_2$.HCl: hydroxylamine hydrochloride
i-Pr$_2$NEt: diisopropylethylamine
i-PrCOCl: isobutyryl chloride
K$_2$CO$_3$: potassium carbonate
KH$_2$PO$_4$: potassium dihydrogen phosphate
KOt-Bu: potassium tert-butoxide
LiCl: lithium chloride
MCPBA: meta-chloroperbenzoic acid
MeI: methyl iodide
MeLi: methyl lithium
MeMgBr: methyl magnesiumbromide
MeOH: methanol
MeONH$_2$.HCl: methoxylamine hydrochloride
MgSO$_4$: magnesium sulfate
N$_2$: nitrogen
Na$_2$CO$_3$: sodium carbonate
Na$_2$SO$_4$: sodium sulfate
NaBH(OAc)$_3$: sodium triacetoxyborohydride
NaBH$_3$CN: sodium cyanoborohydride
NaBH4: sodium borohydride
NaClO$_2$: sodium chlorite
NaH$_2$PO$_4$: sodium dihydrogen phosphate
NaHCO$_3$: sodium bicarbonate
NaOH: sodium hydroxide
NBS: N-bromosuccimide
n-Bu$_4$NI: tetrabutylammonium iodide
NH$_3$.H$_2$O: ammonia
NH$_4$Cl: ammonium chloride
NMO: N-methylmorpholine N-oxide
NMP: N-methylpyrrolidone
n-PrCOCl: butyryl chloride
PCC: pyridinium chlorochromate
Pd(PPh$_3$)$_2$Cl$_2$: dichlorobis(triphenylphosphine)palladium (II)
Pd(PPh$_3$)$_4$: tetrakis(triphenylphosphine)palladium(0)
Pd—C: palladium on activated carbon
POCl$_3$: phosphorus(V) oxyxhloride
PTLC: preparative thin layer chromatography
t-BuOH: tert-butanol
Tf$_2$O: trifluoromethanesulfonic (triflic) anhydride
THF: tetrahydrofuran
TPAP: tetrapropylammonium perruthenate
PTLC: preparative thin layer chromatography
Acetyl chloride, benzyl bromide, 2-bromoethyl methyl ether, cyclopentyl iodide, diisopropylethylamine, 2-dimethylaminoethyl chloride hydrochloride, dimethylcarbamyl chloride, 1-iodobutane, 2-iodobutane, iodoethane, 1-iodohexane, 1-iodopropane, 2-iodopropane, 4-methylbenzene-1sulfonyl chloride, pivaloyl chloride, pyridinium p-toluenesufonate and tetrahydrofuran-3-ol were purchased from Aldrich Chemical Company.

Scheme 3$^a$

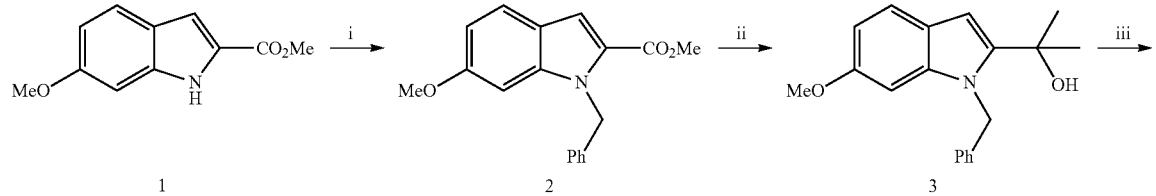

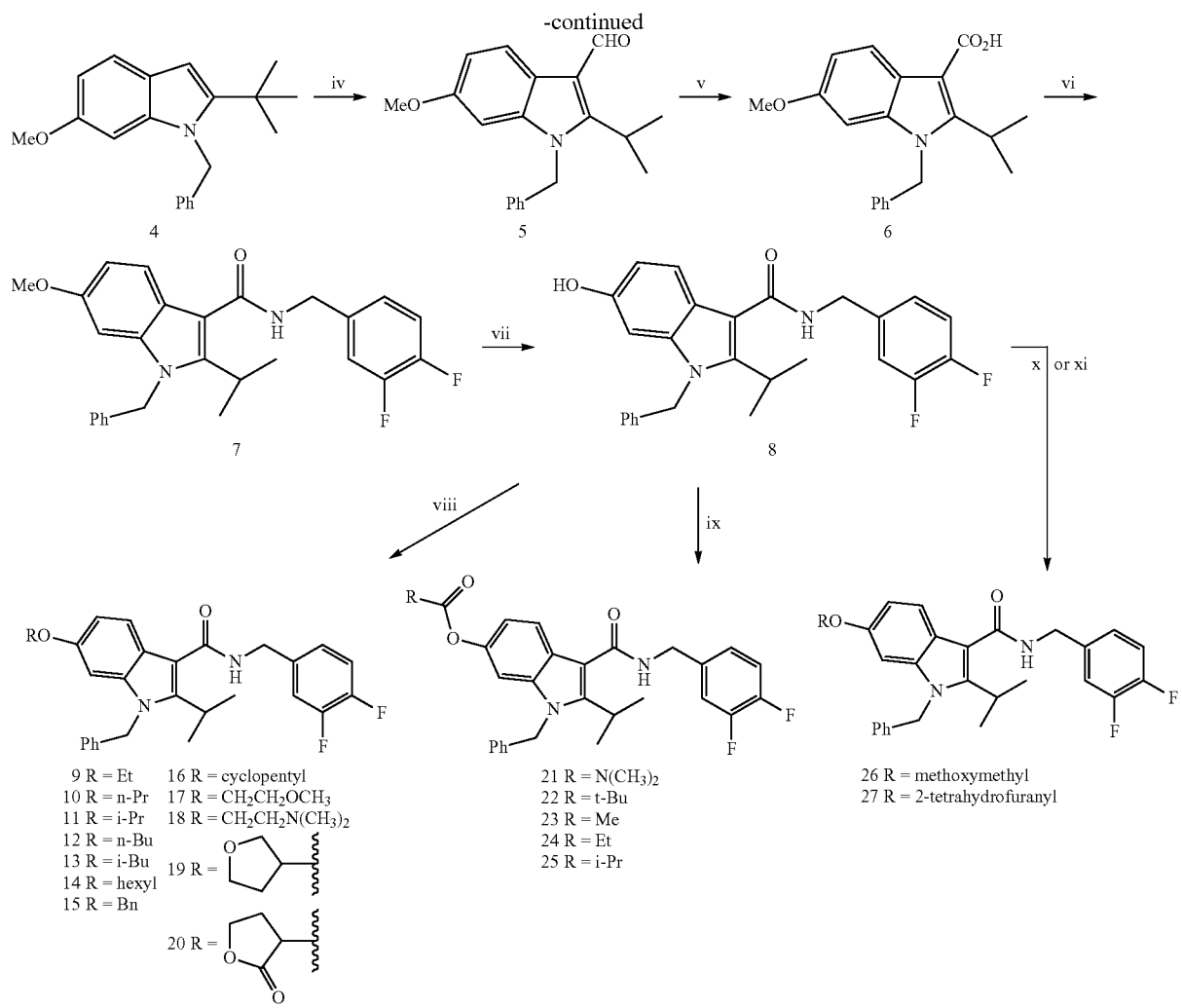

<sup>a</sup>Reagents and conditions: (i) BnBr, K₂CO₃, DMF; (ii) MeLi, THF; (iii) H₂, Pd—C, EtOAc, EtOH, HCl—Et₂O; (iv) POCl₃, DMF; (v) NaClO₂, KH₂PO₄, isobutene, t-BuOH, CH₃CN, H₂O; (vi) 3,4-difluorobenzylamine, EDC, DMAP, CH₂Cl₂; (vii) BBr₃, CH₂Cl₂; (viii) RX, K₂CO₃, DMF; (ix) RCOCl, pyridine; (x) MOMCl, i-Pr₂NEt, CH₂Cl₂; (xi) 2,3-dihydrofuran, PPTS, CH₂Cl₂.

EXAMPLE 2

Methyl 1-Benzyl-6-methoxy-1H-indole-2-carboxylate (Compound 2). To a solution of methyl6-methoxy-1H-indole-2-carboxylate (Compound 1, 1.0 g, 4.9 mmol) in DMF (10 ml) was added K₂CO₃ (2.0 g, 14.6 mmol) and benzyl bromide (0.87 ml, 7.3 mmol). The mixture was stirred at room temperature for 40 h and was diluted with EtOAc, washed with H₂O, brine, dried over Na₂SO₄ and concentrated in vacuo. The residue was purified by crystallization from Et₂O to yield the title compound as an off-white solid.

$^1$H NMR (500 MHz, CHLOROFORM-d) δ ppm 3.81 (s, 3 H), 3.85 (s, 3 H), 5.81 (s, 2 H), 6.73 (d, J=2.0 Hz, 1 H), 6.84 (dd, J=8.8, 2.0 Hz, 1 H), 7.07 (d, J=6.8 Hz, 2 H), 7.19-7.29 (m, 3 H), 7.33 (s, 1 H), 7.58 (d, J=8.8 Hz, 1 H).

EXAMPLE 3

2-(1-Benzyl-6-methoxy-1H-indol-2-yl)propan-2-ol (Compound 3). To a solution of methyl1-benzyl-6-methoxy-1H-indole-2-carboxylate (Compound 2, 4.33 g, 14.7 mmol) in THF (50 ml) at 0° C. under argon was added MeLi (3.0 M in diethoxymethane, 19.6 ml, 58.7 mmol) slowly. After 1 h, the ice-water bath was removed and the reaction was stirred at room temperature for 1 h, cooled to −78° C., quenched with dry ice, diluted with EtOAc, washed with H₂O, brine, dried over Na₂SO₄, concentrated in vacuo to yield the crude title compound as a yellow solid.

$^1$H NMR (500 MHz, CHLOROFORM-d) δ ppm 1.69 (s, 6 H), 3.73 (s, 3 H), 5.76 (s, 2 H), 6.42 (s, 1 H), 6.55 (d, J=2.4 Hz, 1 H), 6.75-6.81 (m, 1 H), 6.96 (d, J=7.3 Hz, 2 H), 7.22 (d, J=7.3 Hz, 1 H), 7.25-7.30 (m, 2 H), 7.49 (d, J=8.8 Hz, 1 H).

EXAMPLE 4

1-Benzyl-2-isopropyl-6-methoxy-1H-indole (Compound 4). To a solution of 2-(1-benzyl-6-methoxy-1H-indol-2-yl)propan-2-ol (Compound 3, 1.05 g, 3.57 mmol) in EtOAc (35 ml) and EtOH (15 ml) was added 10% Pd—C (190 mg, 0.18 mmol) and HCl-Et₂O (1.0 M, 1.25 ml, 1.25 mmol). The mixture was stirred under hydrogen gas (atmospheric pressure) for 1 h and was filtered. To the filtrate was added NaHCO₃ (0.5 g) and H₂O (0.5 ml), followed by Na₂SO₄ and MgSO₄. This was then filtered and concentrated in vacuo to yield the crude title compound as a yellow solid.

¹H NMR (300 MHz, CHLOROFORM-d) δ ppm 1.31 (d, J=6.7 Hz, 6 H), 2.90-3.10 (m, 1 H), 3.79 (s, 3 H), 5.33 (s, 2 H), 6.33 (s, 1 H), 6.68 (d, J=2.1 Hz, 1 H), 6.79 (dd, J=8.5, 2.3 Hz, 1 H), 6.94-7.04 (m, 2 H), 7.20-7.37 (m, 2 H), 7.49 (d, J=8.5 Hz, 1 H).

EXAMPLE 5

1-Benzyl-2-isopropyl-6-methoxy-1H-indole-3-carbaldehyde (Compound 5). $POCl_3$ (0.48 ml, 5.23 mmol) was added dropwise to anhydrous DMF (2 ml) at 0° C. under argon. After stirred for 30 min, this solution was added dropwise to a solution of 1-benzyl-2-isopropyl-6-methoxy-1H-indole (Compound 4, 583 mg, 2.09 mmol) in anhydrous DMF (8 ml) at 0° C. under argon. The reaction was stirred for 1 h at 0° C. and 30 min at room temperature, diluted with EtOAc, washed with aqueous $NaHCO_3$, brine, dried over $Na_2SO_4$, and concentrated in vacuo. The residue was purified by chromatography on silica gel (0→30% EtOAc-hexanes) to yield the title compound as a light yellow syrup.
¹H NMR (500 MHz, CHLOROFORM-d) δ ppm 1.45 (d, J=7.3 Hz, 6 H), 3.40-3.52 (m, 1 H), 3.79 (s, 3 H), 5.40 (s, 2 H), 6.69 (d, J=2.4 Hz, 1 H), 6.94 (dd, J=8.8, 2.0 Hz, 1 H), 7.01 (d, J=7.3 Hz, 2 H), 7.25-7.35 (m, 3 H), 8.28 (d, J=8.8 Hz, 1 H), 10.45 (s, 1 H).

EXAMPLE 6

1-Benzyl-2-isopropyl-6-methoxy-1H-indole-3-carboxylic Acid (Compound 6). To a solution of 1-benzyl-2-isopropyl-6-methoxy-1H-indole-3-carbaldehyde (Compound 5, 608 mg, 1.98 mmol) in t-BuOH (15 ml), $CH_3CN$ (15 ml), and 2-methyl-2-butene (10 ml) was added a solution of $KH_2PO_4$ (5.4 g, 39.6 mmol) and $NaClO_2$ (80%, 4.5 g, 39.6 mmol) in $H_2O$ (50 ml). The mixture was stirred at room temperature and additional 2-methyl-2-butene, $KH_2PO_4$, and $NaClO_2$ were added at the above ratio every 16-24 h until the starting material was consumed. The reaction mixture was extracted with EtOAc (×3) and the combined organic layer was washed with brine, dried over $Na_2SO_4$, and concentrated in vacuo. The residue was purified by chromatography on silica gel (0→25% EtOAc-hexanes) to yield the title compound as a yellow solid.
¹H NMR (500 MHz, CHLOROFORM-d) δ ppm 1.39 (d, J=7.3 Hz, 6 H), 3.75 (s, 3 H), 3.99-4.17 (m, 1 H), 5.45 (s, 2 H), 6.62 (d, J=2.4 Hz, 1 H), 6.90 (dd, J=8.8, 2.4 Hz, 1 H), 6.99 (d, J=7.3 Hz, 2 H), 7.22-7.34 (m, 3 H), 8.18 (d, J=8.8 Hz, 1 H).

EXAMPLE 7

1-Benzyl-N-(3,4-difluorobenzyl)-2-isopropyl-6-methoxy-1H-indole-3-carboxamide (Compound 7). To a solution of 1-benzyl-2-isopropyl-6-methoxy-1H-indole-3-carboxylic acid (Compound 6, 226 mg, 0.70 mmol) in $CH_2Cl_2$ (7.0 ml) was added EDC (202 mg, 1.05 mmol) and DMAP (128 mg, 1.05 mmol) followed by 3,4-difluorobenzylamine (0.25 ml, 2.1 mmol). The reaction was stirred at room temperature for 18 h, diluted with EtOAc, washed with $H_2O$, brine, dried over $Na_2SO_4$ and concentrated in vacuo. The residue was purified by chromatography on silica gel (0→30% EtOAc-hexanes) to yield the title compound as a yellow solid.
¹H NMR (500 MHz, CHLOROFORM-d) δ ppm 1.37 (d, J=7.3 Hz, 6 H), 3.65-3.73 (m, 1 H), 3.74 (s, 3 H), 4.66 (d, J=5.9 Hz, 2 H), 5.40 (s, 2 H), 6.30 (t, J=6.3 Hz, 1 H), 6.63 (d, J=2.0 Hz, 1 H), 6.82 (dd, J=8.8, 2.4 Hz, 1 H), 6.96 (d, J=6.8 Hz, 2 H), 7.11-7.17 (m, 2 H), 7.21-7.31 (m, 4 H), 7.51 (d, J=8.3 Hz, 1 H).

EXAMPLE 8

1-Benzyl-N-(3,4-difluorobenzyl)-6-hydroxy-2-isopropyl-1H-indole-3-carboxamide (Compound 8). To a solution of 1-benzyl-N-(3,4-difluorobenzyl)-2-isopropyl-6-methoxy-1H-indole-3-carboxamide (Compound 7, 452 mg, 1.0 mmol) in $CH_2Cl_2$ (20 ml) at 0° C. was added $BBr_3$ (1.0 M in $CH_2Cl_2$, 3.0 ml, 3.0 mmol) dropwise. The reaction was stirred for 1 h at 0° C. and 1 h at room temperature, quenched with ice, extracted with EtOAc, the organic layer was washed with brine, dried over $Na_2SO_4$, and concentrated in vacuo. The residue was purified by chromatography on silica gel (0→50% EtOAc-hexanes) to yield the title compound as a yellow solid.
¹H NMR (500 MHz, CHLOROFORM-d) δ ppm 1.37 (d, J=7.3 Hz, 6 H), 3.65-3.74 (m, 1 H), 4.66 (d, J=5.9 Hz, 2 H), 4.78 (s, 1 H), 5.37 (s, 2 H), 6.27 (t, J=5.6 Hz, 1 H), 6.60 (d, J=2.4 Hz, 1 H), 6.71 (dd, J=8.5, 2.2 Hz, 1 H), 6.95 (d, J=6.8 Hz, 2 H), 7.11-7.17 (m, 2 H), 7.21-7.32 (m, 4 H), 7.46 (d, J=8.8 Hz, 1 H).

EXAMPLE 9

1-benzyl-N-(3,4-difluorobenzyl)-6-ethoxy-2-isopropyl-1H-indole-3-carboxamide (Compound 9). General Procedure A. To a solution of 1-benzyl-N-(3,4-difluorobenzyl)-6-hydroxy-2-isopropyl-1H-indole-3-carboxamide (Compound 8, 40 mg, 0.092 mmol) in DMF (2.0 ml) was added $K_2CO_3$ (39 mg, 0.28 mmol) and iodoethane (22 µl, 0.28 mmol). The reaction was stirred at room temperature for 48 h, diluted with EtOAc, washed with $H_2O$, brine, dried over $Na_2SO_4$ and concentrated in vacuo. The residue was purified by PTLC on silica gel (30% EtOAc-hexanes) to yield the title compound as an off-white solid.
¹H NMR (500 MHz, CHLOROFORM-d) δ ppm 1.37 (t, J=7.0 Hz, 3 H), 1.38 (d, J=7.3 Hz, 6 H), 3.68-3.75 (m, 1 H), 3.96 (q, J=7.0 Hz, 2 H), 4.67 (d, J=6.3 Hz, 2 H), 5.40 (s, 2 H), 6.31 (t, J=5.4 Hz, 1 H), 6.64 (d, J=2.4 Hz, 1 H), 6.82 (dd, J=8.8, 2.0 Hz, 1 H), 6.97 (d, J=6.8 Hz, 2 H), 7.13-7.17 (m, 2 H), 7.23-7.31 (m, 4 H), 7.52 (d, J=8.3 Hz, 1 H)

EXAMPLE 10

1-Benzyl-N-(3,4-difluorobenzyl)-2-isopropyl-6-propoxy-1H-indole-3-carboxamide (Compound 10). Following General Procedure A, 1-benzyl-N-(3,4-difluorobenzyl)-6-hydroxy-2-isopropyl-1H-indole-3-carboxamide (Compound 8, 8.0 mg, 0.018 mmol) in DMF (1.0 ml) was reacted with $K_2CO_3$ (8.0 mg, 0.055 mmol) and 1-iodopropane (9.0 µl, 0.092 mmol) to yield the title compound as a white solid.
¹H NMR (500 MHz, METHANOL-$d_4$) δ ppm 0.99 (t, J=7.6 Hz, 3 H), 1.32 (d, J=7.3 Hz, 6 H), 1.67-1.77 (m, 2 H), 3.42-3.53 (m, 1 H), 3.84 (t, J=6.6 Hz, 2 H), 4.57 (s, 2 H), 5.46 (s, 2 H), 6.73 (d, J=2.0 Hz, 1 H), 6.78 (dd, J=8.8, 2.4 Hz, 1 H), 6.95 (d, J=6.8 Hz, 2 H), 7.19-7.29 (m, 5 H), 7.30-7.36 (m, 1 H), 7.49 (d, J=8.3 Hz, 1 H).

EXAMPLE 11

1-Benzyl-N-(3,4-difluorobenzyl)-6-isopropoxy-2-isopropyl-1H-indole-3-carboxamide (Compound 11). Following General Procedure A, 1-benzyl-N-(3,4-difluorobenzyl)-6-hydroxy-2-isopropyl-1H-indole-3-carboxamide (Compound 8, 8.0 mg, 0.018 mmol) in DMF (1.0 ml) was reacted with $K_2CO_3$ (8.0 mg, 0.055 mmol) and 2-iodopropane (9.0 µl, 0.092 mmol) to yield the title compound as a white solid.

¹H NMR (500 MHz, METHANOL-d₄) δ ppm 1.21 (d, J=5.9 Hz, 6 H), 1.33 (d, J=7.3 Hz, 6 H), 3.45-3.55 (m, 1 H), 4.41-4.50 (m, 1 H), 4.57 (s, 2 H), 5.46 (s, 2 H), 6.72 (d, J=2.0 Hz, 1 H), 6.74-6.79 (m, 1 H), 6.96 (d, J=7.3 Hz, 2 H), 7.18-7.29 (m, 5 H), 7.30-7.37 (m, 1 H), 7.49 (d, J=8.8 Hz, 1 H).

EXAMPLE 12

1-Benzyl-6-butoxy-N-(3,4-difluorobenzyl)-2-isopropyl-1H-indole-3-carboxamide (Compound 12). Following General Procedure A, 1-benzyl-N-(3,4-difluorobenzyl)-6-hydroxy-2-isopropyl-1H-indole-3-carboxamide (Compound 8, 10.7 mg, 0.025 mmol) in DMF (1.0 ml) was reacted with $K_2CO_3$ (10.0 mg, 0.074 mmol) and 1-iodobutane (14.0 µl, 0.12 mmol) to yield the title compound as a white solid.

¹H NMR (500 MHz, CHLOROFORM-d) δ ppm 0.93 (t, J=7.3 Hz, 3 H), 1.37 (d, J=7.3 Hz, 6 H), 1.40-1.50 (m, 2 H), 1.66-1.74 (m, 2 H), 3.61-3.75 (m, 1 H), 3.88 (t, J=6.6 Hz, 2 H), 4.66 (d, J=6.3 Hz, 2 H), 5.39 (s, 2 H), 6.30 (t, J=5.9 Hz, 1 H), 6.63 (d, J=2.0 Hz, 1 H), 6.81 (dd, J=8.5, 2.2 Hz, 1 H), 6.96 (d, J=6.8 Hz, 2 H), 7.10-7.17 (m, 2 H), 7.21-7.32 (m, 4 H), 7.50 (d, J=8.8 Hz, 1 H).

EXAMPLE 13

1-Benzyl-N-(3,4-difluorobenzyl)-6-isobutoxy-2-isopropyl-1H-indole-3-carboxamide (Compound 13). Following General Procedure A, 1-benzyl-N-(3,4-difluorobenzyl)-6-hydroxy-2-isopropyl-1H-indole-3-carboxamide (Compound 8, 10.7 mg, 0.025 mmol) in DMF (1.0 ml) was reacted with $K_2CO_3$ (10.0 mg, 0.074 mmol) and 2-iodobutane (14.0 µl, 0.12 mmol) to yield the title compound as a white solid.

¹H NMR (500 MHz, CHLOROFORM-d) δ ppm 0.98 (d, J=6.8 Hz, 6 H), 1.36 (d, J=7.3 Hz, 6 H), 1.96-2.08 (m, 1 H), 3.65 (d, J=6.8 Hz, 2 H), 3.65-3.72 (m, 1 H), 4.66 (d, J=6.3 Hz, 2 H), 5.39 (s, 2 H), 6.29 (t, J=5.6 Hz, 1 H), 6.63 (d, J=2.0 Hz, 1 H), 6.82 (dd, J=8.8, 2.0 Hz, 1 H), 6.96 (d, J=6.8 Hz, 2H), 7.11-7.16 (m, 2H), 7.21-7.31 (m, 4 H), 7.50 (d, J=8.8 Hz, 1 H).

EXAMPLE 14

1-Benzyl-N-(3,4-difluorobenzyl)-6-(hexoxy)-2-isopropyl-1H-indole-3-carboxamide (Compound 14). Following General Procedure A, 1-benzyl-N-(3,4-difluorobenzyl)-6-hydroxy-2-isopropyl-1H-indole-3-carboxamide (Compound 8, 10.7 mg, 0.025 mmol) in DMF (1.0 ml) was reacted with $K_2CO_3$ (10.0 mg, 0.074 mmol) and 1-iodohexane (18.0 µl, 0.12 mmol) to yield the title compound as a white solid.

¹H NMR (500 MHz, CHLOROFORM-d) δ ppm 0.85-0.93 (m, 3 H), 1.24-1.33 (m, 4 H), 1.37 (d, J=6.8 Hz, 6 H), 1.38-1.46 (m, 2 H), 1.66-1.77 (m, 2 H), 3.63-3.75 (m, 1 H), 3.87 (t, J=6.6 Hz, 2 H), 4.66 (d, J=5.9 Hz, 2 H), 5.39 (s, 2 H), 6.30 (t, J=5.6 Hz, 1 H), 6.63 (d, J=2.4 Hz, 1 H), 6.81 (dd, J=8.8, 2.4 Hz, 1 H), 6.96 (d, J=6.8 Hz, 2 H), 7.10-7.16 (m, 2 H), 7.21-7.31 (m, 4 H), 7.50 (d, J=8.8 Hz, 1 H).

EXAMPLE 15

1-Benzyl-6-(benzyloxy)-N-(3,4-difluorobenzyl)-2-isopropyl-1H-indole-3-carboxamide (Compound 15). Following General Procedure A, 1-benzyl-N-(3,4-difluorobenzyl)-6-hydroxy-2-isopropyl-1H-indole-3-carboxamide (Compound 8, 10.7 mg, 0.025 mmol) in DMF (1.0 ml) and acetone (1.0 ml) was reacted with $K_2CO_3$ (10.0 mg, 0.074 mmol), benzyl bromide (14.0 µl, 0.12 mmol), and catalytic amount of NaI to yield the title compound as an off-white solid.

¹H NMR (500 MHz, CHLOROFORM-d) δ ppm 1.37 (d, J=7.3 Hz, 6 H), 3.65-3.75 (m, 1 H), 4.66 (d, J=6.3 Hz, 2 H), 4.99 (s, 2 H), 5.37 (s, 2 H), 6.28 (t, J=6.3 Hz, 1 H), 6.71 (d, J=2.0 Hz, 1 H), 6.89 (dd, J=8.8, 2.0 Hz, 1 H), 6.95 (d, J=6.8 Hz, 2 H), 7.11-7.18 (m, 2 H), 7.22-7.30 (m, 5 H), 7.31-7.39 (m, 4 H), 7.51 (d, J=8.8 Hz, 1 H).

EXAMPLE 16

1-Benzyl-6-(cyclopentoxy)-N-(3,4-difluorobenzyl)-2-isopropyl-1H-indole-3-carboxamide (Compound 16). Following General Procedure A, 1-benzyl-N-(3,4-difluorobenzyl)-6-hydroxy-2-isopropyl-1H-indole-3-carboxamide (Compound 8, 40 mg, 0.092 mmol) in DMF (1.0 ml) was reacted with $K_2CO_3$ (38 mg, 0.28 mmol), cyclopentyl iodide (53 µl, 0.46 mmol) to yield the title compound as a white solid.

¹H NMR (300 MHz, CHLOROFORM-d) δ ppm 1.37 (d, J=7.0 Hz, 6 H), 1.48-1.60 (m, 2 H), 1.66-1.86 (m, 6 H), 3.62-3.83 (m, 1 H), 4.56-4.77 (m, 3 H), 5.38 (s, 2 H), 6.32 (t, J=5.9 Hz, 1 H), 6.61 (d, J=2.1 Hz, 1 H), 6.78 (dd, J=8.8, 2.1 Hz, 1 H), 6.91-7.02 (m, 2 H), 7.08-7.17 (m, 2 H), 7.17-7.36 (m, 4 H), 7.49 (d, J=8.5 Hz, 1 H).

EXAMPLE 17

1-Benzyl-N-(3,4-difluorobenzyl)-2-isopropyl-6-(2-methoxyethoxy)-1H-indole-3-carboxamide (Compound 17). Following General Procedure A, 1-benzyl-N-(3,4-difluorobenzyl)-6-hydroxy-2-isopropyl-1H-indole-3-carboxamide (Compound 8, 17 mg, 0.039 mmol) in DMF (1.0 ml) was reacted with $K_2CO_3$ (28 mg, 0.20 mmol), 2-bromoethyl methyl ether (18 µl, 0.20 mmol) to yield the title compound (9 mg, 49%).

¹H NMR (300 MHz, CDCl₃) δ ppm 1.37 (d, J=7.04 Hz, 6 H), 3.40 (s, 3 H), 3.60-3.78 (m, 3 H), 4.04 (dd, J=5.42, 3.96 Hz, 2 H), 4.66 (d, J=5.86 Hz, 2 H), 5.39 (s, 2 H), 6.30 (t, J=5.86 Hz, 1 H), 6.68 (d, J=2.35 Hz, 1 H), 6.85 (dd, J=8.65, 2.20 Hz, 1 H), 6.89-7.01 (m, 2 H), 7.10-7.18 (m, 2 H), 7.17-7.35 (m, 4 H), 7.51 (d, J=8.79 Hz, 1 H).

EXAMPLE 18

1-Benzyl-N-(3,4-difluorobenzyl)-6-(2-(dimethylamino)ethoxy)-2-isopropyl-1H-indole-3-carboxamide (Compound 18). Following General Procedure A, 1-benzyl-N-(3,4-difluorobenzyl)-6-hydroxy-2-isopropyl-1H-indole-3-carboxamide (Compound 8, 17 mg, 0.039 mmol) in DMF (1.0 ml) was reacted with $K_2CO_3$ (28 mg, 0.20 mmol), 2-dimethylamino ethyl chloride hydrochloride (20 mg, 0.20 mmol) to yield the title compound (10 mg, 53%).

¹H NMR (300 MHz, CD₃OD) δ ppm 1.32 (d, J=7.04 Hz, 6 H), 2.30 (s, 6 H), 2.71 (t, J=5.42 Hz, 2 H), 3.37-3.59 (m, 1 H), 4.02 (t, J=5.42 Hz, 2 H), 4.57 (s, 2 H), 5.48 (s, 2 H), 6.73-6.88 (m, 2 H), 6.89-7.02 (m, 2 H), 7.12-7.40 (m, 6 H), 7.50 (d, J=8.50 Hz, 1 H).

EXAMPLE 19

1-Benzyl-N-(3,4-difluorobenzyl)-2-isopropyl-6-(tetrahydrofuran-3-yloxy)-1H-indole-3-carboxamide (Compound 19). To a solution of 1-benzyl-N-(3,4-difluorobenzyl)-6-hydroxy-2-isopropyl-1H-indole-3-carboxamide (Compound 8, 8 mg, 0.039 mmol) in DMF (1.0 ml) was added $K_2CO_3$ (13 mg, 0.092 mmol) and catalytic amount of NaOH, 3-iodotetrahydrofuran (Compound 29, 120 mg, crude). The reaction was stirred at room temperature for 2 days, and purified by a short silica gel column to yield the title compound (8 mg, 86%).

$^1$H NMR (300 MHz, CDCl$_3$) δ ppm 1.38 (d, J=7.04 Hz, 6 H), 1.95-2.14 (m, 2 H), 3.59-4.01 (m, 5 H), 4.66 (d, J=6.16 Hz, 2 H), 4.74-4.88 (m, 1 H), 5.39 (s, 2 H), 6.29 (t, J=4.40 Hz, 1 H), 6.57 (d, J=2.05 Hz, 1 H), 6.69-6.83 (m, 1 H), 6.96 (d, J=7.62 Hz, 2 H), 7.08-7.19 (m, 2 H), 7.18-7.35 (m, 4 H), 7.51 (d, J=8.79 Hz, 1 H).

EXAMPLE 20

1-Benzyl-N-(3,4-difluorobenzyl)-2-isopropyl-6-(2-oxotetrahydrofuran-3-yloxy)-1H-indole-3-carboxamide (Compound 20). Following General Procedure A, 1-benzyl-N-(3,4-difluorobenzyl)-6-hydroxy-2-isopropyl-1 H-indole-3-carboxamide (Compound 8, 19mg, 0.044 mol) in DMF (1.0 ml) was reacted with K$_2$CO$_3$ (30 g, 0.22 mmol), 3-bromodihydrofuran-2(3H)-one (20 mg, 0.22 mmol) to yield the title compound (16mg, 71%).

$^1$H NMR (300 MHz, acetone-d$_6$) δ ppm 1.33 (d, J=5.57 Hz, 6 H), 2.21-2.42 (m, 1 H), 2.68-2.88 (m, 1 H), 3.43-3.65 (m, 1 H), 4.21-4.53 (m, 2 H), 4.66 (d, J=6.16 Hz, 2 H), 5.10-5.24 (m, 1 H), 5.54 (s, 2 H), 6.90 (dd, J=8.65, 2.20 Hz, 1 H), 6.97-7.08 (m, 2 H), 7.11 (d, J=2.35 Hz, 1 H), 7.17-7.35 (m, 5 H), 7.42 (dd, J=12.31, 8.50 Hz, 1 H), 7.62 (d, J=8.79 Hz, 1 H), 7.68-7.78 (m, 1 H).

EXAMPLE 21

1-benzyl-3-(3,4-difluorobenzylcarbamoyl)-2-isopropyl-1H-indol-6-yl Dimethylcarbamate (Compound 21). General Procedure B. To a solution of 1-benzyl-N-(3,4-difluorobenzyl)-6-hydroxy-2-isopropyl-1H-indole-3-carboxamide (Compound 8, 18mg, 0.041mol) in pyridine (1 ml) was added dimethylcarbamyl chloride (40 μl, 0.41 mmol) and stirred at room temperature overnight. The reaction was quenched with water, extracted with ethyl acetate. The combined organic layer was washed with water, brine, dried over Na$_2$SO$_4$, and concentrated in vacuo. The residue was purified by chromatography on silica gel (0→50% EtOAc-hexanes) to yield the title compound as a white solid (17 mg, 82%).

$^1$H NMR (300 MHz, CD$_3$OD) δ ppm 1.32 (d, J=7.04 Hz, 6 H), 2.96 (s, 3 H), 3.09 (s, 3 H), 3.37-3.55 (m, 1 H), 4.58 (s, 2 H), 5.48 (s, 2 H), 6.87 (dd, J=8.65, 1.91 Hz, 1 H), 6.91-6.99 (m, 2 H), 7.02 (d, J=2.05 Hz, 1 H), 7.16-7.39 (m, 6 H), 7.58 (d, J=8.79 Hz, 1 H).

EXAMPLE 22

1-Benzyl-3-(3,4-difluorobenzylcarbamoyl)-2-isopropyl-1H-indol-6-yl Pivalate (Compound 22). Following General Procedure B, 1-benzyl-N-(3,4-difluorobenzyl)-6-hydroxy-2-isopropyl-1H-indole-3-carboxamide (Compound 8, 18 mg, 0.041 mol) in pyridine (1 ml) was reacted with pivaloyl chloride (5.1 μl, 0.41 mmol) to yield the title compound (16 mg, 74%).

$^1$H NMR (300 MHz, CD$_3$OD) δ ppm 1.25-1.40 (m, 15 H), 3.34-3.55 (m, 1 H), 4.58 (d, J=5.86 Hz, 2 H), 5.49 (s, 2 H), 6.73-6.88 (m, 1 H), 6.89-6.99 (m, 2 H), 7.00 (d, J=1.76 Hz, 1 H), 7.14-7.41 (m, 6 H), 7.60 (d, J=8.50 Hz, 1 H).

EXAMPLE 23

1-Benzyl-3-(3,4-difluorobenzylcarbamoyl)-2-isopropyl-1H-indol-6-yl Acetate (Compound 23). Following General Procedure B, 1-benzyl-N-(3,4-difluorobenzyl)-6-hydroxy-2-isopropyl-1H-indole-3-carboxamide (Compound 8, 7 mg, 0.016 mol) in pyridine (1 ml) was reacted with acetyl chloride (1.0 μl, 0. 16 mmol) to yield the title compound (8 mg, 100%).

$^1$H NMR (300 MHz, CDCl$_3$) δ ppm 1.37 (d, J=7.04 Hz, 6 H), 2.26 (s, 3 H), 3.54-3.76 (m, 1 H), 4.66 (d, J=6.16 Hz, 2 H), 5.41 (s, 2 H), 6.28 (t, J=6.01 Hz, 1 H), 6.81-7.01 (m, 4 H), 7.06-7.19 (m, 2 H), 7.18-7.35 (m, 4 H), 7.61 (d, J=9.09 Hz, 1 H).

EXAMPLE 24

1-Benzyl-3-(3,4-difluorobenzylcarbamoyl)-2-isopropyl-1H-indol-6-yl Propionate (Compound 24). Following General Procedure B, 1-benzyl-N-(3,4-difluorobenzyl)-6-hydroxy-2-isopropyl-1H-indole-3-carboxamide (Compound 8, 7 mg, 0.016 mol) in pyridine (1 ml) was reacted with propionyl chloride (1.4 μl, 0.16 mmol) to yield the title compound (8 mg, 100%).

$^1$H NMR (300 MHz, CDCl$_3$) δ ppm 1.23 (t, J=7.48 Hz, 3 H), 1.37 (d, J=7.33 Hz, 6 H), 2.55 (q, J=7.43 Hz, 2 H), 3.53-3.73 (m, 1 H), 4.66 (d, J=5.86 Hz, 2 H), 5.41 (s, 2 H), 6.30 (t, J=5.72 Hz, 1 H), 6.83-7.00 (m, 4 H), 7.06-7.18 (m, 2 H), 7.18-7.35 (m, 4 H), 7.60 (d, J=8.50 Hz, 1 H).

EXAMPLE 25

1-Benzyl-3-(3,4-difluorobenzylcarbamoyl)-2-isopropyl-1H-indol-6-yl Isobutyrate (Compound 25). Following General Procedure B, 1-benzyl-N-(3,4-difluorobenzyl)-6-hydroxy-2-isopropyl-1H-indole-3-carboxamide (Compound 8, 9 mg, 0.021 mol) in pyridine (1 ml) was reacted with isobutyryl chloride (4.1 μl, 0.21 mmol) to yield the title compound (8 mg, 80%).

$^1$H NMR (300 MHz, CDCl$_3$) δ ppm 1.13-1.42 (m, 12 H), 2.47-2.85 (m, 1 H), 3.50-3.74 (m, 1 H), 4.66 (d, J=6.16 Hz, 2 H), 5.41 (s, 2 H), 6.20-6.44 (m, 1 H), 6.74-7.00 (m, 4 H), 7.07-7.18 (m, 2 H), 7.17-7.35 (m, 4 H), 7.60 (d, J=8.50 Hz, 1H).

EXAMPLE 26

1-Benzyl-N-(3,4-difluorobenzyl)-2-isopropyl-6-(methoxymethoxy)-1H-indole-3-carboxamide (Compound 26). To a solution of 1-benzyl-N-(3,4-difluorobenzyl)-6-hydroxy-2-isopropyl-1H-indole-3-carboxamide (Compound 8, 39 mg, 0.090 mmol) in CH$_2$Cl$_2$ (2.0 ml) was added i-Pr$_2$NEt (47 μl, 0.27 mmol) and MOMCl (35 μl, 0.45 mmol). The reaction was stirred at room temperature for 4 h, and was purified directly by PTLC on silica gel (30% EtOAc-hexanes) to yield the title compound as a white solid.

$^1$H NMR (300 MHz, CHLOROFORM-d) δ ppm 1.37 (d, J=7.0 Hz, 6 H), 3.42 (s, 3 H), 3.59-3.78 (m, 1 H), 4.66 (d, J=5.9 Hz, 2 H), 5.10 (s, 2 H), 5.40 (s, 2 H), 6.29 (t, J=5.7 Hz, 1 H), 6.85 (d, J=2.1 Hz, 1 H), 6.89-7.01 (m, 3 H), 7.10-7.17 (m, 2 H), 7.20- 7.34 (m, 4 H), 7.52 (d, J=8.5 Hz, 1 H).

EXAMPLE 27

1-Benzyl-N-(3,4-difluorobenzyl)-2-isopropyl-6-(tetrahydrofuran-2-yloxy)-1H-indole-3-carboxamide (Compound 27). To a solution of 1-benzyl-N-(3,4-difluorobenzyl)-6-hydroxy-2-isopropyl-1H-indole-3-carboxamide (Compound 8, 39 mg, 0.090 mmol) in CH$_2$Cl$_2$ (2.0 ml) was added 2,3-dihydrofuran (68 μl, 0.90 mmol) and catalytic amount of PPTS. The reaction was stirred at room temperature for 4 h, and was purified directly by PTLC on silica gel (30% EtOAc-hexanes) to yield the title compound as a white solid.

$^1$H NMR (300 MHz, CHLOROFORM-d) δ ppm 1.36 (d, J=7.3 Hz, 6 H), 1.85-1.98 (m, 1 H), 2.01-2.19 (m, 3 H), 3.58-3.73 (m, 1 H), 3.85-3.95 (m, 1 H), 3.96-4.07 (m, 1 H), 4.66 (d, J=5.9 Hz, 2 H), 5.40 (s, 2 H), 5.70 (d, J=4.7 Hz, 1 H), 6.29 (t, J=5.7 Hz, 1 H), 6.86 (d, J=2.1 Hz, 1 H), 6.89-6.99 (m, 3 H), 7.11-7.17 (m, 2 H), 7.19-7.32 (m, 4 H), 7.51 (d, J=8.5 Hz, 1 H).

EXAMPLE 28

Tetrahydrofuran-3-yl 4-methylbenzenesulfonate (Compound 28). To a solution of tetrahydrofuran-3-ol (500 mg, 5.67 mmol) in pyridine (10 ml) at 0° C. was added 4-methylbenzene-1-sulfonyl chloride (1.08 g, 5.67 mmol). The reaction was stirred at room temperature overnight. The reaction was quenched with water, extracted with ethyl acetate. The organic layer was washed with water, brine, dried over Na$_2$SO$_4$ and concentrated in vacuo to yield crude oil (1.2 g).

$^1$H NMR (300 MHz, CDCl$_3$) δ ppm 1.91-2.23 (m, 2 H), 3.61-4.05 (m, 4 H), 4.95-5.24 (m, 1 H), 7.36 (d, J=7.92 Hz, 2 H), 7.80 (d, J=8.50 Hz, 2 H).

EXAMPLE 29

3-Iodotetrahydrofuran (Compound 29). To a solution of crude tetrahydrofuran-3-yl 4-methylbenzenesulfonate (Compound 28, 1.2 g, 4.96 mmol) in dry acetone (50 ml) was added NaI (1.1 g, 7.44 mmol). The reacted was heated at 60° C. for 2 days. The mixture was diluted with water and extracted with diethyl ether. The organic layer was washed with water, brine, dried over Na$_2$SO$_4$ and concentrated in vacuo to yield crude oil which was used directly without purification.

$^1$H NMR (300 MHz, CDCl$_3$) δ ppm 2.23-2.55 (m, 2 H), 3.81-4.08 (m, 3 H), 4.08-4.43 (m, 2 H).

Scheme 4

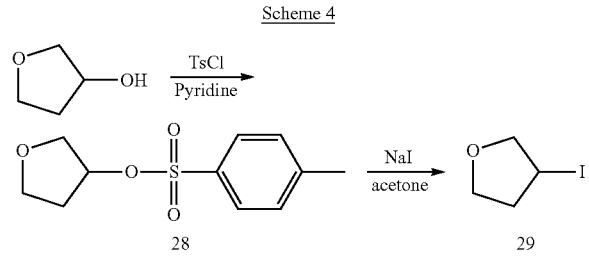

Scheme 5$^a$

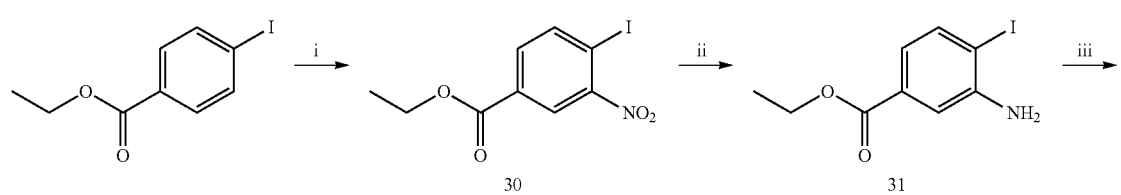

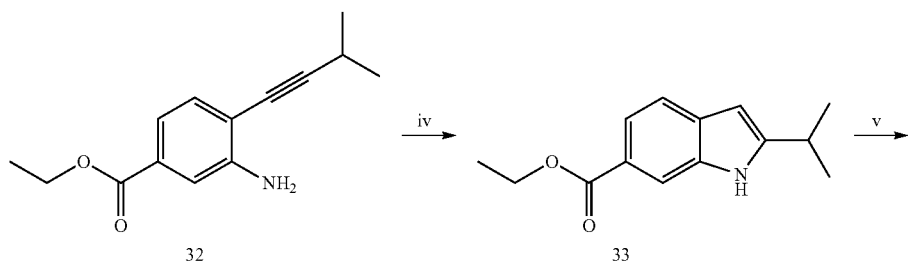

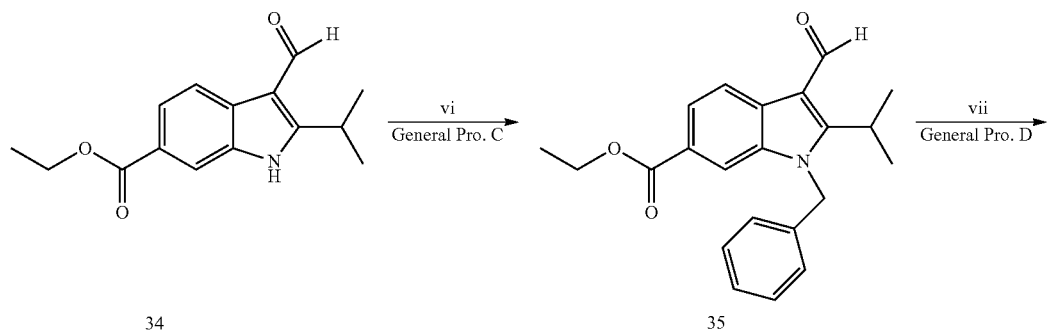

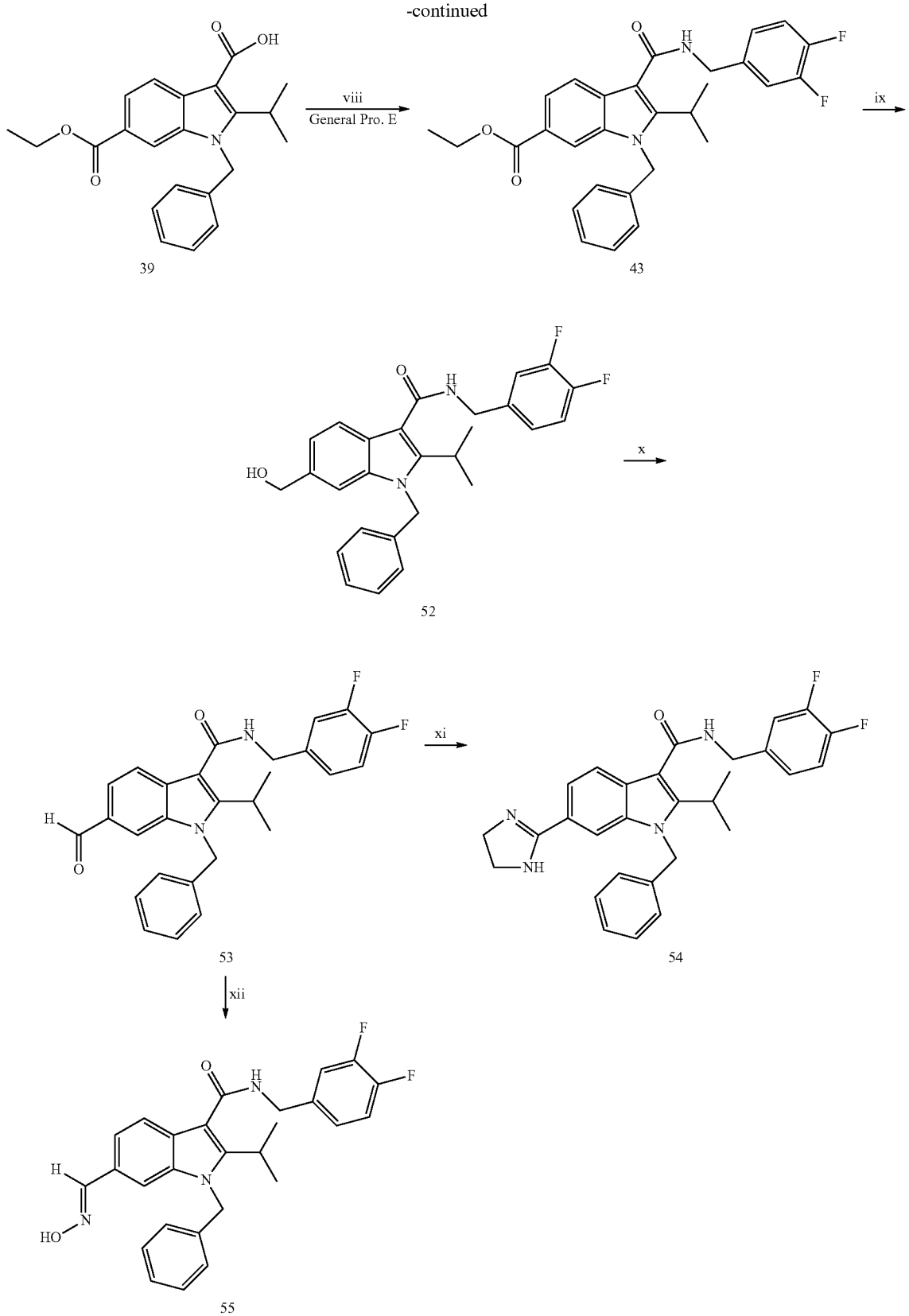
[a]Reagents and conditions: (i) $H_2SO_4$, $HNO_3$; (ii) $SnCl_2 \cdot H_2O$, EtOAC; (iii) $Et_3N$, CuI, $Pd(PPh_3)_2Cl_2$, 3-Methyl-1-butene; (iv) CuI, DMF; (v) $POCl_3$, DMF; (vi) BnBr, $K_2CO_3$, DMF; (vii) $NaClO_2$, $NaH_2PO_4$, Isobutene, t-BuOH, $H_2O$; (viii) 3,4-Difluorobenzylamine, EDC, DMAP; (ix) Dibal-H, $CH_2Cl_2$; (x) NMO, TPAP, $CH_2Cl_2$; (xi) Ethylene diamine, $CH_2Cl_2$, NBS; (xii) $OHNH_2 \cdot HCl$, pyridine.

EXAMPLE 30

Ethyl 4-Iodo-3-nitrobenzoate (Compound 30). To a solution of ethyl-4-iodobenzoate (10.0 g, 36.2 mmol) in $H_2SO_4$ (20 ml) at 0° C. was added dropwise $HNO_3$ (4.7 ml, 72.4 mmol). Reaction was stirred at room temperature for 1 h, cooled to 0° C., quenched with ice, diluted with EtOAc, washed with $H_2O$, brine, dried over $Na_2SO_4$, concentrated in vacuo to yield the crude title compound as a yellow solid.

1H NMR (300 MHz, CHLOROFORM-d) δ ppm 1.41 (t, J=7.09 Hz, 3 H), 4.40 (q, J=7.09 Hz, 2 H), 7.89 (dd, J=6.11, 1.96 Hz, 1 H), 8.19 (d, J=7.62 Hz, 1 H), 8.45 (s, 1 H).

EXAMPLE 31

Ethyl 3-Amino-4-iodobenzoate (Compound 31). To a solution of ethyl4-iodo-3nitrobenzoate (Compound 30, 9.45 g, 29.4 mmol) in ethyl acetate (200 ml) and tin(II) chloride dehydrate (33.1 g, 147 mmol). Reaction was heated to 85° C. for 1 h, cooled to 25° C., quenched with $NaHCO_3$(S), filtered off white solid, and then organic layer was concentrated in vacuo. The residue was purified by chromatography on silica gel (0→50% EtOAc-hexanes) to yield the title compound as a light yellow solid.

1H NMR (300 MHz, CHLOROFORM-d) δ ppm 1.38 (t, J=7.09 Hz, 3 H), 4.34 (q, J=7.18 Hz, 2 H), 7.11 (dd, J=8.21, 2.05 Hz, 1 H), 7.39 (d, J=2.05 Hz, 1 H), 7.71 (d, J=8.06 Hz, 1H).

EXAMPLE 32

Ethyl 3-Amino-4-(3-methylbut-1-ynyl)benzoate (Compound 32). To a solution of ethyl3-amino-4-iodobenzoate (Compound 31, 6.87 g, 23.1 mmol) in triethylamine (50 ml) at 25° C. under argon then added CuI (22 mg, 1.16 mmol), $Pd(PPh_3)_2Cl_2$ (82 mg, 1.16 mmol), and 3-methyl-1-butyne (3.18 g, 46.2 mmol). The reaction was stirred for 20 h at 25° C., filtered off brown solid, and then rinsed solid with EtOAc, organic layer was concentrated in vacuo. The residue was purified by chromatography on silica gel (0→25% EtOAc-hexanes) to yield the title compound as a yellow solid.

1H NMR (300 MHz, CHLOROFORM-d) δ ppm 1.29 (s, 3 H), 1.31 (s, 3 H), 1.38 (t, J=7.11 Hz, 3 H), 2.86 (dt, J=13.67, 6.87 Hz, 1 H), 4.25 (br. s., 2 H), 4.34 (q, J=7.08 Hz, 2 H), 7.29 (s, 1 H), 7.32 (d, J=1.47 Hz, 1 H), 7.33-7.38 (m, 1 H).

EXAMPLE 33

Ethyl 2-Isopropyl-1H-indole-6-carboxylate (Compound 33). To a solution of ethyl3-amino-4-(3-methylbut-1-ynyl)benzoate (Compound 32, 5.30 g, 22.9 mmol) in DMF (50 ml) at 25° C. under argon then added CuI (218 mg, 11.5 mmol). The reaction was heated for 2 h at 160° C., filtered off black solid, and then rinsed solid with EtOAc, organic layer was concentrated in vacuo. The residue was purified by chromatography on silica gel (0→20% EtOAc-hexanes) to yield the title compound as a yellow solid.

1H NMR (300 MHz, CHLOROFORM-d) δ ppm 1.37 (s, 3 H), 1.39 (s, 3 H), 1.40-1.44 (m, 3 H), 1.42 (t, J=7.09 Hz, 3 H), 3.11 (ddd, J=13.71, 6.74, 6.52 Hz, 1 H), 4.39 (q, J=7.08 Hz, 2 H), 6.30 (ddd, J=2.09, 0.99, 0.88 Hz, 1 H), 7.53 (d, J=8.21 Hz, 1 H), 7.78 (dd, J=8.36, 1.47 Hz, 1 H), 8.08 (d, J=0.73 Hz, 1 H), 8.17 (br. s., 1 H).

EXAMPLE 34

Ethyl 3-Formyl-2-isopropyl-1H-indole-6-carboxylate (Compound 34). To a solution of ethyl 2-isopropyl-1H-indole-6-carboxylate (Compound 33, 2.00 g, 8.66 mmol) in DMF (12 ml) at 0° C. under argon then added dropwise $POCl_3$ (1.58 ml, 17.3 mmol) was added dropwise. The reaction was stirred for 30 minutes at 25° C. then cooled to 0° C., quenched with saturated $NaHCO_3$, diluted with EtOAc, washed with brine, dried over $Na_2SO_4$, and concentrated in vacuo. The residue was purified by chromatography on silica gel (0→50% EtOAc-hexanes) to yield the title compound as a light tan solid.

1H NMR (300 MHz, CHLOROFORM-d) δ ppm 1.43 (t, J=7.18 Hz, 3 H), 1.48 (s, 3 H), 1.50 (s, 3 H), 3.84 (dt, J=14.00, 6.93 Hz, 1 H), 4.42 (q, J=7.18 Hz, 2 H), 7.97 (dd, J=8.28, 1.39 Hz, 1 H), 8.18 (d, J=0.73 Hz, 1 H), 8.28 (d, J=8.21 Hz, 1 H), 8.95 (br. s., 1 H), 10.29 (s, 1 H).

EXAMPLE 35

Ethyl 1-Benzyl-3-formyl-2-isopropyl-1H-indole-6-carboxylate (Compound 35). General Procedure C. To a solution of ethyl3-formyl-2-isopropyl-1H-indole-6-carboxylate (Compound 34, 2.08 g, 8.04 mmol) in DMF (15 ml) was added $K_2CO_3$ (3.32 g, 24.1 mmol) and benzyl bromide (1.91 ml, 16.1 mmol). The reaction was stirred at room temperature for 12 h, diluted with EtOAc, washed with $H_2O$, brine, dried over $Na_2SO_4$ and concentrated in vacuo. The residue was purified by chromatography on silica gel (0→35% EtOAc-hexanes) to yield the title compound as a yellow oil.

1H NMR (300 MHz, METHANOL-$d_4$) δ ppm 1.37 (t, J=7.11 Hz, 3 H), 1.44 (s, 3 H), 1.47 (s, 3 H), 3.54-3.76 (m, 0 H), 4.35 (q, J=7.18 Hz, 2 H), 5.67 (s, 2 H), 7.02 (d, J=7.18 Hz, 1 H), 7.18-7.42 (m, 4 H), 7.93 (d, J=8.36 Hz, 1 H), 8.08 (s, 1 H), 8.33 (d, J=8.65 Hz, 1 H), 10.41 (s, 1 H).

EXAMPLE 36

Ethyl 3-Formyl-2-isopropyl-1-(pyridin-2-ylmethyl)-1H-indole-6-carboxylate (Compound 36). Following General Procedure C, ethyl3-formyl-2-isopropyl-1H-indole-6-carboxylate (Compound 34, 278 mg, 1.07 mmol) in DMF (15 ml) was added $K_2CO_3$ (590 mg, 4.28 mmol) and 2-(bromomethyl)pyridine (914 mg, 5.35 mmol). The reaction was stirred at 60° C. for 5 h, diluted with EtOAc, washed with $H_2O$, brine, dried over $Na_2SO_4$ and concentrated in vacuo. The residue was purified by chromatography on silica gel (0→35% EtOAc-hexanes) to yield the title compound as a yellow oil.

1H NMR (300 MHz, METHANOL-$d_4$) δ ppm 1.36 (t, J=7.17 Hz, 3 H), 1.47 (s, 3 H), 1.50 (s, 3 H), 3.62-3.72 (m, 1 H), 4.34 (d, J=7.18 Hz, 2 H), 5.74 (s, 2 H), 7.01 (d, J=7.77 Hz, 1 H), 7.32 (d, J=7.48 Hz, 1 H), 7.75 (td, J=7.70, 1.76 Hz, 1 H), 7.93 (td, J=4.14, 1.39 Hz, 1 H), 8.07 (d, J=0.73 Hz, 1 H), 8.34 (t, J=4.18 Hz, 1 H), 8.52 (ddd, J=4.87, 1.72, 0.88 Hz, 1 H), 10.42 (s, 1 H).

EXAMPLE 37

Ethyl 3-Formyl-2-isopropyl-1-(pyridin-3-ylmethyl)-1H-indole-6-carboxylate (Compound 37). To a solution of ethyl3-formyl-2-isopropyl-1H-indole-6-carboxylate (Compound 34, 1.00 g, 3.86 mmol) in DMF (50 ml) was added NaH (463 mg, 19.3 mmol) and and 3-(bromomethyl)pyridine (2.62 g, 15.4 mmol). The reaction was stirred at 60° C. for 12 h, diluted with EtOAc, washed with $H_2O$, brine, dried over $Na_2SO_4$ and concentrated in vacuo. The residue was purified by chromatography on silica gel (0→70% EtOAc-hexanes) to yield the title compound as a light yellow solid.

1H NMR (300 MHz, METHANOL-$d_4$) δ ppm 1.36 (t, J=7.11 Hz, 3 H), 1.46 (s, 3 H), 1.49 (s, 3 H), 3.66 (dt, J=14.37, 7.18 Hz, 1 H), 4.35 (q, J=7.08 Hz, 2 H), 5.78 (s, 2 H), 7.40 (qd, J=3.81, 3.66 Hz, 3 H), 7.94 (dd, J=8.36, 1.47 Hz, 1 H), 8.10 (d, J=0.73 Hz, 1 H), 8.30-8.40 (m, 1 H), 8.47 (dd, J=4.47, 1.98 Hz, 1 H), 10.43 (s, 1 H).

EXAMPLE 38

Ethyl 3-Formyl-2-isopropyl-1-(oxazol-2-ylmethyl)-1H-indole-6-carboxylate (Compound 38). To a solution of ethyl3-formyl-2-isopropyl-1H-indole-6-carboxylate (Compound 34, 1.22 g, 4.72 mmol) in DMF (10 ml) was added NaH (170 mg, 7.08 mmol) and 2-(chloromethyl)oxazole (1.10 g, 9.44 mmol). The reaction was stirred at 25° C. for 12 h, diluted with EtOAc, washed with $H_2O$, brine, dried over $Na_2SO_4$ and concentrated in vacuo. The residue was purified by chromatography on silica gel (0→50% EtOAc-hexanes) to yield the title compound as a yellow oil.

1H NMR (300 MHz, METHANOL-$d_4$) δ ppm 1.40 (t, J=7.11 Hz, 3 H), 1.54 (s, 3 H), 1.56 (s, 3 H), 3.77 (dt, J=14.33, 7.13 Hz, 1 H), 4.38 (q, J=7.04 Hz, 2 H), 5.80 (s, 2 H), 7.15 (d, J=0.73 Hz, 1 H), 7.80-8.11 (m, 2 H), 8.11-8.52 (m, 2 H), 10.42 (s, 1 H).

EXAMPLE 39

1-Benzyl-6-(ethoxylcarbonyl)-2-isopropyl-1H-indole-3-carboxylic Acid (Compound 39). General Procedure D. To a solution of ethyl1-benzyl-3-formyl-2-isopropyl-1H-indole-6-carboxylate (Compound 35, 220 mg, 0.63 mmol) in t-BuOH (6 ml), $CH_3CN$ (1 ml), and 2-methyl-2-butene (1.76 ml) was added a solution of $NaH_2PO_4$ (1.51 g, 12.6 mmol) and $NaClO_2$ (80%, 1.13 g, 12.6 mmol) in $H_2O$ (6 ml). The mixture was stirred at room temperature fro 12 h. The reaction mixture was extracted with EtOAc (×3) and the combined organic layer was washed with brine, dried over $Na_2SO_4$, and concentrated in vacuo. The residue was purified by chromatography on silica gel (0→20% EtOAc-hexanes) to yield the title compound as a yellow solid.

1H NMR (300 MHz, METHANOL-$d_4$) δ ppm 1.35 (t, J=7.11 Hz, 3 H), 1.37 (s, 3 H), 1.40 (s, 3 H), 3.80-4.08 (m, 1 H), 4.33 (q, J=7.13 Hz, 2 H), 5.67 (s, 2 H), 6.96 (d, J=9.23 Hz, 2 H), 7.20-7.38 (m, 3 H), 7.84 (dd, J=8.50, 1.47 Hz, 1 H), 7.98 (s, 1 H), 8.21 (dd, J=8.50, 0.59 Hz, 1 H).

EXAMPLE 40

6-(Ethoxycarbonyl)-2-isopropyl-1-(pyridin-2-ylmethyl)-1H-indole-3-carboxylic Acid (Compound 40). Following General Procedure D, ethyl3-formyl-2-isopropyl-1-(pyridin-2-ylmethyl)-1H-indole-6-carboxylate (Compound 36, 287 mg, 0.82 mmol) in t-BuOH (6 ml), 2-methyl-2-butene (2.29 ml) was added a solution of $NaH_2PO_4$ (1.97 g, 16.4 mmol) and $NaClO_2$ (80%, 1.48 g, 16.4 mmol) in $H_2O$ (6 ml). The mixture was stirred at room temperature for 12 h. The reaction mixture was extracted with EtOAc (×3) and the combined organic layer was washed with brine, dried over $Na_2SO_4$, and concentrated in vacuo. The residue was purified by chromatography on silica gel (0→50% EtOAc-hexanes) to yield the title compound as a light yellow solid.

1H NMR (300 MHz, METHANOL-$d_4$) δ ppm 1.30-1.47 (m, 9 H), 3.94-4.13 (m, 1 H), 4.33 (q, J=7.13 Hz, 2 H), 5.74 (s, 2 H), 6.76 (d, J=8.06 Hz, 1 H), 7.26-7.37 (m, 1 H), 7.65-7.77 (m, 1 H), 7.85 (d, J=7.04 Hz, 1 H), 7.98 (d, J=0.73 Hz, 1 H), 8.21 (d, J=8.50 Hz, 1 H), 8.55 (dd, J=6.23, 1.25 Hz, 1 H).

EXAMPLE 41

6-(Ethoxycarbonyl)-2-isopropyl-1-(pyridin-2-ylmethyl)-1H-indole-3-carboxylic Acid (Compound 41). Following General Procedure D, ethyl3-formyl-2-isopropyl-1-(pyridin-3-ylmethyl)-1H-indole-6-carboxylate (Compound 37, 754 mg, 1.54 mmol) in t-BuOH (30 ml), 2-methyl-2-butene (6.0 ml) was added a solution of $NaH_2PO_4$ (5.17 g, 30.8 mmol) and $NaClO_2$ (80%, 3.88 g, 30.8 mmol) in $H_2O$ (12 ml). The mixture was stirred at room temperature for 12 h. The reaction mixture was extracted with EtOAc (×3) and the combined organic layer was washed with brine, dried over $Na_2SO_4$, and concentrated in vacuo. The residue was purified by chromatography on silica gel (0→60% EtOAc-hexanes) to yield the title compound as a light yellow solid.

1H NMR (300 MHz, METHANOL-$d_4$) δ ppm 1.36 (t, J=7.11 Hz, 3 H), 1.39 (s, 3 H), 1.42 (s, 3 H), 3.85-4.13 (m, 1 H), 4.33 (q, J=7.08 Hz, 2 H), 5.77 (s, 2 H), 7.36 (t, J=2.05 Hz, 2 H), 7.86 (dd, J=8.50, 1.47 Hz, 1 H), 8.00 (d, J=0.88 Hz, 1 H), 8.22 (dd, J=8.50, 0.73 Hz, 1 H), 8.27 (d, J=1.76 Hz, 1 H), 8.45 (dd, J=4.03, 2.42 Hz, 1 H).

EXAMPLE 42

6-(Ethoxycarbonyl)-2-isopropyl-1-(oxazol-2-ylmethyl)-1H-indole-3-carboxylic Acid (Compound 42). Following General Procedure D, ethyl3-formyl-2-isopropyl-1-(oxazol-2-ylmethyl)-1H-indole-6-carboxylate (Compound 38, 240 mg, 0.70 mmol) in t-BuOH (20 ml), 2-methyl-2-butene (2.0 ml) was added a solution of $NaH_2PO_4$ (1.69 g, 14.0 mmol) and $NaClO_2$ (80%, 1.27 g, 14.0 mmol) in $H_2O$ (4 ml). The mixture was stirred at room temperature for 12 h. The reaction mixture was extracted with EtOAc (×3) and the combined organic layer was washed with brine, dried over $Na_2SO_4$, and concentrated in vacuo. The residue was purified by chromatography on silica gel (0→55% EtOAc-hexanes) to yield the title compound as a light tan solid.

1H NMR (300 MHz, METHANOL-$d_4$) δ ppm 1.40 (t, J=7.11 Hz, 3 H), 1.46 (s, 3 H), 1.48 (s, 3 H), 3.94-4.15 (m, 1 H), 4.38 (q, J=7.18 Hz, 2 H), 5.78 (s, 2 H), 7.14 (d, J=0.73 Hz, 1 H), 7.76-7.93 (m, 2 H), 8.17 (d, J=2.05 Hz, 2 H).

EXAMPLE 43

Ethyl 1-Benzyl-3-(3,4-difluorobenzylcarbamoyl)-2-isopropyl-1H-indole-6-carboxylate (Compound 43). General Procedure E. To a solution of 1-benzyl-6-(ethoxylcarbonyl)-2-isopropyl-1H-indole-3-carboxylic acid (Compound 39, 1.00 g, 2.74 mmol) in $CH_2Cl_2$ (10 ml) was added EDC (1.04 g, 5.84 mmol) and DMAP (500 mg, 4.11 mmol), followed by 3,4-difluorobenzylamine (589 mg, 4.11 mmol). The reaction was stirred at room temperature for 12 h, diluted with EtOAc, washed with $H_2O$, brine, dried over $Na_2SO_4$ and concentrated in vacuo. The residue was purified by chromatography on silica gel (0→35% EtOAc-hexanes) to yield the title compound as a yellow solid.

1H NMR (300 MHz, METHANOL-$d_4$) δ ppm 1.31-1.39 (m, 9 H), 3.47 (m, 1 H), 4.33 (q, J=7.18 Hz, 2 H), 4.59 (s, 2 H), 5.60 (s, 2 H), 6.96 (d, J=8.21 Hz, 1 H), 7.22-7.40 (m, 6 H), 7.67 (d, J=8.36 Hz, 1 H), 7.82 (d, J=1.47 Hz, 1 H), 8.00 (d, J=0.59 Hz, 1 H).

EXAMPLE 44

Ethyl 1-Benzyl-3-((5-fluoropyridin-3-yl)methylcarbamoyl)-2-isopropyl-1H-indole-6-carboxylate (Compound 44). Following General Procedure E, 1-benzyl-6-(ethoxylcarbonyl)-2-isopropyl-1H-indole-3-carboxylic acid (Compound 39, 93 mg, 0.254 mmol) in $CH_2Cl_2$ (6 ml) was added EDC (97 mg, 0.508 mmol) and DMAP (46 mg, 0.381mmol), followed by (5-fluoropyridin-3-yl)methanamine (81 mg, 0.63 mmol). The reaction was stirred at room temperature for 12 h, diluted with EtOAc, washed with $H_2O$, brine, dried over $Na_2SO_4$ and concentrated in vacuo. The residue was purified by chromatography on silica gel (0→80% EtOAc-hexanes) to yield the title compound as a yellow solid.

1H NMR (300 MHz, METHANOL-$d_4$) δ ppm 1.27-1.43 (m, 9 H), 3.40-3.59 (m, 1 H), 4.33 (q, J=7.18 Hz, 2 H), 4.69 (s, 2 H), 5.61 (s, 2 H), 6.95 (dd, J=7.48, 1.03 Hz, 2 H), 7.19-7.34 (m, 3 H), 7.65-7.76 (m, 2 H), 7.82 (dd, J=8.36, 1.47 Hz, 1 H), 8.00 (d, J=1.47 Hz, 1 H), 8.39 (d, J=2.64 Hz, 1 H), 8.52 (s, 1 H).

EXAMPLE 45

Ethyl 3-(3,4-Difluorobenzylcarbamoyl)-2-isopropyl-1-(pyridin-2-ylmethyl)-1H-indole-6-carboxylate (Compound 45). Following General Procedure E, 6-(ethoxycarbonyl)-2-isopropyl-1-(pyridin-2-ylmethyl)-1H-indole-3-carboxylic acid (Compound 40, 150 mg, 0.409 mmol) in $CH_2Cl_2$ (6 ml) was added EDC (157 mg, 0.81 mmol) and DMAP (75 mg, 0.60 mmol), followed by (5-fluoropyridin-3-yl)methanamine (88 mg, 0.63 mmol). The crude material was purified by chromatography on silica gel (0→40% EtOAc-hexanes) to yield the title compound as a light yellow solid.

1H NMR (300 MHz, METHANOL-$d_4$) δ ppm 1.25-1.45 (m, 9 H), 3.40-3.59 (m, 1 H), 4.33 (t, J=7.04 Hz, 2 H), 4.60 (s, 2 H), 5.68 (s, 2 H), 6.74 (d, J=6.89 Hz, 1 H), 7.18-7.43 (m, 4 H), 7.61-7.76 (m, 2 H), 7.82 (dd, J=8.50, 1.47 Hz, 1 H), 8.00 (d, J=0.73 Hz, 1 H), 8.54 (dt, J=5.42, 0.95 Hz, 1 H).

EXAMPLE 46

Ethyl 3-(3,4-Difluorobenzylcarbamoyl)-2-isopropyl-1-(pyridin-3-ylmethyl)-1H-indole-6-carboxylate (Compound 46). Following General Procedure E, 6-(ethoxycarbonyl)-2-isopropyl-1-(pyridin-3-ylmethyl)-1H-indole-3-carboxylic acid (Compound 41, 365 mg, 0.997 mmol) in $CH_2Cl_2$ (12 ml) was added EDC (288 mg, 2.00 mmol) and DMAP (146 mg, 1.50 mmol), followed by 3,4-difluorobenzyl amine (171 mg, 1.50 mmol). The crude material was purified by chromatography on silica gel (0→70% EtOAc-hexanes) to yield the title compound as a white solid.

1H NMR (300 MHz, METHANOL-$d_4$) δ ppm 1.35 (dt, J=7.18, 3.59 Hz, 9 H), 3.47 (m, 1 H), 4.33 (q, J=7.18 Hz, 2 H), 4.59 (s, 2 H), 5.70 (s, 2 H), 7.15-7.41 (m, 5 H), 7.68 (dd, J=8.36, 0.59 Hz, 1 H), 7.82 (dd, J=8.50, 1.47 Hz, 1 H), 8.01 (d, J=0.73 Hz, 1 H), 8.22 (d, J=1.91 Hz, 1 H), 8.43 (dd, J=3.81, 2.64 Hz, 1 H).

EXAMPLE 47

Ethyl 3-(3,4-Difluorobenzylcarbamoyl)-2-isopropyl-1-(oxazol-2-ylmethyl)-1H-indole-6-carboxylate (Compound 47). Following General Procedure E, 6-(ethoxycarbonyl)-2-isopropyl-1-(oxazol-2-ylmethyl)-1H-indole-3-carboxylic acid (Compound 42, 244 mg, 0.685 mmol) in $CH_2Cl_2$ (12 ml) was added EDC (262 mg, 1.37 mmol) and DMAP (125 mg, 1.03 mmol), followed by 3,4-difluorobenzyl amine (197 mg, 1.03 mmol). The crude material was purified by chromatography on silica gel (0→50% EtOAc-hexanes) to yield the title compound as a white solid.

1H NMR (300 MHz, METHANOL-$d_4$) δ ppm 1.33-1.52 (m, 9 H), 3.59 (m, 1 H), 4.37 (q, J=7.18 Hz, 2 H), 4.57 (s, 2 H), 5.70 (s, 2 H), 7.12 (d, J=0.88 Hz, 1 H), 7.18-7.42 (m, 3 H), 7.63 (s, 1 H), 7.81 (dd, J=8.43, 1.39 Hz, 2 H), 7.85 (d, J=0.88 Hz, 1 H), 8.18 (s, 1 H).

EXAMPLE 48

Ethyl 3-(3,5-Difluorobenzylcarbamoyl)-2-isopropyl-1-(pyridin-2-ylmethyl)-1H-indole-6-carboxylate (Compound 48). Following General Procedure E, 6-(ethoxycarbonyl)-2-isopropyl-1-(pyridin-2-ylmethyl)-1H-indole-3-carboxylic acid (Compound 40, 80 mg, 0.22 mmol) in $CH_2Cl_2$ (5 ml) was added EDC (84 mg, 0.42 mmol) and DMAP (40 mg, 0.32 mmol), followed by 3,5-difluorobenzyl amine (47 mg, 0.32mmol). The crude material was purified by chromatography on silica gel (0→40% EtOAc-hexanes) to yield the title compound as an off white solid.

1H NMR (300 MHz, METHANOL-$d_4$) δ ppm 1.28-1.41 (m, 9 H), 3.51 (m, 1 H), 4.32 (q, J=7.03 Hz, 2 H), 4.62 (s, 2 H), 5.68 (s, 2 H), 6.74 (d, J=7.91 Hz, 1 H), 6.85 (tt, J=9.08, 2.34 Hz, 1 H), 7.04 (dd, J=8.50, 2.34 Hz, 2 H), 7.30 (dd, J=6.74, 4.98 Hz, 1 H), 7.59-7.75 (m, 2 H), 7.74-7.88 (m, 1 H), 8.00 (s, 1 H), 8.53 (d, J=4.10 Hz, 1 H).

EXAMPLE 49

Ethyl 3-((5-Fluoropyridin-3-yl)methylcarbamoyl)-2-isopropyl-1-(pyridin-2-ylmethyl)-1H-indole-6-carboxylate (Compound 49). Following General Procedure E, 6-(ethoxycarbonyl)-2-isopropyl-1-(pyridin-2-ylmethyl)-1H-indole-3-carboxylic acid (Compound 40, 150 mg, 0.41 mmol) in $CH_2Cl_2$ (25 ml) was added EDC (236 mg, 0.82 mmol) and DMAP (75 mg, 0.60 mmol), followed by (5-fluoropyridin-3-yl)methanamine (94 mg, 0.82 mmol). The crude material was purified by chromatography on silica gel (0→80% EtOAc-hexanes) to yield the title compound as a white solid.

1H NMR (300 MHz, METHANOL-$d_4$) δ ppm 1.25-1.45 (m, 9 H), 3.42-3.62 (m, 1 H), 4.33 (q, J=7.04 Hz, 2 H), 4.69 (s, 2 H), 5.68 (s, 2 H), 6.69-6.80 (m, 1 H), 7.26-7.36 (m, 1 H), 7.63-7.76 (m, 3 H), 7.79-7.86 (m, 1 H), 8.00 (s, 1 H), 8.39 (s, 1 H), 8.52 (d, J=1.61 Hz, 2 H).

EXAMPLE 50

Ethyl 3-(4-Fluorobenzylcarbamoyl)-2-isopropyl-1-(pyridin-2-ylmethyl)-1H-indole-6-carboxylate (Compound 50). Following General Procedure E, 6-(ethoxycarbonyl)-2-isopropyl-1-(pyridin-2-ylmethyl)-1H-indole-3-carboxylic acid (Compound 40, 80 mg, 0.22 mmol) in $CH_2Cl_2$ (5 ml) was added EDC (84 mg, 0.42 mmol) and DMAP (40 mg, 0.32 mmol), followed by 4-fluorobenzyl amine (47 mg, 0.32 mmol). The crude material was purified by chromatography on silica gel (0→45% EtOAc-hexanes) to yield the title compound as a white solid.

1H NMR (300 MHz, METHANOL-$d_4$) δ ppm 1.27-1.44 (m, 9 H), 3.48 (quin, J=7.25 Hz, 1 H), 4.32 (q, J=7.13 Hz, 2 H), 4.60 (s, 2 H), 5.66 (s, 2 H), 6.72 (d, J=7.91 Hz, 1 H), 7.09 (dd, J=8.79, 4.40 Hz, 2 H), 7.31 (d, J=5.86 Hz, 1 H), 7.47 (dd, J=8.79, 5.27 Hz, 2 H), 7.61-7.72 (m, 2 H), 7.74-7.84 (m, 1 H), 7.98 (s, 1 H), 8.53 (d, J=4.10 Hz, 1 H).

EXAMPLE 51

3,4-Difluorobenzyl 1-Benzyl-6-(ethoxycarbonyl)-2-isopropyl-1H-indole-3-carboxylate (Compound 51). Following General Procedure E,1-benzyl-6-(ethoxylcarbonyl)-2-isopropyl-1H-indole-3-carboxylic acid (Compound 39, 39 mg, 0.1 1 mmol) in $CH_2Cl_2$ (4 ml) was added EDC (35 mg, 0.22 mmol) and DMAP (16 mg, 0.15 mmol), followed by 3,4-difluorobenzyl alcohol (20 mg, 0.15 mmol). The reaction was stirred at room temperature for 12 h, diluted with EtOAc, washed with $H_2O$, brine, dried over $Na_2SO_4$ and concentrated in vacuo. The residue was purified by chromatography on silica gel (0→30% EtOAc-hexanes) to yield the title compound as a yellow oil.

1H NMR (300 MHz, METHANOL-$d_4$) δ ppm 1.21-1.44 (m, 9 H), 3.74-4.03 (m, 1 H), 4.32 (q, J=7.04 Hz, 2 H), 5.39 (s, 2 H), 5.66 (s, 2 H), 6.96 (d, J=6.74 Hz, 2 H), 7.21-7.37 (m, 5 H), 7.38-7.56 (m, 1 H), 7.83 (dd, J=8.50, 1.47 Hz, 1 H), 8.01 (s, 1 H), 8.12 (d, J=8.50 Hz, 1 H).

EXAMPLE 52

1-Benzyl-N-(3,4-difluorobenzyl)-6-(hydroxymethyl)-2-isopropyl-1H-indole-3-carboxamide (Compound 52). To a solution of ethyl1-benzyl-3-(3,4-difluorobenzylcarbamoyl)-2-isopropyl-1H-indole-6-carboxylate (Compound 43, 200 mg, 0.408 mmol) in $CH_2Cl_2$ (10 ml) at −78° C. under argon was added Dibal-H (1.0 M in $CH_2Cl_2$, 1.6 ml, 1.63 mmol) slowly. The reaction was stirred for 3 h, quenched with methanol, celite, diluted with EtOAc, washed with $H_2O$, brine, dried over $Na_2SO_4$, concentrated in vacuo. The residue was purified by chromatography on silica gel (0→50% EtOAc-hexanes) to yield the title compound as a white solid.

1H NMR (300 MHz, METHANOL-$d_4$) δ ppm 1.31 (s, 3 H), 1.33 (s, 3 H), 3.41 (m, 1 H), 4.58 (s, 2 H), 4.62 (s, 2 H), 5.53 (s, 2 H), 5.66 (s, 2 H), 6.96 (dd, J=6.16, 1.76 Hz, 2 H), 7.14 (d, J=8.50 Hz, 1 H), 7.30 (m, 6 H), 7.39 (m, 1 H), 7.60 (d, J=7.91 Hz, 1 H).

EXAMPLE 53

1-Benzyl-N-(3,4-difluorobenzyl)-6-formyl-2-isopropyl-1H-indole-3-carboxamide (Compound 53). To a solution of 1-benzyl-N-(3,4-difluorobenzyl)-6-(hydroxymethyl)-2-isopropyl-1H-indole-3-carboxamide (Compound 52, 340 mg, 0.759 mmol) in $CH_2Cl_2$ (10 ml) at 25° C. under argon was added molecular sieve powder (300 mg), NMO (267 mg, 2.28 mmol), TPAP (26 mg, 0.08 mmol). The reaction was stirred for 10 minutes, then concentrated in vacuo. The residue was purified by chromatography on silica gel (0→25% EtOAc-hexanes) to yield the title compound as a light yellow solid.

1H NMR (300 MHz, METHANOL-$d_4$) δ ppm 1.33 (s, 3 H), 1.35 (s, 3 H), 3.40-3.59 (m, 1 H), 4.59 (s, 2 H), 5.64 (s, 2 H), 6.86-7.06 (m, 2 H), 7.19-7.44 (m, 6 H), 7.61-7.78 (m, 2 H), 7.91 (d, J=0.73 Hz, 1 H), 9.91 (s, 1 H).

EXAMPLE 54

1-Benzyl-N-(3,4-difluorobenzyl)-6-(4,5-dihydro-1H-imidazol-2-yl)-2-isopropyl-1H-indole-3-carboxamide (Compound 54). To a solution of 1-benzyl-N-(3,4-difluorobenzyl)-6-formyl-2-isopropyl-1H-indole-3-carboxamide (Compound 53, 18 mg, 0.040 mmol) in $CH_2Cl_2$ (1 ml) at 0° C. under argon was added ethylene diamine (2.5 mg, 0.042 mmol). The mixture was stirred at 0° C. for 30 minutes, and then added NBS (8 mg, 0.042 mmol). The reaction was stirred at 25° C. for 12 h, quenched with $NaHCO_3$ (aqueous), diluted with EtOAc, washed with $H_2O$, brine, dried over $Na_2SO_4$, concentrated in vacuo. The residue was purified by chromatography on silica gel (100% EtOAc) to yield the title compound as a light yellow solid.

1H NMR (300 MHz, METHANOL-$d_4$) δ ppm 1.31 (s, 3 H), 1.33 (s, 3 H), 3.38-3.52 (m, 1 H), 3.73 (s, 4 H), 4.58 (s, 2 H), 5.57 (s, 2 H), 6.94 (dd, J=7.77, 1.47 Hz, 2 H), 7.15-7.41 (m, 6 H), 7.56-7.60 (m, 1 H), 7.64-7.67 (m, 1 H), 7.82 (d, J=0.73 Hz, 1 H).

EXAMPLE 55

(E)-1-Benzyl-N-(3,4-difluorobenzyl)-6-((hydroxyimino)methyl)-2-isopropyl-1H-indole-3-carboxamide (Compound 55). To a solution of 1-benzyl-N-(3,4-difluorobenzyl)-6-formyl-2-isopropyl-1H-indole-3-carboxamide (Compound 53, 12 mg, 0.027 mmol) in MeOH (6 ml) was hydroxylamine hydrochloride (6.0 mg, 0.081 mmol) and pyridine (3 mg, 0.16 mmol). The mixture was stirred at 65° C. for 12 h, and then added concentrated in vacuo. The residue was purified by chromatography on silica gel (0→40% EtOAc-hexanes) to yield the title compound as a white solid.

1H NMR (300 MHz, METHANOL-$d_4$) δ ppm 1.31 (s, 3 H), 1.33 (s, 3 H), 3.36-3.52 (m, 1 H), 4.58 (s, 2 H), 5.54 (s, 2 H), 6.95 (dd, J=7.99, 1.54 Hz, 2 H), 7.17-7.38 (m, 5 H), 7.42 (dd, J=8.36, 1.32 Hz, 1 H), 7.49 (s, 1 H), 7.61 (d, J=8.36 Hz, 1 H), 8.10 (s, 1 H).

Scheme 6$^a$

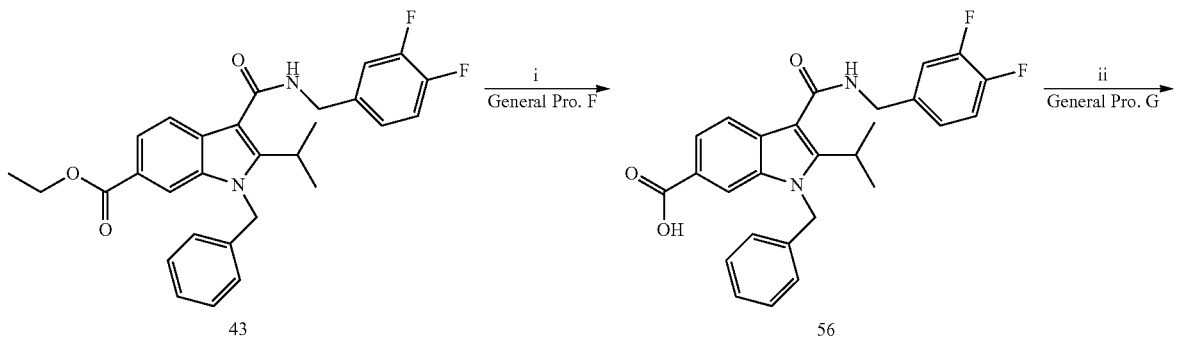

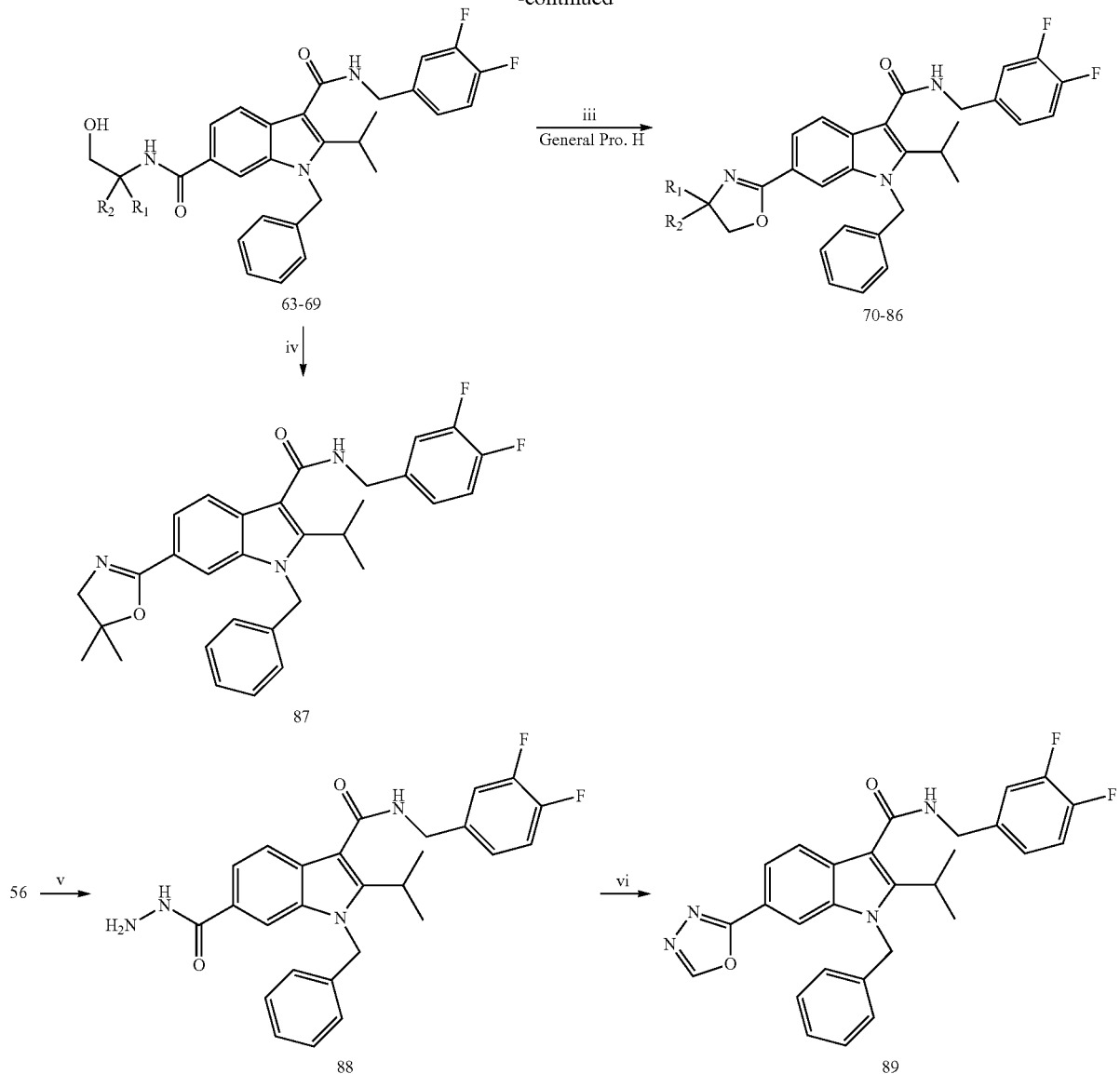

<sup>a</sup>Reagents and conditions: (i) NaOH, EtOH; (ii) Ethanol amine, BOP, DIEPA, DMF; (iii) MsCl, Et₃N, CH₂Cl₂; (iv) P₂O₅, benzene; (v) Hydrazine, EDC, DMAP, CH₂Cl₂; (vi) Triethyl orthoacetate, 145° C.

EXAMPLE 56

1-Benzyl-3-(3,4-difluorobenzylcarbamoyl)-2-isopropyl-1H-indole-6-carboxylic Acid (Compound 56). General Procedure F. To a solution of ethyl1-benzyl-3-(3,4-difluorobenzylcarbamoyl)-2-isopropyl-1H-indole-6-carboxylate (Compound 43, 609 mg, 1.24 mmol) in EtOH (15 ml) was added NaOH (248 mg, 6.21 mmol) and H₂O (1 ml). The reaction was stirred at 50° C. for 12 h, concentrated in vacuo to an oil then acidified to PH=5 with 10% HCl, diluted with EtOAc, washed organic with H₂O, brine, dried over Na₂SO₄ and concentrated in vacuo to yield the title compound as a yellow solid.

1H NMR (300 MHz, METHANOL-d₄) δ ppm 1.32 (s, 3 H), 1.35 (s, 3 H), 3.38-3.59 (m, 1 H), 4.59 (s, 2 H), 5.59 (s, 2 H), 6.96 (d, J=9.38 Hz, 2 H), 7.18-7.44 (m, 6 H), 7.63 (d, J=8.36 Hz, 1 H), 7.80 (dd, J=8.36, 1.32 Hz, 1 H), 8.00 (d, J=0.88 Hz, 1 H).

EXAMPLE 57

1-Benzyl-3-(5-Fluoropyridin-3-yl)methylcarbamoyl)-2-isopropyl-1-indole-6-carboxylic Acid (Compound 57). Following General Procedure F, ethyl1-benzyl-3-((5-fluoropyridin-3-yl)methylcarbamoyl)-2-isopropyl-1H-indole-6-carboxylate (Compound 44, 94 mg, 0.90 mmol) in EtOH (12 ml) was added NaOH (42 mg, 4.5 mmol) and H₂O (1 ml). The reaction was stirred at 50° C. for 12 h, concentrated in vacuo to an oil then acidified to PH=5 with 10% HCl, diluted with EtOAc, washed organic with H₂O, brine, dried over Na₂SO₄ and concentrated in vacuo to yield the title compound as a white solid.

1H NMR (300 MHz, METHANOL-d₄) δ ppm 1.32 (s, 3 H), 1.35 (s, 3 H), 3.40-3.59 (m, 1 H), 4.60 (s, 2 H), 5.62 (s, 2 H), 6.95 (dd, J=7.48, 1.03 Hz, 2 H), 7.19-7.34 (m, 3 H), 7.65-7.76 (m, 2 H), 7.82 (dd, J=8.36, 1.47 Hz, 1 H), 8.00 (d, J=1.47 Hz, 1 H), 8.39 (d, J=2.64 Hz, 1 H), 8.52 (s, 1 H).

EXAMPLE 58

3-(3,4-Difluorobenzylcarbamoyl)-2-isopropyl-1-(pyridin-2-ylmethyl)-1H-indole-6-carboxylic Acid (Compound 58). Following General Procedure F, ethyl3-(3,4-difluorobenzylcarbamoyl)-2-isopropyl-1-(pyridin-2-ylmethyl)-1H-indole-6-carboxylate (Compound 45, 117 mg, 0.238 mmol) in EtOH (10 ml) was added NaOH (47 mg, 1.20 mmol) and $H_2O$ (1 ml). The reaction was stirred at 50° C. for 12 h, concentrated in vacuo to an oil then acidified to PH=5 with 10% HCl, diluted with EtOAc, washed organic with $H_2O$, brine, dried over $Na_2SO_4$ and concentrated in vacuo to yield the title compound as a light yellow solid.

1H NMR (300 MHz, METHANOL-$d_4$) δ ppm 1.32 (s, 3 H), 1.35 (s, 3 H), 3.40-3.59 (m, 1 H), 4.60 (s, 2 H), 5.67 (s, 2 H), 6.74 (d, J=6.89 Hz, 1 H), 7.18-7.43 (m, 4 H), 7.61-7.76 (m, 2 H), 7.82 (dd, J=8.50, 1.47 Hz, 1 H), 8.00 (d, J=0.73 Hz, 1 H), 8.54 (dt, J=5.42, 0.95 Hz, 1 H).

EXAMPLE 59

3-(3,4-Difluorobenzylcarbamoyl)-2-isopropyl-1-(pyridin-3-ylmethyl)-1H-indole-6-carboxylic Acid (Compound 59). Following General Procedure F, ethyl3-(3,4-difluorobenzylcarbamoyl)-2-isopropyl-1-(pyridin-3-ylmethyl)-1H-indole-6-carboxylate (Compound 46, 439 mg, 0.896 mmol) ) in EtOH (12 ml) was added NaOH (179 mg, 4.48 mmol) and $H_2O$ (1 ml). The reaction was stirred at 25° C. for 12 h, concentrated in vacuo to an oil then acidified to PH=5 with 10% HCl, diluted with EtOAc, washed organic with $H_2O$, brine, dried over $Na_2SO_4$ and concentrated in vacuo to yield the title compound as a light yellow solid.

1H NMR (300 MHz, METHANOL-$d_4$) δ ppm 1.32 (s, 3 H), 1.35 (s, 3 H), 3.40-3.59 (m, 1 H), 4.59 (s, 2 H), 5.70 (s, 2 H), 7.15-7.41 (m, 5 H), 7.68 (dd, J=8.36, 0.59 Hz, 1 H), 7.82 (dd, J=8.50, 1.47 Hz, 1 H), 8.01 (d, J=0.73 Hz, 1 H), 8.22 (d, J=1.91 Hz, 1 H), 8.43 (dd, J=3.81, 2.64 Hz, 1 H).

EXAMPLE 60

3-(3,4-Difluorobenzylcarbamoyl)-2-isopropyl-1-(oxazol-2-ylmethyl)-1H-indole-6-carboxylic Acid (Compound 60). Following General Procedure F, ethyl3-(3,4-difluorobenzylcarbamoyl)-2-isopropyl-1-(oxazol-2-ylmethyl)-1H-indole-6-carboxylate (Compound 47, 197 mg, 0.414 mmol) in EtOH (12 ml) was added NaOH (82 mg, 2.07 mmol) and $H_2O$ (1 ml). The reaction was stirred at 25° C. for 12 h, concentrated in vacuo to an oil then acidified to PH=5 with 10% HCl, diluted with EtOAc, washed organic with $H_2O$, brine, dried over $Na_2SO_4$ and concentrated in vacuo to yield the title compound as a white solid.

1H NMR (300 MHz, METHANOL-$d_4$) δ ppm 1.32 (s, 3 H), 1.35 (s, 3 H), 3.59 (m, 1 H), 4.57 (s, 2 H), 5.70 (s, 2 H), 7.12 (d, J=0.88 Hz, 1 H), 7.18-7.42 (m, 3 H), 7.63 (s, 1 H), 7.81 (dd, J=8.43, 1.39 Hz, 2 H), 7.85 (d, J=0.88 Hz, 1 H), 8.18 (s, 1 H).

EXAMPLE 61

3-(3,5-Difluorobenzylcarbamoyl)-2-isopropyl-1-(pyridin-2-ylmethyl)-1H-indole-6-carboxylic Acid (Compound 61). Following General Procedure F, ethyl3-(3,5-difluorobenzylcarbamoyl)-2-isopropyl-1-(pyridin-2-ylmethyl)-1H-indole-6-carboxylate (Compound 48, 92 mg, 0.187 mmol) in EtOH (10 ml) was added NaOH (40 mg, 0.94 mmol) and $H_2O$ (1 ml). The reaction was stirred at 55° C. for 4 h, concentrated in vacuo to an oil then acidified to PH=5 with 10% HCl, diluted with EtOAc, washed organic with $H_2O$, brine, dried over $Na_2SO_4$ and concentrated in vacuo to yield the title compound as a white solid.

1H NMR (300 MHz, METHANOL-$d_4$) δ ppm 1.32 (s, 3 H), 1.35 (s, 3 H), 3.51 (m, 1 H), 4.62 (s, 2 H), 5.68 (s, 2 H), 6.74 (d, J=7.91 Hz, 1 H), 6.85 (tt, J=9.08, 2.34 Hz, 1 H), 7.04 (dd, J=8.50, 2.34 Hz, 2 H), 7.30 (dd, J=6.74, 4.98 Hz, 1 H), 7.59-7.75 (m, 2 H), 7.74-7.88 (m, 1 H), 8.00 (s, 1 H), 8.53 (d, J=4.10 Hz, 1 H).

EXAMPLE 62

3-(4-Fluorobenzylcarbamoyl)-2-isopropyl-1-(pyridin-2-ylmethyl)-1H-indole-6-carboxylic Acid (Compound 62). Following General Procedure F, ethyl3-(4-fluorobenzylcarbamoyl)-2-isopropyl-1-(pyridin-2-ylmethyl)-1H-indole-6-carboxylate (Compound 50, 90 mg, 0.18 mmol) in EtOH (6 ml) was added NaOH (39 mg, 0.90 mmol) and $H_2O$ (1 ml). The reaction was stirred at 55° C. for 12 h, concentrated in vacuo to an oil then acidified to PH=5 with 10% HCl, diluted with EtOAc, washed organic with $H_2O$, brine, dried over $Na_2SO_4$ and concentrated in vacuo to yield the title compound as a white solid.

1H NMR (300 MHz, METHANOL-$d_4$) δ ppm 1.32 (s, 3 H), 1.35 (s, 3 H), 3.48 (m, 1 H), 4.60 (s, 2 H), 5.66 (s, 2 H), 6.72 (d, J=7.91 Hz, 1 H), 7.09 (dd, J=8.79, 4.40 Hz, 2 H), 7.31 (d, J=5.86 Hz, 1 H), 7.47 (dd, J=8.79, 5.27 Hz, 2 H), 7.61-7.72 (m, 2 H), 7.74-7.84 (m, 1 H), 7.98 (s, 1 H), 8.53 (d, J=4.10 Hz, 1 H).

EXAMPLE 63

1-Benzyl-N3-(3,4-difluorobenzyl)-N6-(2-hydroxyethyl)-2-isopropyl-1H-indole-3,6-dicarboxamide (Compound 63). General Procedure G. To a solution of 1-benzyl-3-(3,4-difluorobenzylcarbamoyl)-2-isopropyl-1H-indole-6-carboxylic acid (Compound 56, 30 mg, 0.065 mmol) in DMF (3 ml) was added BOP (35 mg, 0.090 mmol) and DIPEA (17 mg, 0.098 mmol), followed by ethanolamine (6 mg, 0.098 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as a yellow oil.

1H NMR (300 MHz, METHANOL-$d_4$) δ ppm 1.31 (s, 3 H), 1.34 (s, 3 H), 3.37-3.46 (m, 1 H), 3.49 (t, J=5.86 Hz, 2 H), 3.65-3.74 (m, 2 H), 4.59 (s, 2 H), 5.60 (s, 2 H), 6.94 (dd, J=7.92, 1.61 Hz, 2 H), 7.17-7.42 (m, 6 H), 7.65 (dd, J=2.35, 1.03 Hz, 2 H), 7.91 (s, 1 H).

EXAMPLE 64

1-Benzyl-N3-(3,4-difluorobenzyl)-N6-(1-hydroxy-2-methylpropan-2-yl)-2-isopropyl-1H-indole-3,6-dicarboxamide (Compound 64). Following General Procedure G, 1-benzyl-3-(3,4-difluorobenzylcarbamoyl)-2-isopropyl-1H-indole-6-carboxylic acid (Compound 56, 35 mg, 0.076 mmol) in DMF (3 ml) was added BOP (40 mg, 0.091 mmol) and DIPEA (20 mg, 0.10 mmol), followed by 2-amino-2-methylpropan-1-ol (15 mg, 0.15 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as a yellow oil.

1H NMR (300 MHz, METHANOL-$d_4$) δ ppm 1.31 (s, 3 H), 1.34 (s, 3 H), 1.39 (s, 6 H), 3.43 (dt, J=14.18, 7.05 Hz, 1 H), 3.66 (s, 2 H), 4.58 (s, 2 H), 5.59 (s, 2 H), 6.96 (d, J=1.61

Hz, 2 H), 7.16-7.49 (m, 5 H), 7.52-7.60 (m, 1 H), 7.60-7.68 (m, 1 H), 7.84 (s, 1 H), 7.97 (s, 1 H).

EXAMPLE 65

(S)-1-Benzyl-N3-((5-fluoropyridin-3-yl)methyl)-N6-(1-hydroxypropan-2-yl)-2-isopropyl-1H-indole-3,6-dicarboxamide (Compound 65). Following General Procedure G, 1-benzyl-3-(5-fluoropyridin-3-yl)methylcarbamoyl)-2-isopropyl-1H-indole-6-carboxylic acid (Compound 57, 104 mg, 0.237 mmol) in DMF (6 ml) was added BOP (124 mg, 0.284 mmol) and DIPEA (61 mg, 0.355 mmol), followed by L-alanol (26 mg, 0.355 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as a white solid.

1H NMR (300 MHz, METHANOL-$d_4$) δ ppm 1.23 (s, 3 H), 1.30 (s, 3 H), 1.32 (s, 3 H), 3.37-3.48 (m, 1 H), 3.54-3.61 (m, 2 H), 4.12-4.23 (m, 1 H), 4.69 (s, 2 H), 5.60 (s, 2 H), 6.95 (dd, J=7.62, 1.03 Hz, 2 H), 7.19-7.31 (m, 3 H), 7.63-7.76 (m, 4 H), 7.93 (s, 1 H), 8.39 (d, J=2.35 Hz, 1 H).

EXAMPLE 66

(R)-1-Benzyl-N3-(3,4-difluorobenzyl)-N6-(1-hydroxypropan-2-yl)-2-isopropyl-1H-indole-3,6-dicarboxamide (Compound 66). Following General Procedure G, 1-benzyl-3-(3,4-difluorobenzylcarbamoyl)-2-isopropyl-1H-indole-6-carboxylic acid (Compound 56, 37 mg, 0.08 mmol) in DMF (3 ml) was added BOP (42 mg, 0.10 mmol) and DIPEA (16 mg, 0.10 mmol), followed by D-alanol (16 mg, 0.10 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as a white solid.

1H NMR (300 MHz, METHANOL-$d_4$) δ ppm 1.22 (d, J=6.89 Hz, 3 H), 1.31 (s, 3 H), 1.33 (s, 3 H), 3.38-3.48 (m, 1 H), 3.58 (d, J=5.57 Hz, 2 H), 4.17 (q, J=6.89 Hz, 1 H), 4.59 (s, 2 H), 5.59 (s, 2 H), 6.94 (dd, J=7.92, 1.61 Hz, 2 H), 7.18-7.41 (m, 6 H), 7.65 (s, 2 H), 7.91 (s, 1 H).

EXAMPLE 67

(S)-1-Benzyl-N3-(3,4-difluorobenzyl)-N6-(1-hydroxybutan-2-yl)-2-isopropyl-1H-indole-3,6-dicarboxamide (Compound 67). Following General Procedure G, 1-benzyl-3-(3,4-difluorobenzylcarbamoyl)-2-isopropyl-1H-indole-6-carboxylic acid (Compound 56, 42 mg, 0.089 mmol) in DMF (4 ml) was added BOP (48 mg, 0.11 mmol) and DIPEA (23 mg, 0.10 mmol), followed by (S)-2-aminobutan-1-ol (16 mg, 0.10 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as a light yellow solid.

1H NMR (300 MHz, METHANOL-$d_4$) δ ppm 0.97 (t, J=7.16 Hz 3 H), 1.24 (t, J=7.11 Hz, 4 H), 1.32 (s, 3 H), 1.34 (s, 3 H), 3.38-3.52 (m, 1 H), 3.61-3.78 (m, 2 H), 3.83-3.95 (m, 1 H), 4.59 (s, 2 H), 5.61 (s, 2 H), 6.96 (d, J=8.21 Hz, 2 H), 7.18-7.43 (m, 6 H), 7.66 (s, 2 H), 7.92 (d, J=1.03 Hz, 1 H).

EXAMPLE 68

1-Benzyl-N3-(3,4-difluorobenzyl)-N6-(2-hydroxy-2-methylpropyl)-2-isopropyl-1H-indole-3,6-dicarboxamide (Compound 68). Following General Procedure G, 1-benzyl-3-(3,4-difluorobenzylcarbamoyl)-2-isopropyl-1H-indole-6-carboxylic acid (Compound 56, 35 mg, 0.080 mmol) in DMF (4 ml) was added BOP (40 mg, 0.10 mmol) and DIPEA (20 mg, 0.11 mmol), followed by 1-amino-2-methylpropan-2-ol (10 mg, 0.10 mmol). The reaction was stirred at room temperature for 12 h, diluted with EtOAc, washed with $H_2O$, brine, dried over $Na_2SO_4$ and concentrated in vacuo. The residue was purified by chromatography on silica gel (5:95 MeOH—$CH_2Cl_2$) to yield the title compound as yellow oil.

1H NMR (300 MHz, METHANOL-$d_4$) δ ppm 1.21 (s, 6 H), 1.31 (s, 3 H), 1.34 (s, 3 H), 3.39 (s, 2 H), 3.40-3.51 (m, 1 H), 4.59 (s, 2 H), 5.59 (s, 2 H), 6.96 (d, J=1.76 Hz, 2 H), 7.16-7.40 (m, 6 H), 7.66 (dd, J=3.30, 1.10 Hz, 2 H), 7.91 (s, 1 H).

EXAMPLE 69

1-Benzyl-N3-(3,4-difluorobenzyl)-2-isopropyl-N6-(prop-2-ynyl)-1H-indole-3,6-dicarboxamide (Compound 69). Following General Procedure G, 1-benzyl-3-(3,4-difluorobenzylcarbamoyl)-2-isopropyl-1H-indole-6-carboxylic acid (Compound 56, 35 mg, 0.080 mmol) in in $CH_2Cl_2$ (3 ml) was added EDC (25 mg, 0.15 mmol) and DMAP (15 mg, 0.09 mmol), followed by propargyl amine (7 mg, 0.09 mmol). The crude material was purified by chromatography on silica gel (0→50% EtOAc-hexanes) to yield the title compound as an oil.

1H NMR (500 MHz, METHANOL-$d_4$) δ ppm 1.32 (s, 3 H), 1.33 (s, 3 H), 2.55 (t, J=2.57 Hz, 1 H), 3.44 (dt, J=14.27, 7.11 Hz, 1 H), 4.13 (s, 2 H), 4.58 (s, 2 H), 5.58 (s, 2 H), 6.94 (d, J=6.97 Hz, 2 H), 7.18-7.30 (m, 5 H), 7.31-7.41 (m, 1 H), 7.59-7.70 (m, 2 H), 7.89 (d, J=0.73 Hz, 1 H).

EXAMPLE 70

1-Benzyl-N-(3,4-difluorobenzyl)-6-(4,5-dihydrooxazol-2-yl)-2-isopropyl-1H-indole-3-carboxamide (Compound 70). General Procedure H. To a solution of 1-benzyl-N3-(3,4-difluorobenzyl)-N6-(2-hydroxyethyl)-2-isopropyl-1H-indole-3,6-dicarboxamide (Compound 63, 17 mg, 0.033 mmol) in $CH_2Cl_2$ (2 ml) at 0° C under argon was added $Et_3N$ (0.03 ml, 0.2 mmol), and then added MsCl (7 mg, 0.066 mmol). The reaction was stirred at 25° C. for 3 h, quenched with $H_2O$ diluted with EtOAc, washed with brine, dried over $Na_2SO_4$, concentrated in vacuo. The residue was purified by chromatography on silica gel (100% EtOAc) to yield the title compound as a yellow solid.

1H NMR (300 MHz, METHANOL-$d_4$) δ ppm 1.32 (s, 3 H), 1.35 (s, 3 H), 3.41-3.56 (m, 1 H), 3.98 (t, J=9.38 Hz, 2 H), 4.45 (t, J=9.53 Hz, 2 H), 4.59 (d, J=4.10 Hz, 2 H), 5.57 (s, 2 H), 6.94 (d, J=6.16 Hz, 2 H), 7.13-7.43 (m, 6 H), 7.55-7.79 (m, 2 H), 7.87 (s, 1 H), 8.71 (t, J=5.13 Hz, 1 H).

EXAMPLE 71

1-Benzyl-N-(3,4-difluorobenzyl)-6-(4,4-dimethyl-4,5-dihydrooxazol-2-yl)-2-isopropyl-1H-indole-3-carboxamide (Compound 71). The title compound was prepared from 1-benzyl-N3-(3,4-difluorobenzyl)-N6-(1-hydroxy-2-methylpropan-2-yl)-2-isopropyl-1H-indole-3,6-dicarboxamide (Compound 64) by General Procedure H.

1H NMR (300 MHz, METHANOL-d$_4$) δ ppm 1.18-1.47 (m, 12 H), 3.37-3.53 (m, 1 H), 4.20-4.46 (m, 2 H), 4.59 (d, J=5.57 Hz, 2 H), 5.59 (s, 2 H), 6.94 (d, J=3.96 Hz, 2 H), 7.06-7.43 (m, 6 H), 7.55-7.84 (m, 2 H), 7.89-7.96 (m, 1 H), 8.78 (d, J=1.17 Hz, 1 H).

EXAMPLE 72

(S)-1-Benzyl-N-((5-fluoropyridin-3-yl)methyl)-2-isopropyl-6-(4-methyl-4,5-dihydrooxazol-2-yl)-1H-indole-3-carboxamide (Compound 72). The title compound was prepared from (S)-1-benzyl-N3-((5-fluoropyridin-3-yl)methyl)-N6-(1-hydroxypropan-2-yl)-2-isopropyl-1H-indole-3,6-dicarboxamide (Compound 65) by General Procedure H.

1H NMR (300 MHz, METHANOL-d$_4$) δ ppm 1.26-1.36 (m, 9 H), 3.39-3.53 (m, 1 H), 4.04 (t, J=7.99 Hz, 1 H), 4.27-4.46 (m, 1 H), 4.61 (d, J=8.36 Hz, 1 H), 4.69 (d, J=5.72 Hz, 2 H), 5.59 (s, 2 H), 6.89-7.03 (m, 2 H), 7.12-7.35 (m, 3 H), 7.56-7.78 (m, 3 H), 7.91 (s, 1 H), 8.39 (d, J=2.64 Hz, 1 H), 8.51 (s, 1 H), 8.82 (t, J=7.84 Hz, 1 H).

EXAMPLE 73

(S)-1-Benzyl-6-(4-ethyl-4,5-dihydrooxazol-2-yl)-N-((5-fluoropyridin-3-yl)methyl)-2-isopropyl-1H-indole-3-carboxamide (Compound 73). The title compound was prepared from (S)-1-benzyl-N3-((5-fluoropyridin-3-yl)methyl)-N6-(1-hydroxypropan-2-yl)-2-isopropyl-1H-indole-3,6-dicarboxamide (Compound 65) by General Procedure H.

1H NMR (300 MHz, METHANOL-d$_4$) δ ppm 0.96 (t, J=7.40 Hz, 3 H), 1.31 (s, 3 H), 1.33 (s, 3 H), 1.51-1.81 (m, 2 H), 3.39-3.57 (m, 1 H), 4.11 (dd, J=7.48, 6.45 Hz, 2 H), 4.50 (dd, J=8.94, 7.92 Hz, 1 H), 4.68 (s, 2 H), 5.58 (s, 2 H), 6.94 (dd, J=7.77, 1.47 Hz, 2 H), 7.14-7.35 (m, 4 H), 7.62-7.81 (m, 3 H), 7.90 (s, 1 H), 8.39 (d, J=2.64 Hz, 1 H), 8.51 (s, 1 H).

EXAMPLE 74

(R)-1-Benzyl-N-(3,4-difluorobenzyl)-2-isopropyl-6-(4-methyl-4,5-dihydrooxazol-2-yl)-1H-indole-3-carboxamide (Compound 74). The title compound was prepared from (R)-1-benzyl-N3-(3,4-difluorobenzyl)-N6-(1-hydroxypropan-2-yl)-2-isopropyl-1H-indole-3,6-dicarboxamide (Compound 66) by General Procedure H.

1H NMR (300 MHz, METHANOL-d$_4$) δ ppm 1.26 (s, 3 H), 1.37 (s, 3 H), 3.36-3.51 (m, 1 H), 4.09 (t, J=7.11 Hz, 1 H), 4.26-4.42 (m, 1 H), 4.59 (s, 2 H), 4.71 (m, 1H), 5.60 (s, 2 H), 6.89-7.02 (m, 2 H), 7.16-7.44 (m, 6 H), 7.59-7.75 (m, 2 H), 7.90 (s, 1 H).

EXAMPLE 75

(S)-1-Benzyl-N-(3,4-difluorobenzyl)-6-(4-ethyl-4,5-dihydrooxazol-2-yl)-2-isopropyl-1H-indole-3-carboxamide (Compound 75). The title compound was prepared from (S)-1-benzyl-N3-(3,4-difluorobenzyl)-N6-(1-hydroxybutan-2-yl)-2-isopropyl-1H-indole-3,6-dicarboxamide (Compound 67) by General Procedure H.

1H NMR (300 MHz, METHANOL-d$_4$) δ ppm 0.96 (t, J=7.40 Hz, 3 H), 1.32 (s, 3 H), 1.34 (s, 3 H), 1.52-1.81 (m, 2 H), 3.38-3.52 (m, 1H), 4.12 (d, J=7.62 Hz, 1H), 4.15-4.29 (m, 1 H), 4.51 (dd, J=8.94, 7.92 Hz, 1 H), 4.57-4.62 (m, 2 H), 5.58 (s, 2 H), 6.95 (d, J=1.76 Hz, 2 H), 7.08-7.45 (m, 6 H), 7.51-7.82 (m, 3 H), 7.89 (d, J=0.59 Hz, 1H), 8.72 (t, J=7.84 Hz, 1H).

EXAMPLE 76

(S)-1-Benzyl-N-(3,4-difluorobenzyl)-2-isopropyl-6-(4-methyl-4,5-dihydrooxazol-2-yl)-1H-indole-3-carboxamide (Compound 76). The title compound was prepared from (S)-1-benzyl-N3-(3,4-difluorobenzyl)-N6-(1-hydroxypropan-2-yl)-2-isopropyl-1H-indole-3,6-dicarboxamide by General Procedure H.

1H NMR (300 MHz, METHANOL-d$_4$) δ ppm 1.21-1.41 (m, 9 H), 3.39-3.56 (m, 1H), 4.12 (t, J=8.21 Hz, 1H), 4.59 (s, 2 H), 4.65 (d, J=8.50 Hz, 1H), 5.60 (s, 2 H), 6.88-6.99 (m, 2 H), 7.15-7.41 (m, 6 H), 7.63-7.78 (m, 2 H), 7.93 (s, 1H).

EXAMPLE 77

(S)-1-Benzyl-N-(3,4-difluorobenzyl)-2-isopropyl-6-(4-(methoxymethyl)-4,5-dihydrooxazol-2-yl)-1H-indole-3-carboxamide (Compound 77). The title compound was prepared from (R)-1-benzyl-N3-(3,4-difluorobenzyl)-N6-(1-hydroxy-3-methoxypropan-2-yl)-2-isopropyl-1H-indole-3,6-dicarboxamide by General Procedure H.

1H NMR (300 MHz, METHANOL-d$_4$) δ ppm 1.34 (s, 3 H), 1.36 (s, 3 H), 3.37 (s, 3 H), 3.44-3.61 (m, 2 H), 4.31-4.57 (m, 2 H), 4.60 (d, J=5.57 Hz, 2 H), 5.60 (s, 2 H), 6.97 (d, J=1.76 Hz, 2 H), 7.17-7.45 (m, 6 H), 7.63-7.80 (m, 2 H), 7.93 (s, 1H), 8.74 (s, 1H).

EXAMPLE 78

(R)—N-(3,4-Difluorobenzyl)-2-isopropyl-6-(4-methyl-4,5-dihydrooxazol-2-yl)-1-(pyridin-2-ylmethyl)-1H-indole-3-carboxamide (Compound 78). The title compound was prepared from (R)—N3-(3,4-difluorobenzyl)-N6-(1-hydroxypropan-2-yl)-2-isopropyl-1-(pyridin-2-ylmethyl)-1H-indole-3,6-dicarboxamide by General Procedure H.

1H NMR (300 MHz, METHANOL-d$_4$) δ ppm 1.32 (m, 9 H), 3.43-3.55 (m, 1H), 4.00 (t, J=8.06 Hz, 1H), 4.28-4.38 (m, 1H), 4.52-4.64 (m, 3 H), 5.65 (s, 1H), 6.71 (d, J=7.62 Hz, 1 H), 7.20-7.40 (m, 4 H), 7.63-7.75 (m, 3 H), 7.88 (s, 1H), 8.53 (d, J=4.10 Hz, 1H), 8.72 (t, 1 H).

EXAMPLE 79

(S)—N-(3,4-Difluorobenzyl)-2-isopropyl-6-(4-methyl-4,5-dihydrooxazol-2-yl)-1-(pyridin-2-ylmethyl)-1H-indole-3-carboxamide (Compound 79). The title compound was prepared from (S)—N3-(3,4-difluorobenzyl)-N6-(1-hydroxypropan-2-yl)-2-isopropyl-1-(pyridin-2-ylmethyl)-1H-indole-3,6-dicarboxamide by General Procedure H.

1H NMR (300 MHz, METHANOL-d$_4$) δ ppm 1.24-1.39 (m, 9 H), 3.42-3.60 (m, 1H), 4.00 (t, J=8.06 Hz, 1 H), 4.25 (m, 1 H), 4.38 (m, 1 H), 4.56 (s, 2 H), 5.65 (s, 2 H), 6.70 (d, J=7.62 Hz, 1 H), 7.18-7.40 (m, 4 H), 7.60-7.77 (m, 3 H), 7.88 (d, J=0.73 Hz, 1 H), 8.54 (d, J=5.57 Hz, 1 H).

EXAMPLE 80

(S)—N-(3,4-Difluorobenzyl)-6-(4-ethyl-4,5-dihydrooxazol-2-yl)-2-isopropyl-1-(pyridin-2-ylmethyl)-1H-indole-3-carboxamide (Compound 80). The title compound was prepared from (S)—N3-(3,4-difluorobenzyl)-N6-(1-hydroxybutan-2-yl)-2-isopropyl-1-(pyridin-2-ylmethyl)-1H-indole-3,6-dicarboxamide by General Procedure H.

1H NMR (300 MHz, METHANOL-d$_4$) δ ppm 0.96 (t, J=7.61 Hz, 3 H), 1.32 (s, 3 H), 1.35 (s, 3 H), 1.49-1.85 (m, 2 H), 3.40-3.59 (m, 1 H), 4.02-4.11 (m, 1 H), 4.49 (t, J=8.79 Hz, 1 H), 4.56 (s, 2 H), 5.65 (s, 2 H), 6.70 (d, J=7.62 Hz, 1 H), 7.18-7.40 (m, 4 H), 7.60-7.77 (m, 3 H), 7.88 (d, J=0.73 Hz, 1 H), 8.54 (d, J=5.57 Hz, 1 H).

EXAMPLE 81

(S)—N-(3,4-Difluorobenzyl)-6-(4-(hydroxymethyl)-4,5-dihydrooxazol-2-yl)-2-isopropyl-1-(pyridin-2-ylmethyl)-1H-indole-3-carboxamide (Compound 81)

Following General Procedure H, (S)-6-(4-(benzyloxymethyl)-4,5-dihydrooxazol-2-yl)-N-(3,4-difluorobenzyl)-2-isopropyl-1-(pyridin-2-ylmethyl)-1H-indole-3-carboxamide was prepared (10 mg, 0.015 mmol), was then reacted with $BBr_3$ (1M in $CH_2Cl_2$, 0.05 ml, 0.05 mmol) in $CH_2Cl_2$ (2 ml) at −78° C. for 1 h, quenched with water, diluted with EtOAc, washed organic with brine, dried over $Na_2SO_4$ and concentrated in vacuo. The residue was purified by chromatography on silica gel (5:95 MeOH—$CH_2Cl_2$) to yield the title compound as a white solid.

1H NMR (300 MHz, METHANOL-$d_4$) δ ppm 1.32 (s, 3 H), 1.34 (s, 3 H), 3.41-3.57 (m, 1 H), 3.59-3.76 (m, 2 H), 4.27-4.43 (m, 1 H), 4.50 (t, J=8.28 Hz, 1 H), 4.59 (s, 2 H), 5.65 (s, 2 H), 6.70 (d, J=7.92 Hz, 1 H), 7.18-7.42 (m, 4 H), 7.61-7.79 (m, 3 H), 7.91 (s, 1 H), 8.53 (d, J=4.98 Hz, 1 H).

EXAMPLE 82

(S)—N-(3,4-Difluorobenzyl)-2-isopropyl-6-(4-methyl-4,5-dihydrooxazol-2-yl)-1-(pyridin-3-ylmethyl)-1H-indole-3-carboxamide (Compound 82). The title compound was prepared from (S)—N3-(3,4-difluorobenzyl)-N6-(1-hydroxypropan-2-yl)-2-isopropyl-1-(pyridin-3-ylmethyl)-1H-indole-3,6-dicarboxamide by General Procedure H.

1H NMR (300 MHz, METHANOL-$d_4$) δ ppm 1.22-1.42 (m, 9 H), 3.41-3.62 (m, 1 H), 3.99 (t, J=8.06 Hz, 1 H), 4.31 (dd, J=9.52, 6.89 Hz, 1 H), 4.54 (d, J=8.20 Hz, 1 H), 4.59 (s, 2 H), 5.67 (s, 2 H), 7.08-7.31 (m, 2 H), 7.29-7.49 (m, 3 H), 7.56-7.80 (m, 2 H), 7.89 (s, 1H), 8.21 (s, 1 H), 8.43 (d, J=3.52 Hz, 1 H).

EXAMPLE 83

(S)—N-(3,4-Difluorobenzyl)-6-(4-ethyl-4,5-dihydrooxazol-2-yl)-2-isopropyl-1-(oxazol-2-ylmethyl)-1H-indole-3-carboxamide (Compound 83). The title compound was prepared from (S)—N3-(3,4-difluorobenzyl)-N6-(1-hydroxybutan-2-yl)-2-isopropyl-1-(oxazol-2-ylmethyl)-1H-indole-3,6-dicarboxamide by General Procedure H.

1H NMR (500 MHz, METHANOL-$d_4$) δ ppm 1.00 (t, J=7.46 Hz, 3 H), 1.38 (s, 3 H), 1.40 (s, 3 H), 1.55-1.87 (m, 2 H), 3.57 (dt, J=14.18, 7.09 Hz, 1 H), 4.17 (t, J=7.83 Hz, 1H), 4.25 (ddd, J=14.73, 7.27, 7.09 Hz, 1 H), 4.57 (s, 2 H), 5.67 (s, 2 H), 7.11 (s, 1 H), 7.19-7.28 (m, 2 H), 7.34 (d, J=7.82 Hz, 1 H), 7.61 (d, J=8.31 Hz, 1 H), 7.73 (d, J=8.56 Hz, 1 H), 7.84 (s, 1 H), 8.05 (s, 1 H), 8.71 (br. s., 1 H).

EXAMPLE 84

(S)—N-(3,5-Difluorobenzyl)-2-isopropyl-6-(4-methyl-4,5-dihydrooxazol-2-yl)-1-(pyridin-2-ylmethyl)-1H-indole-3-carboxamide (Compound 84). The title compound was prepared from (S)—N3-(3,5-difluorobenzyl)-N6-(1-hydroxypropan-2-yl)-2-isopropyl-1-(pyridin-2-ylmethyl)-1H-indole-3,6-dicarboxamide by General Procedure H.

1H NMR (300 MHz, METHANOL-$d_4$) δ ppm 1.23-1.42 (m, 9 H), 3.41-3.58 (m, 1 H), 3.98 (t, 1 H), 4.23-4.38 (m, 1 H), 4.47-4.58 (m, 1 H), 4.62 (m, 1 H), 5.65 (s, 2 H), 6.76 (d, J=7.91, Hz, 1 H), 6.76-6.91 (m, 1 H), 7.00-7.11 (m, 1 H), 7.21-7.36 (m, 1 H), 7.61-7.79 (m, 4 H), 7.88 (s, 1 H), 8.44-8.58 (m, 1 H).

EXAMPLE 85

(S)—N-(3,5-Difluorobenzyl)-6-(4-ethyl-4,5-dihydrooxazol-2-yl)-2-isopropyl-1-(pyridin-2-ylmethyl)-1H-indole-3-carboxamide (Compound 85). The title compound was prepared from (S)—N3-(3,5-difluorobenzyl)-N6-(1-hydroxybutan-2-yl)-2-isopropyl-1-(pyridin-2-ylmethyl)-1H-indole-3,6-dicarboxamide by General Procedure H.

1H NMR (300 MHz, METHANOL-$d_4$) δ ppm 0.96 (t, J=7.61 Hz, 3 H), 1.32 (s, 3 H), 1.35 (s, 3 H), 1.49-1.85 (m, 2 H), 3.40-3.59 (m, 1 H), 4.12 (t, J=7.61 Hz, 2 H), 4.14-4.30 (m, 1 H), 4.49 (t, J=8.79 Hz, 1 H), 4.63 (s, 2 H), 5.65 (s, 2 H), 6.71 (d, J=7.91 Hz, 1 H), 6.79-6.90 (m, 1 H), 6.99-7.10 (m, 1 H), 7.25-7.33 (m, 1 H), 7.62-7.78 (m, 4 H), 7.89 (s, 1 H), 8.52 (d, J=5.57 Hz, 1 H).

EXAMPLE 86

(S)—N-(4-Fluorobenzyl)-2-isopropyl-6-(4-methyl-4,5-dihydrooxazol-2-yl)-1-(pyridin-2-ylmethyl)-1H-indole-3-carboxamide (Compound 86). The title compound was prepared from (S)—N3-(4-fluorobenzyl)-N6-(1-hydroxypropan-2-yl)-2-isopropyl-1-(pyridin-2-ylmethyl)-1H-indole-3,6-dicarboxamide by General Procedure H.

1H NMR (300 MHz, METHANOL-$d_4$) δ ppm 1.34 (m, 9 H), 3.41-3.61 (m, 1 H), 3.95 (t, J=7.91 Hz, 1 H), 4.25-4.43 (m, 1 H), 4.54 (t, J=8.79 Hz, 1 H), 4.63 (s, 2 H), 5.65 (s, 2 H), 6.63 (d, J=7.91 Hz, 1 H), 7.01-7.14 (m, 2 H), 7.23-7.33 (m, 1 H), 7.40-7.54 (m, 2 H), 7.61-7.76 (m, 3 H), 7.90 (s, 1 H), 8.53 (d, J=5.57 Hz, 1 H).

EXAMPLE 87

6-(5,5-Dimethyl-4,5-dihydrooxazol-2-yl)-N-(4-fluorobenzyl)-2-isopropyl-1-(pyridin-2-ylmethyl)-1H-indole-3-carboxamide (Compound 87). To a solution of N3-(4-fluorobenzyl)-N6-(2-hydroxy-2-methylpropyl)-2-isopropyl-1-(pyridin-2-ylmethyl)-1H-indole-3,6-dicarboxamide (Compound 68, 23 mg, 0.043 mmol) in benzene (6 ml) at 25° C. was added $P_2O_5$ (120 mg, 0.86 mmol). The mixture was stirred at 50° C. for 4 h, quenched with 6N NaOH (1 ml), extracted several times with EtOAc, washed with $H_2O$, brine, dried over $Na_2SO_4$, concentrated in vacuo. The residue was purified by chromatography on silica gel (100% EtOAc) to yield the title compound as yellow oil.

1H NMR (300 MHz, METHANOL-$d_4$) δ ppm 1.31 (s, 3 H), 1.34 (s, 3 H), 1.46 (s, 6 H), 3.35-3.54 (m, 1 H), 3.71 (s, 2 H), 4.58 (s, 2 H), 5.57 (s, 2 H), 6.94 (d, J=6.16 Hz, 2 H), 7.24 (dd, J=3.59, 1.39 Hz, 6 H), 7.67 (dd, J=2.05, 1.03 Hz, 2 H), 7.85 (s, 1 H).

EXAMPLE 88

1-Benzyl-N-(3,4-difluorobenzyl)-6-(hydrazinecarbonyl)-2-isopropyl-1H-indole-3-carboxamide (Compound 88). Following General Procedure E, 1-benzyl-3-(3,4-difluorobenzylcarbamoyl)-2-isopropyl-1H-indole-6-carboxylic acid (Compound 56, 82 mg, 0.176 mmol) in CH$_2$Cl$_2$ (8 ml) was added EDC (51 mg, 0.264 mmol) and DMAP (26 mg, 0.256 mmol), followed by hydrazine (7 mg, 0.264 mmol). The reaction was stirred at room temperature for 12 h, diluted with EtOAc, washed with H$_2$O, brine, dried over Na$_2$SO$_4$ and concentrated in vacuo. The residue was purified by chromatography on silica gel (0→100% EtOAc-hexanes) to yield the title compound as a yellow oil.

1H NMR (300 MHz, METHANOL-d$_4$) δ ppm 1.29-1.41 (m, 6 H), 3.38-3.54 (m, 1 H), 4.59 (s, 2 H), 5.59 (s, 2 H), 6.88-7.02 (m, 2 H), 7.14-7.43 (m, 6 H), 7.52-7.73 (m, 2 H), 7.73-7.88 (m, 1 H), 8.00 (br. s., 1 H), 8.71 (d, J=2.93 Hz, 1 H).

EXAMPLE 89

1-Benzyl-N-(3,4-difluorobenzyl)-2-isopropyl-6-(1,3,4-oxadiazol-2-yl)-1H-indole-3-carboxamide (Compound 89). 1-benzyl-N-(3,4-difluorobenzyl)-6-(hydrazinecarbonyl)-2-isopropyl-1H-indole-3-carboxamide (Compound 88, 21 mg, 0.044 mmol) in triethyl orthoformate (5 ml) was heated to 145° C. for 5 h, then concentrated in vacuo. The residue was purified by chromatography on silica gel (0→55% EtOAc-hexanes) to yield the title compound as a white solid.

1H NMR (300 MHz, METHANOL-d$_4$) δ ppm 1.34 (s, 3 H), 1.36 (s, 3 H), 3.39-3.59 (m, 1 H), 4.60 (s, 2 H), 5.63 (s, 2 H), 6.98 (d, J=8.06 Hz, 2 H), 7.15-7.47 (m, 6 H), 7.70-7.90 (m, 2 H), 8.02 (d, J=0.59 Hz, 1 H), 8.90 (s, 1 H).

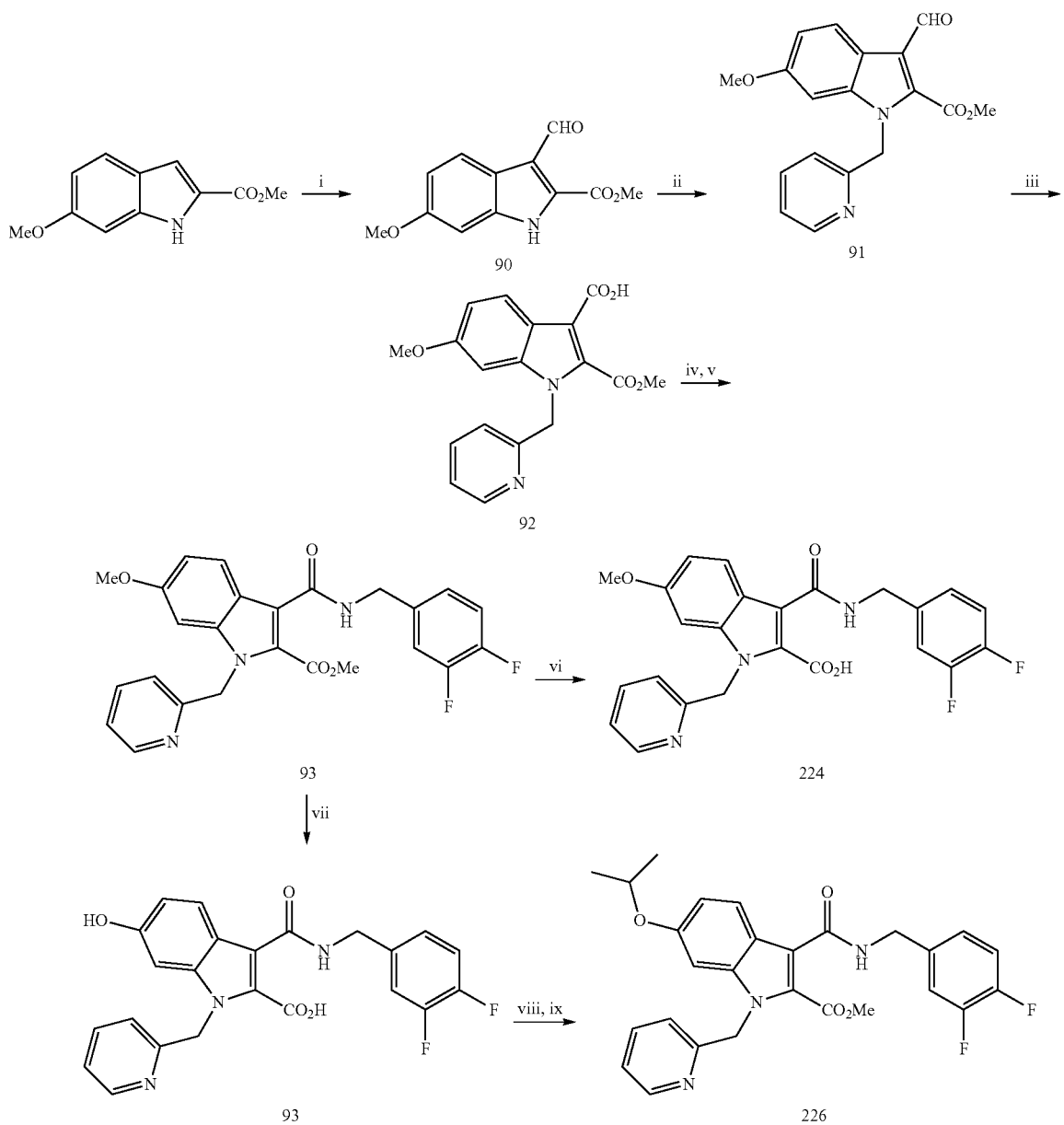

Scheme 7$^a$ $^a$Reagents and conditions: (i) POCl$_3$, DMF; (ii) 2-bromomethylpyridine, K$_2$CO$_3$, DMF, 60° C.; (iii) NaClO$_2$, NaH$_2$PO$_4$, isobutene, t-BuOH, dioxane, H$_2$O; (iv) (COCl)$_2$, cat. DMF CH$_2$Cl$_2$; (v) 3,4-difluorobenzylamine, Et$_3$N, CH$_2$Cl$_2$; (vi) BBr$_3$, CH$_2$Cl$_2$; (vii) AlCl$_3$, EtSH, CH$_2$Cl$_2$; (viii) MeOH, cat. H$_2$SO$_4$, 80° C.; (ix) i-PrI, K$_2$CO$_3$, DMF.

EXAMPLE 90

Methyl 3-Formyl-6-methoxy-1H-indole-2-carboxylate (Compound 90). General Procedure I. POCl$_3$ (2.94 ml, 32.2 mmol) was added dropwise to anhydrous DMF (10 ml) at 0° C. under argon. After stirred for 30 min, this solution was added dropwise to a solution of methyl6-methoxy-1H-indole-2-carboxylate (Aldrich, 2.2 g, 10.7 mmol) in anhydrous DMF (20 ml) at 0° C. under argon. The reaction was stirred for 20 h at room temperature, quenched with ice, diluted with EtOAc, a precipitate formed and was filtered and washed with H$_2$O (×3) to give the title compound as an off-white solid.

1H NMR (300 MHz, DMSO-d$_6$) δ ppm 3.81 (s, 3 H), 3.97 (s, 3 H), 6.79-7.09 (m, 2 H), 8.09 (d, J=9.1 Hz, 1 H), 10.57 (s, 1 H), 12.66 (s, 1 H).

EXAMPLE 91

Methyl 3-Formyl-6-methoxy-1-(pyridin-2-ylmethyl)-1H-indole-2-carboxylate (Compound 91). General Procedure J. 2-Bromomethylpyridine.HBr salt (7.0 g, 27.7 mmol) was treated with NaOH (4M, 6.9 ml, 27.6 mmol) in Et$_2$O (20 ml). The ether layer was separated, washed with brine, and dried over MgSO$_4$, filtered into a flask containing a suspension of methyl3-formyl-6-methoxy-1H-indole-2-carboxylate (Compound 90, 1.29 g, 5.54 mmol) and K$_2$CO$_3$ (2.3 g, 16.6 mmol) in DMF (25 ml). The reaction was stirred at 60° C. for 3 h, cooled to room temperature, quenched with H$_2$O and extracted with EtOAc (×2). The combined organic layer was washed with brine, dried over Na$_2$SO$_4$, and concentrated in vacuo. The residue was purified by washing with H$_2$O (×3) and filtration to yield the title compound as a golden brown solid.

1H NMR (300 MHz, CHLOROFORM-d) δ ppm 3.80 (s, 3 H), 3.99 (s, 3 H), 5.89 (s, 2 H), 6.82 (d, J=2.3 Hz, 1 H), 6.86 (d, J=7.9 Hz, 1 H), 7.00 (dd, J=8.8, 2.3 Hz, 1 H), 7.19 (ddd, J=7.5, 4.8, 1.2 Hz, 1 H), 7.57 (td, J=7.7, 1.9 Hz, 1 H), 8.40 (d, J=9.1 Hz, 1 H), 8.59 (ddd, J=4.7, 1.8, 0.9 Hz, 1 H), 10.65 (s, 1 H).

EXAMPLE 92

6-Methoxy-2-(methoxycarbonyl)-1-(pyridin-2-ylmethyl)-1H-indole-3-carboxylic Acid (Compound 92). General Procedure K. To a suspension of methyl3-formyl-6-methoxy-1-(pyridin-2-ylmethyl)-1H-indole-2-carboxylate (Compound 91, 1.64 g, 5.07 mmol) in t-BuOH (120 ml) and dioxane (20 ml) was added 2-methyl-2-butene (25 ml) and a solution of NaH$_2$PO$_4$ (7.3 g, 61 mmol) and NaClO$_2$ (80%, 5.7 g, 50.7 mmol) in H$_2$O (100 ml). The reaction was stirred at room temperature for 6 h, extracted with EtOAc (×2). The combined organic layer was washed with brine, dried over Na$_2$SO$_4$, and concentrated in vacuo. The residue was purified by chromatography on silica gel (0→100% EtOAc-hexanes) to yield the title compound as an off-white solid.

1H NMR (300 MHz, CHLOROFORM-d) δ ppm 3.82 (s, 3 H), 3.92 (s, 3 H), 5.76 (s, 2 H), 6.66-6.79 (m, 2 H), 7.02 (dd, J=9.1, 2.1 Hz, 1 H), 7.22 (dd, J=7.3, 5.3 Hz, 1 H), 7.59 (td, J=7.8, 1.8 Hz, 1 H), 8.52 (d, J=8.8 Hz, 1 H), 8.62 (d, J=5.0 Hz, 1 H).

EXAMPLE 93

Methyl 3-(3,4-Difluorobenzylcarbamoyl)-6-methoxy-1-(pyridin-2-ylmethyl)-1H-indole-2-carboxylate (Compound 93). To a solution of 6-methoxy-2-(methoxycarbonyl)-1-(pyridin-2-ylmethyl)-1H-indole-3-carboxylic acid (Compound 92, 1.59 g, 4.7 mmol) in anhydrous CH$_2$Cl$_2$ (50 ml) was added DMF (3 drops, catalytic amount) and (COCl)$_2$ (2M in CH$_2$Cl$_2$, 5.9 ml, 11.8 mmol). The resulting mixture was stirred at room temperature for 1 h, and was concentrated in vacuo. To a solution of the crude product in CH$_2$Cl$_2$ (50 ml) was added 3,4-difluorobenzylamine (0.84 ml, 7.05 mmol), followed by Et$_3$N (2.0 ml, 14.1 mmol). The reaction was stirred at room temperature for 1 h, diluted with EtOAc, washed with H$_2$O and brine, dried over Na$_2$SO$_4$, and concentrated in vacuo. The residue was purified by chromatography on silica gel (0→100% EtOAc-hexanes) to yield the title compound as a white solid.

1H NMR (300 MHz, CHLOROFORM-d) δ ppm 3.78 (s, 3 H), 3.80 (s, 3 H), 4.64 (d, J=5.9 Hz, 2 H), 5.73 (s, 2 H), 6.71 (d, J=2.1 Hz, 1 H), 6.77 (d, J=7.9 Hz, 1 H), 6.93 (dd, J=8.9, 2.2 Hz, 1 H), 7.09-7.22 (m, 3 H), 7.22-7.32 (m, 1 H), 7.55 (td, J=7.6, 1.8 Hz, 1 H), 8.14 (d, J=9.1 Hz, 2 H), 8.58 (d, J=4.1 Hz, 1 H).

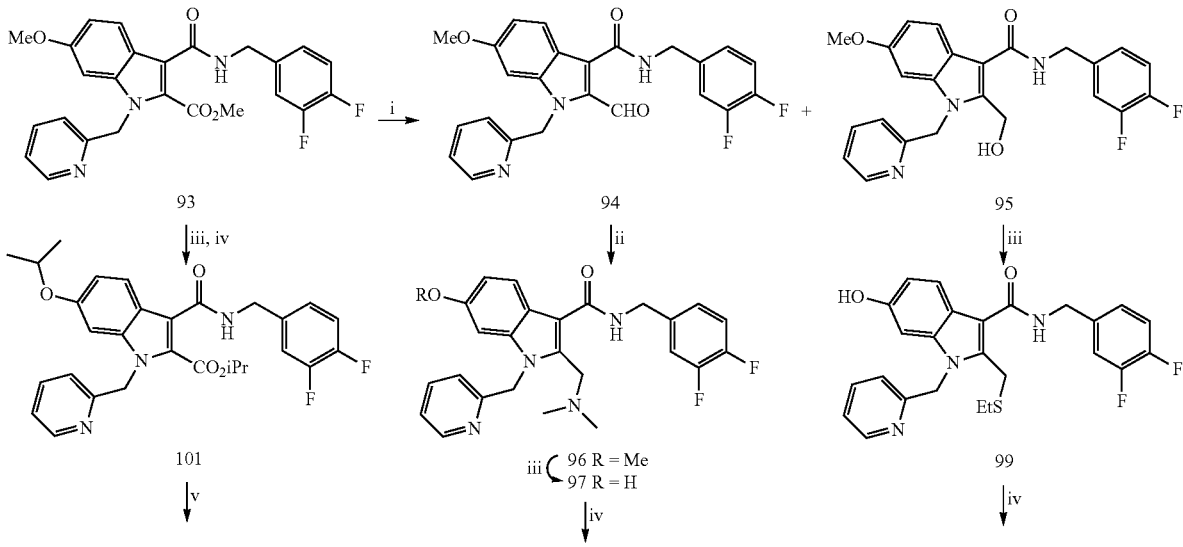

Scheme 8$^a$

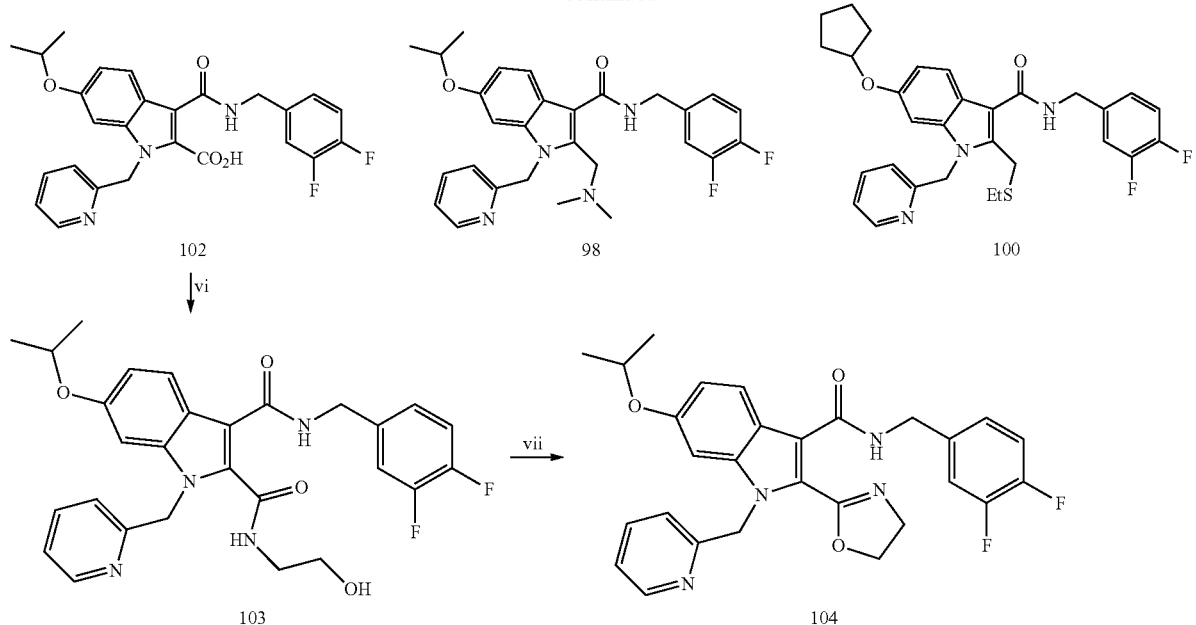

*Reagents and conditions: (i) DIBAL, CH₂Cl₂, -78° C.; (ii) amines, ClCH₂CH₂Cl, HOAc, NaBH(OAc)₃; (iii) AlCl₃, EtSH, CH₂Cl₂; (iv) i-PrI or c-C₅H₉I, K₂CO₃, DMF; (v) NaOH, MeOH; (vi) ethanolamine, BOP, iPr₂NEt, DMF; (vii) MsCl, Et₃N, CH₂Cl₂.

EXAMPLE 94

N-(3,4-Difluorobenzyl)-2-formyl-6-methoxy-1-(pyridin-2-ylmethyl)-1H-indole-3-carboxamide (Compound 94). General Procedure O. To a solution of methyl3-(3,4-difluorobenzylcarbamoyl)-6-methoxy-1-(pyridin-2-ylmethyl)-1H-indole-2-carboxylate (Compound 93, 515 mg, 1.11 mmol) in CH₂Cl₂ (20 ml) at −78° C. was added DIBAL (1 M in CH₂Cl₂, 4.4 ml, 4.44 mmol) slowly. The reaction was stirred at −78° C. for 2 h, quenched with H₂O, diluted with EtOAc, washed with NaOH and brine, dried over Na₂SO₄, and concentrated in vacuo. The residue was purified by chromatography on silica gel (0→100% EtOAc-hexanes) to yield the title compound as a beige solid.

1H NMR (500 MHz, METHANOL-d₄) δ ppm 3.81 (s, 3 H), 4.62 (s, 2 H), 5.98 (s, 2 H), 6.89-6.96 (m, 3 H), 7.22-7.30 (m, 3 H), 7.31-7.37 (m, 1 H), 7.65-7.72 (m, 1 H), 7.80 (d, J=9.8 Hz, 1 H), 8.48 (d, J=5.1 Hz, 1 H), 10.15 (s, 1 H).

EXAMPLE 95

N-(3,4-Difluorobenzyl)-2-(hydroxymethyl)-6-methoxy-1-(pyridin-2-ylmethyl)-1H-indole-3-carboxamide (Compound 95). The title compound was also isolated in the synthesis of Compound 94.

1H NMR (500 MHz, METHANOL-d₄) δ ppm 3.75 (s, 3 H), 4.60 (s, 2 H), 4.95 (s, 2 H), 5.62 (s, 2 H), 6.80-6.88 (m, 2 H), 7.01 (d, J=8.3 Hz, 1 H), 7.20-7.26 (m, 2 H), 7.26- 7.37 (m, 2 H), 7.71 (td, J=7.8, 1.6 Hz, 1 H), 7.75 (d, J=8.8 Hz, 1 H), 8.51 (d, J=4.6 Hz, 1 H).

EXAMPLE 96

N-(3,4-Difluorobenzyl)-2-((dimethylamino)methyl)-6-methoxy-1-(pyridin-2-ylmethyl)-1H-indole-3-carboxamide (Compound 96). General Procedure P. To a solution of N-(3,4-difluorobenzyl)-2-formyl-6-methoxy-1-(pyridin-2-ylmethyl)-1H-indole-3-carboxamide (Compound 94, 70 mg, 0.16 mmol) in ClCH₂CH₂Cl (10 ml) at room temperature was added dimethylamine (2 M in THF, 0.24 ml, 0.48 mmol), HOAc (14 µl, 0.24 mmol), and NaBH(OAc)₃ (102 mg, 0.48 mmol). The reaction was stirred at room temperature for 16 h, diluted with EtOAc, washed with aqueous Na₂CO₃ and brine, dried over Na₂SO₄, and concentrated in vacuo. The residue was purified by chromatography on silica gel (EtOAc, then 9:1 EtOAc-Et₃N, then 7:2:1 CH₂Cl₂-MeOH-Et₃N) to yield the title compound as an off-white solid.

1H NMR (300 MHz, METHANOL-d₄) δ ppm 2.07 (s, 6 H), 3.70 (s, 2 H), 3.76 (s, 3 H), 4.54 (s, 2 H), 5.61 (s, 2 H), 6.76-6.93 (m, 3 H), 7.15-7.37 (m, 4 H), 7.66 (td, J=7.6, 1.8 Hz, 1 H), 8.01 (d, J=8.8 Hz, 1 H), 8.51 (d, J=5.0 Hz, 1 H).

EXAMPLE 97

N-(3,4-Difluorobenzyl)-2-((dimethylamino)methyl)-6-hydroxy-1-(pyridin-2-ylmethyl)-1H-indole-3-carboxamide (Compound 97). The title compound was prepared from N-(3,4-difluorobenzyl)-2-((dimethylamino)methyl)-6-methoxy-1-(pyridin-2-ylmethyl)-1H-indole-3-carboxamide (Compound 96) by General Procedure M.

1H NMR (300 MHz, CHLOROFORM-d) δ ppm 2.06 (s, 6 H), 3.56 (s, 2 H), 4.57 (d, J=5.3 Hz, 2 H), 5.41 (s, 2 H), 6.50 (d, J=7.9 Hz, 1 H), 6.70 (d, J=2.1 Hz, 1 H), 6.85 (dd, J=8.6, 2.2 Hz, 1 H), 7.03-7.24 (m, 4 H), 7.42-7.53 (m, 1 H), 8.20 (d, J=8.5 Hz, 1 H), 8.53 (d, J=5.0 Hz, 1 H), 9.96-10.14 (m, J=5.6 Hz, 1 H).

EXAMPLE 98

N-(3,4-Difluorobenzyl)-2-((dimethylamino)methyl)-6-isopropoxy-1-(pyridin-2-ylmethyl)-1H-indole-3-carboxamide (Compound 98). The title compound was prepared from N-(3,4-difluorobenzyl)-2-((dimethylamino)methyl)-6-hydroxy-1-(pyridin-2-ylmethyl)-1H-indole-3-carboxamide (Compound 97) by General Procedure N.

1H NMR (300 MHz, CHLOROFORM-d) δ ppm 1.30 (d, J=6.2 Hz, 6 H), 2.09 (s, 6 H), 3.57 (s, 2 H), 4.42-4.63 (m, 3 H), 5.49 (s, 2 H), 6.51 (d, J=6.4 Hz, 1 H), 6.75 (d, J=2.1 Hz, 1 H), 6.92 (dd, J=8.8, 2.1 Hz, 1 H), 7.04-7.25 (m, 4 H), 7.43-7.57 (m, 1 H), 8.27 (d, J=9.4 Hz, 1 H), 8.59 (d, J=4.4 Hz, 1 H), 9.96 (s, 1 H).

EXAMPLE 99

N-(3,4-Difluorobenzyl)-2-(ethylthiomethyl)-6-hydroxy-1-(pyridin-2-ylmethyl)-1H-indole-3-carboxamide (Compound 99). The title compound was prepared from N-(3,4-difluorobenzyl)-2-(hydroxymethyl)-6-methoxy-1-(pyridin-2-ylmethyl)-1H-indole-3-carboxamide (Compound 95) by General Procedure M.

1H NMR (300 MHz, METHANOL-$d_4$) δ ppm 1.09 (t, J=7.3 Hz, 3 H), 2.41 (q, J=7.3 Hz, 2 H), 4.24 (s, 2 H), 4.58 (s, 2 H), 5.54 (s, 2 H), 6.62 (d, J=1.8 Hz, 1 H), 6.69-6.83 (m, 2 H), 7.17-7.40 (m, 4 H), 7.61 (d, J=8.2 Hz, 1 H), 7.63-7.72 (m, 1 H), 8.52 (d, J=5.6 Hz, 1 H).

EXAMPLE 100

6-(Cyclopentyloxy)-N-(3,4-difluorobenzyl)-2-(ethylthiomethyl)-1-(pyridin-2-ylmethyl)-1H-indole-3-carboxamide (Compound 100). The title compound was prepared from N-(3,4-difluorobenzyl)-2-(ethylthiomethyl)-6-hydroxy-1-(pyridin-2-ylmethyl)-1H-indole-3-carboxamide (Compound 99) by General Procedure N.

1H NMR (300 MHz, CHLOROFORM-d) δ ppm 1.19 (t, J=7.5 Hz, 3 H), 1.47-1.65 (m, 4 H), 1.69-1.87 (m, 4 H), 2.55 (q, J=7.3 Hz, 2 H), 4.28 (s, 2 H), 4.61-4.75 (m, 3 H), 5.54 (s, 2 H), 6.61-6.72 (m, 2 H), 6.84 (dd, J=8.8, 2.1 Hz, 1 H), 7.09-7.31 (m, 4 H), 7.48-7.58 (m, 1 H), 7.67 (d, J=9.4 Hz, 1 H), 8.60 (d, J=5.0 Hz, 1 H).

EXAMPLE 101

Isopropyl 3-(3,4-Difluorobenzylcarbamoyl)-6-isopropoxy-1-(pyridin-2-ylmethyl)-1H-indole-2-carboxylate (Compound 101). The title compound was prepared from methyl 3-(3,4-difluorobenzylcarbamoyl)-6-methoxy-1-(pyridin-2-ylmethyl)-1H-indole-2-carboxylate (Compound 93) by General Procedure M and General Procedure N.

1H NMR (300 MHz, METHANOL-$d_4$) δ ppm 1.17 (d, J=6.4 Hz, 6 H), 1.25 (d, J=6.2 Hz, 6 H), 4.51-4.64 (m, 3 H), 5.05-5.18 (m, 1 H), 5.84 (s, 2 H), 6.80-6.89 (m, 3 H), 7.16-7.29 (m, 3 H), 7.30-7.40 (m, 1 H), 7.56-7.71 (m, 2 H), 8.49 (d, J=5.0 Hz, 1 H).

EXAMPLE 102

3-(3,4-Difluorobenzylcarbamoyl)-6-isopropoxy-1-(pyridin-2-ylmethyl)-1H-indole-2-carboxylic Acid (Compound 102). A solution of isopropyl 3-(3,4-difluorobenzylcarbamoyl)-6-isopropoxy-1-(pyridin-2-ylmethyl)-1H-indole-2-carboxylate (Compound 101, 551 mg, 1.06 mmol) in MeOH (15 ml) and NaOH (1 M, 5.3 ml, 5.3 mmol) was stirred at room temperature for 4 h. The reaction was quenched cautiously with 6 M HCl at 0° C., extracted with EtOAc (×3). The combined organic layer was washed with brine, dried over $Na_2SO_4$, and concentrated in vacuo. The residue was purified by chromatography on silica gel (EtOAc, then 8:2 EtOAc-MeOH, then 7:2:1 EtOAc-MeOH-$Et_3N$) to yield the title compound as its $Et_3N$ salt.

1H NMR (300 MHz, METHANOL-$d_4$) δ ppm 1.22 (d, J=5.9 Hz, 6 H), 4.43-4.55 (m, 1 H), 4.57 (s, 2 H), 5.86 (s, 2 H), 6.72 (d, J=2.1 Hz, 1 H), 6.79 (dd, J=8.8, 2.3 Hz, 1 H), 6.88 (d, J=7.9 Hz, 1 H), 7.15-7.36 (m, 4 H), 7.58-7.69 (m, 1 H), 8.23 (d, J=8.8 Hz, 1 H), 8.49 (d, J=5.0 Hz, 1 H).

EXAMPLE 103

$N^3$-(3,4-Difluorobenzyl)-$N^2$-(2-hydroxyethyl)-6-isopropoxy-1-(pyridin-2-ylmethyl)-1H-indole-2,3-dicarboxamide (Compound 103). To a solution of 3-(3,4-difluorobenzylcarbamoyl)-6-isopropoxy-1-(pyridin-2-ylmethyl)-1H-indole-2-carboxylic acid (Compound 102, 73 mg, 0.12 mmol) in DMF (2 ml) was added 2-aminoethanol (11 μl, 0.17 mmol), BOP (64 mg, 0.14 mmol), and i-$Pr_2NEt$ 30 μl, 0.17 mmol). The reaction was stirred at room temperature for 16 h, diluted with EtOAc, washed with $H_2O$ and brine, dried over $Na_2SO_4$, and concentrated in vacuo. The residue was purified by chromatography on silica gel (0→100% EtOAc-hexanes) to yield the title compound as a yellow syrup.

1H NMR (300 MHz, CHLOROFORM-d) δ ppm 1.29 (d, J=5.9 Hz, 6 H), 3.55-3.69 (m, 2 H), 3.74-3.85 (m, 2 H), 4.45-4.58 (m, 1 H), 4.63 (d, J=5.9 Hz, 2 H), 5.63 (s, 2 H), 6.77 (d, J=2.1 Hz, 1 H), 6.87 (dd, J=8.9, 2.2 Hz, 1 H), 7.06-7.28 (m, 4 H), 7.32 (d, J=7.9 Hz, 1 H), 7.63-7.74 (m, 1 H), 7.80-7.96 (m, 2 H), 8.52 (d, J=4.1 Hz, 1 H), 9.93-10.08 (m, 1 H).

EXAMPLE 104

N-(3,4-Difluorobenzyl)-2-(4,5-dihydrooxazol-2-yl)-6-isopropoxy-1-(pyridin-2-ylmethyl)-1H-indole-3-carboxamide (Compound 104). To a solution of $N^3$-(3,4-difluorobenzyl)-$N^2$-(2-hydroxyethyl)-6-isopropoxy-1-(pyridin-2-ylmethyl)-1H-indole-2,3-dicarboxamide (Compound 103, 36 mg, 0.069 mmol) in $CH_2Cl_2$ (3 ml) at 0° C was added $Et_3N$ (58 μl, 0.41 mmol) and methanesulfonyl chloride (11 μl, 0.14 mmol). The reaction was stirred at room temperature for 0.5 h, diluted with EtOAc, washed with $H_2O$ and brine, dried over $Na_2SO_4$, and concentrated in vacuo. The residue was purified by chromatography on silica gel (0→100% EtOAc-hexanes) to yield the title compound as a yellow film.

1H NMR (300 MHz, METHANOL-$d_4$) δ ppm 1.25 (d, J=6.2 Hz, 6 H), 3.94 (t, J=10.0 Hz, 2 H), 4.31 (t, J=9.8 Hz, 2 H), 4.47-4.64 (m, 3 H), 5.85 (s, 2 H), 6.79-6.92 (m, 3 H), 7.16-7.42 (m, 4 H), 7.61-7.73 (m, 1 H), 7.85 (d, J=9.4 Hz, 1 H), 8.49 (d, J=5.0 Hz, 1 H).

Scheme 9<sup>a</sup>

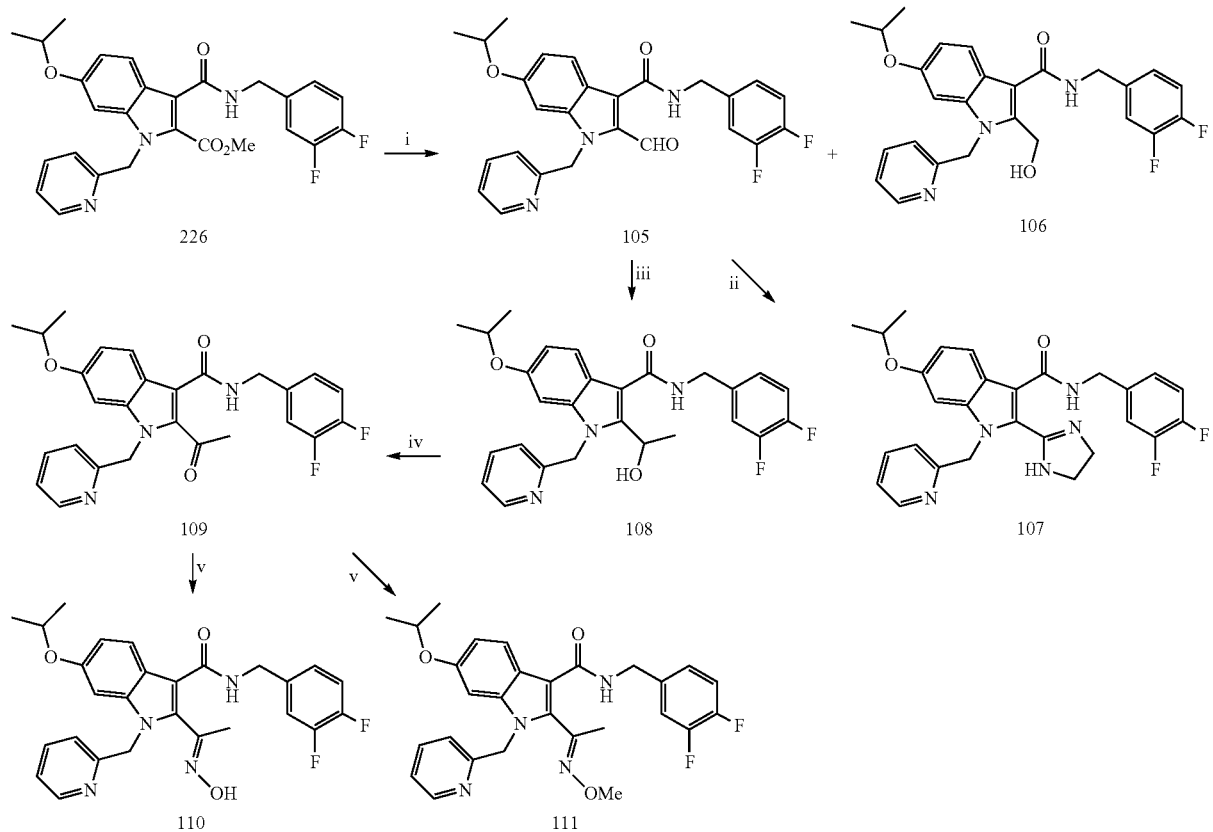

<sup>a</sup>Reagents and conditions: (i) DIBAL, CH$_2$Cl$_2$, -78° C.; (ii) ethane-1,2-diamine, CH$_2$Cl$_2$, then NBS; (iii) MeMgBr, 1,2-dimethoxyethane; (iv) TPAP, NMO, CH$_2$Cl$_2$; (v) HONH$_2$•HCl or MeONH$_2$•HCl, pyridine, MeOH.

EXAMPLE 105

N-(3,4-Difluorobenzyl)-2-formyl-6-isopropoxy-1-(pyridin-2-ylmethyl)-1H-indole-3-carboxamide (Compound 105). The title compound was prepared from methyl3-(3,4-difluorobenzylcarbamoyl)-6-isopropoxy-1-(pyridin-2-ylmethyl)-1H-indole-2-carboxylate (Compound 96) by General Procedure O.

1H NMR (300 MHz, METHANOL-d$_4$) δ ppm 1.27 (d, J=6.2 Hz, 6 H), 4.51-4.70 (m, 3 H), 5.96 (s, 2 H), 6.86-7.00 (m, 3 H), 7.19-7.41 (m, 4 H), 7.63-7.74 (m, 1 H), 7.78 (d, J=9.7 Hz, 1 H), 8.48 (d, J=5.0 Hz, 1 H), 10.16 (s, 1 H).

EXAMPLE 106

N-(3,4-Difluorobenzyl)-2-(hydroxymethyl)-6-isopropoxy-1-(pyridin-2-ylmethyl)-1H-indole-3-carboxamide (Compound 106). The title compound was also isolated in the synthesis of Compound 105.

1H NMR (300 MHz, CHLOROFORM-d) δ ppm 1.32 (d, J=5.9 Hz, 6 H), 4.47-4.60 (m, 1 H), 4.64 (d, J=5.9 Hz, 2 H), 4.95 (s, 2 H), 5.38 (s, 2 H), 6.02 (s, 1 H), 6.79-6.91 (m, 3 H), 7.07-7.32 (m, 4 H), 7.68 (td, J=7.8, 1.8 Hz, 1 H), 7.85 (d, J=8.5 Hz, 1 H), 8.48 (d, J=4.4 Hz, 1 H).

EXAMPLE 107

N-(3,4-Difluorobenzyl)-2-(4,5-dihydro-1H-imidazol-2-yl)-6-isopropoxy-1-(pyridin-2-ylmethyl)-1H-indole-3-carboxamide (Compound 107). To a solution of N-(3,4-difluorobenzyl)-2-formyl-6-isopropoxy-1-(pyridin-2-ylmethyl)-1H-indole-3-carboxamide (Compound 105, 27 mg, 0.058 mmol) in CH$_2$Cl$_2$ (2 ml) was added 1,2-ethylene-diamine (5 µl, 0.070 mmol). The reaction was stirred at room temperature for 1 h and NBS (13 mg, 0.070 mmol) was added. The reaction was stirred for 16 h and the solvent was removed in vacuo. The residue was purified by chromatography on silica gel (9:1 EtOAc-Et$_3$N, then 8:2:1 EtOAc-MeOH-Et$_3$N) followed by PTLC eluted with EtOAc to yield the title compound.

1H NMR (300 MHz, CHLOROFORM-d) δ ppm 1.30 (d, J=6.2 Hz, 6 H), 3.78 (s, 4 H), 4.43-4.58 (m, 1 H), 4.62 (s, 2 H), 5.51 (s, 2 H), 6.66 (d, J=2.1 Hz, 1 H), 6.87 (dd, J=8.9, 2.2 Hz, 1 H), 7.06-7.32 (m, 4 H), 7.38 (d, J=7.9 Hz, 1 H), 7.68-7.82 (m, 1 H), 8.24 (d, J=8.8 Hz, 1 H), 8.53 (d, J=5.0 Hz, 1 H), 9.95 (s, 1 H).

EXAMPLE 108

N-(3,4-Difluorobenzyl)-2-(1-hydroxyethyl)-6-isopropoxy-1-(pyridin-2-ylmethyl)-1H-indole-3-carboxamide (Compound 108). To a solution of N-(3,4-difluorobenzyl)-2-formyl-6-isopropoxy-1-(pyridin-2-ylmethyl)-1H-indole-3-carboxamide (Compound 105, 102 mg, 0.23 mmol) in 1,2-dimethoxy-ethane (15 ml) was added MeMgBr (1.4 M in toluene-THF, 0.5 ml, 0.70 mmol) at 0° C. The reaction was stirred at room temperature for 2 h and more MeMgBr (1.0 ml, 1.4 mmol) was added. The reaction was stirred at room temperature for another 2 h and was quenched with ice, extracted with EtOAc. The organic layer was washed with brine, dried over $Na_2SO_4$, and concentrated in vacuo. The residue was purified by chromatography on silica gel (0→100% EtOAc-hexanes) to yield the title compound.

1H NMR (300 MHz, METHANOL-$d_4$) δ ppm 1.23 (dd, J=6.0, 1.3 Hz, 6 H), 1.44 (d, J=6.7 Hz, 3 H), 4.41-4.67 (m, 3 H), 5.43 (q, J=6.9 Hz, 1 H), 5.56-5.76 (m, 2 H), 6.75-6.91 (m, 3 H), 7.15-7.39 (m, 4 H), 7.61-7.74 (m, 1 H), 7.79 (d, J=8.8 Hz, 1 H), 8.52 (d, J=4.7 Hz, 1 H).

EXAMPLE 109

2-Acetyl-N-(3,4-difluorobenzyl)-6-isopropoxy-1-(pyridin-2-ylmethyl)-1H-indole-3-carboxamide (Compound 109). To a solution of N-(3,4-difluorobenzyl)-2-(1-hydroxyethyl)-6-isopropoxy-1-(pyridin-2-ylmethyl)-1H-indole-3-carboxamide (Compound 108, 8.0 mg, 0.017 mmol) in $CH_2Cl_2$ (1 ml) was added NMO (6.0 mg, 0.051 mmol) and TPAP (0.6 mg, 0.0017 mmol). The reaction was stirred at room temperature for 1 h and was purified directly by PTLC (75% EtOAc-hexanes) to yield the title compound.

1H NMR (300 MHz, CHLOROFORM-d) δ ppm 1.29 (dd, J=6.0, 0.7 Hz, 6 H), 2.59 (s, 3 H), 4.46-4.60 (m, 1 H), 4.67 (d, J=5.9 Hz, 2 H), 5.67 (s, 2 H), 6.55 (t, J=6.3 Hz, 1 H), 6.79 (d, J=2.1 Hz, 1 H), 6.83-6.89 (m, 1 H), 6.94 (d, J=7.6 Hz, 1 H), 7.07-7.35 (m, 4 H), 7.48-7.63 (m, 2 H), 8.54 (d, J=4.7 Hz, 1 H).

EXAMPLE 110

(E)-N-(3,4-Difluorobenzyl)-2-(1-(hydroxyimino)ethyl)-6-isopropoxy-1-(pyridin-2-ylmethyl)-1H-indole-3-carboxamide (Compound 110). General Procedure Q. To a solution of 2-acetyl-N-(3,4-difluorobenzyl)-6-isopropoxy-1-(pyridin-2-ylmethyl)-1H-indole-3-carboxamide (Compound 109, 18 mg, 0.038 mmol) in MeOH (3 ml) was added $HONH_2·HCl$ (8.0 mg, 0.11 mmol) and pyridine (30 μl, 0.38 mmol). The reaction was stirred at 65° C. for 20 h and the solvent was removed in vacuo. The residue was purified by PTLC (75% EtOAc-hexanes) to yield the title compound.

1H NMR (300 MHz, CHLOROFORM-d) δ ppm 1.26 (d, J=5.9 Hz, 6 H), 2.08 (s, 3 H), 4.40-4.53 (m, 1 H), 4.58 (d, J=5.9 Hz, 2 H), 5.46 (s, 2 H), 6.59-6.71 (m, 3 H), 6.89 (dd, J=8.8, 2.2 Hz, 1 H), 7.03-7.24 (m, 4 H), 7.41-7.55 (m, 1 H), 7.92 (d, J=8.8 Hz, 1 H), 8.50 (d, J=4.1 Hz, 1 H), 10.61 (s, 1 H).

EXAMPLE 111

(E)-N-(3,4-Difluorobenzyl)-6-isopropoxy-2-(1-(methoxyimino)ethyl)-1-(pyridin-2-ylmethyl)-1H-indole-3-carboxamide (Compound 111). The title compound was prepared from 2-acetyl-N-(3,4-difluorobenzyl)-6-isopropoxy-1-(pyridin-2-ylmethyl)-1H-indole-3-carboxamide (Compound 109) and $MeONH_2·HCl$ by General Procedure Q.

1H NMR (300 MHz, CHLOROFORM-d) δ ppm 1.27 (d, J=6.2 Hz, 6 H), 2.12 (s, 3 H), 3.82 (s, 3 H), 4.42-4.56 (m, 1 H), 4.61 (d, J=5.6 Hz, 2 H), 5.40 (s, 2 H), 6.69 (d, J=2.1 Hz, 1 H), 6.37-6.85 (m, 2 H), 6.89 (dd, J=8.8, 2.1 Hz, 1 H), 7.03-7.25 (m, 4 H), 7.49-7.59 (m, 1 H), 7.94 (d, J=8.8 Hz, 1 H), 8.58 (d, J=4.4 Hz, 1 H).

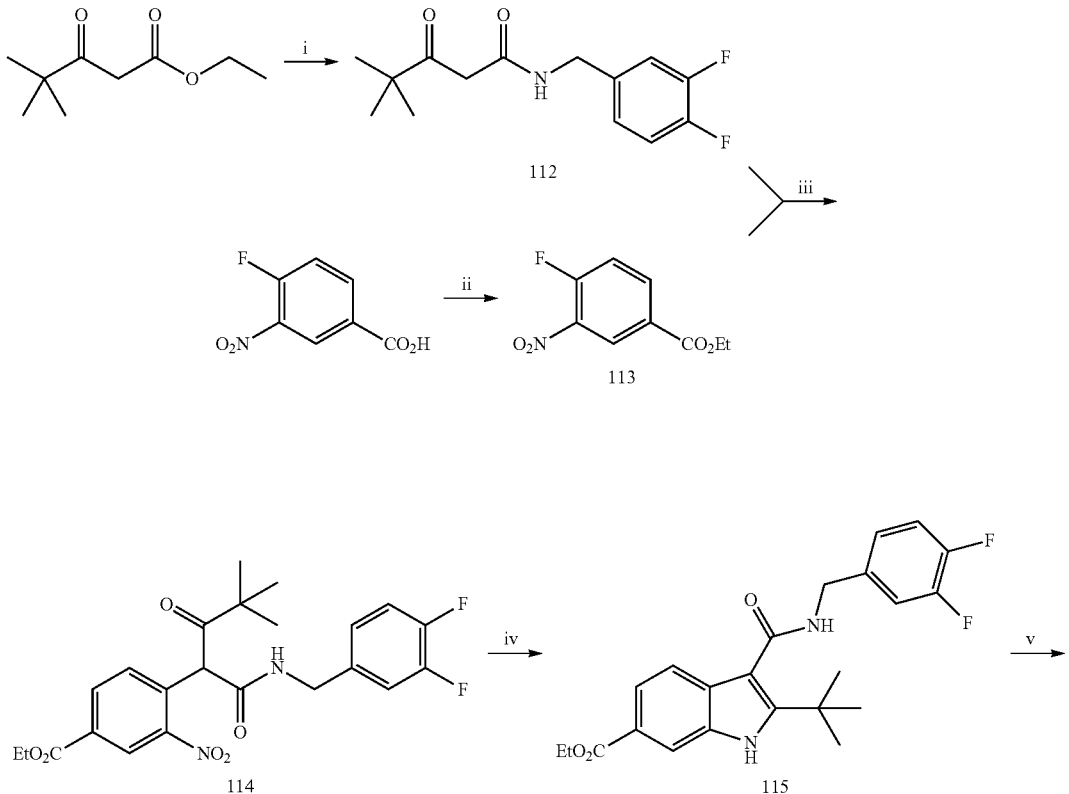

Scheme 10$^a$

-continued

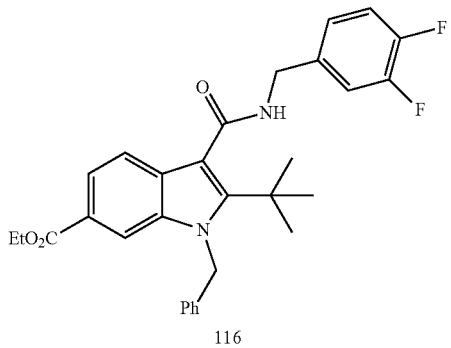

116

<sup>a</sup>Reagents and conditions: (i) 3,4-difluorobenzylamine, toluene; (ii) EtOH, cat. H₂SO₄; (iii) K₂CO₃, DMSO; (iv) Zn dust, MeOH, aq. NH₄Cl; (v) BnBr, K₂CO₃, DMF.

EXAMPLE 112

N-(3,4-Difluorobenzyl)-4,4-dimethyl-3-oxopentanamide (Compound 112). A solution of ethyl4,4-dimethyl-3-oxopentanoate (Alfa Aesar, 2.4 g, 14 mmol) and 3,4-difluorobenzylamine (Aldrich, 2.0 g, 14 mmol) in toluene (15 ml) was refluxed for 24 h. The solvent was removed to yield the title compound as an off-white wax. Used without further purification.

1H NMR (300 MHz, CHLOROFORM-d) δ ppm 1.18 (s, 9 H), 3.55 (s, 2 H), 4.42 (d, J=6.2 Hz, 2 H), 6.95-7.31 (m, 3 H), 7.57 (s, 1 H).

EXAMPLE 113

Ethyl 4-Fluoro-3-nitrobenzoate (Compound 113). A solution of 4-fluoro-3-nitrobenzoic acid (Alfa Aesar, 10.0 g, 54 mmol) and concentrated H₂SO₄ (0.2 ml, 4.1 mmol) in EtOH (200 ml) was refluxed for 40 h. The mixture was cooled to 0° C., solid NaHCO₃ and MgSO₄ was added, and the suspension was filtered and concentrated in vacuo. The residue was purified by chromatography on silica gel (0→30% EtOAc-hexanes) to yield the title compound as an off-white solid.

1H NMR (300 MHz, CHLOROFORM-d) δ ppm 1.43 (t, J=7.0 Hz, 3 H), 4.44 (q, J=7.2 Hz, 2 H), 7.39 (dd, J=10.3, 8.8 Hz, 1 H), 8.33 (ddd, J=8.6, 4.2, 2.1 Hz, 1 H), 8.74 (dd, J=7.2, 2.2 Hz, 1 H).

EXAMPLE 114

Ethyl 4-(1-(3,4-Difluorobenzylamino)-4,4-dimethyl-1,3-dioxopentan-2-yl)-3-nitrobenzoate (Compound 114). To a solution of N-(3,4-difluorobenzyl)-4,4-dimethyl-3-oxopentanamide (Compound 112, 126 mg, 0.47 mmol) and ethyl4-fluoro-3-nitrobenzoate (Compound 113, 100 mg, 0.47 mmol) in DMSO (1 ml) was added K₂CO₃ (130 mg, 0.94 mmol). The mixture was stirred at room temperature for 16 h, diluted with EtOAc, washed with 1 M HCl, H₂O, and brine, dried over Na₂SO₄, and concentrated in vacuo. The residue was purified by chromatography on silica gel (0→30% EtOAc-hexanes) to yield the title compound as a yellow solid.

1H NMR (300 MHz, CHLOROFORM-d) δ ppm 1.17 (s, 9 H), 1.41 (t, J=7.2 Hz, 3 H), 4.35 (dd, J=5.9, 1.8 Hz, 2 H), 4.42 (q, J=7.0 Hz, 2 H), 5.86 (s, 1 H), 6.63 (t, J=5.9 Hz, 1 H), 6.86-7.14 (m, 3 H), 7.77 (d, J=8.2 Hz, 1 H), 8.21 (dd, J=8.2, 1.8 Hz, 1 H), 8.50 (d, J=1.8 Hz, 1 H).

Example 115

Ethyl 2-tert-Butyl-3-(3,4-difluorobenzylcarbamoyl)-1H-indole-6-carboxylate (Compound 115). General Procedure R. To a solution of ethyl4-(1-(3,4-difluorobenzylamino)-4,4-dimethyl-1,3-dioxopentan-2-yl)-3-nitrobenzoate (Compound 114, 91 mg, 0.20 mmol) in MeOH (10 ml) and saturated aqueous NH₄Cl (5 ml) was added zinc dust (320 mg, 4.9 mmol). The mixture was stirred at room temperature for 0.5 h, filtered and concentrated. The remaining aqueous suspension was extracted with EtOAc (×3). The combined organic layer was washed with brine, dried over Na₂SO₄, and concentrated in vacuo. The residue was purified by chromatography on silica gel (0→50% EtOAc-hexanes) to yield the title compound.

1H NMR (300 MHz, CHLOROFORM-d) δ ppm 1.39 (t, J=7.2 Hz, 3 H), 1.53 (s, 9 H), 4.37 (q, J=7.1 Hz, 2 H), 4.64 (d, J=6.2 Hz, 2 H), 6.39 (t, J=6.0 Hz, 1 H), 7.07-7.29 (m, 3 H), 7.53 (d, J=8.5 Hz, 1 H), 7.79 (dd, J=8.5, 1.5 Hz, 1 H), 8.12 (d, J=1.2 Hz, 1 H), 8.89 (s, 1 H).

EXAMPLE 116

Ethyl 1-Benzyl-2-tert-butyl-3-(3,4-difluorobenzylcarbamoyl)-1H-indole-6-carboxylate (Compound 116). To a solution of ethyl2-tert-butyl-3-(3,4-difluorobenzylcarbamoyl)-1H-indole-6-carboxylate (Compound 115, 33 mg, 0.080 mmol) in DMF (1 ml) was added benzyl bromide (47 μl, 0.40 mmol) and K₂CO₃ (33 mg, 0.24 mmol). The mixture was stirred at room temperature for 24 h, diluted with EtOAc, washed with H₂O and brine, dried over Na₂SO₄, and concentrated in vacuo. The residue was purified by chromatography on silica gel (0→30% EtOAc-hexanes) followed by PTLC (5% MeOH—CH₂Cl₂) to yield the title compound.

1H NMR (300 MHz, CHLOROFORM-d) δ ppm 1.33 (t, J=7.2 Hz, 3 H), 1.49 (s, 9 H), 4.30 (q, J=7.0 Hz, 2 H), 4.65 (d, J=5.9 Hz, 2 H), 5.67 (s, 2 H), 6.26 (t, J=6.0 Hz, 1 H), 6.87 (dd, J=7.9, 1.8 Hz, 2 H), 7.12-7.35 (m, 6 H), 7.45 (d, J=9.1 Hz, 1 H), 7.72-7.82 (m, 2 H).

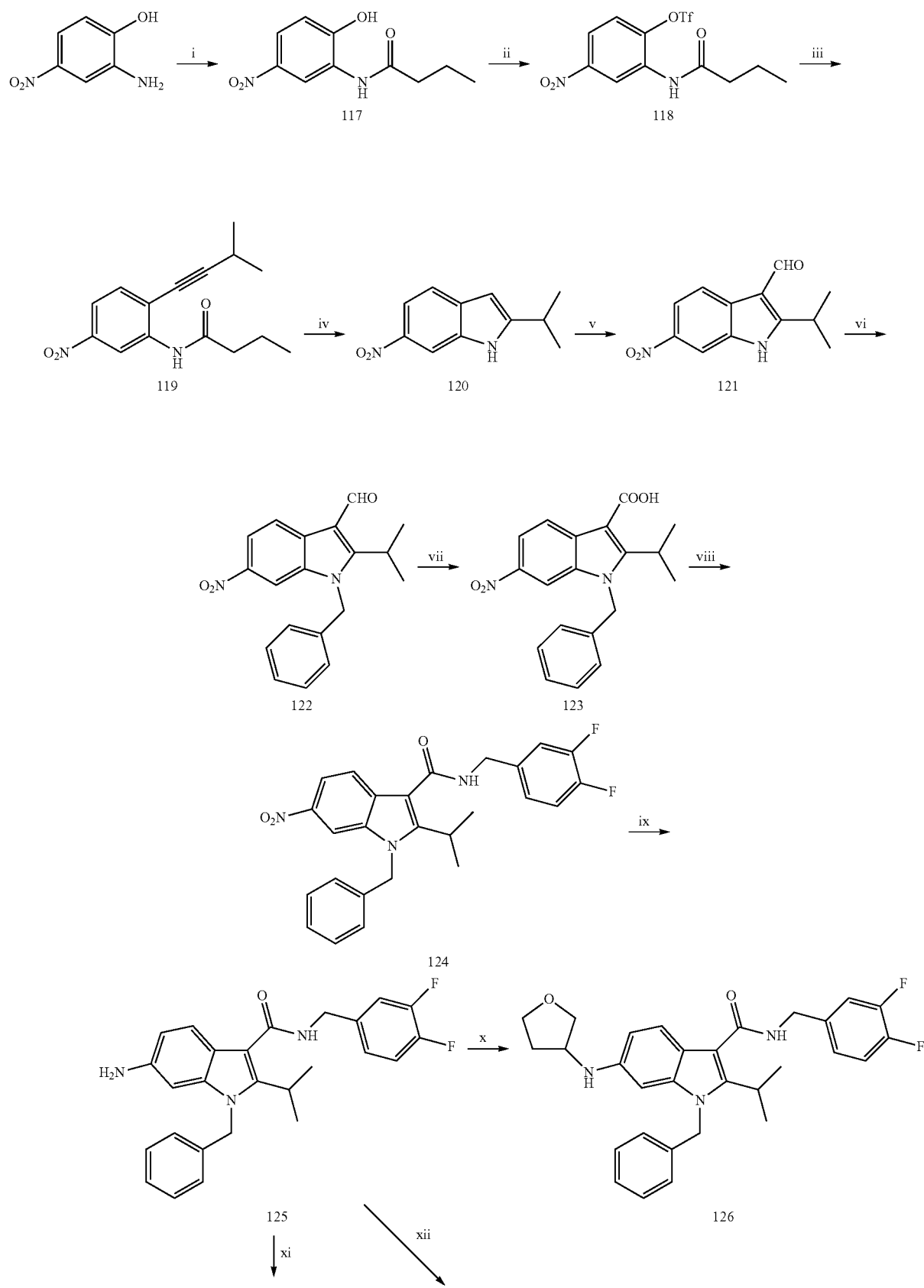

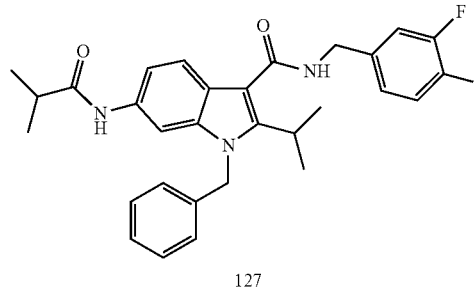

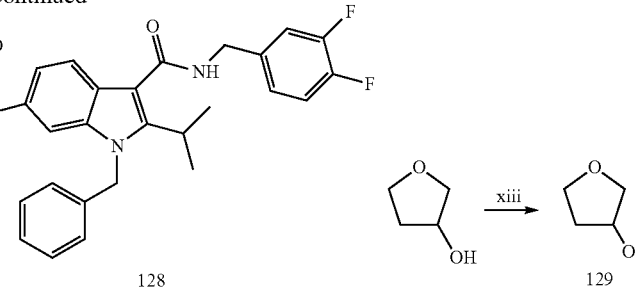

127  128  129

<sup>a</sup>Reagents and conditions: (i) n-PrCOCl, Pyridine, THF, reflux; (ii) Tf₂O, Et₃N, CH₂Cl₂; (iii) 3-methyl-1-butyne, Pd(PPh₃)₄, CuI, nBu₄NI, Et₃N, MeCN; (iv) t-BuOK, NMP; (v) POCl₃, DMF; (vi) Benzyl bromide, K₂CO₃, DMF; (vii) NaClO₂, NaH₂PO₄, t-BuOH, isobutene, H₂O; (viii) 3,4-difluorobenzyl amine, EDCI, DMAP, CH₂Cl₂; (ix) H₂, 10% wt Pd—C, EtOAc (x) compound 45, NaCNBH₃, MeOH, HOAc; (xi) i-PrCOCl, DMAP, CH₂Cl₂; (xii) Br(CH₂)₃COOCH₃, NMP; (xiii) PCC, CH₂Cl₂.

EXAMPLE 117

N-(2-Hydroxy-5-nitrophenyl)butyramide (Compound 117). To a solution of 2-amino-4-nitrophenol (Aldrich, 1.0 g, 6.5 mmol) in THF (25 ml) was added n-PrCOCl (694 mg, 6.5 mmol) and pyridine (2.6 ml, 32.4 mmol). The reaction was refluxed for 5 days, diluted with EtOAc, washed with H₂O and brine, dried over Na₂SO₄, and concentrated in vacuo. The residue was purified by chromatography on silica gel (0→50% EtOAc-hexanes) to yield the title compound as a brown solid.

1H NMR (300 MHz, acetone) δ ppm 0.99 (t, J=7.5 Hz, 3 H), 1.60-1.89 (m, 2 H), 2.54 (t, J=7.5 Hz, 2 H), 7.07 (d, J=8.8 Hz, 1 H), 7.92 (dd, J=8.9, 2.8 Hz, 1 H), 8.83 (d, J=2.9 Hz, 1 H), 9.10 (s, 1 H), 10.68 (s, 1 H).

EXAMPLE 118

2-Butyramido-4-nitrophenyl trifluoromethanesulfonate (Compound 118). To a solution of N-(2-hydroxy-5-nitrophenyl)butyramide (Compound 117, 1.75 g, 7.8 mmol) in CH₂Cl₂ (40 ml) at 0° C. was added Et₃N (1.4 ml, 10.1 mmol) and Tf₂O (1.7 ml, 10.2 mmol). After 10 min, the reaction was diluted with CH₂Cl₂, washed with H₂O and brine, dried over Na₂SO₄, and concentrated in vacuo. The residue was purified by chromatography on silica gel (0→25% EtOAc-hexanes) to yield the title compound.

1H NMR (300 MHz, CHLOROFORM-d) δ ppm 1.05 (t, J=7.5 Hz, 3 H), 1.73-1.89 (m, 2 H), 2.46 (t, J=7.5 Hz, 2 H), 7.44 (s, 1 H), 7.49 (d, J=9.1 Hz, 1 H), 8.05 (dd, J=9.1, 2.6 Hz, 1 H), 9.34 (d, J=2.6 Hz, 1 H).

EXAMPLE 119

N-(2-(3-Methylbut-1-ynyl)-5-nitrophenyl)butyramide (Compound 119). A mixture of 2-butyramido-4-nitrophenyl trifluoromethanesulfonate (Compound 118, 200 mg, 0.56 mmol), CuI (32 mg, 0.17 mmol), and n-Bu₄NI (311 mg, 0.84 mmol) in CH₃CN (5 ml) and Et₃N (1 ml) was purged with N₂ for 10 min and Pd(PPh₃)₄ (64 mg, 0.056 mmol) was added and the mixture was purged with N₂ for another 5 min. The mixture was then cooled to 0° C. and 3-methyl-1-butyne (76 mg, 1.12 mmol) was added. After 5 min, the reaction was quenched with aqueous NaHCO₃, extracted with EtOAc (×3). The combined organic layer was washed with brine, dried over Na₂SO₄, and concentrated in vacuo. The residue was purified by chromatography on silica gel (0→20% EtOAc-hexanes) to yield the title compound.

1H NMR (300 MHz, CHLOROFORM-d) δ ppm 1.06 (t, J=7.5 Hz, 3 H), 1.36 (d, J=6.7 Hz, 6 H), 1.72-1.92 (m, 2 H), 2.44 (t, J=7.5 Hz, 2 H), 2.85-3.01 (m, 1 H), 7.49 (d, J=8.5 Hz, 1 H), 7.88 (dd, J=8.8, 2.3 Hz, 1 H), 8.04 (s, 1 H), 9.33 (d, J=2.3 Hz, 1 H).

EXAMPLE 120

2-Isopropyl-6-nitro-1H-indole (Compound 120). To a solution of N-(2-(3-methylbut-1-ynyl)-5-nitrophenyl)butyramide (Compound 119, 900 mg, 3.29 mmol) in NMP (10 ml) was added KOt-Bu (552 mg, 4.94 mmol) and the mixture was stirred at 70° C. for 16 h, cooled to room temperature, diluted with EtOAc, washed with brine, dried over Na₂SO₄, and concentrated in vacuo. The residue was purified by chromatography on silica gel (0→25% EtOAc-hexanes) to yield the title compound.

1H NMR (300 MHz, CHLOROFORM-d) δ ppm 1.41 (d, J=7.0 Hz, 6 H), 3.07-3.22 (m, 1 H), 6.38 (d, J=2.3 Hz, 1 H), 7.56 (d, J=8.8 Hz, 1 H), 8.00 (dd, J=8.8, 2.1 Hz, 1 H), 8.28 (d, J=2.1 Hz, 1 H).

EXAMPLE 121

2-isopropyl-6-nitro-1H-indole-3-carbaldehyde (Compound 121). POCl₃ (0.12 ml, 1.4 mmol) was added dropwise to anhydrous DMF (1.5 ml) at 0° C. under argon. After stirred for 20 min, a solution of 2-isopropyl-6-nitro-1H-indole (Compound 120, 115 mg, 0.56 mmol) in anhydrous DMF (1.5 ml) was added slowly to the above reaction and stirred for 1 h at 0° C. and 2 h at room temperature. The reaction was diluted with EtOAc, washed with H₂O and brine, dried over Na₂SO₄, and concentrated in vacuo. The residue was purified by chromatography on silica gel (0→50% EtOAc-hexanes) to yield the title compound.

1H NMR (300 MHz, CHLOROFORM-d) δ ppm 1.44 (d, J=7.0 Hz, 6 H), 3.65-3.84 (m, 1 H), 7.38 (s, 1 H), 8.04-8.12 (m, 1 H), 8.18-8.32 (m, 2 H), 10.13 (s, 1 H).

EXAMPLE 122

1-Benzyl-2-isopropyl-6-nitro-1H-indole-3-carbaldehyde (Compound 122). To a solution of 2-isopropyl-6-nitro-1H-indole-3-carbaldehyde (Compound 121, 244 mg, 1.05 mmol) in DMF (10 ml) was added benzyl bromide (0.62 ml, 5.26 mmol) and K₂CO₃ (726 mg, 5.26 mmol). The reaction was stirred at room temperature for 16 h, diluted with EtOAc, washed with H₂O and brine, dried over Na₂SO₄, and concentrated in vacuo. The residue was purified by chromatography on silica gel (0→50% EtOAc-hexanes) to yield the title compound.

1H NMR (300 MHz, CHLOROFORM-d) δ ppm 1.49 (d, J=7.0 Hz, 6 H), 3.45-3.60 (m, 1 H), 5.54 (s, 2 H), 6.94-7.02 (m, 2 H), 7.29-7.41 (m, 3 H), 8.16-8.24 (m, 2 H), 8.49 (d, J=8.5 Hz, 1 H), 10.51 (s, 1 H).

EXAMPLE 123

1-Benzyl-2-isopropyl-6-nitro-1H-indole-3-carboxylic acid (Compound 123). The title compound was prepared from 1-benzyl-2-isopropyl-6-nitro-1H-indole-3-carbaldehyde (Compound 122) by General Procedure K.

1H NMR (300 MHz, METHANOL-$d_4$) δ ppm 1.40 (d, J=7.3 Hz, 6 H), 3.87-4.10 (m, 1 H), 5.72 (s, 2 H), 6.98 (dd, J=7.3, 1.5 Hz, 2 H), 7.22-7.41 (m, 3 H), 8.07 (dd, J=8.9, 2.2 Hz, 1 H), 8.22-8.35 (m, 2 H).

EXAMPLE 124

1-Benzyl-N-(3,4-difluorobenzyl)-2-isopropyl-6-nitro-1H-indole-3-carboxamide (Compound 124). The title compound was prepared from 1-benzyl-2-isopropyl-6-nitro-1H-indole-3-carboxylic acid (Compound 123) by General Procedure C.

1H NMR (300 MHz, CHLOROFORM-d) δ ppm 1.42 (d, J=7.3 Hz, 6 H), 3.51-3.67 (m, 1 H), 4.70 (d, J=6.2 Hz, 2 H), 5.53 (s, 2 H), 6.28 (t, J=6.9 Hz, 1 H), 6.94 (dd, J=7.2, 1.9 Hz, 2 H), 7.12-7.19 (m, 2 H), 7.19-7.37 (m, 4 H), 7.69 (d, J=8.8 Hz, 1 H), 8.08 (dd, J=8.8, 2.1 Hz, 1 H), 8.18 (d, J=1.8 Hz, 1 H).

EXAMPLE 125

6-Amino-1-benzyl-N-(3,4-difluorobenzyl)-2-isopropyl-1H-indole-3-carboxamide (Compound 125). General Procedure S. A solution of 1-benzyl-N-(3,4-difluorobenzyl)-2-isopropyl-6-nitro-1H-indole-3-carboxamide (Compound 124, 300 mg, 0.65 mmol) in EtOAc (5 ml) was treated with 10% Pd—C (6.8 mg, 0.065 mmol) and hydrogen gas under atmospheric pressure at room temperature for 16 h. The mixture was filtered and concentrated in vacuo. The residue was purified by chromatography on silica gel (0→50% EtOAc-hexanes) to yield the title compound as a yellow oil.

1H NMR (300 MHz, METHANOL-$d_4$) δ ppm 1.31 (d, J=7.3 Hz, 6 H), 3.38-3.58 (m, 1 H), 4.56 (s, 2 H), 5.41 (s, 2 H), 6.58-6.73 (m, 2 H), 6.89-7.01 (m, 2 H), 7.16-7.37 (m, 6 H), 7.39 (d, J=8.5 Hz, 1 H).

EXAMPLE 126

1-Benzyl-N-(3,4-difluorobenzyl)-2-isopropyl-6-(tetrahydrofuran-3-ylamino)-1H-indole-3-carboxamide (Compound 126). General Procedure T. To a solution of 6-amino-1-benzyl-N-(3,4-difluorobenzyl)-2-isopropyl-1H-indole-3-carboxamide (Compound 125, 15 mg, 0.035 mmol) in MeOH (1 ml) was added dihydrofuran-3(2H)-one (Compound 129, 6.0 mg, 0.069 mmol), NaBH$_3$CN (2.2 mg, 0.035 mmol), and HOAc (1 drop). The reaction was stirred at room temperature for 3 h, diluted with EtOAc, washed with aqueous Na$_2$CO$_3$ and brine, dried over Na$_2$SO$_4$, and concentrated in vacuo. The residue was purified by chromatography on silica gel (0→50% EtOAc-hexanes) to yield the title compound.

1H NMR (300 MHz, CHLOROFORM-d) δ ppm 1.38 (d, J=7.0 Hz, 6 H), 1.69-1.83 (m, 1 H), 2.08-2.23 (m, 1 H), 3.61 (dd, J=9.4, 2.9 Hz, 1 H), 3.70-3.94 (m, 4 H), 3.96-4.05 (m, 1 H), 4.66 (d, J=5.9 Hz, 2 H), 5.38 (s, 2 H), 6.23-6.34 (m, 2 H), 6.53 (dd, J=8.5, 1.8 Hz, 1 H), 7.00 (d, J=8.2 Hz, 2 H), 7.11-7.19 (m, 2 H), 7.20-7.34 (m, 4 H), 7.43 (d, J=8.8 Hz, 1 H).

EXAMPLE 127

1-Benzyl-N-(3,4-difluorobenzyl)-6-isobutyramido-2-isopropyl-1H-indole-3-carboxamide (Compound 127). To a solution of 6-amino-1-benzyl-N-(3,4-difluorobenzyl)-2-isopropyl-1H-indole-3-carboxamide (Compound 125, 18 mg, 0.042 mmol) in CH$_2$Cl$_2$ (1 ml) was added i-PrCOCl (8.7 μl, 0.089 mmol) and DMAP (10 mg, 0.089 mmol). The reaction was stirred at room temperature for 2 h, diluted with EtOAc, washed with aqueous Na$_2$CO$_3$ and brine, dried over Na$_2$SO$_4$, and concentrated in vacuo. The residue was purified by chromatography on silica gel (0→50% EtOAc-hexanes) to yield the title compound.

1H NMR (300 MHz, CHLOROFORM-d) δ ppm 1.21 (d, J=6.7 Hz, 6 H), 1.34 (d, J=7.0 Hz, 6 H), 2.38-2.56 (m, 1 H), 3.48-3.65 (m, 1 H), 4.65 (d, J=6.2 Hz, 2 H), 5.39 (s, 2 H), 6.31 (t, J=6.0 Hz, 1 H), 6.88-6.95 (m, 2 H), 6.99 (dd, J=8.5, 1.8 Hz, 1 H), 7.09-7.17 (m, 2 H), 7.19-7.29 (m, 4 H), 7.32 (s, 1 H), 7.51 (d, J=8.5 Hz, 1 H), 7.84 (d, J=1.5 Hz, 1 H).

EXAMPLE 128

1-Benzyl-N-(3,4-difluorobenzyl)-2-isopropyl-6-(2-oxopyrrolidin-1-yl)-1H-indole-3-carboxamide (Compound 128). A solution of 6-amino-1-benzyl-N-(3,4-difluorobenzyl)-2-isopropyl-1H-indole-3-carboxamide (Compound 125, 20 mg, 0.046 mmol) and ethyl 4-bromobutanoate (13 μl, 0.092 mmol) in NMP (1 ml) was heated at 168° C. for 16 h, cooled to room temperature, diluted with EtOAc, washed with brine, dried over Na$_2$SO$_4$, and concentrated in vacuo. The residue was purified by chromatography on silica gel (0→50% EtOAc-hexanes) to yield the title compound.

1H NMR (300 MHz, CHLOROFORM-d) δ ppm 1.37 (d, J=7.0 Hz, 6 H), 2.06-2.20 (m, 2 H), 2.57 (t, J=8.1 Hz, 2 H), 3.59-3.74 (m, 1 H), 3.78-3.88 (m, 2 H), 4.66 (d, J=5.9 Hz, 2 H), 5.44 (s, 2 H), 6.30 (t, J=6.4 Hz, 1 H), 6.94 (dd, J=7.9, 1.8 Hz, 2 H), 7.10-7.18 (m, J=8.8, 4.7 Hz, 2 H), 7.20-7.33 (m, 5 H), 7.56-7.63 (m, 2 H).

EXAMPLE 129

Dihydrofuran-3(2H)-one (Compound 129). To a suspension of PCC (4.2 g, 19.3 mmol) and 4 Å molecular sieves (2.0 g) in CH$_2$Cl$_2$ (40 ml) was added a solution of tetrahydrofuran-3-ol (Aldrich, 0.92 ml, 11.4 mmol) in CH$_2$Cl$_2$ (20 ml) and the mixture was heated to reflux for 16 h, cooled to room temperature, filtered through Celite, diluted with Et$_2$O, filtered again through Celite, washed successively with 2 M HCl, H$_2$O, and brine, dried over Na$_2$SO$_4$, and concentrated in vacuo. The crude was used without further purification.

EXAMPLE 130

1-Benzyl-6-(cyclopentylamino)-N-(3,4-difluorobenzyl)-2-isopropyl-1H-indole-3-carboxamide (Compound 130). The title compound was prepared from 6-amino-1-benzyl-N-(3,4-difluorobenzyl)-2-isopropyl-1H-indole-3-carboxamide (Compound 125) and cyclopentanone by General Procedure T.

1H NMR (300 MHz, CHLOROFORM-d) δ ppm 1.31-1.47 (m, 1 H), 1.37 (d, J=7.3 Hz, 6 H), 1.50-1.76 (m, 3 H), 1.84-2.02 (m, 3 H), 2.12-2.23 (m, 1 H), 3.61-3.86 (m, 2 H), 4.66 (d, J=6.2 Hz, 2 H), 5.37 (s, 2 H), 6.25-6.37 (m, 2 H), 6.53 (dd, J=8.6, 1.9 Hz, 1 H), 6.96-7.06 (m, 2 H), 7.10-7.18 (m, 2 H), 7.19-7.34 (m, 4 H), 7.40 (d, J=8.5 Hz, 1 H).

EXAMPLE 131

1-Benzyl-N-(3,4-difluorobenzyl)-2-isopropyl-6-(1,3-oxazol-2-ylmethoxy)-1H-indole-3-carboxamide (Compound 131). The title compound was prepared from 1-benzyl-N-(3,4-difluorobenzyl)-6-hydroxy-2-isopropyl-1H-indole-3-carboxamide (Compound 8) and 2-(chloromethyl)oxazole by General Procedure N.

1H NMR (300 MHz, CHLOROFORM-d) δ ppm 1.38 (d, J=7.3 Hz, 6 H), 3.62-3.79 (m, 1 H), 4.67 (d, J=5.9 Hz, 2 H), 5.09 (s, 2 H), 5.40 (s, 2 H), 6.30 (t, J=6.0 Hz, 1H), 6.79 (d, J=2.1 Hz, 1 H), 6.88-7.00 (m, 3 H), 7.07 (s, 1 H), 7.11-7.19 (m, 2 H), 7.19-7.34 (m, 4 H), 7.54 (d, J=8.5 Hz, 1 H), 7.61 (s, 1 H).

EXAMPLE 132

1-Benzyl-N-(3,4-difluorobenzyl)-2-isopropyl-6-(1,3-thiazol-2-yloxy)-1H-indole-3-carboxamide (Compound 132). General Procedure U. To a solution of 1-benzyl-N-(3,4-difluorobenzyl)-6-hydroxy-2-isopropyl-1H-indole-3-carboxamide (Compound 8, 12 mg, 0.028 mmol) in DMF (1 ml) was added $K_2CO_3$ (19 mg, 0.14 mmol) and 2-bromothiazole (23 mg, 0.14 mmol). The mixture was stirred at room temperature overnight and a small amount of NaOH was added. The reaction was kept stirring for 72 h, diluted with EtOAc, washed with brine, dried over $Na_2SO_4$, and concentrated in vacuo. The residue was purified by chromatography on silica gel (0→50% EtOAc-hexanes) to yield the title compound.

1H NMR (300 MHz, CHLOROFORM-d) δ ppm 1.39 (d, J=7.0 Hz, 6 H), 3.61-3.76 (m, 1 H), 4.67 (d, J=5.6 Hz, 2 H), 5.42 (s, 2 H), 6.24-6.32 (m, 1 H), 6.74 (d, J=3.8 Hz, 1 H), 6.94 (dd, J=8.1, 1.3 Hz, 3 H), 7.06-7.32 (m, 8 H), 7.65 (d, J=9.1 Hz, 1 H).

EXAMPLE 133

1-Benzyl-N-(3,4-difluorobenzyl)-2-isopropyl-6-(tetrahydro-2H-pyran-4-yloxy)-1H-indole-3-carboxamide (Compound 133). The title compound was prepared from 1-benzyl-N-(3,4-difluorobenzyl)-6-hydroxy-2-isopropyl-1H-indole-3-carboxamide (Compound 8) and 4-iodotetrahydro-2H-pyran (Maybridge) by General Procedure N.

1H NMR (300 MHz, CHLOROFORM-d) δ ppm 1.38 (d, J=7.0 Hz, 6 H), 1.62-1.78 (m, 2 H), 1.83-1.96 (m, 2 H), 3.42-3.56 (m, 2 H), 3.65-3.80 (m, 1 H), 3.87-3.99 (m, 2 H), 4.28-4.41 (m, 1 H), 4.66 (d, J=5.9 Hz, 2 H), 5.39 (s, 2 H), 6.28 (t, J=5.7 Hz, 1 H), 6.66 (d, J=2.1 Hz, 1 H), 6.83 (dd, J=8.6, 2.2 Hz, 1 H), 6.93-7.01 (m, 2 H), 7.10-7.18 (m, 2 H), 7.18-7.34 (m, 4 H), 7.51 (d, J=8.8 Hz, 1 H).

Scheme 12$^a$

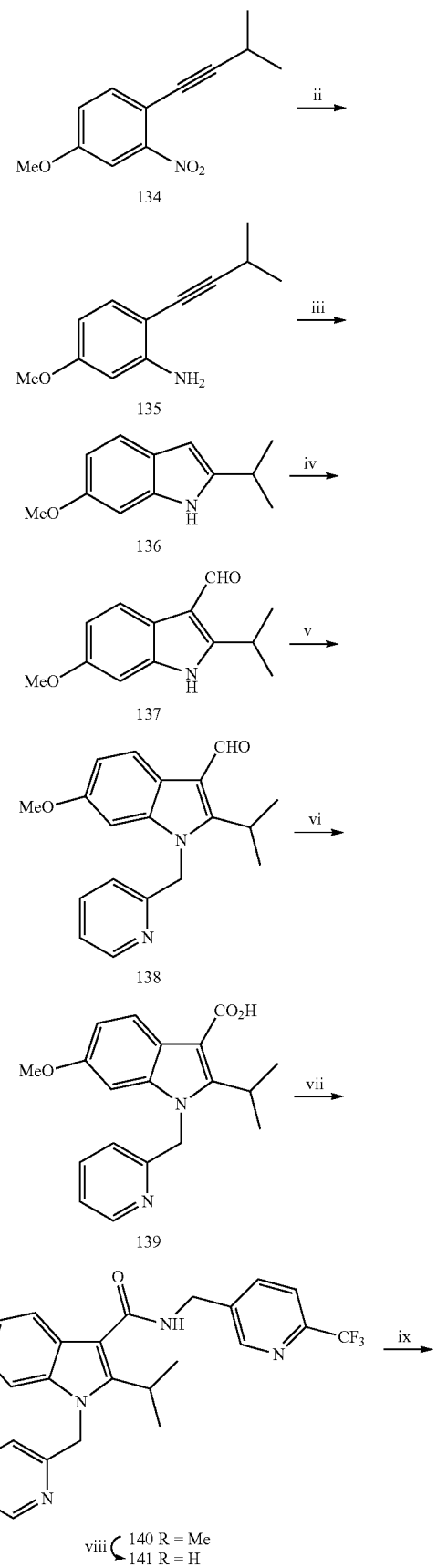

-continued

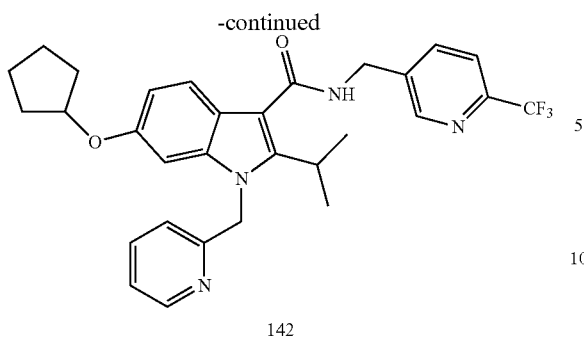

142

<sup>a</sup>Reagents and conditions: (i) 3-methyl-1-butyne, Pd(PPh₃)₂Cl₂, CuI, Et₃N, DMF; (ii) SnCl₂, NaBH₄, THF, EtOH; (iii) CuI, DMF; (iv) POCl₃, DMF; (v) 2-bromomethylpyridine•HBr, K₂CO₃, DMF; (vi) NaClO₂, NaH₂PO₄, t-BuOH, isobutene, H₂O; (vii) (6-(trifluoromethyl)pyridin-3-yl)methanamine, EDCI, DMAP, CH₂Cl₂; (viii) BBr₃, CH₂Cl₂; (ix) c-C₅H₉I, K₂CO₃, DMF.

EXAMPLE 134

4-Methoxy-1-(3-methylbut-1-ynyl)-2-nitrobenzene (Compound 134). To a solution of 1-iodo-4-methoxy-2-nitrobenzene (Aldrich, 10 g, 35.8 mmol) in Et₃N (60 ml) and DMF (6 ml) was added CuI (34 mg, 0.18 mmol), Pd(PPh₃)₂Cl₂ (126 mg, 0.18 mmol), and 3-methyl-1-butyne (5.0 ml, 73.5 mmol). The mixture was stirred at room temperature for 16 h and was concentrated. The resulting mixture was diluted with EtOAc, washed with H₂O, brine, dried over Na₂SO₄ and concentrated in vacuo. The residue was purified by chromatography on silica gel (0→15% EtOAc-hexanes) to yield the title compound as a brown oil.

1H NMR (300 MHz, CHLOROFORM-d) δ ppm 1.27 (d, J=6.4 Hz, 6 H), 2.70-2.92 (m, 1 H), 3.86 (s, 3 H), 7.06 (dd, J=8.9, 2.8 Hz, 1 H), 7.40-7.50 (m, 2 H).

EXAMPLE 135

5-Methoxy-2-(3-methylbut-1-ynyl)aniline (Compound 135). To a solution of 4-methoxy-1-(3-methylbut-1-ynyl)-2-nitrobenzene (Compound 134, 2.97 g, 13.6 mmol) in THF (45 ml) and EtOH (15 ml) at 0° C. was added SnCl₂ (12.9 g, 68 mmol), followed by NaBH₄ (3.1 g, 81.6 mmol) in three equal portions with one hour between each addition. The reaction was stirred at 0° C. for a total of 3.5 h and was quenched with aqueous ammonia, filtered through a pad of Celite, extracted with EtOAc (×3). The combined organic layer was washed with brine, dried over Na₂SO₄, and concentrated in vacuo. The residue was purified by chromatography on silica gel (0→20% EtOAc-hexanes) to yield the title compound.

1H NMR (300 MHz, CHLOROFORM-d) δ ppm 1.27 (d, J=7.0 Hz, 6 H), 2.73-2.90 (m, 1 H), 3.75 (s, 3 H), 4.16 (s, 2 H), 6.16-6.34 (m, 2 H), 7.15 (d, J=8.2 Hz, 1 H).

EXAMPLE 136

2-Isopropyl-6-methoxy-1H-indole (Compound 136). To a solution of 5-methoxy-2-(3-methylbut-1-ynyl)aniline (Compound 135, 1.8 g, 9.5 mmol) in DMF (20 ml) was added CuI (101 mg, 0.53 mmol). The reaction was stirred at 160° C. for 1.5 h. The solvent was removed in vacuo and the residue was purified by chromatography on silica gel (0→25% EtOAc-hexanes) to yield the title compound as a brownish red solid.

1H NMR (300 MHz, CHLOROFORM-d) δ ppm 1.34 (d, J=7.0 Hz, 6 H), 2.97-3.10 (m, 1 H), 3.83 (s, 3 H), 6.13-6.19 (m, 1 H), 6.74 (dd, J=8.5, 2.3 Hz, 1 H), 6.83 (d, J=2.3 Hz, 1 H), 7.39 (d, J=8.8 Hz, 1 H), 7.76 (s, 1 H).

EXAMPLE 137

2-Isopropyl-6-methoxy-1H-indole-3-carbaldehyde (Compound 137). The title compound was prepared from 2-isopropyl-6-methoxy-1H-indole (Compound 136) by General Procedure I.

1H NMR (300 MHz, CHLOROFORM-d) δ ppm 1.44 (d, J=7.0 Hz, 6 H), 3.70-3.82 (m, 1 H), 3.84 (s, 3 H), 6.86 (d, J=2.1 Hz, 1 H), 6.91 (dd, J=8.8, 2.3 Hz, 1 H), 8.14 (d, J=8.8 Hz, 1 H), 8.36 (s, 1 H), 10.21 (s, 1 H).

EXAMPLE 138

2-Isopropyl-6-methoxy-1-(pyridin-2-ylmethyl)-1H-indole-3-carbaldehyde (Compound 138). The title compound was prepared from 2-isopropyl-6-methoxy-1H-indole-3-carbaldehyde (Compound 139) by General Procedure J.

1H NMR (300 MHz, CHLOROFORM-d) δ ppm 1.45 (d, J=7.0 Hz, 6 H), 3.43-3.64 (m, 1 H), 3.79 (s, 3 H), 5.50 (s, 2 H), 6.59-6.77 (m, 2 H), 6.94 (dd, J=8.5, 2.1 Hz, 1 H), 7.17-7.26 (m, 1 H), 7.50-7.67 (m, 1 H), 8.28 (d, J=8.8 Hz, 1 H), 8.62 (d, J=5.3 Hz, 1 H), 10.44 (s, 1 H).

EXAMPLE 139

2-Isopropyl-6-methoxy-1-(pyridin-2-ylmethyl)-1H-indole-3-carboxylic acid (Compound 139). The title compound was prepared from 2-isopropyl-6-methoxy-1-(pyridin-2-ylmethyl)-1H-indole-3-carbaldehyde (Compound 138) by General Procedure K.

1H NMR (300 MHz, CHLOROFORM-d) δ ppm 1.39 (d, J=7.0 Hz, 6 H), 3.76 (s, 3 H), 4.06-4.29 (m, 1 H), 5.58 (s, 2 H), 6.56 (d, J=7.9 Hz, 1 H), 6.62 (d, J=2.3 Hz, 1 H), 6.92 (dd, J=8.8, 2.3 Hz, 1 H), 7.16-7.24 (m, 1 H), 7.49-7.60 (m, 1 H), 8.15 (d, J=9.1 Hz, 1 H), 8.64 (d, J=5.3 Hz, 1 H).

EXAMPLE 140

2-Isopropyl-6-methoxy-1-(pyridin-2-ylmethyl)-N-((6-(trifluoromethyl)pyridin-3-yl)methyl)-1H-indole-3-carboxamide (Compound 140). The title compound was prepared from 2-isopropyl-6-methoxy-1-(pyridin-2-ylmethyl)-1H-indole-3-carboxylic acid (Compound 139) and (6-(trifluoromethyl)pyridin-3-yl)methanamine by General Procedure C.

1H NMR (300 MHz, CHLOROFORM-d) δ ppm 1.37 (d, J=7.0 Hz, 6 H), 3.68-3.87 (m, 4 H), 4.81 (d, J=6.2 Hz, 2 H), 5.52 (s, 2 H), 6.41 (t, J=5.9 Hz, 1 H), 6.52 (d, J=7.9 Hz, 1 H), 6.64 (d, J=2.1 Hz, 1 H), 6.85 (dd, J=8.6, 2.2 Hz, 1 H), 7.19 (dd, J=7.5, 4.8 Hz, 1 H), 7.47-7.58 (m, 2 H), 7.69 (d, J=7.9 Hz, 1 H), 7.98 (d, J=8.5 Hz, 1 H), 8.62 (d, J=4.7 Hz, 1 H), 8.79 (s, 1 H).

EXAMPLE 141

6-Hydroxy-2-isopropyl-1-(pyridin-2-ylmethyl)-N-((6-(trifluoromethyl)pyridin-3-yl)methyl)-1H-indole-3-carboxamide (Compound 141). The title compound was prepared from 2-isopropyl-6-methoxy-1-(pyridin-2-ylmethyl)-N-((6-(trifluoromethyl)pyridin-3-yl)methyl)-1H-indole-3-carboxamide (Compound 140) by General Procedure L.

1H NMR (300 MHz, CHLOROFORM-d) δ ppm 1.36 (d, J=7.3 Hz, 6 H), 3.71-3.86 (m, 1 H), 4.80 (d, J=6.2 Hz, 2 H), 5.49 (s, 2 H), 6.40 (t, J=6.2 Hz, 1 H), 6.52-6.60 (m, 2 H), 6.74

(dd, J=8.5, 2.1 Hz, 1 H), 7.15-7.23 (m, 1 H), 7.45-7.59 (m, 2 H), 7.69 (d, J=8.2 Hz, 1 H), 7.98 (dd, J=7.3, 2.3 Hz, 1 H), 8.56 (d, J=4.7 Hz, 1 H), 8.79 (d, J=2.3 Hz, 1 H).

EXAMPLE 142

6-(Cyclopentyloxy)-2-isopropyl-1-(pyridin-2-ylmethyl)-N-((6-(trifluoromethyl)pyridin-3-yl)methyl)-1H-indole-3-carboxamide (Compound 142). The title compound was prepared from 6-hydroxy-2-isopropyl-1-(pyridin-2-ylmethyl)-N-((6-(trifluoromethyl)pyridin-3-yl)methyl)-1H-indole-3-carboxamide (Compound 141) and cyclopentyl iodide by General Procedure N.

1H NMR (300 MHz, CHLOROFORM-d) δ ppm 1.36 (d, J=7.0 Hz, 6 H), 1.49-1.64 (m, 2 H), 1.67-1.88 (m, 6 H), 3.71-3.91 (m, 1 H), 4.67 (s, 1 H), 4.80 (d, J=5.9 Hz, 2 H), 5.51 (s, 2 H), 6.46 (t, J=5.9 Hz, 1 H), 6.53 (d, J=7.9 Hz, 1 H), 6.62 (d, J=2.1 Hz, 1 H), 6.81 (dd, J=8.8, 2.1 Hz, 1 H), 7.18 (dd, J=7.3, 5.0 Hz, 1 H), 7.46-7.57 (m, 2 H), 7.68 (d, J=8.2 Hz, 1 H), 7.97 (d, J=7.9 Hz, 1 H), 8.61 (d, J=4.1 Hz, 1 H), 8.78 (s, 1 H).

EXAMPLE 143

N-(3,4-Difluorobenzyl)-2-isopropyl-1-(pyridin-2-ylmethyl)-6-(tetrahydro-2H-pyran-4-yloxy)-1H-indole-3-carboxamide (Compound 143). The title compound was prepared from 2-isopropyl-6-methoxy-1-(pyridin-2-ylmethyl)-1H-indole-3-carboxylic acid (Compound 139) by, in order, General Procedure C, General Procedure L, and General Procedure N.

1H NMR (300 MHz, CHLOROFORM-d) δ ppm 1.38 (d, J=7.0 Hz, 6 H), 1.62-1.79 (m, 2 H), 1.84-1.98 (m, 2 H), 3.44-3.57 (m, 2 H), 3.71-3.87 (m, 1 H), 3.87-4.00 (m, 2 H), 4.31-4.44 (m, 1 H), 4.67 (d, J=6.2 Hz, 2 H), 5.50 (s, 2 H), 6.28 (t, J=5.4 Hz, 1 H), 6.54 (d, J=7.9 Hz, 1 H), 6.68 (d, J=2.1 Hz, 1 H), 6.85 (dd, J=8.6, 2.2 Hz, 1 H), 7.09-7.31 (m, 4 H), 7.45-7.58 (m, 2 H), 8.62 (d, J=4.7 Hz, 1 H).

Scheme 13<sup>a</sup>

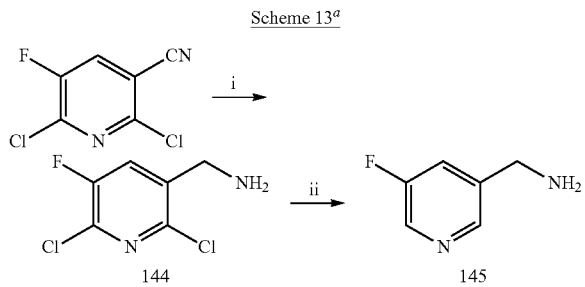

<sup>a</sup>Reagents and conditions: (i) 50 psi H₂, Pd—C, 6M HCl, MeOH; (ii) 51 psi H₂, Pd—C, 28% NH₃·H₂O, MeOH.

EXAMPLE 144

(2,6-Dichloro-5-fluoropyridin-3-yl)methanamine (Compound 144). To a Parr reaction bottle was added Pd—C (10%, 560 mg, 0.52 mmol), followed by 6 M HCl (50 ml) and a solution of 2,6-dichloro-5-fluoronicotinonitrile (Aldrich, 10.0 g, 52.4 mmol) in MeOH (100 ml). The mixture was placed under 50 psi H₂ on a shaker type Parr apparatus for 21 h, filtered and concentrated. The crude was dissolved in EtOAc, basified with aqueous NaOH, and the layers were separated. The organic layer was washed with brine, dried over Na₂SO₄, and concentrated in vacuo to yield the title compound as crude light yellow oil. Used without further purification.

1H NMR (300 MHz, METHANOL-d₄) δ ppm 4.31 (s, 2 H), 8.06 (d, J=8.2 Hz, 1 H).

EXAMPLE 145

(5-Fluoropyridin-3-yl)methanamine (Compound 145). To a Parr reaction bottle was added Pd—C (10%, 560 mg, 0.52 mmol), followed by 28% NH₃.H₂O (50 ml) and a solution of (2,6-dichloro-5-fluoropyridin-3-yl)methanamine (Compound 144, 10.1 g, 52 mmol) in MeOH (100 ml). The mixture was placed under 51 psi H₂ on a shaker type Parr apparatus for 16 h, filtered and concentrated. The resulting aqueous solution was basified with NaOH, extracted with EtOAc (×3). The combined organic layer was washed with brine, dried over Na₂SO₄, and concentrated in vacuo. The crude product was purified by distillation under vacuum to yield the title compound as colorless oil.

1H NMR (300 MHz, METHANOL-d₄) δ ppm 3.87 (s, 2 H), 7.61-7.73 (m, 1 H), 8.25-8.44 (m, 2 H).

EXAMPLE 146

N-((5-Fluoropyridin-3-yl)methyl)-2-isopropyl-6-methoxy-1-(pyridin-2-ylmethyl)-1H-indole-3-carboxamide (Compound 146). The title compound was prepared from 2-isopropyl-6-methoxy-1-(pyridin-2-ylmethyl)-1H-indole-3-carboxylic acid (Compound 139) and (5-fluoropyridin-3-yl)methanamine (Compound 145) by General Procedure C.

1H NMR (300 MHz, METHANOL-d₄) δ ppm 1.30 (d, J=7.0 Hz, 6 H), 3.38-3.57 (m, 1 H), 3.73 (s, 3 H), 4.67 (s, 2 H), 5.56 (s, 2 H), 6.63 (d, J=7.9 Hz, 1 H), 6.76-6.85 (m, 2 H), 7.29 (dd, J=6.9, 5.1 Hz, 1 H), 7.52 (d, J=9.1 Hz, 1 H), 7.62-7.75 (m, 2 H), 8.38 (d, J=2.6 Hz, 1 H), 8.50 (s, 1 H), 8.54 (d, J=4.1 Hz, 1 H).

EXAMPLE 147

N-((5-Fluoropyridin-3-yl)methyl)-6-hydroxy-2-isopropyl-1-(pyridin-2-ylmethyl)-1H-indole-3-carboxamide (Compound 147). The title compound was prepared from N-((5-fluoropyridin-3-yl)methyl)-2-isopropyl-6-methoxy-1-(pyridin-2-ylmethyl)-1H-indole-3-carboxamide (Compound 146) by General Procedure L.

1H NMR (300 MHz, METHANOL-d₄) δ ppm 1.30 (d, J=7.0 Hz, 6 H), 3.44-3.57 (m, 1 H), 4.67 (s, 2 H), 5.48 (s, 2 H), 6.57-6.65 (m, 2 H), 6.70 (dd, J=8.4, 1.9 Hz, 1 H), 7.29 (dd, J=7.2, 4.8 Hz, 1 H), 7.46 (d, J=8.8 Hz, 1 H), 7.61-7.74 (m, 2 H), 8.38 (d, J=2.6 Hz, 1 H), 8.50 (s, 1 H), 8.54 (d, J=5.0 Hz, 1 H).

EXAMPLE 148

6-(Cyclopentyloxy)-N-((5-fluoropyridin-3-yl)methyl)-2-isopropyl-1-(pyridin-2-ylmethyl)-1H-indole-3-carboxamide (Compound 148). The title compound was prepared from N-((5-fluoropyridin-3-yl)methyl)-6-hydroxy-2-isopropyl-1-(pyridin-2-ylmethyl)-1H-indole-3-carboxamide (Compound 147) by General Procedure N.

1H NMR (300 MHz, CHLOROFORM-d) δ ppm 1.37 (d, J=7.0 Hz, 6 H), 1.50-1.61 (m, 2 H), 1.67-1.84 (m, 6 H), 3.73-3.88 (m, 1 H), 4.62-4.71 (m, 1 H), 4.75 (d, J=5.9 Hz, 2 H), 5.50 (s, 2 H), 6.37 (t, J=6.0 Hz, 1 H), 6.53 (d, J=7.9 Hz, 1 H), 6.61 (d, J=2.1 Hz, 1 H), 6.76-6.85 (m, 1 H), 7.18 (dd, J=7.6, 5.0 Hz, 1 H), 7.47-7.57 (m, 3 H), 8.40 (d, J=2.3 Hz, 1 H), 8.49 (s, 1 H), 8.61 (d, J=3.8 Hz, 1 H).

EXAMPLE 149

N-((5-Fluoropyridin-3-yl)methyl)-6-isobutoxy-2-isopropyl-1-(pyridin-2-ylmethyl)-1H-indole-3-carboxamide (Compound 149). The title compound was prepared from N-((5-fluoropyridin-3-yl)methyl)-6-hydroxy-2-isopropyl-1-(pyridin-2-ylmethyl)-1H-indole-3-carboxamide (Compound 147) by General Procedure N.

1H NMR (300 MHz, METHANOL-$d_4$) δ ppm 0.98 (d, J=6.4 Hz, 6 H), 1.30 (d, J=7.3 Hz, 6 H), 1.91-2.06 (m, 1 H), 3.42-3.58 (m, 1 H), 3.66 (d, J=6.4 Hz, 2 H), 4.67 (s, 2 H), 5.54 (s, 2 H), 6.63 (d, J=7.9 Hz, 1 H), 6.75 (d, J=2.1 Hz, 1 H), 6.81 (dd, J=8.6, 2.2 Hz, 1 H), 7.29 (dd, J=7.3, 5.0 Hz, 1 H), 7.52 (d, J=8.8 Hz, 1 H), 7.61-7.75 (m, 2 H), 8.38 (d, J=2.6 Hz, 1 H), 8.50 (s, 1 H), 8.54 (d, J=5.0 Hz, 1 H).

EXAMPLE 150

N-(3,4-Difluorobenzyl)-2-isopropyl-1-(pyridin-2-ylmethyl)-6-(thiazol-2-yloxy)-1H-indole-3-carboxamide (Compound 150). The title compound was prepared from 2-isopropyl-6-methoxy-1-(pyridin-2-ylmethyl)-1H-indole-3-carboxylic acid (Compound 139) by, in order, General Procedure C, General Procedure L, and General Procedure U.

1H NMR (300 MHz, CHLOROFORM-d) δ ppm 1.37 (d, J=7.3 Hz, 6 H), 3.65-3.79 (m, 1 H), 4.66 (d, J=5.9 Hz, 2 H), 5.50 (s, 2 H), 6.31-6.41 (m, 1 H), 6.56 (d, J=7.9 Hz, 1 H), 6.74 (d, J=3.8 Hz, 1 H), 7.05-7.31 (m, 7 H), 7.48-7.58 (m, 1 H), 7.65 (d, J=9.1 Hz, 1 H), 8.58 (d, J=5.0 Hz, 1 H).

EXAMPLE 151

N-(3,4-Difluorobenzyl)-6-hydroxy-2-isopropyl-1-(pyridin-3-ylmethyl)-1H-indole-3-carboxamide (Compound 151). The title compound was prepared from 2-isopropyl-6-methoxy-1H-indole-3-carbaldehyde (Compound 137) and 3-(bromomethyl)pyridine.HBr by, in order, General Procedure J, General Procedure K, General Procedure C, and General Procedure L.

1H NMR (300 MHz, CHLOROFORM-d) δ ppm 1.37 (d, J=7.0 Hz, 6 H), 3.66-3.81 (m, 1 H), 4.66 (d, J=6.2 Hz, 2 H), 5.36 (s, 2 H), 6.28-6.36 (m, 1 H), 6.53 (d, J=1.2 Hz, 1 H), 6.73 (d, J=7.0 Hz, 1 H), 7.08-7.31 (m, 6 H), 7.46 (d, J=8.5 Hz, 1 H), 8.41 (d, J=36.9 Hz, 1 H).

EXAMPLE 152

N-(3,4-Difluorobenzyl)-2-isopropyl-1-(pyridin-3-ylmethyl)-6-(thiazol-2-yloxy)-1H-indole-3-carboxamide (Compound 152). The title compound was prepared from N-(3,4-difluorobenzyl)-6-hydroxy-2-isopropyl-1-(pyridin-3-ylmethyl)-1H-indole-3-carboxamide (Compound 151) by General Procedure U.

1H NMR (300 MHz, METHANOL-$d_4$) δ ppm 1.35 (d, J=7.3 Hz, 6 H), 3.40-3.54 (m, 1 H), 4.59 (s, 2 H), 5.61 (s, 2 H), 6.95 (d, J=3.8 Hz, 1 H), 7.08 (dd, J=8.4, 2.2 Hz, 1 H), 7.18 (d, J=4.1 Hz, 1 H), 7.21-7.28 (m, 2 H), 7.29-7.41 (m, 4 H), 7.68 (d, J=8.5 Hz, 1 H), 8.20 (d, J=1.2 Hz, 1 H), 8.41 (dd, J=4.4, 1.8 Hz, 1 H).

EXAMPLE 153

6-(Cyclopentyloxy)-N-(3,4-difluorobenzyl)-2-isopropyl-1-(pyridin-3-ylmethyl)-1H-indole-3-carboxamide (Compound 153). The title compound was prepared from N-(3,4-difluorobenzyl)-6-hydroxy-2-isopropyl-1-(pyridin-3-ylmethyl)-1H-indole-3-carboxamide (Compound 151) by General Procedure N.

1H NMR (300 MHz, METHANOL-$d_4$) δ ppm 1.34 (d, J=7.3 Hz, 6 H), 1.52-1.63 (m, 2 H), 1.64-1.87 (m, 6 H), 3.43-3.57 (m, 1 H), 4.57 (s, 2 H), 4.67-4.77 (m, 1 H), 5.55 (s, 2 H), 6.70 (d, J=2.1 Hz, 1 H), 6.76 (dd, J=8.6, 2.2 Hz, 1 H), 7.19-7.27 (m, 2 H), 7.28-7.40 (m, 3 H), 7.49 (d, J=8.5 Hz, 1 H), 8.22 (s, 1 H), 8.41 (dd, J=4.4, 2.1 Hz, 1 H).

EXAMPLE 154

N-(3,4-Difluorobenzyl)-6-isopropoxy-2-isopropyl-1-(pyridin-3-ylmethyl)-1H-indole-3-carboxamide (Compound 154). The title compound was prepared from N-(3,4-difluorobenzyl)-6-hydroxy-2-isopropyl-1-(pyridin-3-ylmethyl)-1H-indole-3-carboxamide (Compound 151) by General Procedure N.

1H NMR (300 MHz, METHANOL-$d_4$) δ ppm 1.21 (d, J=6.2 Hz, 6 H), 1.33 (d, J=7.3 Hz, 6 H), 3.42-3.57 (m, 1 H), 4.43-4.54 (m, 1 H), 4.57 (s, 2 H), 5.55 (s, 2 H), 6.74-6.83 (m, 2 H), 7.19-7.27 (m, 2 H), 7.28-7.39 (m, 3 H), 7.50 (d, J=9.1 Hz, 1 H), 8.21 (s, 1 H), 8.41 (dd, J=4.3, 2.2 Hz, 1 H).

EXAMPLE 155

2-Isopropyl-6-methoxy-1H-indole-3-carboxylic acid (Compound 155). The title compound was prepared from 2-isopropyl-6-methoxy-1H-indole-3-carbaldehyde (Compound 137) by General Procedure K.

1H NMR (300 MHz, CHLOROFORM-d) δ ppm 1.30 (d, J=6.7 Hz, 6 H), 2.51-2.74 (m, 1 H), 3.89 (s, 3 H), 6.63 (dd, J=8.9, 2.5 Hz, 1 H), 8.03 (d, J=9.1 Hz, 1 H), 8.48 (d, J=2.3 Hz, 1 H), 11.15 (s, 1 H).

EXAMPLE 156

N-(3,4-Difluorobenzyl)-2-isopropyl-6-methoxy-1H-indole-3-carboxamide (Compound 156). To a solution of 2-isopropyl-6-methoxy-1H-indole-3-carboxylic acid (Compound 155, 10 mg, 0.046 mmol) in $CH_2Cl_2$ (1 ml) was added i-$Pr_2$NEt (17 μl, 0.098 mmol) and 3,4-difluorobenzylamine (11 μl, 0.092 mmol), followed by BOP. After completion, the reaction was diluted with EtOAc, washed with $H_2O$ and brine, dried over $Na_2SO_4$, and concentrated in vacuo. The residue was purified by chromatography on silica gel (0→25% EtOAc-hexanes) to yield the title compound.

1H NMR (300 MHz, CHLOROFORM-d) δ ppm 1.27 (d, J=6.7 Hz, 6 H), 2.53-2.68 (m, 1 H), 3.86 (s, 3 H), 4.56 (d, J=5.9 Hz, 2 H), 6.47 (dd, 1 H), 6.57 (dd, J=8.8, 2.6 Hz, 1 H), 7.01-7.22 (m, 3 H), 7.39 (d, J=8.8 Hz, 1 H), 8.41 (d, J=2.6 Hz, 1 H), 11.57 (s, 1 H).

EXAMPLE 157

N-(3,4-Difluorobenzyl)-1-isobutyl-2-isopropyl-6-methoxy-1H-indole-3-carboxamide (Compound 157). The title compound was prepared from 2-isopropyl-6-methoxy-1H-indole-3-carbaldehyde (Compound 137) and 1-iodo-2-methylpropane by, in order, General Procedure J, General Procedure K, and General Procedure C.

1H NMR (300 MHz, CHLOROFORM-d) δ ppm 0.96 (d, J=6.7 Hz, 6 H), 1.50 (d, J=7.0 Hz, 6 H), 2.13-2.26 (m, 1 H), 3.28-3.41 (m, 1 H), 3.86 (s, 3 H), 3.89 (d, J=7.6 Hz, 2 H), 4.65 (d, J=6.2 Hz, 2 H), 6.20-6.28 (m, 1 H), 6.76-6.83 (m, 2 H), 7.10-7.17 (m, 2 H), 7.19-7.30 (m, 1 H), 7.47 (d, J=8.5 Hz, 1 H).

EXAMPLE 158

N-(3,4-Difluorobenzyl)-6-hydroxy-1-isobutyl-2-isopropyl-1H-indole-3-carboxamide (Compound 158). The title compound was prepared from N-(3,4-difluorobenzyl)-1-isobutyl-2-isopropyl-6-methoxy-1H-indole-3-carboxamide (Compound 157) by General Procedure L.

1H NMR (300 MHz, CHLOROFORM-d) δ ppm 0.95 (d, J=6.7 Hz, 6 H), 1.49 (d, J=7.0 Hz, 6 H), 2.11-2.27 (m, 1 H), 3.26-3.40 (m, 1 H), 3.86 (d, J=7.6 Hz, 2 H), 4.65 (d, J=6.2 Hz, 2 H), 4.79 (s, 1 H), 6.23 (t, J=6.2 Hz, 1 H), 6.68 (dd, J=8.5, 1.8 Hz, 1 H), 6.77 (d, J=2.3 Hz, 1 H), 7.09-7.16 (m, 2 H), 7.18-7.28 (m, 1 H), 7.42 (d, J=8.5 Hz, 1 H).

EXAMPLE 159

6-(Cyclopentyloxy)-N-(3,4-difluorobenzyl)-1-isobutyl-2-isopropyl-1H-indole-3-carboxamide (Compound 159). The title compound was prepared from N-(3,4-difluorobenzyl)-6-hydroxy-1-isobutyl-2-isopropyl-1H-indole-3-carboxamide (Compound 158) by General Procedure N.

1H NMR (300 MHz, CHLOROFORM-d) δ ppm 0.96 (d, J=6.7 Hz, 6 H), 1.49 (d, J=7.0 Hz, 6 H), 1.59-1.70 (m, 2 H), 1.73-1.97 (m, 6 H), 2.12-2.26 (m, 1 H), 3.27-3.40 (m, 1 H), 3.88 (d, J=7.6 Hz, 2 H), 4.65 (d, J=5.9 Hz, 2 H), 4.76-4.84 (m, 1 H), 6.24 (t, J=6.6 Hz, 1 H), 6.74-6.81 (m, 2 H), 7.09-7.16 (m, 2 H), 7.18-7.28 (m, 1 H), 7.42-7.48 (m, 1 H).

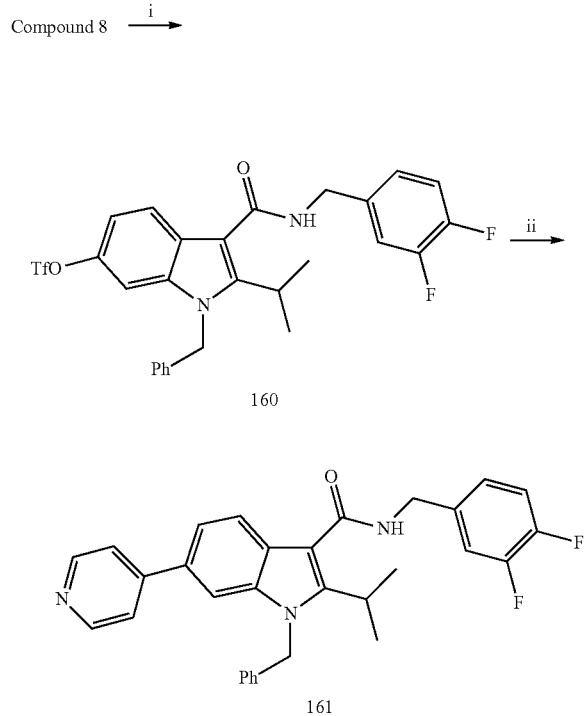

[a]Reagents and conditions: (i) 2-[N,N-Bis(trifluoromethylsulphonyl)amino]-5-chloropyridine, DMAP, CH$_2$Cl$_2$; (ii) pyridin-4-ylboronic acid, Pd(PPh$_3$)$_4$, K$_2$CO$_3$, LiCl, toluene, MeOH, H$_2$O.

EXAMPLE 160

1-Benzyl-3-(3,4-difluorobenzylcarbamoyl)-2-isopropyl-1H-indol-6-yl trifluoromethanesulfonate (Compound 160). General Procedure V. To a solution of 1-benzyl-N-(3,4-difluorobenzyl)-6-hydroxy-2-isopropyl-1H-indole-3-carboxamide (Compound 8, 48 mg, 0.11 mmol) in CH$_2$Cl$_2$ (2 ml) was added 2-[N,N-bis(trifluoromethylsulphonyl)amino]-5-chloropyridine (48 mg, 0.12 mmol) and DMAP (15 mg, 0.12 mmol). The reaction was stirred at room temperature for 16 h, diluted with EtOAc, washed with brine, dried over Na$_2$SO$_4$, and concentrated in vacuo. The residue was purified by chromatography on silica gel (0→30% EtOAc-hexanes) to yield the title compound.

1H NMR (300 MHz, CHLOROFORM-d) δ ppm 1.39 (d, J=7.3 Hz, 6 H), 3.57-3.72 (m, 1 H), 4.65 (d, J=5.9 Hz, 2 H), 5.43 (s, 2 H), 6.30 (t, J=5.7 Hz, 1 H), 6.89-6.98 (m, 2 H), 7.02-7.09 (m, 2 H), 7.11-7.18 (m, 2 H), 7.18-7.36 (m, 4 H), 7.66 (d, J=9.4 Hz, 1 H).

EXAMPLE 161

1-Benzyl-N-(3,4-difluorobenzyl)-2-isopropyl-6-(pyridin-4-yl)-1H-indole-3-carboxamide (Compound 161). General Procedure W. A mixture of 1-benzyl-3-(3,4-difluorobenzylcarbamoyl)-2-isopropyl-1H-indol-6-yl trifluoromethanesulfonate (Compound 160, 50 mg, 0.088 mmol), pyridin-4-ylboronic acid (22 mg, 0.18 mmol), Pd(PPh$_3$)$_4$ (5.0 mg, 0.0043 mmol), K$_2$CO$_3$ (61 mg, 0.44 mmol), and LiCl (19 mg, 0.44 mmol) in toluene (3 ml), MeOH (1 ml), and H$_2$O (0.5 ml) was heated at 90° C. for 16 h. The reaction was then cooled to room temperature, diluted with EtOAc, washed with brine, dried over Na$_2$SO$_4$, and concentrated in vacuo. The residue was purified by chromatography on silica gel (0→100% EtOAc-hexanes) to yield the title compound.

1H NMR (300 MHz, METHANOL-d$_4$) δ ppm 1.35 (d, J=7.0 Hz, 6 H), 3.41-3.58 (m, 1 H), 4.60 (s, 2 H), 5.63 (s, 2 H), 6.94-7.06 (m, 2 H), 7.16-7.44 (m, 5 H), 7.49-7.81 (m, 6 H), 8.47 (dd, J=4.7, 1.8 Hz, 2 H).

EXAMPLE 162

N-((5-Fluoropyridin-3-yl)methyl)-6-hydroxy-2-isopropyl-1-(pyridin-3-ylmethyl)-1H-indole-3-carboxamide (Compound 162). The title compound was prepared from 2-isopropyl-6-methoxy-1H-indole-3-carbaldehyde (Compound 137), 3-(bromomethyl)pyridine.HBr, and (5-fluoropyridin-3-yl)methanamine (Compound 145) by, in order, General Procedure J, General Procedure K, General Procedure C, and General Procedure L.

1H NMR (300 MHz, METHANOL-d$_4$) δ ppm 1.32 (d, J=7.0 Hz, 6 H), 3.41-3.58 (m, 1 H), 4.67 (d, J=6.2 Hz, 2 H), 5.50 (s, 2 H), 6.61 (d, J=2.1 Hz, 1 H), 6.71 (dd, J=8.5, 2.1 Hz, 1 H), 7.29-7.39 (m, 2 H), 7.46 (d, J=8.5 Hz, 1 H), 7.69 (d, J=9.1 Hz, 1 H), 7.90 (s, 1 H), 8.21 (s, 1 H), 8.35-8.44 (m, 2 H), 8.50 (s, 1 H), 8.60 (t, J=5.7 Hz, 1 H).

EXAMPLE 163

6-(Cyclopentyloxy)-N-((5-fluoropyridin-3-yl)methyl)-2-isopropyl-1-(pyridin-3-ylmethyl)-1H-indole-3-carboxamide (Compound 163). The title compound was prepared from N-((5-fluoropyridin-3-yl)methyl)-6-hydroxy-2-isopropyl-1-(pyridin-3-ylmethyl)-1H-indole-3-carboxamide (Compound 162) and cyclopentyl iodide by General Procedure N.

1H NMR (300 MHz, METHANOL-d$_4$) δ ppm 1.33 (d, J=7.3 Hz, 6 H), 1.50-1.64 (m, 2 H), 1.64-1.90 (m, 6 H), 3.44-3.58 (m, 1 H), 4.67 (s, 2 H), 4.70-4.77 (m, 1 H), 5.56 (s, 2 H), 6.72 (d, J=2.1 Hz, 1 H), 6.77 (dd, J=8.8, 2.1 Hz, 1 H), 7.30-7.41 (m, 2 H), 7.51 (d, J=8.8 Hz, 1 H), 7.65-7.75 (m, 1 H), 8.22 (s, 1 H), 8.35-8.45 (m, 2 H), 8.50 (s, 1 H).

EXAMPLE 164

N-(3,4-Difluorobenzyl)-2-isopropyl-1-(pyridin-2-ylmethyl)-6-(pyridin-4-yl)-1H-indole-3-carboxamide (Compound 164). The title compound was prepared from 2-isopropyl-6-methoxy-1-(pyridin-2-ylmethyl)-1H-indole-3-carboxylic acid (Compound 139), 3,4-difluorobenzylamine, and pyridin-4-ylboronic acid by, in order, General Procedure C, General Procedure L, General Procedure V, and General Procedure W.

1H NMR (300 MHz, METHANOL-d₄) δ ppm 1.35 (d, J=7.0 Hz, 6 H), 3.44-3.57 (m, 1 H), 4.60 (s, 2 H), 5.71 (s, 2 H), 6.74 (d, J=7.9 Hz, 1 H), 7.21-7.42 (m, 4 H), 7.56 (dd, J=8.2, 1.8 Hz, 1 H), 7.62-7.79 (m, 5 H), 8.49 (d, J=6.2 Hz, 2 H), 8.54 (d, J=4.1 Hz, 1 H).

EXAMPLE 165

6-Cyclobutoxy-N-(3,4-difluorobenzyl)-2-isopropyl-1-(pyridin-3-ylmethyl)-1H-indole-3-carboxamide (Compound 165). The title compound was prepared from 2-isopropyl-6-methoxy-1H-indole-3-carbaldehyde (Compound 137), 3-(bromomethyl)pyridine.HBr, 3,4-difluorobenzylamine, and cyclobutyl bromide by, in order, General Procedure J, General Procedure K, General Procedure C, General Procedure L, and General Procedure N.

1H NMR (500 MHz, CHLOROFORM-d) δ ppm 1.39 (d, J=7.3 Hz, 6 H), 1.60-1.74 (m, 2 H), 2.04-2.15 (m, 2 H), 2.27-2.39 (m, 2 H), 3.70-3.81 (m, 1 H), 4.50-4.60 (m, 1 H), 4.66 (d, J=5.9 Hz, 2 H), 5.41 (s, 2 H), 6.29 (t, J=5.6 Hz, 1 H), 6.49 (d, J=2.2 Hz, 1 H), 6.75 (dd, J=8.7, 2.1 Hz, 1 H), 7.11-7.18 (m, 3 H), 7.18-7.28 (m, 2 H), 7.50 (d, J=8.6 Hz, 1 H), 8.43 (s, 1 H), 8.52 (s, 1 H).

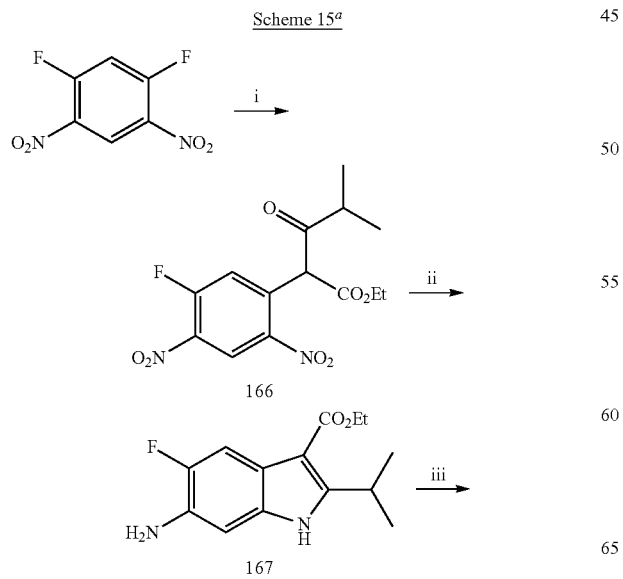

Scheme 15ᵃ

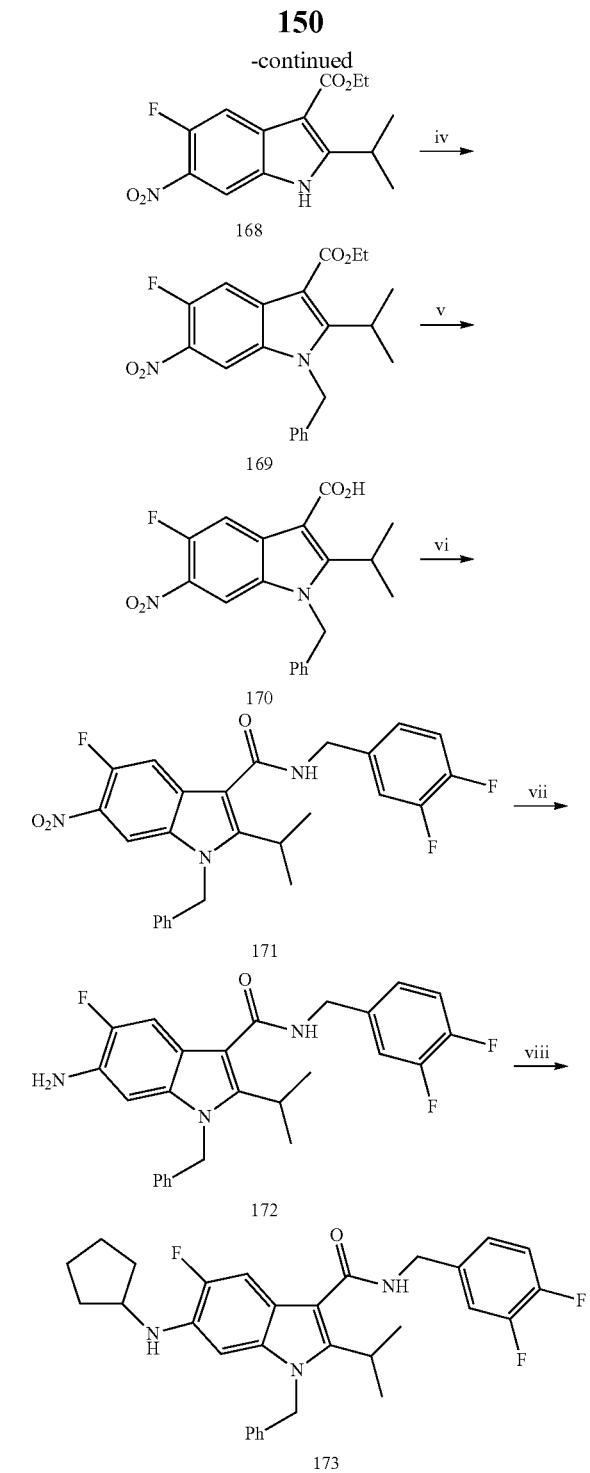

ᵃReagents and conditions: (i) ethyl isobutyryl acetate, K₂CO₃, THF; (ii) Zn dust, aqueous NH₄Cl, MeOH; (iii) MCPBA, aqueous NaHCO₃, acetone, CH₂Cl₂; (iv) BnBr, K₂CO₃, DMF; (v) NaOH, EtOH; (vi) 3,4-difluorobenzylamine, EDC, DMAP, CH₂Cl₂; (vii) H₂, Pd—C, EtOAc; (viii) cyclopentanone, NaBH₃CN, HOAc, MeOH.

EXAMPLE 166

Ethyl 2-(5-Fluoro-2,4-dinitrophenyl)-4-methyl-3-oxopentanoate (Compound 166). General Procedure X. To a solution of 1,5-difluoro-2,4-dinitrobenzene (Aldrich, 10.6 g, 52.0 mmol) in THF (100 ml) was added ethyl isobutyryl acetate (8.4 ml, 52.0 mmol) and K₂CO₃ (8.6 g, 62.3 mmol). The mixture was stirred at room temperature for 2 h, diluted with EtOAc, washed with aqueous HCl and brine, dried over Na₂SO₄, and concentrated in vacuo. The residue was purified by chromatography on silica gel (0→25% EtOAc-hexanes) to yield the title compound as a yellow oil.

1H NMR (300 MHz, CHLOROFORM-d) δ ppm 1.07 (d, J=6.7 Hz, 3 H), 1.13 (t, J=7.0 Hz, 3 H), 1.19 (d, J=6.7 Hz, 3 H), 2.22-2.48 (m, 1 H), 3.91-4.38 (m, 2 H), 7.24 (d, J=10.3 Hz, 1 H), 8.79 (d, J=7.0 Hz, 1 H), 13.21 (d, J=1.5 Hz, 1 H).

EXAMPLE 167

Ethyl 6-Amino-5-fluoro-2-isopropyl-1H-indole-3-carboxylate (Compound 167). The title compound was prepared from ethyl2-(5-fluoro-2,4-dinitrophenyl)-4-methyl-3-oxopentanoate (Compound 166) by General Procedure R.

1H NMR (300 MHz, CHLOROFORM-d) δ ppm 1.34 (d, J=7.0 Hz, 6 H), 1.44 (t, J=7.0 Hz, 3 H), 3.70 (s, 2 H), 3.99-4.15 (m, 1 H), 4.37 (q, J=7.1 Hz, 2 H), 6.71 (d, J=7.6 Hz, 1 H), 7.69 (d, J=12.0 Hz, 1 H), 8.12 (s, 1 H).

EXAMPLE 168

Ethyl 5-fluoro-2-isopropyl-6-nitro-1H-indole-3-carboxylate (Compound 92). General Procedure Y. To a solution of ethyl6-amino-5-fluoro-2-isopropyl-1H-indole-3-carboxylate (Compound 167, 1.92 g, 7.3 mmol) in acetone (20 ml) and CH₂Cl₂ (20 ml) was added saturated aqueous NaHCO₃ (10 ml) and MCPBA (6.3 g, 36.5 mmol). The resulting reddish brown solution was stirred at room temperature for 2 h, extracted with EtOAc (×3). The combined organic layer was washed with brine, dried over Na₂SO₄, and concentrated in vacuo. The residue was purified by chromatography on silica gel (0→35% EtOAc-hexanes) to yield the title compound as a yellow solid.

1H NMR (300 MHz, CHLOROFORM-d) δ ppm 1.41 (d, J=7.0 Hz, 6 H), 1.46 (t, J=7.0 Hz, 3 H), 4.06-4.21 (m, 1 H), 4.42 (q, J=7.1 Hz, 2 H), 7.94 (d, J=12.3 Hz, 1 H), 8.16 (d, J=6.2 Hz, 1 H), 8.65 (s, 1 H).

EXAMPLE 169

Ethyl 1-Benzyl-5-fluoro-2-isopropyl-6-nitro-1H-indole-3-carboxylate (Compound 169). The title compound was prepared from ethyl5-fluoro-2-isopropyl-6-nitro-1H-indole-3-carboxylate (Compound 168) and benzyl bromide by General Procedure J.

1H NMR (500 MHz, CHLOROFORM-d) δ ppm 1.41 (d, J=7.3 Hz, 6 H), 1.50 (t, J=7.2 Hz, 3 H), 3.90-4.04 (m, 1 H), 4.45 (q, J=7.1 Hz, 2 H), 5.54 (s, 2 H), 6.93 (d, J=6.4 Hz, 2 H), 7.29-7.36 (m, 3 H), 7.96 (d, J=6.1 Hz, 1 H), 8.00 (d, J=12.7 Hz, 1 H).

EXAMPLE 170

1-Benzyl-5-fluoro-2-isopropyl-6-nitro-1H-indole-3-carboxylic acid (Compound 170). General Procedure Z. To a solution of ethyl1-benzyl-5-fluoro-2-isopropyl-6-nitro-1H-indole-3-carboxylate (Compound 169, 546 mg, 1.54 mmol) in EtOH (10 ml) was added 5 M NaOH (3.1 ml, 15.5 mmol). The reaction was heated at 80° C. for 5 h, diluted with EtOAc, washed with brine, dried over Na₂SO₄, and concentrated in vacuo. The residue was purified by chromatography on silica gel (0→50% EtOAc-hexanes) to yield the title compound as a brown solid.

1H NMR (300 MHz, CHLOROFORM-d) δ ppm 1.46 (d, J=7.0 Hz, 6 H), 3.94-4.16 (m, 1 H), 5.57 (s, 2 H), 6.91-7.01 (m, 2 H), 7.32 (t, J=6.4 Hz, 3 H), 7.92-8.01 (m, 1 H), 8.16 (d, J=12.3 Hz, 1 H).

EXAMPLE 171

1-Benzyl-N-(3,4-difluorobenzyl)-5-fluoro-2-isopropyl-6-nitro-1H-indole-3-carboxamide (Compound 171). The title compound was prepared from 1-benzyl-5-fluoro-2-isopropyl-6-nitro-1H-indole-3-carboxylic acid (Compound 170) and 3,4-difluorobenzylamine by General Procedure C.

1H NMR (300 MHz, CHLOROFORM-d) δ ppm 1.40 (d, J=7.0 Hz, 6 H), 3.48-3.63 (m, 1 H), 4.67 (d, J=5.9 Hz, 2 H), 5.48 (s, 2 H), 6.21 (t, J=6.0 Hz, 1 H), 6.92 (dd, J=7.5, 2.2 Hz, 2 H), 7.12-7.36 (m, 6 H), 7.43 (d, J=12.0 Hz, 1 H), 7.98 (d, J=5.9 Hz, 1 H).

EXAMPLE 172

6-Amino-1-benzyl-N-(3,4-difluorobenzyl)-5-fluoro-2-isopropyl-1H-indole-3-carboxamide (Compound 172). The title compound was prepared from 1-benzyl-N-(3,4-difluorobenzyl)-5-fluoro-2-isopropyl-6-nitro-1H-indole-3-carboxamide (Compound 171) by General Procedure S.

1H NMR (300 MHz, METHANOL-d₄) δ ppm 1.30 (d, J=7.3 Hz, 6 H), 3.39-3.52 (m, 1 H), 4.56 (s, 2 H), 5.40 (s, 2 H), 6.70 (d, J=7.3 Hz, 1 H), 6.93 (dd, J=7.9, 1.5 Hz, 2 H), 7.16-7.38 (m, 7 H).

EXAMPLE 173

1-Benzyl-6-(cyclopentylamino)-N-(3,4-difluorobenzyl)-5-fluoro-2-isopropyl-1H-indole-3-carboxamide (Compound 173). The title compound was prepared from 6-amino-1-benzyl-N-(3,4-difluorobenzyl)-5-fluoro-2-isopropyl-1H-indole-3-carboxamide (Compound 172) and cyclopentanone by General Procedure T.

1H NMR (300 MHz, METHANOL-d₄) δ ppm 1.33 (d, J=7.3 Hz, 6 H), 1.36-2.10 (m, 8 H), 3.46-3.59 (m, 1 H), 3.58-3.70 (m, 1 H), 4.56 (s, 2 H), 5.43 (s, 2 H), 6.46 (d, J=7.3 Hz, 1 H), 6.93-7.03 (m, 2 H), 7.13-7.41 (m, 7 H), 8.40 (s, 1 H).

EXAMPLE 174

1-Benzyl-N-cyclopentyl-3-(3,4-difluorobenzylcarbamoyl)-5-fluoro-2-isopropyl-N,N-dimethyl-1H-indol-6-aminium chloride (Compound 174). To a solution of 1-benzyl-6-(cyclopentylamino)-N-(3,4-difluorobenzyl)-5-fluoro-2-isopropyl-1H-indole-3-carboxamide (Compound 173, 12 mg, 0.023 mmol) in DMF (2 ml) was added MeI (15 μl, 0.23 mmol) and K₂CO₃ (32 mg, 0.23 mmol). The reaction was stirred at room temperature for 16 h, diluted with EtOAc, washed with H₂O and brine, dried over Na₂SO₄, and concentrated in vacuo. The residue was purified by reverse phase chromatography on C18 bonded silica gel (90% MeOH—H₂O) to yield the title compound.

1H NMR (300 MHz, METHANOL-d₄) δ ppm 1.33 (d, J=7.0 Hz, 6 H), 1.57-1.89 (m, 8 H), 3.36-3.54 (m, 1 H), 3.65 (s, 6 H), 4.58 (s, 2 H), 4.74-4.83 (m, 1 H), 5.69 (s, 2 H), 6.92-7.01 (m, 2 H), 7.19-7.40 (m, 7 H), 7.60 (d, J=15.2 Hz, 1 H), 7.75 (d, J=6.7 Hz, 1 H), 8.77 (t, J=6.0 Hz, 1 H).

EXAMPLE 175

N-(3,4-Difluorobenzyl)-6-isopropoxy-1-(pyridin-2-ylmethyl)-2-(pyrrolidin-1-ylmethyl)-1H-indole-3-carboxamide (Compound 175). The title compound was prepared from N-(3,4-difluorobenzyl)-2-formyl-6-methoxy-1-(pyridin-2-ylmethyl)-1H-indole-3-carboxamide (Compound 94) and pyrrolidine by, in order, General Procedure P, General Procedure M, and General Procedure N.

1H NMR (300 MHz, CHLOROFORM-d) δ ppm 1.30 (d, J=6.2 Hz, 6 H), 1.55 (s, 4 H), 2.34 (s, 4 H), 3.76 (s, 2 H), 4.45-4.62 (m, 3 H), 5.50 (s, 2 H), 6.51 (d, J=7.6 Hz, 1 H), 6.75 (d, J=1.8 Hz, 1 H), 6.92 (dd, J=8.5, 1.8 Hz, 1 H), 7.05-7.30 (m, 4 H), 7.45-7.56 (m, 1 H), 8.29 (d, J=8.8 Hz, 1 H), 8.58 (d, J=4.7 Hz, 1 H), 10.15 (t, J=4.5 Hz, 1 H).

EXAMPLE 176

1-((3-(3,4-Difluorobenzylcarbamoyl)-6-isopropoxy-1-(pyridin-2-ylmethyl)-1H-indol-2-yl)methyl)-1-methylpyrrolidinium iodide (Compound 176). To a solution of N-(3,4-difluorobenzyl)-6-isopropoxy-1-(pyridin-2-ylmethyl)-2-(pyrrolidin-1-ylmethyl)-1H-indole-3-carboxamide (Compound 175, 17 mg, 0.033 mmol) in acetone (1 ml) was added MeI (0.1 ml, 1.6 mmol). The reaction was stirred at room temperature for 16 h and the solvent was removed in vacuo. The residue was purified by PTLC on silica gel (10% MeOH-EtOAc) to yield the title compound.

1H NMR (300 MHz, acetone) δ ppm 1.22 (d, J=5.9 Hz, 6 H), 2.25 (s, 4 H), 3.35 (s, 3 H), 3.72-3.97 (m, 4 H), 4.52-4.67 (m, 1 H), 4.70 (t, J=5.3 Hz, 2 H), 5.63 (s, 2 H), 6.84 (dd, J=8.8, 2.1 Hz, 1 H), 7.01 (d, J=2.1 Hz, 1 H), 7.20-7.54 (m, 5 H), 7.70-7.79 (m, 1 H), 7.88 (d, J=9.1 Hz, 1 H), 8.19 (t, J=6.3 Hz, 1 H), 8.44 (d, J=4.1 Hz, 1 H).

EXAMPLE 177

1-Benzyl-N-(3,4-difluorobenzyl)-6-(3,4-dihydro-2H-pyrrol-5-ylamino)-5-fluoro-2-isopropyl-1H-indole-3-carboxamide (Compound 177). A mixture of 2-pyrrolidinone (47 mg, 0.55 mmol) and POCl$_3$ (0.10 ml, 1.1 mmol) was stirred at 0° C. to room temperature for 2h. To the above mixture was then added a solution of 6-amino-1-benzyl-N-(3,4-difluorobenzyl)-5-fluoro-2-isopropyl-1H-indole-3-carboxamide (Compound 172, 50 mg, 0.11 mmol) in toluene (3 ml). The reaction was heated to 110° C. for 16 h and was cooled to room temperature, diluted with EtOAc, washed with brine, dried over Na$_2$SO$_4$, and concentrated in vacuo. The residue was purified by reverse phase chromatography on C18 bonded silica gel (MeOH) to yield the title compound as a white solid.

1H NMR (300 MHz, METHANOL-d$_4$) δ ppm 1.26-1.37 (m, 8 H), 2.53 (t, J=7.8 Hz, 2 H), 3.37-3.57 (m, 3 H), 4.57 (s, 2 H), 5.47 (s, 2 H), 6.90-7.02 (m, 3 H), 7.15-7.41 (m, 7 H).

EXAMPLE 178

1-Benzyl-N-(3,4-difluorobenzyl)-6-(4,5-dihydrothiazol-2-ylamino)-5-fluoro-2-isopropyl-1H-indole-3-carboxamide (Compound 178). General Procedure AA. To a solution of 6-amino-1-benzyl-N-(3,4-difluorobenzyl)-5-fluoro-2-isopropyl-1H-indole-3-carboxamide (Compound 172, 39 mg, 0.086 mmol) in CH$_2$Cl$_2$ (1 ml) was added 2-chloroethyl isothiocyanate (25 µl, 0.26 mmol) and Et$_3$N (1 drop). The reaction was stirred at room temperature for 16 h and was purified directly by chromatography on silica gel (0→60% EtOAc-hexanes) to yield the title compound.

1H NMR (300 MHz, CHLOROFORM-d) δ ppm 1.36 (d, J=7.0 Hz, 6 H), 3.28 (t, J=7.0 Hz, 2 H), 3.58-3.70 (m, 1 H), 3.79 (t, J=6.9 Hz, 2 H), 4.65 (d, J=5.6 Hz, 2 H), 5.38 (s, 2 H), 6.17-6.25 (m, 1 H), 6.96 (d, J=6.4 Hz, 2 H), 7.10-7.18 (m, 2 H), 7.20-7.35 (m, 6 H).

EXAMPLE 179

1-Benzyl-N-(3,4-difluorobenzyl)-5-fluoro-6-iodo-2-isopropyl-1H-indole-3-carboxamide (Compound 179). To a solution of 6-amino-1-benzyl-N-(3,4-difluorobenzyl)-5-fluoro-2-isopropyl-1H-indole-3-carboxamide (Compound 96, 324 mg, 0.72 mmol) in MeOH (5 ml) at −10° C. was added 2 M H$_2$SO$_4$ (3 ml, 6.0 mmol) followed by sodium nitrite (50 mg, 0.72 mmol). The reaction was stirred at −10° C. for 0.5 h and a solution of potassium iodide (477 mg, 2.9 mmol) in H$_2$O (3 ml) was added. The mixture was stirred for another 0.5 h and was extracted with EtOAc (×3). The combined organic layer was washed with brine, dried over Na$_2$SO$_4$, and concentrated in vacuo. The residue was purified by chromatography on silica gel (0→30% EtOAc-hexanes) to yield the title compound.

1H NMR (300 MHz, METHANOL-d$_4$) δ ppm 1.32 (d, J=7.3 Hz, 6 H), 3.37-3.52 (m, 1 H), 4.57 (s, 2 H), 5.47-5.53 (m, 2 H), 6.82-6.97 (m, 2 H), 7.17-7.39 (m, 8 H).

EXAMPLE 180

1-Benzyl-N-(3,4-difluorobenzyl)-5-fluoro-2-isopropyl-6-methoxy-1H-indole-3-carboxamide (Compound 180). To a mixture of sodium methoxide (freshly prepared from 25 mg sodium and 1 ml MeOH) and CuI (30 mg, 0.16 mmol) was added a solution of 1-benzyl-N-(3,4-difluorobenzyl)-5-fluoro-6-iodo-2-isopropyl-1H-indole-3-carboxamide (Compound 179, 30 mg, 0.053 mmol) in DMF (0.5 ml). The reaction was heated to 110° C. for 16 h, and was filtered and concentrated. The residue was purified by chromatography on silica gel (0→30% EtOAc-hexanes) to yield the title compound.

1H NMR (300 MHz, METHANOL-d$_4$) δ ppm 1.31 (d, J=7.0 Hz, 6 H), 3.37-3.51 (m, 1 H), 3.76 (s, 3 H), 4.56 (s, 2 H), 5.50 (s, 2 H), 6.88-6.98 (m, 3 H), 7.17-7.38 (m, 7 H).

EXAMPLE 181

N-(3,4-Difluorobenzyl)-2-isopropyl-6-nitro-1-(pyridin-2-ylmethyl)-1H-indole-3-carboxamide (Compound 181). The title compound was prepared from 1-fluoro-2,4-dinitrobenzene and methyl isobutyryl acetate by, in order, General Procedure X, General Procedure R, General Procedure Y, General Procedure J, General Procedure Z, and General Procedure C.

1H NMR (300 MHz, METHANOL-d$_4$) δ ppm 1.34 (d, J=7.3 Hz, 6 H), 3.41-3.58 (m, 1 H), 4.59 (s, 2 H), 5.72 (s, 2 H), 6.90 (d, J=7.9 Hz, 1 H), 7.19-7.41 (m, 4 H), 7.67-7.78 (m, 2 H), 8.04 (dd, J=8.8, 2.1 Hz, 1 H), 8.33 (d, J=2.1 Hz, 1 H), 8.51 (d, J=4.1 Hz, 1 H).

EXAMPLE 182

6-Amino-N-(3,4-difluorobenzyl)-2-isopropyl-1-(pyridin-2-ylmethyl)-1H-indole-3-carboxamide (Compound 182). The title compound was prepared from N-(3,4-difluorobenzyl)-2-isopropyl-6-nitro-1-(pyridin-2-ylmethyl)-1H-indole-3-carboxamide (Compound 181) by General Procedure S.

1H NMR (300 MHz, METHANOL-d₄) δ ppm 1.30 (d, J=7.0 Hz, 6 H), 3.41-3.58 (m, 1 H), 4.56 (s, 2 H), 5.48 (s, 2 H), 6.54-6.62 (m, 2 H), 6.66 (dd, J=8.5, 1.8 Hz, 1 H), 7.17-7.37 (m, 4 H), 7.39 (d, J=8.5 Hz, 1 H), 7.58-7.70 (m, 1 H), 8.53 (d, J=4.1 Hz, 1 H).

EXAMPLE 183

6-(Cyclopentylamino)-N-(3,4-difluorobenzyl)-2-isopropyl-1-(pyridin-2-ylmethyl)-1H-indole-3-carboxamide (Compound 183). The title compound was prepared from 6-amino-N-(3,4-difluorobenzyl)-2-isopropyl-1-(pyridin-2-ylmethyl)-1H-indole-3-carboxamide (Compound 182) by General Procedure T.

1H NMR (300 MHz, METHANOL-d₄) δ ppm 1.32 (d, J=7.3 Hz, 6 H), 1.34-1.75 (m, 6 H), 1.80-1.95 (m, 2 H), 3.47-3.60 (m, 1 H), 3.61-3.73 (m, 1 H), 4.56 (s, 2 H), 5.49 (s, 2 H), 6.39 (d, J=1.8 Hz, 1 H), 6.58-6.67 (m, 2 H), 7.19-7.36 (m, 4 H), 7.38 (d, J=8.8 Hz, 1 H), 7.60-7.71 (m, 1 H), 8.54 (d, J=5.0 Hz, 1 H).

EXAMPLE 184

N-(3,4-Difluorobenzyl)-6-(4,5-dihydrothiazol-2-ylamino)-2-isopropyl-1-(pyridin-2-ylmethyl)-1H-indole-3-carboxamide (Compound 184). The title compound was prepared from 6-amino-N-(3,4-difluorobenzyl)-2-isopropyl-1-(pyridin-2-ylmethyl)-1H-indole-3-carboxamide (Compound 106) by General Procedure AA.

1H NMR (300 MHz, METHANOL-d₄) δ ppm 1.32 (d, J=7.3 Hz, 6 H), 3.24 (t, J=7.0 Hz, 2 H), 3.43-3.58 (m, 1 H), 3.79 (t, J=7.2 Hz, 2 H), 4.57 (s, 2 H), 5.54 (s, 2 H), 6.65 (d, J=7.9 Hz, 1 H), 6.93 (dd, J=8.5, 1.8 Hz, 1 H), 7.14-7.39 (m, 5 H), 7.51 (d, J=8.5 Hz, 1 H), 7.61-7.69 (m, 1 H), 8.53 (d, J=4.1 Hz, 1 H).

EXAMPLE 185

N-(3,4-Difluorobenzyl)-6-(4,5-dihydrothiazol-2-ylamino)-2-isopropyl-1-(pyridin-2-ylmethyl)-1H-indole-3-carboxamide, hydrogen chloride salt (Compound 185). The title compound was also isolated in the synthesis of Compound 184.

1H NMR (300 MHz, METHANOL-d₄) δ ppm 1.32 (d, J=7.3 Hz, 6 H), 3.41-3.54 (m, 1 H), 3.58 (t, J=7.5 Hz, 2 H), 3.99 (t, J=7.6 Hz, 2 H), 4.59 (s, J=4.1 Hz, 2 H), 5.61 (s, 2 H), 6.81 (d, J=7.9 Hz, 1 H), 7.04-7.12 (m, 1 H), 7.19-7.41 (m, 5 H), 7.64-7.77 (m, 2 H), 8.51 (d, J=4.1 Hz, 1 H), 8.67 (t, J=6.0 Hz, 1 H).

EXAMPLE 186

N-(3,4-Difluorobenzyl)-6-(4,5-dihydrooxazol-2-ylamino)-2-isopropyl-1-(pyridin-2-ylmethyl)-1H-indole-3-carboxamide (Compound 186). To a solution of 6-amino-N-(3,4-difluorobenzyl)-2-isopropyl-1-(pyridin-2-ylmethyl)-1H-indole-3-carboxamide (Compound 182, 48 mg, 0.11 mmol) in CH₂Cl₂ (1 ml) was added chloroethyl isocyanate (10 μl, 0.12 mmol). The reaction was stirred at room temperature for 16 h, and the solvent was removed. To the residue was added H₂O and the mixture was heated at 80° C. for 3 h, diluted with EtOAc, washed with aqueous K₂CO₃ and brine, dried over Na₂SO₄, and concentrated in vacuo. The residue was purified by chromatography on silica gel (0→100% EtOAc-hexanes) to yield the title compound.

1H NMR (300 MHz, METHANOL-d₄) δ ppm 1.30 (d, J=7.3 Hz, 6 H), 3.40-3.53 (m, 1 H), 3.72 (t, J=8.4 Hz, 2 H), 4.34 (t, J=8.4 Hz, 2 H), 4.57 (s, 2 H), 5.55 (s, 2 H), 6.65 (d, J=7.9 Hz, 1 H), 7.01 (dd, J=8.5, 1.8 Hz, 1 H), 7.19-7.38 (m, 5 H), 7.52 (d, J=8.8 Hz, 1 H), 7.60-7.68 (m, 1 H), 8.52 (d, J=4.1 Hz, 1 H).

EXAMPLE 187

6-(3-(2-Chloroethyl)ureido)-N-(3,4-difluorobenzyl)-2-isopropyl-1-(pyridin-2-ylmethyl)-1H-indole-3-carboxamide (Compound 187). The title compound was also isolated in the synthesis of Compound 186.

1H NMR (300 MHz, METHANOL-d₄) δ ppm 1.31 (d, J=7.0 Hz, 6 H), 3.42-3.54 (m, 3 H), 3.55-3.67 (m, 2 H), 4.57 (s, 2 H), 5.54 (s, 2 H), 6.65 (d, J=7.9 Hz, 1 H), 6.99 (dd, J=8.5, 2.1 Hz, 1 H), 7.17-7.38 (m, 4 H), 7.46-7.56 (m, 2 H), 7.61-7.72 (m, 1 H), 8.53 (d, J=4.7 Hz, 1 H).

EXAMPLE 188

N-(3,4-Difluorobenzyl)-2-isopropyl-1-(pyridin-2-ylmethyl)-6-(pyrrolidin-1-yl)-1H-indole-3-carboxamide (Compound 188). To a solution of 6-amino-N-(3,4-difluorobenzyl)-2-isopropyl-1-(pyridin-2-ylmethyl)-1H-indole-3-carboxamide (Compound 182, 64 mg, 0.15 mmol) in toluene (2 ml) was added 1,4-dibromobutane (19 μl, 0.16 mmol) and i-Pr₂NEt (77 μl, 0.44 mmol). The reaction was heated at 110° C. for 16 h, and was purified directly by chromatography on silica gel (0→100% EtOAc-hexanes) to yield the title compound.

1H NMR (300 MHz, METHANOL-d₄) δ ppm 1.31 (d, J=7.0 Hz, 6 H), 1.92-2.00 (m, 4 H), 3.04-3.26 (m, 4 H), 3.40-3.65 (m, 1 H), 4.57 (s, 2 H), 5.50 (s, 2 H), 6.17-6.35 (m, 1 H), 6.50-6.67 (m, J=8.4, 8.4 Hz, 2 H), 7.19-7.38 (m, 4 H), 7.45 (d, J=8.5 Hz, 1 H), 7.58-7.70 (m, 1 H), 8.54 (d, J=5.0 Hz, 1 H).

EXAMPLE 189

1-Benzyl-6-(cyclopentyl(methyl)amino)-N-(3,4-difluorobenzyl)-2-isopropyl-1H-indole-3-carboxamide (Compound 189). The title compound was prepared from 1-benzyl-6-(cyclopentylamino)-N-(3,4-difluorobenzyl)-2-isopropyl-1H-indole-3-carboxamide (Compound 130) by General Procedure T.

1H NMR (300 MHz, METHANOL-d₄) δ ppm 1.34 (d, J=7.0 Hz, 6 H), 1.41-1.57 (m, 4 H), 1.57-1.77 (m, 4 H), 2.68 (s, 3 H), 3.45-3.61 (m, 1 H), 3.69-3.81 (m, 1 H), 4.57 (s, 2 H), 5.47 (s, 2 H), 6.78 (d, J=1.8 Hz, 1 H), 6.88-7.01 (m, 3 H), 7.15-7.39 (m, 6 H), 7.50 (d, J=8.8 Hz, 1 H).

EXAMPLE 190

1-Benzyl-6-(cyclobutylamino)-N-(3,4-difluorobenzyl)-2-isopropyl-1H-indole-3-carboxamide (Compound 190). The title compound was prepared from 6-amino-1-benzyl-N-(3,4-difluorobenzyl)-2-isopropyl-1H-indole-3-carboxamide (Compound 125) by General Procedure T.

1H NMR (300 MHz, METHANOL-d₄) δ ppm 1.32 (d, J=7.2 Hz, 6 H), 1.66-1.86 (m, 4 H), 2.18-2.32 (m, 2 H), 3.44-3.60 (m, 1 H), 3.73-3.88 (m, 1 H), 4.56 (s, 2 H), 5.41 (s, 2 H), 6.36 (d, J=1.9 Hz, 1 H), 6.57 (dd, J=8.6, 2.0 Hz, 1 H), 6.94-7.01 (m, 2 H), 7.18-7.35 (m, 6 H), 7.38 (d, J=8.5 Hz, 1 H).

EXAMPLE 191

1-Benzyl-6-(cyclopentylamino)-N-(3,5-difluorobenzyl)-2-isopropyl-1H-indole-3-carboxamide (Compound 191). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.32 (d, J=7.0 Hz, 6 H), 1.35-1.47 (m, 2 H), 1.47-1.59 (m, 2 H), 1.60-1.73 (m, 2 H), 1.79-1.93 (m, 2 H), 3.46-3.59 (m, 1 H), 3.61-3.73 (m, 1 H), 4.55-4.64 (m, 2 H), 5.41 (s, 2 H), 6.45 (d, J=1.8 Hz, 1 H), 6.62 (dd, J=8.5, 2.1 Hz, 1 H), 6.76-6.88 (m, 1 H), 6.93-7.08 (m, 4 H), 7.13-7.29 (m, 3 H), 7.41 (d, J=8.5 Hz, 1 H), 8.38 (t, J=6.2 Hz, 1 H).

EXAMPLE 192

1-Benzyl-6-(cyclopentylamino)-N-(4-fluorobenzyl)-2-isopropyl-1H-indole-3-carboxamide (Compound 192). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.32 (d, J=7.3 Hz, 6 H), 1.35-1.45 (m, 2 H), 1.50-1.59 (m, 2 H), 1.62-1.75 (m, 2 H), 1.79-1.93 (m, 2 H), 3.44-3.58 (m, 1 H), 3.61-3.73 (m, 1 H), 4.58 (d, J=5.9 Hz, 2 H), 5.41 (s, 2 H), 6.44 (d, J=1.8 Hz, 1 H), 6.60 (dd, J=8.5, 2.1 Hz, 1 H), 6.95-6.99 (m, 2 H), 7.03-7.12 (m, 2 H), 7.17-7.29 (m, 3 H), 7.36 (d, J=8.8 Hz, 1 H), 7.40-7.50 (m, 2 H), 8.30 (t, J=6.0 Hz, 1 H).

EXAMPLE 193

1-Benzyl-6-(cyclopentylamino)-N-((5-fluoropyridin-3-yl)methyl)-2-isopropyl-1H-indole-3-carboxamide (Compound 193). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.31 (d, J=7.3 Hz, 6 H), 1.34-1.45 (m, 2 H), 1.47-1.60 (m, 2 H), 1.61-1.75 (m, 2 H), 1.80-1.94 (m, 2 H), 3.46-3.58 (m, 1 H), 3.60-3.72 (m, 1 H), 4.65 (s, 2 H), 5.40 (s, 2 H), 6.44 (d, J=1.8 Hz, 1 H), 6.62 (dd, J=8.6, 1.9 Hz, 1 H), 6.94-7.00 (m, 2 H), 7.15-7.30 (m, 3 H), 7.40 (d, J=8.8 Hz, 1 H), 7.68 (dd, J=9.4, 2.1 Hz, 1 H), 8.36 (d, J=2.6 Hz, 1 H), 8.49 (s, 1 H).

EXAMPLE 194

1-Benzyl-6-(cyclobutylamino)-N-(3,5-difluorobenzyl)-2-isopropyl-1H-indole-3-carboxamide (Compound 194). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.32 (d, J=7.3 Hz, 6 H), 1.67-1.82 (m, 4 H), 2.20-2.31 (m, 2 H), 3.46-3.61 (m, 1 H), 3.73-3.87 (m, 1 H), 4.56-4.62 (m, 2 H), 5.41 (s, 2 H), 6.36 (d, J=2.1 Hz, 1 H), 6.58 (dd, J=8.6, 1.9 Hz, 1 H), 6.77-6.88 (m, 1 H), 6.93-7.07 (m, 4 H), 7.16-7.30 (m, 3 H), 7.41 (d, J=8.5 Hz, 1 H), 8.40 (t, J=6.0 Hz, 1 H).

EXAMPLE 195

1-Benzyl-6-(cyclobutylamino)-N-(4-fluorobenzyl)-2-isopropyl-1H-indole-3-carboxamide (Compound 195). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.31 (d, J=7.3 Hz, 6 H), 1.67-1.83 (m, 4 H), 2.18-2.33 (m, 2 H), 3.44-3.61 (m, 1 H), 3.72-3.86 (m, 1 H), 4.53-4.62 (m, 2 H), 5.40 (s, 2 H), 6.35 (d, J=2.1 Hz, 1 H), 6.55 (dd, J=8.5, 2.1 Hz, 1 H), 6.92-7.00 (m, 2 H), 7.01-7.13 (m, 2 H), 7.15-7.30 (m, 3 H), 7.36 (d, J=8.5 Hz, 1 H), 7.40-7.49 (m, 2 H), 8.29 (t, J=6.3 Hz, 1 H).

EXAMPLE 196

1-Benzyl-6-(cyclobutylamino)-N-((5-fluoropyridin-3-yl)methyl)-2-isopropyl-1H-indole-3-carboxamide (Compound 196). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.30 (d, J=7.3 Hz, 6 H), 1.64-1.86 (m, 4 H), 2.18-2.32 (m, 2 H), 3.44-3.60 (m, 1 H), 3.72-3.86 (m, 1 H), 4.64 (s, 2 H), 5.40 (s, 2 H), 6.36 (d, J=1.8 Hz, 1 H), 6.58 (dd, J=8.6, 1.9 Hz, 1 H), 6.91-7.01 (m, 2 H), 7.15-7.31 (m, 3 H), 7.40 (d, J=8.8 Hz, 1 H), 7.63-7.73 (m, 1 H), 8.36 (d, J=2.6 Hz, 1 H), 8.48 (s, 1 H).

EXAMPLE 197

6-(Cyclobutylamino)-N-(3,4-difluorobenzyl)-2-isopropyl-1-(pyridin-2-ylmethyl)-1H-indole-3-carboxamide (Compound 197). The title compound was prepared from 1-fluoro-2,4-dinitrobenzene and methyl isobutyryl acetate by, in order, General Procedure X, General Procedure R, General Procedure Y, General Procedure J, General Procedure Z, General Procedure C, General Procedure S, and General Procedure T.

1H NMR (300 MHz, METHANOL-$d_4$) δ ppm 1.31 (d, J=7.3 Hz, 6 H), 1.67-1.83 (m, 4 H), 2.19-2.32 (m, 2 H), 3.46-3.61 (m, 1 H), 3.73-3.87 (m, 1 H), 4.56 (s, 2 H), 5.48 (s, 2 H), 6.31 (d, J=1.8 Hz, 1 H), 6.54-6.64 (m, 2 H), 7.17-7.43 (m, 5 H), 7.58-7.69 (m, 1 H), 8.54 (d, J=4.1 Hz, 1 H).

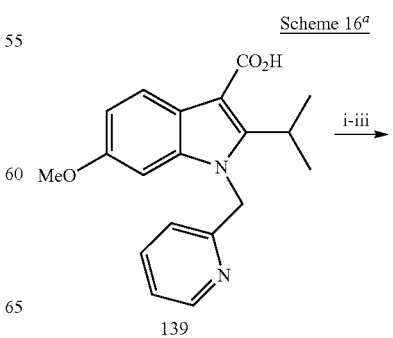

Scheme 16$^a$

139

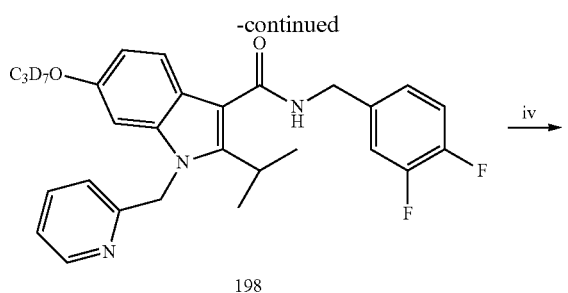

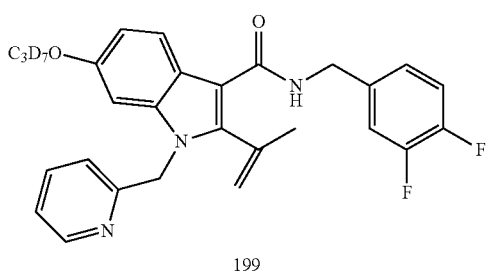

198

199 aReagents and conditions: (i) (COCl)₂, cat. DMF, CH₂Cl₂, then 3,4-difluorobenzylamine, Et₃N, CH₂Cl₂; (ii) BBr₃, CH₂Cl₂; (iii) C₃D₇I, K₂CO₃, DMF; (iv) HCl—Et₂O, air.

EXAMPLE 198

N-(3,4-Difluorobenzyl)-6-isopropoxy-2-isopropyl-1-(pyridin-2-ylmethyl)-1H-indole-3-carboxamide-d7 (Compound 198). The title compound was prepared from 2-isopropyl-6-methoxy-1-(pyridin-2-ylmethyl)-1H-indole-3-carboxylic acid (Compound 139) by General Procedure C, General Procedure L, and General Procedure N.

1H NMR (300 MHz, CHLOROFORM-d) δ ppm 1.37 (d, J=7.0 Hz, 6 H), 3.69-3.89 (m, 1 H), 4.67 (d, J=5.9 Hz, 2 H), 5.51 (s, 2 H), 6.30 (t, J=6.0 Hz, 1 H), 6.53 (d, J=7.9 Hz, 1 H), 6.65 (d, J=1.8 Hz, 1 H), 6.82 (dd, J=8.6, 2.2 Hz, 1 H), 7.09-7.32 (m, 4 H), 7.45-7.57 (m, 2 H), 8.62 (d, J=4.7 Hz, 1 H).

EXAMPLE 199

N-(3,4-Difluorobenzyl)-2-isopropenyl-6-isopropoxy-1-(pyridin-2-ylmethyl)-1H-indole-3-carboxamide-d7 (Compound 199). To a solution of N-(3,4-difluorobenzyl)-6-isopropoxy-2-isopropyl-1-(pyridin-2-ylmethyl)-1H-indole-3-carboxamide-d7 (Compound 198, 71 mg, 0.15 mmol) in Et₂O (5 ml) under air was added HCl (2 M in Et₂O, 0.15 ml, 0.30 mmol). The solvent was removed and the residue was purified by PTLC (50% EtOAc-hexanes) to yield the title compound as a side product.

1H NMR (300 MHz, METHANOL-d₄) δ ppm 2.00 (t, J=1.2 Hz, 3 H), 4.55 (s, 2 H), 5.18-5.25 (m, 1 H), 5.44 (s, 2 H), 5.57 (t, J=1.6 Hz, 1 H), 6.71 (d, J=1.8 Hz, 1 H), 6.76 (d, J=7.9 Hz, 1 H), 6.81 (dd, J=8.8, 2.3 Hz, 1 H), 7.14-7.37 (m, 4 H), 7.62-7.73 (m, 1 H), 7.82 (d, J=8.8 Hz, 1 H), 8.50 (d, J=5.0 Hz, 1 H).

Scheme 17ᵃ

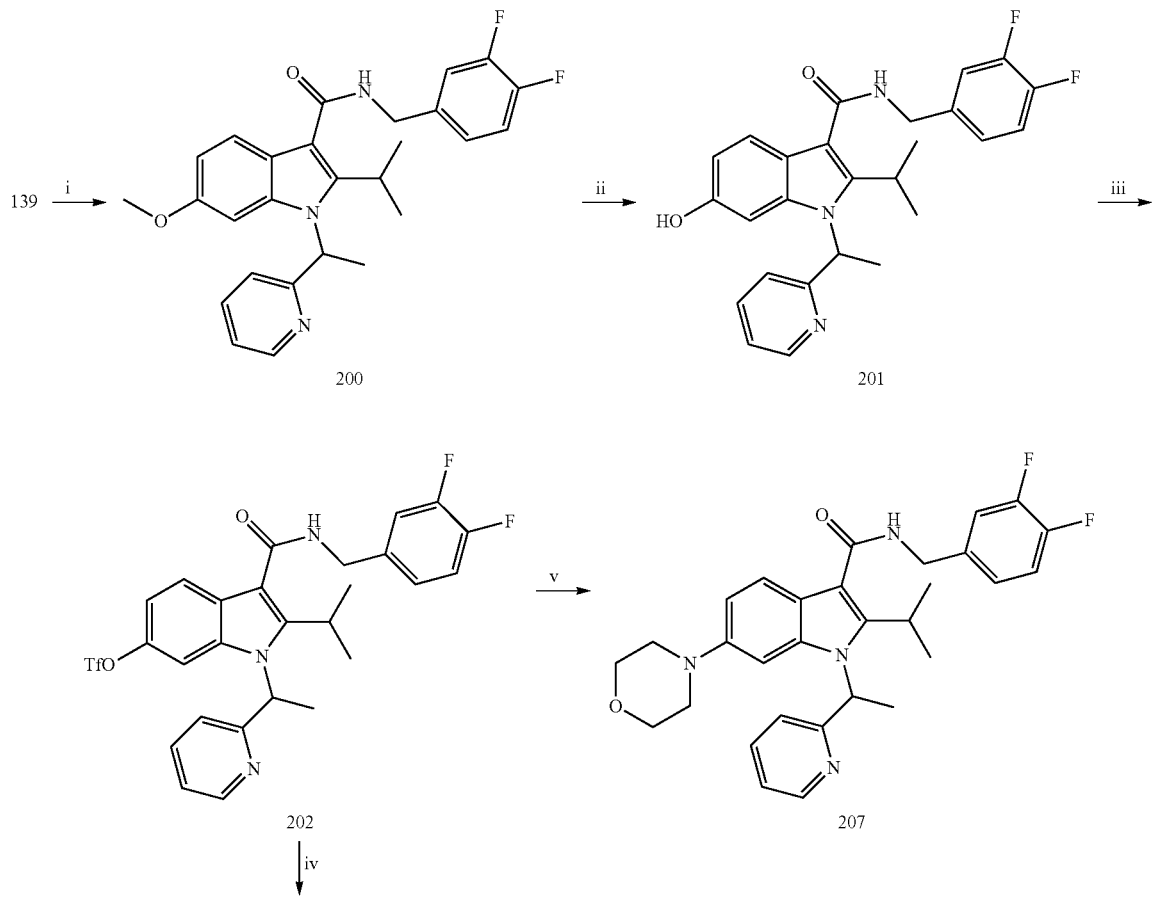

-continued

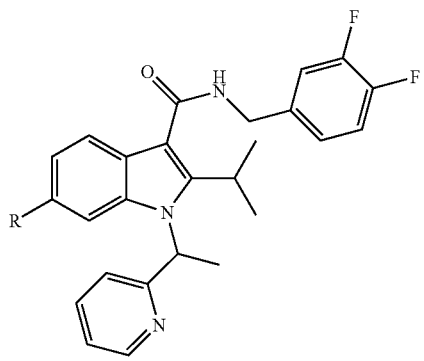

203

*Reagents and conditions: (i) (COCl)$_2$, cat. DMF, CH$_2$Cl$_2$, then 3,4-difluorobenzylamine, Et$_3$N, CH$_2$Cl$_2$; (ii) BBr$_3$, CH$_2$Cl$_2$; (iii) 2-[N,N-Bis(trifluoromethyl-sulfonyl)amino]-5-chloropyridine, CH$_2$Cl$_2$; (iv) R-B(OH)$_2$, toluene, MeOH, H$_2$O, LiCl, K$_2$CO$_3$, Pd(PPh$_3$)$_4$, 85° C.; (v) Morpholine, LiN(TMS)$_2$, X-Phos, Pd$_2$(dba)$_3$, 110° C.

EXAMPLE 200

N-(3,4-Difluorobenzyl)-2-isopropyl-6-methoxy-1-(pyridin-2-ylmethyl)-1H-indole-3-carboxamide (Compound 200). To a solution of 2-isopropyl-6-methoxy-1-(pyridin-2-ylmethyl)-1H-indole-3-carboxylic acid (Compound 139, 415 mg, 1.28 mmol) in CH$_2$Cl$_2$ (20 ml) at 0° C. was added (COCl)$_2$ (2 M in CH$_2$Cl$_2$, 1.6 ml, 3.20 mmol) and a catalytic amount of DMF. The mixture was stirred at room temperature for 1 h, and was concentrated in vacuo. The residue was dissolved in CH$_2$Cl$_2$ (20 ml), cooled to 0° C., and 3,4-difluorobenzylamine (0.23 ml, 1.92 mmol) was added, followed by Et$_3$N (0.53 ml, 3.84 mmol). The reaction was stirred at room temperature for 4 h, diluted with EtOAc, washed with H$_2$O, brine, dried over Na$_2$SO$_4$, and concentrated in vacuo. The residue was purified by chromatography on silica gel (0→100% EtOAc-hexanes) to yield the title compound as a yellow solid.

1H NMR (300 MHz, CHLOROFORM-d) δ ppm 1.36 (d, J=7.0 Hz, 6 H), 3.74 (s, 3 H), 3.74-3.83 (m, 1 H), 4.65 (d, J=6.2 Hz, 2 H), 5.51 (s, 2 H), 6.37 (t, J=5.9 Hz, 1 H), 6.52 (d, J=7.9 Hz, 1 H), 6.62 (d, J=2.3 Hz, 1 H), 6.82 (dd, J=8.6, 2.2 Hz, 1 H), 7.08-7.30 (m, 4 H), 7.46-7.57 (m, 2 H), 8.61 (d, J=4.1 Hz, 1 H).

EXAMPLE 201

N-(3,4-Difluorobenzyl)-6-hydroxy-2-isopropyl-1-(pyridin-2-ylmethyl)-1H-indole-3-carboxamide (Compound 201). To a solution of N-(3,4-difluorobenzyl)-2-isopropyl-6-methoxy-1-(pyridin-2-ylmethyl)-1H-indole-3-carboxamide (Compound 200, 735 mg, 1.64 mmol) in CH$_2$Cl$_2$ (25 ml) at 0° C. was added BBr$_3$ (1.0 M in CH$_2$Cl$_2$, 6.6 ml, 6.56 mmol) dropwise. The reaction was stirred for 1 h at 0° C. and 1 h at room temperature, quenched with ice, extracted with EtOAc, the organic layer was washed with brine, dried over Na$_2$SO$_4$, and concentrated in vacuo. The residue was purified by chromatography on silica gel (0→85% EtOAc-hexanes) to yield the title compound as a yellow oil.

1H NMR (500 MHz, METHANOL-d$_4$) δ ppm 1.30 (s, 3 H), 1.32 (s, 3 H), 3.43-3.57 (m, 1 H), 4.57 (s, 2 H), 5.48 (s, 2 H), 6.54-6.64 (m, 2 H), 6.68 (dd, J=8.56, 2.20 Hz, 1 H), 7.19-7.37 (m, 4 H), 7.43 (d, J=8.56 Hz, 1 H), 7.66 (td, J=7.76, 1.59 Hz, 1 H), 8.54 (d, J=4.89 Hz, 1 H).

EXAMPLE 202

3-(3,4-Difluorobenzylcarbamoyl)-2-isopropyl-1-(pyridin-2-ylmethyl)-1H-indol-6-yl trifluoromethanesulfonate (Compound 202). To a solution of N-(3,4-difluorobenzyl)-6-hydroxy-2-isopropyl-1-(pyridin-2-ylmethyl)-1H-indole-3-carboxamide (Compound 201, 1.20 g, 2.76 mmol) in CH$_2$Cl$_2$ (50 ml) at 0° C. was added 2-[N,N-Bis(trifluoromethylsulfonyl)amino]-5-chloropyridine (1.20 g, 3.04 mmol) and DMAP (370 mg, 3.04 mmol). The reaction was stirred at room temperature for 12 h, quenched with water, extracted with EtOAc, the organic layer was washed with brine, dried over Na$_2$SO$_4$, and concentrated in vacuo. The residue was purified by chromatography on silica gel (0→40% EtOAc-hexanes) to yield the title compound as a white solid.

1H NMR (500 MHz, METHANOL-d$_4$) δ ppm 1.33 (s, 3 H), 1.34 (s, 3 H), 3.42-3.54 (m, 1 H), 4.58 (s, 2 H), 5.62 (s, 2 H), 6.78 (d, J=7.83 Hz, 1 H), 7.11 (dd, J=8.68, 1.83 Hz, 1 H), 7.21-7.39 (m, 5 H), 7.68 (d, J=8.80 Hz, 2 H), 8.52 (d, J=4.89 Hz, 1 H), 8.73 (br. s., 1 H).

EXAMPLE 203

N-(3,4-Difluorobenzyl)-2-isopropyl-1-(pyridin-2-ylmethyl)-6-(pyrimidin-5-yl)-1H-indole-3-carboxamide (Compound 203). General Procedure BB. To a solution of 3-(3,4-difluorobenzylcarbamoyl)-2-isopropyl-1-(pyridin-2-ylmethyl)-1H-indol-6-yl trifluoromethanesulfonate (Compound 202, 33 mg, 0.06 mmol) in toluene (8 ml) and MeOH (1 ml) at 25° C., bubbled with argon then added LiCl (8 mg, 0.18 mmol), Na$_2$CO$_3$ (aqueous) (2M, 0.1 ml), Pd(PPh$_3$)$_4$ (3.4 mg, 0.003 mmol), and 5-pyrimidine boronic acid (11 mg, 0.09 mmol). The reaction was stirred for 12 h at 80° C., diluted with EtOAc, the organic layer was washed with brine, dried over Na$_2$SO$_4$, and concentrated in vacuo. The residue was purified by chromatography on silica gel (0→100% EtOAc-hexanes) to yield the title compound as a white solid.

1H NMR (300 MHz, METHANOL-d$_4$) δ ppm 1.34 (s, 3 H), 1.36 (s, 3 H), 3.50 (ddd, J=14.54, 7.14, 6.89 Hz, 1 H), 4.61 (s, 2 H), 5.71 (s, 2 H), 6.76 (d, J=7.62 Hz, 1 H), 7.18-7.42 (m, 4 H), 7.46-7.63 (m, 1 H), 7.62-7.74 (m, 2 H), 7.78 (d, J=8.35 Hz, 1 H), 8.53 (dd, J=4.98, 0.88 Hz, 1 H), 9.00-9.09 (m, 3 H).

EXAMPLE 204

N-(3,4-Difluorobenzyl)-2-isopropyl-6-(1H-pyrazol-5-yl)-1-(pyridin-2-ylmethyl)-1H-indole-3-carboxamide (Compound 204). Following General Procedure BB, 3-(3,4-difluorobenzylcarbamoyl)-2-isopropyl-1-(pyridin-2-ylmethyl)-1H-indol-6-yl trifluoromethanesulfonate (Compound 202, 29 mg, 0.05 mmol), was reacted with 1H-pyrazole boronic acid (9 mg, 0.08 mmol), LiCl (7 mg, 0.18 mmol), $Na_2CO_3$ (aqueous) (2M, 0.1 ml), $Pd(PPh_3)_4$ (3 mg, 0.003 mmol) to yield the title compound as a white solid.

1H NMR (300 MHz, METHANOL-$d_4$) δ ppm 1.32 (s, 3 H), 1.34 (s, 3 H), 3.49 (m, 1 H), 4.60 (s, 2 H), 5.65 (s, 2 H), 6.61 (d, J=2.05 Hz, 1 H), 6.69 (d, J=8.06 Hz, 1 H), 7.19-7.42 (m, 4 H), 7.52-7.77 (m, 5 H), 8.54 (d, J=4.83 Hz, 1 H).

EXAMPLE 205

N-(3,4-Difluorobenzyl)-2-isopropyl-6-(1-methyl-1H-pyrazol-5-yl)-1-(pyridin-2-ylmethyl)-1H-indole-3-carboxamide (Compound 205). Following General Procedure BB, 3-(3,4-difluorobenzylcarbamoyl)-2-isopropyl-1-(pyridin-2-ylmethyl)-1H-indol-6-yl trifluoromethanesulfonate (Compound 202, 39 mg, 0.07 mmol), was reacted with 1-methyl-1H-pyrazole-5-boronic acid pinocol ester (21 mg, 0.09 mmol), LiCl (9 mg, 0.18 mmol), $Na_2CO_3$ (aqueous) (2M, 0.1 ml), $Pd(PPh_3)_4$ (4 mg, 0.003 mmol) to yield the title compound as a white solid 1H NMR (300 MHz, METHANOL-$d_4$) δ ppm 1.32 (s, 3 H), 1.34 (s, 3 H), 3.49 (m, 1 H), 3.75 (s, 3H), 4.60 (s, 2 H), 5.65 (s, 2 H), 6.35 (d, J=2.05 Hz, 1 H), 6.69 (d, J=8.06 Hz, 1 H), 7.19-7.42 (m, 4 H), 7.52-7.77 (m, 5 H), 8.54 (d, J=4.83 Hz, 1 H).

EXAMPLE 206

N-(3,4-Difluorobenzyl)-6-(3,5-dimethylisoxazol-4-yl)-2-isopropyl-1-(pyridin-2-ylmethyl)-1H-indole-3-carboxamide (Compound 206). Following General Procedure BB, 3-(3,4-difluorobenzylcarbamoyl)-2-isopropyl-1-(pyridin-2-ylmethyl)-1H-indol-6-yl trifluoromethanesulfonate (Compound 202, 57 mg, 0. 10 mmol), was reacted with 3,5-dimethylisoxazol-4-ylboronic acid (21 mg, 0.15 mmol), LiCl (13 mg, 0.30 mmol), $Na_2CO_3$ (aqueous) (2M, 0.2 ml), $Pd(PPh_3)_4$ (6 mg, 0.006 mmol) to yield the title compound as a yellow solid.

1H NMR (300 MHz, METHANOL-$d_4$) δ ppm 1.36 (s, 3 H), 1.39 (s, 3 H), 2.12 (s, 3 H), 2.29 (s, 3 H), 3.50-3.65 (m, 1 H), 4.60 (s, 2 H), 5.64 (s, 2 H), 6.74 (d, J=7.91 Hz, 1 H), 7.09 (dd, J=8.28, 1.39 Hz, 1 H), 7.17 (d, J=0.88 Hz, 1 H), 7.22-7.41 (m, 5 H), 7.70 (dd, J=8.20, 0.59 Hz, 2 H), 8.53 (ddd, J=4.91, 1.76, 0.81 Hz, 1 H).

EXAMPLE 207

N-(3,4-Difluorobenzyl)-2-isopropyl-6-morpholino-1-(pyridin-2-ylmethyl)-1H-indole-3-carboxamide (Compound 207). To a solution of 3-(3,4-difluorobenzylcarbamoyl)-2-isopropyl-1-(pyridin-2-ylmethyl)-1H-indol-6-yl trifluoromethanesulfonate (Compound 202, 100 mg, 0.18 mmol) in toluene (10 ml) at 25° C., bubbled with argon then added morpholine (22 mg, 0.25 mmol), $LiN(TMS)_2$ (1M in THF, 0.37 ml, 0.40 mmol), $Pd_2(dba)_3$ (3.2 mg, 0.0035 mmol), and X-Phos (4 mg, 0.011 mmol). The reaction was stirred for 12 h at 110° C., diluted with EtOAc, the organic layer was washed with brine, dried over $Na_2SO_4$, and concentrated in vacuo. The residue was purified by chromatography on silica gel (0→100% EtOAc-hexanes) to yield the title compound as a light brown solid.

1H NMR (300 MHz, <cd3od>) δ ppm 1.30 (s, 3 H), 1.32 (s, 3 H), 3.05 (t, J=4.98, 4 H), 3.49 (m, 1 H), 3.78 (t, J=4.98, 4 H), 4.57 (s, 2 H), 5.55 (s, 2 H), 6.62 (d, J=8.20 Hz, 1 H), 6.77 (d, J=1.76 Hz, 1 H), 6.93 (dd, J=8.79, 2.05 Hz, 1 H), 7.20-7.38 (m, 4 H), 7.52 (d, J=8.79 Hz, 1 H), 7.65 (td, J=7.76, 1.76 Hz, 2 H), 8.54 (d, J=4.40 Hz, 2 H).

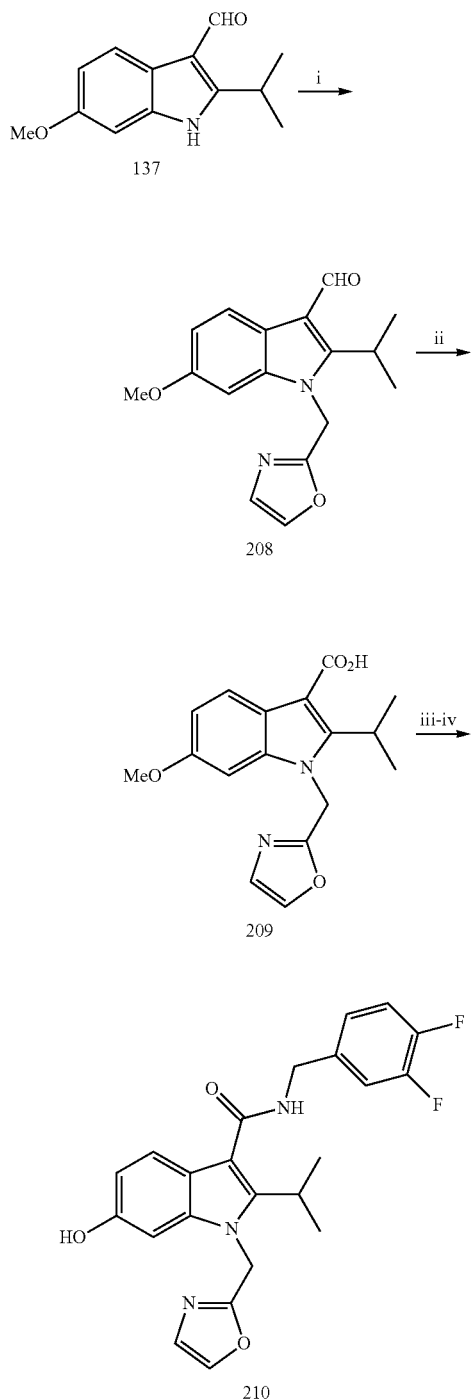

Scheme 18[a].

-continued

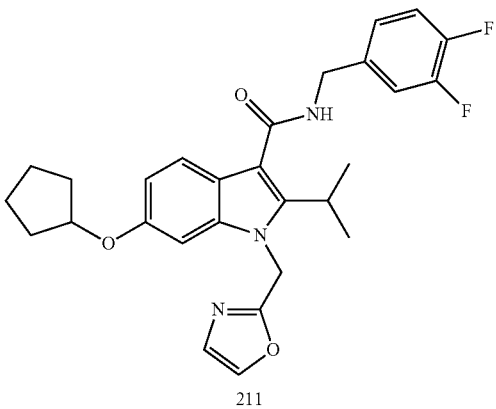

211

<sup>a</sup>Reagents and conditions: (i) 2-(chloromethyl)oxazole, NaH, DMF; (ii) NaClO$_2$, NaH$_2$PO$_4$, t-BuOH, isobutene, H$_2$O; (iii) 3,4-difluorobenzylamine, EDCI, DMAP, CH$_2$Cl$_2$; (iv) BBr$_3$, CH$_2$Cl$_2$; (v) c-C$_5$H$_9$I, K$_2$CO$_3$, DMF.

EXAMPLE 208

2-Isopropyl-6-methoxy-1-(oxazol-2-ylmethyl)-1H-indole-3-carbaldehyde (Compound 208). 2-Isopropyl-6-methoxy-1H-indole-3-carbaldehyde (Compound 137, 0.54 g, 2.49 mmol) and 2-(chloromethyl)oxazole (0.58 g, 4.4 mmol) were reacted as described in General Procedure J to give the title compound as an oil.

1H NMR (300 MHz, METHANOL-d$_4$) δ ppm 1.52 (d, J=7.0 Hz, 6 H), 3.71 (p, J=7.0 Hz, 1 H), 3.82 (s, 3 H), 5.66 (s, 2 H), 6.87 (dd, J=8.8, 2.2 Hz, 1 H), 7.04 (d, J=2.2 Hz, 1 H), 7.15 (s, 1 H), 7.88 (s, 1 H), 8.08 (d, J=8.8 Hz, 1 H), 10.32 (s, 1 H).

EXAMPLE 209

2-Isopropyl-6-methoxy-1-(oxazol-2-ylmethyl)-1H-indole-3-carboxylic Acid (Compound 209). 2-Isopropyl-6-methoxy-1-(oxazol-2-ylmethyl)-1H-indole-3-carbaldehyde (Compound 208, 0.40 g, 1.34 mmol) was oxidized to the title compound by General Procedure K.

1H NMR (300 MHz, METHANOL-d$_4$) δ ppm 1.42 (d, J=7.0 Hz, 6 H), 3.80 (s, 3 H), 4.04 (p, J=7.0 Hz, 1 H), 5.62 (s, 2 H), 6.81 (dd, J=8.5, 2.0 Hz, 1 H), 6.95 (d, J=2.0 Hz, 1 H), 7.15 (s, 1 H), 7.83 (s, 1 H), 7.96 (d, J=8.5 Hz, 1 H).

EXAMPLE 210

N-(3,4-Difluorobenzyl)-6-hydroxy-2-isopropyl-1-(oxazol-2-ylmethyl)-1H-indole-3-carboxamide (Compound 210). 2-Isopropyl-6-methoxy-1-(oxazol-2-ylmethyl)-1H-indole-3-carboxylic acid (Compound 209, 0.83 g, 2.64 mmol) was converted to the title compound by utilizing, in order, General Procedure C and General Procedure L.

1H NMR (300 MHz, METHANOL-d$_4$) δ ppm 1.41 (d, J=7.0 Hz, 6 H), 3.59 (p, J=7.0 Hz, 1 H), 4.58 (s, 2 H), 5.52 (s, 2 H), 6.70 (dd, J=8.5, 2.2 Hz, 1 H), 6.82 (d, J=2.2 Hz, 1 H), 7.15 (s, 1 H), 7.19-7.36 (m, 3 H), 7.40 (d, J=8.5 Hz, 1 H), 7.86 (s, 1 H).

EXAMPLE 211

6-(Cyclopentyloxy)-N-(3,4-difluorobenzyl)-2-isopropyl-1-(oxazol-2-ylmethyl)-1H-indole-3-carboxamide (Compound 211). N-(3,4-difluorobenzyl)-6-hydroxy-2-isopropyl-1-(oxazol-2-ylmethyl)-1H-indole-3-carboxamide (Compound 210, 68 mg, 0.16 mmol) was reacted according to General Procedure N to give the title compound as an oil.

1H NMR (300 MHz, METHANOL-d$_4$) δ ppm 1.41 (d, J=7.0 Hz, 6 H), 1.60-2.00 (m, 8 H), 3.50 (p, J=7.0 Hz, 1 H), 4.58 (s, 2 H), 5.54 (s, 2 H), 6.74 (dd, J=8.5, 2.2 Hz, 1 H), 6.83 (d, J=2.2 Hz, 1 H), 7.13 (s, 1 H), 7.20-7.38 (m, 3 H), 7.42 (d, J=8.5 Hz, 1 H), 7.83 (s, 1 H).

EXAMPLE 212

N-(3,4-Difluorobenzyl)-2-isopropyl-1-(oxazol-2-ylmethyl)-6-propoxy-1H-indole-3-carboxamide (Compound 212). The title compound was prepared from N-(3,4-difluorobenzyl)-6-hydroxy-2-isopropyl-1-(oxazol-2-ylmethyl)-1H-indole-3-carboxamide (Compound 210) and n-propyl iodide by General Procedure N.

1H NMR (300 MHz, METHANOL-d$_4$) δ ppm 1.04 (t, J=7.5 Hz, 3 H), 1.39 (d, J=7.0 Hz, 6 H), 1.78 (m, 2 H), 3.57 (p, J=7.0 Hz, 1 H), 3.94 (t, J=6.5 Hz, 2 H), 4.55 (s, 2 H), 5.55 (s, 2 H), 6.78 (dd, J=8.8, 2.1 Hz, 1 H), 6.95 (d, J=2.1 Hz, 1 H), 7.11-7.36 (m, 4 H), 7.43 (d, J=8.8 Hz, 1 H), 7.83 (d, J=0.88 Hz, 1 H).

EXAMPLE 213

N-(3,4-Difluorobenzyl)-6-isopropoxy-2-isopropyl-1-(oxazol-2-ylmethyl)-1H-indole-3-carboxamide (Compound 213). The title compound was prepared from N-(3,4-difluorobenzyl)-6-hydroxy-2-isopropyl-1-(oxazol-2-ylmethyl)-1H-indole-3-carboxamide (Compound 210) and isopropyl iodide by General Procedure N.

1H NMR (300 MHz, METHANOL-d$_4$) δ ppm 1.29 (d, J=6.0 Hz, 6 H), 1.39 (d, J=7.0 Hz, 6 H), 3.59 (p, J=7.0 Hz, 1 H), 4.55 (s, 2 H), 4.57 (p, J=6.0 Hz, 1 H), 5.54 (s, 2 H), 6.74 (dd, J=8.5, 2.4 Hz, 1 H), 6.78 (d, J=2.4 Hz, 1 H), 7.12 (s, 1 H), 7.20-7.38 (m, 3 H), 7.40 (d, J=8.5 Hz, 1 H), 7.83 (s, 1 H).

EXAMPLE 214

N-(3,4-Difluorobenzyl)-2-isopropyl-1-(oxazol-2-ylmethyl)-6-(thiazol-2-yloxy)-1H-indole-3-carboxamide (Compound 214). The title compound was prepared from N-(3,4-difluorobenzyl)-6-hydroxy-2-isopropyl-1-(oxazol-2-ylmethyl)-1H-indole-3-carboxamide (Compound 210), 2-bromothiazole and DMSO with heating following General Procedure N.

1H NMR (300 MHz, METHANOL-d$_4$) δ ppm 1.40 (d, J=7.0 Hz, 6 H), 3.57 (p, J=7.0 Hz, 0 H), 4.57 (s, 2 H), 5.61 (s, 2 H), 6.99 (d, J=3.81 Hz, 1 H), 7.07 (dd, J=8.5, 1.8 Hz, 1 H), 7.11 (d, J=0.88 Hz, 1 H), 7.19-7.39 (m, 4 H), 7.48 (d, J=1.8 Hz, 1 H), 7.62 (d, J=8.5 Hz, 1 H), 7.83 (d, J=0.88 Hz, 1 H).

EXAMPLE 215

6-(5-Bromothiazol-2-yloxy)-N-(3,4-difluorobenzyl)-2-isopropyl-1-(oxazol-2-ylmethyl)-1H-indole-3-carboxamide (Compound 215). The title compound was also isolated in the synthesis of Compound 214.

1H NMR (300 MHz, METHANOL-d$_4$) δ ppm 1.40 (d, J=7.3 Hz, 6 H), 3.58 (p, J=7.3 Hz, 0 H), 4.56 (s, 2 H), 5.62 (s, 2 H), 7.08 (dd, J=8.8, 2.1 Hz, 1 H), 7.11 (d, J=0.88 Hz, 1 H), 7.20-7.39 (m, 4 H), 7.50 (d, J=1.8 Hz, 1 H), 7.63 (d, J=8.8 Hz, 1 H), 7.83 (d, J=0.88 Hz, 1 H).

EXAMPLE 216

2-Isopropyl-6-methoxy-1-((5-methylisoxazol-3-yl)methyl)-1H-indole-3-carbaldehyde (Compound 216). The title compound was prepared from 2-isopropyl-6-methoxy-1H-indole-3-carbaldehyde (Compound 137) and 3-(bromomethyl)-5-methylisoxazole by General Procedure J.

1H NMR (300 MHZ, METHANOL-D4) δ ppm 1.50 (d, J=7.3 Hz, 6 H), 2.35 (s, 3 H), 3.65 (p, J=7.3 Hz), 3.82 (s, 3 H), 5.53 (s, 2 H), 5.89 (s, 1 H), 6.88 (dd, J=2.3, 8.7 Hz, 1 H), 7.00 (d, J=2.3 Hz, 1 H), 8.10 (d, J=8.7 Hz, 1 H), 10.23 (s, 1 H).

EXAMPLE 217

2-Isopropyl-6-methoxy-1-((5-methylisoxazol-3-yl)methyl)-1H-indole-3-carboxylic Acid (Compound 217). The title compound was prepared from 2-isopropyl-6-methoxy-1-((5-methylisoxazol-3-yl)methyl)-1H-indole-3-carbaldehyde (Compound 213) by General Procedure K.

1H NMR (300 MHZ, METHANOL-D4) δ ppm 1.42 (d, J=7.0 Hz, 6 H), 2.31 (s, 3 H), 3.55 (p, J=7.0 Hz), 3.80 (s, 3 H), 5.55 (s, 2 H), 5.78 (s, 1 H), 6.82 (dd, J=2.0, 8.5 Hz, 1 H), 6.93 (d, J=2.0 Hz, 1 H), 7.90 (d, J=8.5 Hz, 1 H).

EXAMPLE 218

N-(3,4-Difluorobenzyl)-6-hydroxy-2-isopropyl-1-((5-methylisoxazol-3-yl)methyl)-1H-indole-3-carboxamide (Compound 218). The title compound was prepared from 2-isopropyl-6-methoxy-1-((5-methylisoxazol-3-yl)methyl)-1H-indole-3-carboxylic acid (Compound 217) by utilizing, in order, General Procedure C and General Procedure L.

1H NMR (300 MHZ, METHANOL-D4) δ ppm 1.36 (d, J=7.0 Hz, 6 H), 2.32 (s, 3 H), 3.54 (p, J=7.0 Hz), 4.55 (s, 2 H), 5.38 (s, 2 H), 5.74 (s, 1 H), 6.67 (dd, J=2.2, 8.5 Hz, 1 H), 6.74 (d, J=2.2 Hz, 1 H), 7.20-7.35 (m, 3 H), 7.38 (d, J=8.5 Hz, 1 H).

EXAMPLE 219

6-(Cyclopentyloxy)-N-(3,4-difluorobenzyl)-2-isopropyl-1-((5-methylisoxazol-3-yl)methyl)-1H-indole-3-carboxamide (Compound 219). The title compound was prepared from N-(3,4-difluorobenzyl)-6-hydroxy-2-isopropyl-1-((5-methylisoxazol-3-yl)methyl)-1H-indole-3-carboxamide (Compound 218) by General Procedure N.

1H NMR (300 MHZ, METHANOL-D4) δ ppm 1.38 (d, J=7.0 Hz, 6 H), 1.60-1.95 (m, 8 H), 2.31 (s, 3 H), 3.55 (p, J=7.0 Hz), 4.55 (s, 2 H), 5.43 (s, 2 H), 5.75 (s, 1 H), 6.74 (dd, J=2.0, 8.8 Hz, 1 H), 6.85 (d, J=2.0 Hz, 1 H), 7.20-7.35 (m, 3 H), 7.43 (d, J=8.8 Hz, 1 H).

Scheme 19<sup>a</sup>.

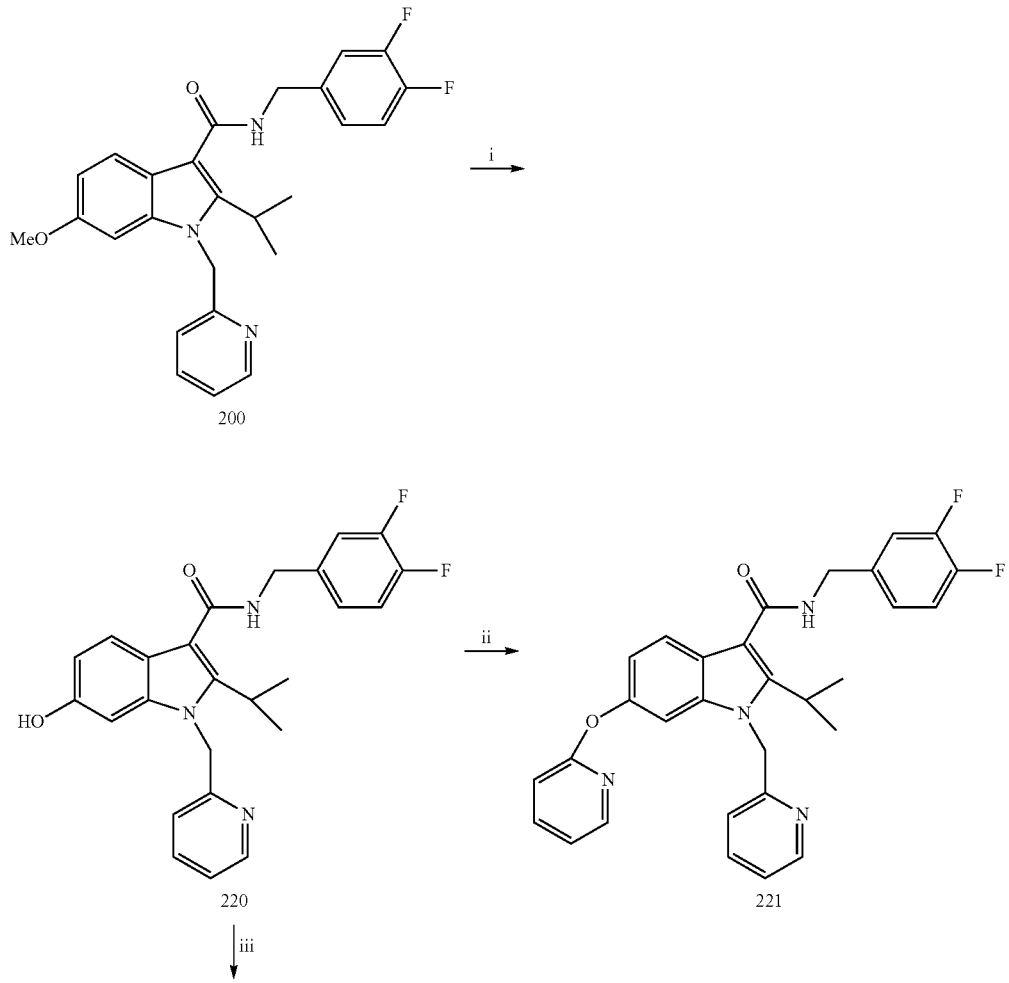

-continued

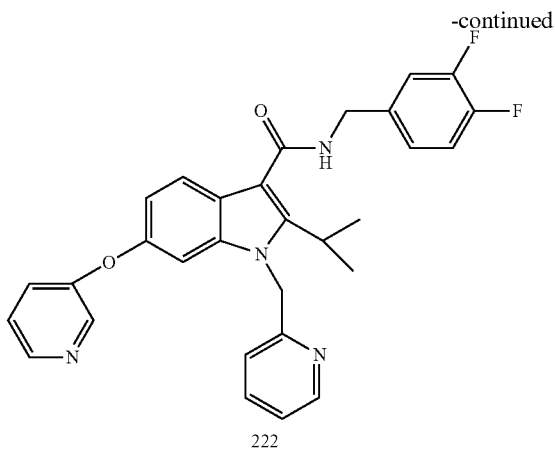

222

<sup>a</sup>Reagents and conditions: (i) BBr<sub>3</sub>, CH<sub>2</sub>Cl<sub>2</sub>; (ii) 2-iodopyridine, Cs<sub>2</sub>CO<sub>3</sub>, Cu, DMF; (iii) 3-bromopyridine, KOH, Cu, DMA.

EXAMPLE 220

N-(3,4-Difluorobenzyl)-6-hydroxy-2-isopropyl-1-(pyridin-2-ylmethyl)-1H-indole-3-carboxamide (Compound 220). The title compound was prepared from N-(3,4-difluorobenzyl)-2-isopropyl-6-methoxy-1-(pyridin-2-ylmethyl)-1H-indole-3-carboxamide (Compound 200) by General Procedure L.

1H NMR (300 MHz, METHANOL-$d_4$) δ ppm 1.23 (t, J=7.0 Hz, 1 H), 1.31 (d, J=7.0 Hz, 7 H), 3.46 (p, J=7.18 Hz, 1 H), 4.09 (q, 1 H), 4.57 (s, 2 H), 5.63 (s, 2 H), 6.58 (d, J=1.8 Hz, 1 H), 6.71 (dd, J=8.6, 2.2 Hz, 1 H), 6.88 (d, J=8.2 Hz, 1 H), 7.19-7.38 (m, 3 H), 7.44 (d, J=8.5 Hz, 1 H), 7.60 (d, J=5.57 Hz, 1 H), 8.01 (td, J=7.8, 1.6 Hz, 1 H), 8.68 (d, J=4.4 Hz, 1 H).

EXAMPLE 221

N-(3,4-Difluorobenzyl)-2-isopropyl-1-(pyridin-2-ylmethyl)-6-(pyridin-2-yloxy)-1H-indole-3-carboxamide (Compound 221). To a solution of N-(3,4-difluorobenzyl)-2-isopropyl-6-hydroxy-1-(pyridin-2-ylmethyl)-1H-indole-3-carboxamide (Compound 220, 26 mg, 0.060 mmol) in dimethylformamide (1 ml) stirring at room temperature, was added cesium carbonate (83 mg, 0.25 mmol) and the reaction stirred for 5 minutes. 2-iodopyridine (0.05 mL, 0.09 g, 0.47 mmol) and then copper powder (7.0 mg, 0.11 mmol) was then directly added and the resulting mixture heated at 100° C. for 18 h. The reaction was cooled to room temperature, quenched with water, extracted with EtOAc, washed with brine, dried over Na<sub>2</sub>SO<sub>4</sub>, and concentrated under reduced pressure. The residue was purified by flash column chromatography on silica gel (50% EtOAc-hexanes, 100 % EtOAc) to yield the title compound as a white solid.

1H NMR (300 MHz, METHANOL-$d_4$) δ ppm 1.34 (d, J=7.2 Hz, 6 H), 3.51 (p, J=7.2 Hz, 1 H), 4.60 (d, J=5.9 Hz, 2 H), 5.55 (s, 2 H), 6.73 (d, J=7.9 Hz, 1 H), 6.81 (d, J=8.2 Hz, 1 H), 6.91 (dd, J=8.5, 2.2 Hz, 1 H), 7.01-7.10 (m, 2 H), 7.20-7.42 (m, 4 H), 7.65 (d, J=8.5 Hz, 1 H), 7.69 (dd, J=7.9, 1.8 Hz, 1 H), 7.74 (ddd, J=8.2, 7.2, 2.0 Hz, 1 H), 8.07 (dt, J=5.7, 1.9 Hz, 1H), 8.50 (dt, J=4.8, 1.3 Hz, 1 H), 8.67 (t, J=5.9 Hz, 1 H).

EXAMPLE 222

N-(3,4-Difluorobenzyl)-2-isopropyl-1-(pyridin-2-ylmethyl)-6-(pyridin-3-yloxy)-1H-indole-3-carboxamide (Compound 222). General Procedure G. To a solution of N-(3,4-difluorobenzyl)-2-isopropyl-6-hydroxy-1-(pyridin-2-ylmethyl)-1H-indole-3-carboxamide (Compound 220, 30 mg, 0.069 mmol) in N,N-dimethylacetamide (1.50 ml) stirring at room temperature, was added potassium hydroxide (80 mg, 1.43 mmol) and the reaction stirred for 5 minutes. 3-bromopyridine (0.05 mL, 0.08 g, 0.51 mmol) and then Copper powder (9.0 mg, 0.14 mmol) was then directly added and the resulting mixture heated at 120-140° C. for 18 h. The reaction was cooled to room temperature, quenched with water, extracted with EtOAc, washed with brine, dried over Na<sub>2</sub>SO<sub>4</sub>, and concentrated under reduced pressure. The residue was purified by flash column chromatography on silica gel (50% EtOAc-hexanes, 100 % EtOAc) to yield N-(3,4-difluorobenzyl)-2-isopropyl-1-(pyridin-2-ylmethyl)-6-(pyridin-3-yloxy)-1H-indole-3-carboxamide (Compound 222) as a yellow solid (2.3 mg). 1H NMR (300 MHz, METHANOL-$d_4$) δ ppm 1.34 (d, J=7.0 Hz, 6 H), 4.59 (s, 2 H), 5.55 (s, 2 H), 6.72 (d, J=8.2 Hz, 1 H), 6.92 (dd, J=8.6, 2.2 Hz, 1 H), 7.02 (d, J=2.0 Hz, 1 H), 7.19-7.42 (m, 6 H), 7.62-7.74 (m, 2 H), 8.14-8.24 (m, 2 H), 8.49 (d, J=5.0 Hz, 1 H).

EXAMPLE 223

Ethyl 2-(6-(Cyclopentyloxy)-3-(3,4-difluorobenzylcarbamoyl)-2-isopropyl-1H-indol-1-yl)acetate (Compound 223). The title compound was prepared from 2-isopropyl-6-methoxy-1H-indole-3-carbaldehyde (Compound 137) and ethyl2-bromoacetate by following, in order, General Procedure J, General Procedure K, General Procedure C, General Procedure L, and General Procedure N.

1H NMR (300 MHz, METHANOL-$d_4$) δ ppm 1.25 (t, J=7.0 Hz, 3 H), 1.39 (d, J=7.3 Hz, 6 H), 1.60-2.00 (m, 8 H), 3.48 (p, J=7.3 Hz, 1 H), 4.21 (q, J=7.0 Hz, 2 H), 4.56 (s, 2 H), 5.02 (s, 2 H), 6.76 (dd, J=9.0, 2.1 Hz, 1 H), 6.77 (d, J=2.1 Hz, 1 H), 7.20-7.36 (m, 3 H), 7.45 (d, J=9.0 Hz, 1 H).

EXAMPLE 224

3-(3,4-Difluorobenzylcarbamoyl)-6-methoxy-1-(pyridin-2-ylmethyl)-1H-indole-2-carboxylic Acid (Compound 224). General Procedure L. To a solution of methyl3-(3,4-difluorobenzylcarbamoyl)-6-methoxy-1-(pyridin-2-ylmethyl)-1H-indole-2-carboxylate (Compound 93, 149 mg, 0.32 mmol) in CH$_2$Cl$_2$ (10 ml) was added BBr$_3$ (1M in CH$_2$Cl$_2$, 1.6 ml, 1.6 mmol) slowly at 0° C. The mixture was stirred at room temperature for 2 h, and was quenched with ice, extracted with EtOAc (×3). The combined organic layer was washed with brine, dried over Na$_2$SO$_4$, and concentrated in vacuo. The residue was purified by PTLC on silica gel (10% MeOH—CH$_2$Cl$_2$) to yield the title compound.

1H NMR (300 MHz, METHANOL-d$_4$) δ ppm 3.74 (s, 3 H), 4.57 (s, 2 H), 5.91 (s, 2 H), 6.77 (d, J=2.3 Hz, 1 H), 6.80-6.92 (m, J=8.9, 2.2 Hz, 2 H), 7.12-7.37 (m, 4 H), 7.56-7.69 (m, 1 H), 8.18 (d, J=8.2 Hz, 1 H), 8.48 (s, 1 H).

EXAMPLE 225

3-(3,4-Difluorobenzylcarbamoyl)-6-hydroxy-1-(pyridin-2-ylmethyl)-1H-indole-2-carboxylic Acid (Compound 225). General Procedure M. To a solution of AlCl$_3$ (1.8 g, 13.5 mmol) in EtSH (25 ml) at room temperature was added a solution of methyl 3-(3,4-difluorobenzylcarbamoyl)-6-methoxy-1-(pyridin-2-ylmethyl)-1H-indole-2-carboxylate (Compound 93, 1.26 g, 2.7 mmol) in CH$_2$Cl$_2$ (75 ml). The reaction was stirred for 2 h and was quenched with ice. The mixture was concentrated in vacuo, and the resulting white suspension in aqueous solution was acidified with 1M HCl and filtered. The cake was washed with H$_2$O (×3), taken in MeOH, dried over MgSO$_4$, and concentrated in vacuo to yield the title compound as a crude yellowish white solid contaminated with unknown inorganic product. The crude was used without further purification.

1H NMR (300 MHz, METHANOL-d$_4$) δ ppm 4.63 (s, 2 H), 5.92 (s, 2 H), 6.73 (d, J=1.5 Hz, 1 H), 6.82 (dd, J=8.8, 2.1 Hz, 1 H), 6.94 (d, J=7.9 Hz, 1 H), 7.17-7.30 (m, 2 H), 7.30-7.44 (m, 2 H), 7.65-7.84 (m, 2 H), 8.47-8.57 (m, 1 H).

EXAMPLE 226

Methyl 3-(3,4-Difluorobenzylcarbamoyl)-6-isopropoxy-1-(pyridin-2-ylmethyl)-1H-indole-2-carboxylate (Compound 226). A solution of 3-(3,4-difluorobenzylcarbamoyl)-6-hydroxy-1-(pyridin-2-ylmethyl)-1H-indole-2-carboxylic acid (Compound 225, crude 6.5 g) and concentrated H$_2$SO$_4$ (0.1 ml, catalytic amount) in MeOH (100 ml) was heated to 90° C. for 16 h. The mixture was cooled and the suspension was filtered. The filtrate was concentrated, diluted with EtOAc, washed with H$_2$O and brine, dried over Na$_2$SO$_4$, and concentrated in vacuo to give a pale brown solid as the crude product. General Procedure N. To a solution of the crude product in DMF (10 ml) was added 2-iodopropane (2.2 ml, 22 mmol) and K$_2$CO$_3$ (1.8 g, 13.2 mmol). The reaction was stirred at room temperature for 16 h and was diluted with EtOAc, washed with H$_2$O and brine, dried over Na$_2$SO$_4$, and concentrated in vacuo. The residue was purified by chromatography on silica gel (0→100% EtOAc-hexanes) to yield the title compound as a white solid.

1H NMR (300 MHz, METHANOL-d$_4$) δ ppm 1.26 (d, J=6.2 Hz, 6 H), 3.69 (s, 3 H), 4.50-4.66 (m, 3 H), 5.87 (s, 2 H), 6.79-6.93 (m, 3 H), 7.20-7.31 (m, 3 H), 7.33-7.44 (m, 1 H), 7.59 (dd, J=8.5, 0.9 Hz, 1 H), 7.67 (td, J=7.8, 1.8 Hz, 1 H), 8.48 (ddd, J=5.0, 1.8, 0.9 Hz, 1 H).

The foregoing description details specific methods and compositions that can be employed to practice the present invention, and represents the best mode contemplated. Thus, however detailed the foregoing may appear in text, it should not be construed as limiting the overall scope hereof, rather, the ambit of the present invention was to be governed only by the lawful construction of the appended claims. In particular, the present invention includes a 6-substituted indole-3-carboxylic acid-N-arylmethyl amide having sphingosine-1-phosphate antagonist activity wherein the 6-substituent is represented by the formula -A$^1$-(X$^1$)$_r$-A$^2$-B wherein X$_1$ is O;
r is 0 or 1;
A$^2$ is absent or is (CH$_2$)$_v$, wherein v is 1 or 2;
B is OR$^6$ or NR$^8$R$^9$, wherein R$^6$, R$^8$ and R$^9$ are methyl; or
B is CR$^{10}$=NO R$^{11}$R$^{10}$ wherein R$^{10}$ is H and R$^{11}$ is methyl or i-butyl; or B is CONR$^8$R$^9$, wherein R$^8$ and R$^9$ are selected from the group consisting of H, methyl, ethyl and propyl or R$^8$ and R$^9$, together with N, form a 5-membered ring; or B is OR$^6$, wherein R$^6$ is H; or
B is COR$^{10}$, wherein R$^{10}$ is methyl.

What is claimed is:
1. A compound represented by the formula I having sphingosine-1-phosphate receptor agonist and or antagonist biological activity:

Formula I wherein:
R$^1$ is selected from the group consisting of hydrogen, straight or branched chain alkyl having 1 to 12 carbons, heterocyclic groups having up to 20 carbon atoms and at least one of oxygen, nitrogen and/or sulfur in the ring, halo, C$_1$ to C$_{12}$ haloalkyl, hydroxyl, C$_1$ to C$_{12}$ alkoxy, C$_1$ to C$_{12}$ alkylcarbonyl, formyl, C$_1$ to C$_{12}$ alkyl carboxylate, C$_1$ to C$_{12}$ alkyl amide, aminocarbonyl, amino, cyano, nitro and sulfonyl groups;
R$^2$ is selected from the group consisting of hydrogen and halo;
R$^3$ is selected from the group consisting of straight or branched chain alkyl having 3 to 12 carbons, carbocyclic hydrocarbon groups having from 3 to 20 carbon atoms, heterocyclic groups having up to 20 carbon atoms and at least one of oxygen, nitrogen and/or sulfur in the ring, C$_1$ to C$_{12}$ alkoxy, C$_1$ to C$_{12}$ alkylcarbonyl and C$_1$ to C$_{12}$ alkyl carboxylate;
R$^4$ is selected from the group consisting of hydrogen, halo and C$_1$ to C$_{12}$ haloalkyl;
X is NR$^5$;
X$^1$ is selected from the group consisting of NR$^5$, O and S;
R$^5$ is hydrogen;
Y is a phenyl or a pyridyl group and wherein said phenyl or pyridyl group may be bonded to A at any position;
Z is O;
n is 0 or an integer of from 1 to 5;
o is an integer of from 1 to 3;
p is 1;
q is 1;
r is 0 or 1;
A is selected from the group consisting of (CH$_2$)$_v$ wherein v is an integer of from 1 to 12;

$A^1$ and $A^2$ are independently selected from the group consisting of $(CN_2)_v$, wherein v is 0 or an integer of from 1 to 12, and branched chain alkyl having 3 to 12 carbons;

B is selected from the group consisting of hydrogen, $OR^6$, $COOR^7$, $NR^8R^9$, $CONR^8R^9$, $COR^{10}$, $CH=NOR^{11}$, and $CH=NNR^{12}R^{13}$; and wherein $R^6$, $R^7$, $R^{10}$ and $R^{11}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, and a heterocyclic group having up to 20 carbon atoms and at least one of oxygen, nitrogen and/or sulfur in the ring, $R^8$, $R^9$, $R^{12}$ and $R^{13}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, and a heterocyclic group having up to 20 carbon atoms and at least one of oxygen, nitrogen and/or sulfur in the ring, or $R^8$ and $R^9$ and/or $R^{12}$ and $R^{13}$, together, can form a divalent carbon radical of 2 to 5 carbons to form a heterocyclic ring with nitrogen, wherein any of $R^6$, $R^7$, $R^8$, $R^9$, $R^{10}$, $R^{11}$, $R^{12}$ or $R^{13}$ may be substituted with one or more halogen, hydroxy, alkyloxy, cyano, nitro, mercapto or thiol radical; provided however, when v is 0, and r is 0, B is not hydrogen; or B is a carbocyclic hydrocarbon group having from 3 to 20 carbon atoms, or a heterocyclic group having up to 20 carbon atoms and at least one of oxygen, nitrogen and/or sulfur in the ring, and wherein when said B is a carbocyclic or heterocyclic group B may be bonded to $A^2$ at any position, or a pharmaceutically acceptable salt of said compound.

2. The compound of claim 1 wherein A is $CH_2$.

3. The compound of claim 2 wherein n is 0 or an integer of 1 or 2 and $R^4$ is fluoro.

4. The compound of claim 3 wherein $R^1$ is i-propyl.

5. The compound of claim 4 wherein $A^1$ and $A^2$ are absent.

6. The compound of claim 5 wherein B is $OR^6$.

7. The compound of claim 5 wherein B is $COOR^7$.

8. A compound represented by the formula I having sphingosine-1-phosphate receptor agonist and or antagonist biological activity:

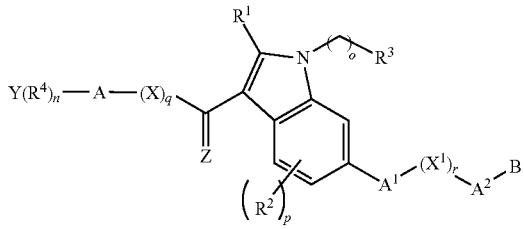

Formula I wherein:
$R^1$ is isopropyl;
$R^2$ is selected from the group consisting of hydrogen and halo;
$R^3$ is selected from the group consisting of straight or branched chain alkyl having 3 to 12 carbons, carbocyclic hydrocarbon groups having from 3 to 20 carbon atoms, heterocyclic groups having up to 20 carbon atoms and at least one of oxygen, nitrogen and/or sulfur in the ring, $C_1$ to $C_{12}$ alkoxy, $C_1$ to $C_{12}$ alkylcarbonyl and $C_1$ to $C_{12}$ alkyl carboxylate;

$R^4$ is selected from the group consisting of hydrogen, halo and $C_1$ to $C_{12}$ haloalkyl;
X $NR^5$;
$X^1$ is O;
$R^5$ is hydrogen;
Y is a phenyl or a pyridyl group and wherein said phenyl or pyridyl group may be bonded to A at any position;
Z is O;
n is 0 or an integer of from 1 to 5;
o is an integer of from 1 to 3;
p is 1;
q is 1;
r is 1;
A is selected from the group consisting of $(CH_2)_v$ wherein v is an integer of from 1 to 12;
$A^1$ is absent;
$A^2$ is $(CH_2)_v$, wherein v is 1 or 2;
B is $OR^6$ or $NR^8R^9$;
$R^6$ is selected from the group consisting of hydrogen, straight or branched chain alkyl having 1 to 12 carbons, a carbocyclic hydrocarbon group having from 3 to 20 carbon atoms, and a heterocyclic group having up to 20 carbon atoms and at least one of oxygen, nitrogen and/or sulfur in the ring;
$R^8$ is selected from the group consisting of hydrogen, straight or branched chain alkyl having 1 to 12 carbons, a carbocyclic hydrocarbon group having from 3 to 20 carbon atoms, and a heterocyclic group having up to 20 carbon atoms and at least one of oxygen, nitrogen and/or sulfur in the ring;
$R^9$ is selected from the group consisting of hydrogen, straight or branched chain alkyl having 1 to 12 carbons, a carbocyclic hydrocarbon group having from 3 to 20 carbon atoms, and a heterocyclic group having up to 20 carbon atoms and at least one of oxygen, nitrogen and/or sulfur in the ring;
or $R^8$ and $R^9$, together, can form a divalent carbon radical of 2 to 5 carbons to form a heterocyclic ring with nitrogen;
any of $R^6$, $R^8$ and $R^9$ may be substituted with one or more halogen, hydroxy, alkyloxy, cyano, nitro, mercapto or thiol moiety.

9. The compound of claim 8 wherein $R^6$, $R^8$ and $R^9$ are methyl.

10. The compound of claim 5 wherein B is $CH=NOR^{11}$ wherein $R^{11}$ is methyl or i-butyl.

11. The compound of claim 5 wherein B is $CONR^8R^9$ wherein $R^8$ and $R^9$ are selected from the group consisting of H, methyl, ethyl and propyl, or $R^8$ and $R^9$, together with N, form a 5-member ring.

12. The compound of claim 4 wherein $A^1$ is absent, r is 0, $A^2$ is $CH_2$ and B is $OR^6$, wherein $R^6$ is H.

13. The compound of claim 5 wherein $A^1$ is absent, r is 1 and B is $COR^{10}$ wherein $R^{10}$ is methyl.

14. The compound of claim 1 having sphingosine-1-phosphate antagonist activity, wherein
$X^1$ is O;
r is 0 or 1;
$A^2$ is absent or is $(CH_2)_v$ wherein v is 1 or 2;
B is $OR^6$ or $NR^8R^9$, wherein $R^6$, $R^8$ and $R^9$ are methyl; or
B is $CH=NOR^{11}$;
$R^{11}$ is methyl or i-butyl; or
B is $CONR^8R^9$, wherein $R^8$ and $R^9$ are selected from the group consisting of H, methyl, ethyl and propyl or $R^8$ and $R^9$, together with N, form a 5-membered ring; or B is $OR^6$, wherein $R^6$ is H; or B is $COR^{10}$, wherein $R^{10}$ is methyl.

* * * * *

UNITED STATES PATENT AND TRADEMARK OFFICE
CERTIFICATE OF CORRECTION

PATENT NO. : 8,524,917 B2  
APPLICATION NO. : 12/013239  
DATED : September 3, 2013  
INVENTOR(S) : Richard L. Beard et al.

Page 1 of 7

It is certified that error appears in the above-identified patent and that said Letters Patent is hereby corrected as shown below:

Title page, in Item (57), under "Abstract", in column 2, line 3, delete "and or" and insert -- and/or --, therefor.

On Title page 2, in column 1, Item (56), under "Other Publications", line 5, delete "Methoxybras Sinin B" and insert -- Methoxy brassinin B --, therefor.

On Title page 2, in column 1, Item (56), under "Other Publications", line 5, delete "Postional" and insert -- Positional --, therefor.

In the Specification

In column 1, line 52, delete "sphingomeyeline" and insert -- sphingomyelin --, therefor.

In column 1, line 55, delete "spingosine" and insert -- sphingosine --, therefor.

In column 2, line 10, delete "spingosine" and insert -- sphingosine --, therefor.

In column 2, line 63, delete "spingosine" and insert -- sphingosine --, therefor.

In column 2, line 65, delete "spingosine" and insert -- sphingosine --, therefor.

In column 3, line 14, delete "and or" and insert -- and/or --, therefor.

In column 4, line 9, delete "$R^9$," and insert -- $R^9$, --, therefor.

In column 4, line 31, delete "carbocylic" and insert -- carbocyclic --, therefor.

In column 4, line 38, delete "isooxazole," and insert -- isoxazole, --, therefor.

In column 4, line 43, delete "coumarinone." and insert -- coumaranone. --, therefor.

In column 43, line 63, delete "flouro" and insert -- fluoro --, therefor.

In column 6, line 11, delete "ethylcarbodimide" and insert -- ethylcarbodiimide --, therefor.

In column 6, line 13, delete "difluorophenylmethyl6" and insert -- difluorophenylmethyl-6 --, therefor.

In column 7, line 2, delete "ethyl4" and insert -- ethyl-4 --, therefor.

In column 9, line 36, delete "3-pyridylmethyl1" and insert -- 3-pyridylmethyl-1 --, therefor.

Signed and Sealed this  
Tenth Day of December, 2013

Margaret A. Focarino  
*Commissioner for Patents of the United States Patent and Trademark Office*

CERTIFICATE OF CORRECTION (continued)
U.S. Pat. No. 8,524,917 B2

In column 9, lines 41-42, delete "3-pyridylmethyl1" and insert -- 3-pyridylmethyl-1 --, therefor.

In column 11, line 32, delete "alkyaryl," and insert -- alkylaryl, --, therefor.

In column 12, line 35, delete "Levenburg" and insert -- Levenberg --, therefor.

In column 88, line 22, delete "NaBH4:" and insert -- $NaBH_4$: --, therefor.

In column 88, line 27, delete "N-bromosuccimide" and insert -- N-bromosuccinimide --, therefor.

In column 88, line 38, delete "oxyxhloride" and insert -- oxychloride --, therefor.

In column 88, line 48, delete "dimethylcarbamyl" and insert -- dimethylcarbamoyl --, therefor.

In column 88, line 51, delete "p-toluenesufonate" and insert -- p-toluenesulfonate --, therefor.

In column 89, line 48, delete "Methyl 1" and insert -- Methyl-1 --, therefor.

In column 89, line 49, delete "methyl6" and insert -- methyl-6 --, therefor.

In column 89, line 65, delete "methyl1" and insert -- methyl-1 --, therefor.

In column 95, line 19, delete "-1 H-" and insert -- -1H- --, therefor.

In column 95, line 41, delete "dimethylcarbamyl" and insert -- dimethylcarbamoyl --, therefor.

In column 98, line 3, delete "3-yl4" and insert -- 3-yl-4 --, therefor.

In column 98, line 18, delete "3-yl4" and insert -- 3-yl-4 --, therefor.

In column 101, line 3, delete "Ethyl 4" and insert -- Ethyl-4 --, therefor.

In column 101, line 17, delete "Ethyl 3" and insert -- Ethyl-3 --, therefor.

In column 101, line 18, delete "ethyl4" and insert -- ethyl-4 --, therefor.

In column 101, line 34, delete "Ethyl 3" and insert -- Ethyl-3 --, therefor.

In column 101, line 35, delete "ethyl3" and insert -- ethyl-3 --, therefor.

In column 101, line 53, delete "Ethyl 2" and insert -- Ethyl-2 --, therefor.

In column 101, line 54, delete "ethyl3" and insert -- ethyl-3 --, therefor.

In column 102, line 3, delete "Ethyl 3" and insert -- Ethyl-3 --, therefor.

In column 102, line 4, delete "ethyl 2" and insert -- ethyl-2 --, therefor.

In column 102, line 22, delete "Ethyl 1" and insert -- Ethyl-1 --, therefor.

In column 102, line 24, delete "ethyl3" and insert -- ethyl-3 --, therefor.

In column 102, line 40, delete "Ethyl 3" and insert -- Ethyl-3 --, therefor.

In column 102, line 42, delete "ethyl3" and insert -- ethyl-3 --, therefor.

In column 102, line 60, delete "Ethyl 3" and insert -- Ethyl-3 --, therefor.

In column 102, line 62, delete "ethyl3" and insert -- ethyl-3 --, therefor.

In column 102, line 64, delete "and and" and insert -- and --, therefor.

In column 103, line 12, delete "Ethyl 3" and insert -- Ethyl-3 --, therefor.

In column 103, line 14, delete "ethyl3" and insert -- ethyl-3 --, therefor.

In column 103, line 31, delete "(ethoxylcarbonyl)" and insert -- (ethoxycarbonyl) --, therefor.

CERTIFICATE OF CORRECTION (continued)
U.S. Pat. No. 8,524,917 B2

In column 103, line 33, delete "ethyl1" and insert -- ethyl-1 --, therefor.

In column 103, line 38, delete "fro" and insert -- for --, therefor.

In column 103, line 54, delete "ethyl3" and insert -- ethyl-3 --, therefor.

In column 104, line 9, delete "ethyl3" and insert -- ethyl-3 --, therefor.

In column 104, line 32, delete "ethyl3" and insert -- ethyl-3 --, therefor.

In column 104, line 51, delete "Ethyl 1" and insert -- Ethyl-1 --, therefor.

In column 104, line 53, delete "(ethoxylcarbonyl)" and insert -- (ethoxycarbonyl) --, therefor.

In column 105, line 3, delete "Ethyl 1" and insert -- Ethyl-1 --, therefor.

In column 105, lines 5-6, delete "(ethoxylcarbonyl)" and insert -- (ethoxycarbonyl) --, therefor.

In column 105, line 8, delete "0.381mmol)," and insert -- 0.381 mmol), --, therefor.

In column 105, line 9, delete "methanamine" and insert -- methenamine --, therefor.

In column 105, line 24, delete "Ethyl 3" and insert -- Ethyl-3 --, therefor.

In column 105, line 30, delete "methanamine" and insert -- methenamine --, therefor.

In column 105, line 42, delete "Ethyl 3" and insert -- Ethyl-3 --, therefor.

In column 105, line 61, delete "Ethyl 3" and insert -- Ethyl-3 --, therefor.

In column 106, line 13, delete "Ethyl 3" and insert -- Ethyl-3 --, therefor.

In column 106, line 33, delete "Ethyl 3" and insert -- Ethyl-3 --, therefor.

In column 106, line 40, delete "methanamine" and insert -- methenamine --, therefor.

In column 106, line 52, delete "Ethyl 3" and insert -- Ethyl-3 --, therefor.

In column 107, line 3, delete "Difluorobenzyl 1" and insert -- Difluorobenzyl-1 --, therefor.

In column 107, line 7, delete "0.1 1 mmol)" and insert -- 0.11 mmol) --, therefor.

In column 107, line 25, delete "ethyl1" and insert -- ethyl-1 --, therefor.

In column 109, line 54, delete "ethyl1" and insert -- ethyl-1 --, therefor.

In column 110, line 53, delete "-1-" and insert -- -1H- --, therefor.

In column 110, line 54, delete "ethyl1" and insert -- ethyl-1 --, therefor.

In column 111, line 5, delete "ethyl3" and insert -- ethyl-3 --, therefor.

In column 111, lines 6-7, delete "1 H" and insert -- 1H --, therefor.

In column 111, line 24, delete "ethyl3" and insert -- ethyl-3 --, therefor.

In column 111, line 43, delete "ethyl3" and insert -- ethyl-3 --, therefor.

In column 111, line 52, delete "ethyl3" and insert -- ethyl-3 --, therefor.

In column 112, line 15, delete "ethyl3" and insert -- ethyl-3 --, therefor.

In columns 119-120, line 6, delete "93" and insert -- 225 --, therefor.

In column 121, line 3, delete "Methyl 3" and insert -- Methyl-3 --, therefor.

In column 121, line 7, delete "methyl6" and insert -- methyl-6 --, therefor.

In column 121, line 21, delete "Methyl 3" and insert -- Methyl-3 --, therefor.

In column 121, line 27, delete "methyl3" and insert -- methyl-3 --, therefor.

In column 122, line 5, delete "methyl3" and insert -- methyl-3 --, therefor.

In column 122, line 22, delete "Methyl 3" and insert -- Methyl-3 --, therefor.

In column 123, line 35, delete "methyl3" and insert -- methyl-3 --, therefor.

In column 125, line 56, delete "Isopropyl3" and insert -- Isopropyl-3 --, therefor.

In column 125, line 60, delete "methyl3" and insert -- methyl-3 --, therefor.

In column 126, line 5, delete "isopropyl 3" and insert -- isopropyl-3 --, therefor.

In column 127, line 43, delete "methyl3" and insert -- methyl-3 --, therefor.

In column 131, line 22, delete "ethyl4" and insert -- ethyl-4 --, therefor.

In column 131, line 36, delete "Ethyl 4" and insert -- Ethyl-4 --, therefor.

In column 131, line 53, delete "Ethyl 4" and insert -- Ethyl-4 --, therefor.

In column 132, line 25, delete "Ethyl 2" and insert -- Ethyl-2 --, therefor.

In column 132, line 27, delete "ethyl4" and insert -- ethyl-4 --, therefor.

In column 132, line 48, delete "Ethyl 1" and insert -- Ethyl-1 --, therefor.

In column 132, line 50, delete "ethyl2" and insert -- ethyl-2 --, therefor.

In column 138, line 28, delete "ethyl4" and insert -- ethyl-4 --, therefor.

In column 142, line 47, delete "methanamine" and insert -- methenamine --, therefor.

In column 143, line 59, delete "methanamine" and insert -- methenamine --, therefor.

In column 144, line 9, delete "methanamine" and insert -- methenamine --, therefor.

In column 144, line 12, delete "methanamine" and insert -- methenamine --, therefor.

In column 144, line 32, delete "methanamine" and insert -- methenamine --, therefor.

In column 148, line 48, delete "methanamine" and insert -- methenamine --, therefor.

In column 150, line 63, delete "Ethyl 2" and insert -- Ethyl-2 --, therefor.

In column 151, line 13, delete "Ethyl 6" and insert -- Ethyl-6 --, therefor.

In column 151, line 15, delete "ethyl2" and insert -- ethyl-2 --, therefor.

In column 151, line 25, delete "Ethyl 5" and insert -- Ethyl-5 --, therefor.

In column 151, line 27, delete "ethyl6" and insert -- ethyl-6 --, therefor.

In column 151, line 45, delete "Ethyl 1" and insert -- Ethyl-1 --, therefor.

In column 151, line 47, delete "ethyl5" and insert -- ethyl-5 --, therefor.

In column 151, line 60, delete "ethyl1" and insert -- ethyl-1 --, therefor.

In columns 159-160, line 2, structure 1, delete " 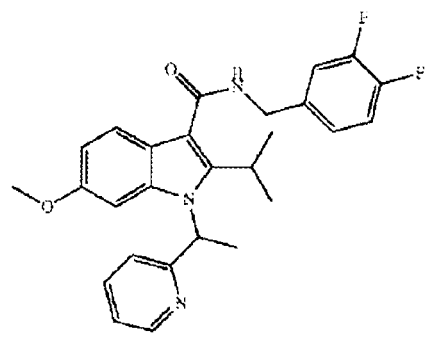 " and
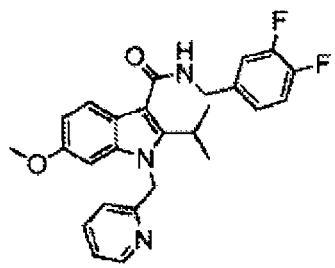
insert -- -- , therefor.
In columns 159-160, structure 2, line 2, delete " 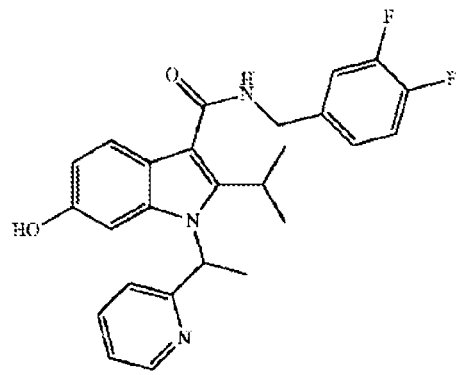 " and
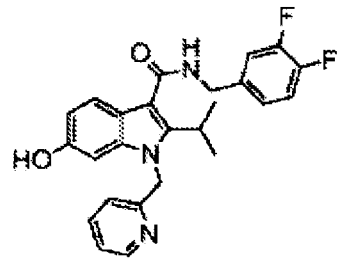
insert -- -- , therefor.

In columns 159-160, structure 1, line 3, delete " 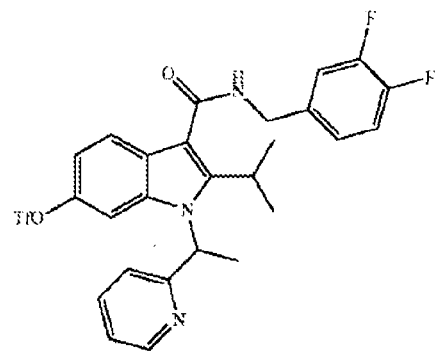 " and
insert -- 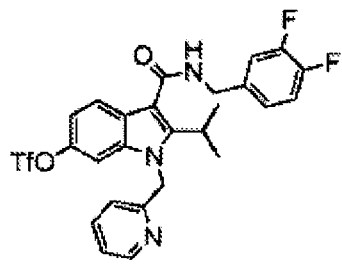 --, therefor.
In columns 159-160, structure 2, line 3, delete " 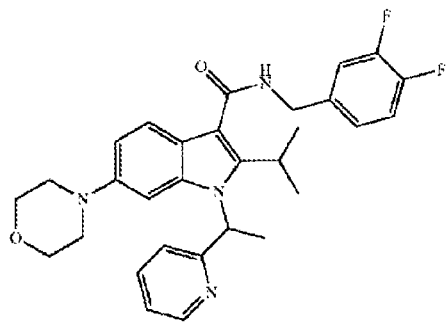 " and
insert -- 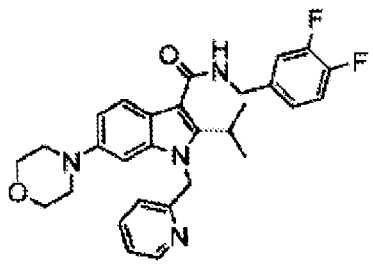 --, therefor.

CERTIFICATE OF CORRECTION (continued)
U.S. Pat. No. 8,524,917 B2

In column 161, line 1, delete " 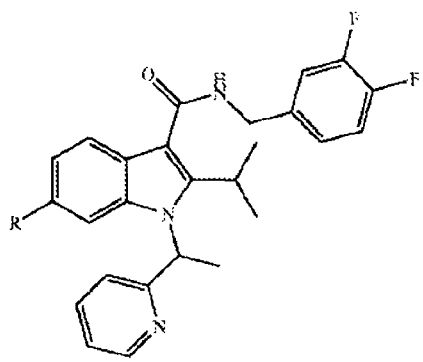 " and insert -- 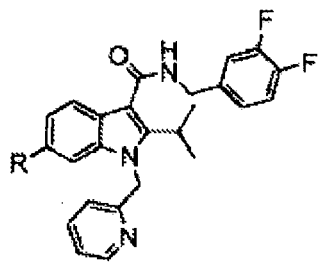 --, therefor.

In column 163, line 26, delete "pinocol" and insert -- pinacol --, therefor.

In column 170, line 48, delete "Ethyl 2" and insert -- Ethyl-2 --, therefor.

In column 170, line 65, delete "methyl3" and insert -- methyl-3 --, therefor.

In column 171, line 19, delete "methyl3" and insert -- methyl-3 --, therefor.

In column 171, line 37, delete "Methyl 3" and insert -- Methyl-3 --, therefor.

In the Claims

In column 172, line 19, in claim 1, delete "and or" and insert -- and/or --, therefor.

In column 173, line 15, in claim 1, delete "$R^9$," and insert -- $R^9$, --, therefor.

In column 173, line 44, in claim 8, delete "and or" and insert -- and/or --, therefor.

In column 174, line 3, in claim 8, delete "X $NR^5$;" and insert -- X is $NR^5$; --, therefor.

In column 174, line 39, in claim 8, delete "$R^6$," and insert -- $R^6$, --, therefor.

In column 174, line 60, in claim 14, delete "CH=$NOR^{11}$;" and insert -- CH=$NOR^{11}$; --, therefor.